(12) United States Patent
Kuball et al.

(10) Patent No.: US 12,161,669 B2
(45) Date of Patent: Dec. 10, 2024

(54) COMPOSITIONS AND METHODS FOR CELL TARGETING THERAPIES

(71) Applicant: UMC UTRECHT HOLDING B.V., Utrecht (NL)

(72) Inventors: Jürgen Herbert Ernst Kuball, Utrecht (NL); Zsolt Sebestyen, Utrecht (NL); Dennis Beringer, Utrecht (NL); Anna Vyborova, Utrecht (NL)

(73) Assignee: UMC UTRECHT HOLDING B.V., Utrecht (NL)

( * ) Notice: Subject to any disclaimer, the term of this patent is extended or adjusted under 35 U.S.C. 154(b) by 785 days.

(21) Appl. No.: 16/614,691

(22) PCT Filed: May 18, 2018

(86) PCT No.: PCT/EP2018/063210
§ 371 (c)(1),
(2) Date: Nov. 18, 2019

(87) PCT Pub. No.: WO2018/211115
PCT Pub. Date: Nov. 22, 2018

(65) Prior Publication Data
US 2020/0368278 A1 Nov. 26, 2020

Related U.S. Application Data

(60) Provisional application No. 62/508,272, filed on May 18, 2017, provisional application No. 62/508,833, filed on May 19, 2017.

(51) Int. Cl.
| | | |
|---|---|---|
| *A61K 35/17* | (2015.01) | |
| *A61K 38/17* | (2006.01) | |
| *A61P 35/00* | (2006.01) | |
| *C07K 14/725* | (2006.01) | |
| *C07K 16/28* | (2006.01) | |

(52) U.S. Cl.
CPC .......... *A61K 35/17* (2013.01); *A61K 38/1774* (2013.01); *A61P 35/00* (2018.01); *C07K 14/7051* (2013.01); *C07K 16/2827* (2013.01); *C07K 2319/00* (2013.01)

(58) Field of Classification Search
CPC ................ A61P 35/00; C07K 14/7051; C07K 16/2827
See application file for complete search history.

(56) References Cited

U.S. PATENT DOCUMENTS

| | | | |
|---|---|---|---|
| 5,122,464 A | 6/1992 | Wilson et al. | |
| 5,260,223 A | 11/1993 | Brenner et al. | |
| 5,595,756 A * | 1/1997 | Bally .................. | A61K 9/1272 264/4.1 |
| 5,723,309 A | 3/1998 | Bonneville | |
| 5,770,359 A | 6/1998 | Wilson et al. | |
| 5,858,358 A | 1/1999 | June et al. | |
| 5,883,223 A | 3/1999 | Gray | |
| 5,885,827 A | 3/1999 | Wabl et al. | |
| 6,165,782 A | 12/2000 | Naldini et al. | |
| 6,207,455 B1 | 3/2001 | Chang | |
| 6,218,181 B1 | 4/2001 | Verma et al. | |
| 6,277,633 B1 | 8/2001 | Olsen | |
| 6,323,031 B1 | 11/2001 | Cichutek | |
| 6,352,694 B1 | 3/2002 | June et al. | |
| 6,534,055 B1 | 3/2003 | June et al. | |
| 6,692,964 B1 | 2/2004 | June et al. | |
| 6,797,514 B2 | 9/2004 | Berenson et al. | |
| 6,867,041 B2 | 3/2005 | Berenson et al. | |
| 6,887,466 B2 | 5/2005 | June et al. | |
| 6,905,680 B2 | 6/2005 | June et al. | |
| 6,905,681 B1 | 6/2005 | June et al. | |
| 6,905,874 B2 | 6/2005 | Berenson et al. | |
| 7,067,318 B2 | 6/2006 | June et al. | |
| 7,144,575 B2 | 12/2006 | June et al. | |
| 7,172,869 B2 | 2/2007 | June et al. | |
| 7,175,843 B2 | 2/2007 | June et al. | |
| 7,232,566 B2 | 6/2007 | June et al. | |
| 8,603,950 B2 | 12/2013 | Bowers et al. | |
| 8,999,715 B2 | 4/2015 | Bonini et al. | |
| 9,891,211 B2 * | 2/2018 | Kuball .................. | C12N 15/85 |
| 10,324,083 B2 | 6/2019 | Kuball et al. | |
| 11,299,708 B2 * | 4/2022 | Jakobovits ............. | A61P 29/00 |
| 2002/0011914 A1 | 1/2002 | Ikeura et al. | |
| 2002/0119149 A1 | 8/2002 | Jakobsen et al. | |

(Continued)

FOREIGN PATENT DOCUMENTS

| | | |
|---|---|---|
| CA | 2996887 A1 | 3/2017 |
| CN | 1379041 A | 11/2002 |

(Continued)

OTHER PUBLICATIONS

Sebestyen et al., RhoB mediates phosphoantigen recognition by Vγ9Vδ2 T cell receptor, May 2016, Cell Reports, vol. 15, Issue 9, pp. 1-26 (Year: 2016).*
Gogoi and Chiplunkar, Targeting gamma delta T cells for cancer immunotherapy: bench to bedside, Nov. 2013, Indian Journal of Medical Research, vol. 138, pp. 755-761 (Year: 2013).*
Heppner and Miller Tumor heterogeneity: biological implications and therapeutic consequences, 1983, Cancer Metastasis Reviews, vol. 2, pp. 5-23 (Year: 1983).*
Hsiao et al., Synthesis of a Phosphoantigen Prodrug that Potently Activates Vγ9Vδ2 T-Lymphocytes, Aug. 2014, Chemistry & Biology, vol. 21, pp. 945-954 (Year: 2014).*
Huang et al., RhoB facilitates c-Myc turnover by supporting efficient nuclear accumulation of GSK-3, 2006, Oncogene, vol. 25, pp. 1281-1289 (Year: 2006).*

(Continued)

Primary Examiner — Jeffrey Stucker
Assistant Examiner — Brittney E Donoghue
(74) Attorney, Agent, or Firm — POLSINELLI PC

(57) ABSTRACT

The current disclosure provides polypeptide constructs and cells comprising CDR3 regions of γ9. δ2 or both, that selectively bind a J-configuration of CD277 on a target cell. The disclosure also provides pharmaceutical compositions with the disclosed polypeptides or cells and methods of using these compositions in the treatment of cancer.

8 Claims, 29 Drawing Sheets
Specification includes a Sequence Listing.

(56) References Cited

U.S. PATENT DOCUMENTS

| | | |
|---|---|---|
| 2002/0142389 A1 | 10/2002 | Jakobsen et al. |
| 2006/0093613 A1 | 5/2006 | Jakobsen et al. |
| 2006/0121005 A1 | 6/2006 | Berenson et al. |
| 2006/0155115 A1 | 7/2006 | Jakobsen et al. |
| 2007/0036812 A1 | 2/2007 | Sato et al. |
| 2008/0131415 A1 | 6/2008 | Riddell et al. |
| 2009/0105133 A1 | 4/2009 | Boulter |
| 2010/0151467 A1 | 6/2010 | Wohlgemuth et al. |
| 2014/0120622 A1 | 5/2014 | Gregory et al. |
| 2014/0219975 A1 | 8/2014 | June et al. |
| 2014/0308250 A1 | 10/2014 | Handgretinger et al. |
| 2014/0356398 A1 | 12/2014 | Riddell et al. |
| 2015/0017137 A1 | 1/2015 | Spencer et al. |
| 2015/0050670 A1 | 2/2015 | Kuball et al. |
| 2015/0306142 A1 | 10/2015 | Bonini et al. |
| 2015/0344844 A1 | 12/2015 | Better et al. |
| 2015/0353643 A1* | 12/2015 | Olive ............ A61K 39/001129 424/172.1 |
| 2016/0367664 A1 | 12/2016 | Wang et al. |
| 2017/0174741 A1 | 6/2017 | Kuball et al. |
| 2019/0169260 A1 | 6/2019 | Kuball et al. |
| 2019/0209613 A1 | 7/2019 | Kuball et al. |
| 2019/0271688 A1 | 9/2019 | Kuball et al. |

FOREIGN PATENT DOCUMENTS

| | | |
|---|---|---|
| CN | 101155829 A | 4/2008 |
| CN | 102453701 A | 5/2012 |
| CN | 102532269 A | 7/2012 |
| CN | 105296431 A | 2/2016 |
| EP | 1080193 A2 | 3/2001 |
| EP | 1066380 B1 | 11/2001 |
| EP | 2099902 A1 | 9/2009 |
| EP | 1956080 B1 | 9/2011 |
| EP | 2710123 A2 | 3/2014 |
| EP | 3102609 A2 | 12/2016 |
| EP | 3144388 A1 | 3/2017 |
| WO | 9208796 A1 | 5/1992 |
| WO | WO-199412648 A2 | 6/1994 |
| WO | 9428143 A1 | 12/1994 |
| WO | WO9960120 A2 | 11/1999 |
| WO | WO-199958557 A2 | 11/1999 |
| WO | WO-200224718 | 3/2002 |
| WO | WO-2003060097 A2 | 7/2003 |
| WO | 03090694 A2 | 11/2003 |
| WO | WO-2004016225 A2 | 2/2004 |
| WO | 2004033685 A1 | 4/2004 |
| WO | WO-2005016962 A2 | 2/2005 |
| WO | WO-2005019258 A2 | 3/2005 |
| WO | 2006000830 A2 | 1/2006 |
| WO | WO-2006056733 A1 | 6/2006 |
| WO | WO-2009136874 A1 | 11/2009 |
| WO | WO2010058023 A1 | 5/2010 |
| WO | WO-2010087335 A1 | 8/2010 |
| WO | WO-2013147606 A1 | 10/2013 |
| WO | WO-2014179202 A1 | 11/2014 |
| WO | WO-2015063069 A1 | 5/2015 |
| WO | WO-2015075939 A1 | 5/2015 |
| WO | WO-2015174439 A1 | 11/2015 |
| WO | WO-2016195086 A1 | 12/2016 |
| WO | WO-2017096239 A1 | 6/2017 |
| WO | 2017197347 A1 | 11/2017 |
| WO | 2017212074 A1 | 12/2017 |
| WO | WO-2017212072 A1 | 12/2017 |
| WO | 2018162563 A1 | 9/2018 |
| WO | WO-2018211115 A1 | 11/2018 |
| WO | 2019156566 A1 | 8/2019 |
| WO | 2019219979 A1 | 11/2019 |

OTHER PUBLICATIONS

Kabelitz, CD277 takes the lead in human γδ T-cell activation, Sep. 2012, Blood, vol. 20, No. 11, pp. 2159-2161 (Year: 2012).*

Kabelitz and Dechanet-Merville, Editorial: "Recent advances in gamma/delta T cell biology: new ligands, new functions, and new translational perspectives", Jul. 2015, Frontiers in Immunology, vol. 6, Article 371, pp. 1-6 (Year: 2015).*

Karunakaran and Hermann, The Vγ9Vδ2 T cell antigen receptor and butyrophilin-3 A1: models of interaction, the possibility of co-evolution, and the case of dendritic epidermal T cells, Dec. 2014, Frontiers in Immunology, vol. 5, Article 648, pp. 1-13 (Year: 2014).*

Palakodeti et al., The Molecular Basis for Modulation of Human Vγ9Vδ2 T Cell Responses by CD277/Butyrophilin-3 (BTN3A)-specific Antibodies, Jul. 2012, The Journal of Biological Chemistry, vol. 287, No. 39, pp. 32780-32790 (Year: 2012).*

Sandstrom et al., The Intracellular B30.2 Domain of Butyrophilin 3A1 Binds Phosphoantigens to Mediate Activation of Human Vγ9Vδ2 T Cells, Apr. 2014, Immunity, vol. 40, pp. 490-500 (Year: 2014).*

Scheper et al., Cancer immunotherapy using γδT cells: dealing with diversity, Nov. 2014, Frontiers in Immunology, vol. 5, Article 601, pp. 1-9 (Year: 2014).*

Scheper, γδT cells for immunotherapy in cancer, Mar. 3, 2015, Thesis, pp. 1-172 (Year: 2015).*

Sicard et al., Synthetic Phosphoantigens Enhance Human Vγ9Vδ2 T Lymphocytes Killing of Non-Hodgkin's B Lymphoma, Oct. 2001, Molecular Medicine, vol. 7, No. 10, pp. 711-722 (Year: 2001).*

Vavassori et al., Butyrophilin 3A1 binds phosphorylated antigens and stimulates human γδT cells, Sep. 2013, Nature Immunology, vol. 14, No. 9, pp. 908-918 (Year: 2013).*

Peng et al., Loss of PTEN Promotes Resistance to T Cell-Mediated Immunotherapy, 2016, Cancer Discovery, vol. 6, Issue 2, pp. 202-216 (Year: 2016).*

Sporn and Suh, Chemoprevention of Cancer, Carcinogenesis, 2000, vol. 21, Issue 3, pp. 525-530 (Year: 2000).*

Auerbach et al., Angiogenesis assays: Problems and pitfalls, Cancer and Metastasis Reviews, 2000, vol. 19, pp. 167-172 (Year: 2000).*

Gura, Systems for Identifying New Drugs are Often Faulty, Science, 1997, vol. 278, pp. 1041-1042 (Year: 1997).*

Jain, Barriers to Drug Delivery in Solid Tumors, Scientific American, 1994, pp. 58-65 (Year: 1994).*

Hait, Anticancer drug development: the grand challenges, Nature Reviews/Drug Discovery, 2010, vol. 9, pp. 253-254 (Year: 2010).*

Gravanis et al., The changing world of cancer drug development: the regulatory bodies' perspective, Chinese Clinical Oncology, 2014, vol. 3, Issue 2, pp. 1-5 (Year: 2014).*

Beans, Targeting metastasis to halt cancer's spread, PNAS, 2018, vol. 115, No. 50, pp. 12539-12543 (Year: 2018).*

Cooper, The Development and Cause of Cancer, The Cell: A molecular Approach, 2000, 2nd edition (Year: 2000).*

Laydon et al., Estimating T-cell repertoire diversity: limitations of classical estimators and a new approach, 2015, Philos Trans R Soc Lond B Biol Sci, Issue 370, pp. 1-11 (Year: 2015).*

Krishna et al., Genetic and environmental determinants of human TCR repertoire diversity, 2020, Immunity & Ageing, vol. 17, Article 26, pp. 1-7 (Year: 2020).*

Vajdos et al. (J Mol Biol. Jul. 5, 2002;320(2):415-28 (Year: 2002).*

Brown et al. (J Immunol. May 1996; 156(9):3285-91 (Year: 1996).*

Aagaard et al (Advanced Drug Delivery Reviews 59 (2007) 75-86 (Year: 2007).*

Warzocha et al (Leukemia and Lymphoma (1997) vol. 24. pp. 267-281 (Year: 1997).*

McKeague et al (J Nucleic Acids. 2012;2012:748913. Epub Oct. 24, 2012 (Year: 2012).*

Guido et al.(Curr Med Chem. 2008; 15(1):37-46 (Year: 2008).*

Clark et al.(J. Med. Chem., 2014, 57 (12), pp. 5023-5038 (Year: 2014).*

Sporn et al., Chemoprevention of Cancer, 2000, Carcinogenesis, vol. 21, No. 3, pp. 525-530 (Year: 2000).*

Auerbach et al., Angiogenesis assays: Problems and pitfalls, 2000, Cancer and Metastasis Reviews, vol. 19, pp. 167-172 (Year: 2000).*

Gura et al., Systems for Identifying New Drugs Are Often Faulty, 1997, Science, vol. 278, pp. 1041-1042 (Year: 1997).*

Jain et al., Barriers to Drug Delivery in Solid Tumors, 1994, Scientific American, pp. 58-65 (Year: 1994).*

(56) References Cited

OTHER PUBLICATIONS

Hogenesch et al., Challenges in pre-clinical testing of anti-cancer drugs in cell culture and in animal models, 2012, Journal of Control Release, vol. 164, Issue 2, pp. 183-186 (Year: 2012).*
Christiansen et al., Biological impediments to monoclonal antibody-based cancer immunotherapy, 2004, Molecular Cancer Therapeutics, vol. 4, Issue 3, pp. 1493-1501 (Year: 2004).*
Topp et al., Antibody transport in cultured tumor cell layers, 1998, Journal of Controlled Release, 1998, vol. 53, pp. 15-23 (Year: 1998).*
Harley et al., Key implication of CD277/butyrophilin-3 (BTN3A) in cellular stress sensing by a major human γδ T-cell subset, Sep. 2012, Blood, vol. 120, No. 11, pp. 2269-2279 (Year: 2012).*
Skolnick et al (Trends Biotechnol. Jan. 2000;18(1):34-9) (Year: 2000).*
Burgess et al. (J. Cell Biol. 111:2129-2138, 1990) (Year: 1990).*
Lazar et al. (Mol. Cell. Biol., 8:1247-1252, 1988) (Year: 1988).*
Miosge (Proc Natl Acad Sci U S A. Sep. 15, 2015;112(37):E5189-98) (Year: 2015).*
Bork (Genome Research, 2000, 10:398-400) (Year: 2000).*
Kulmanov et al.(Bioinformatics, 34(4), 2018, 660-668) (Year: 2018).*
Davey et al., Recasting Human Vδ1 Lymphocytes in an Adaptive Role. Davey et al. Willcox Trends Immunol. Jun. 2018; 39(6): 446-459.
European Appl. No. 177339994.2 Office Action dated Feb. 24, 2020.
Halary et al, Shared reactivity of V2neg T cells against cytomegalovirus-infected cells and tumor intestinal epithelial cells, J Exp Med. May 16, 2005; 201(10): 1567-1578.
International Search Report and Written Opinion dated Jul. 8, 2019 for PCT/EP2019/063004 (Published as WO2019/219979)—Applicant: UMC Utrecht Holding B.V.
Lal, Nareej et al., Endothelial protein C receptor is overexpressed in colorectal cancer as a result of amplification and hypomethylation of chromosome 20q, The Journal of Pathology Clinical Research, Jul. 2017; 3(3):155-170.
Melandri et al., The γδ T cell receptor combines innate with adaptive immunity by utilizing spatially distinct regions for agonist-selection and antigen responsiveness, Nat Immunol.. Nat Immunol. Dec. 1, 2019; 19(12): 1352-1365.
Non-Final Office Action mailed Feb. 7, 2020, for U.S. Appl. No. 16/275,070.
Willcox et al., Butyrophilin-like 3 Directly Binds a Human Vγ4+T Cell Receptor Using a Modality Distinct from Clonally-Restricted Antigen, Immunity. Nov. 19, 2019; 51(5): 813-825.
XP-002789044 Database Geneseq [Online] Jan. 11, 2018 , Human:BES28452 Database Accession No. BES28452.
XP-002789045 Database Geneseq [online] Feb. 8, 2018, TCR Delta CDR3 peptide VD2#4, retrieved from EBI accession No. GP:BES28452 Database Accession No. BES28452.
Zsolt, Sebestyen et al., RhoB Mediates Phosphoantigen Recognition by V[gamma]9V[delta]2 T Cell Receptor, Cell Reports, vol. 15, No. 9, May 1, 2016.
Morita, Craig T., et al., Nonpeptide antigens, presentation mechanisms, and immunological memory of human Vγ2Vδ2 T cells: discriminating friend from foe through the recognition of prenyl pyrophosphate antigens, Immunological Reviews 2007, vol. 215: 59-76.
Yu, Songtao et al. T cell receptor γδ phenotypic lymphocyte with tumor immunity, "Overseas Medicine (Immunology division)", No. 2, 1997 (machine translation of the abstract provided).
Airoldi, I., et al. (2015). gammadelta T-cell reconstitution after HLA-haploidentical hematopoietic transplantation depleted of TCR-alphabeta+/CD19+ lymphocytes. Blood 125: 2349-58.
Altschul, et al. Basic local alignment search tool. J Mol Biol. Oct. 5, 1990;215(3):403-10.
Amado and Chen, Lentiviral vectors—the promise of gene therapy within reach?, 1999, Science 285: 674-6.
Anderson, W. French, Human gene therapy, 1998, Nature 392: pp. 25-30.

Anonymous: "EM_STD:BC030554", Dec. 2, 2006 (Dec. 2, 2006), XP055403988, Retrieved from the Internet: URL:http://ibis.internal.epo.org/exam/dbfetch.jsp?id=EM_STD:BC030554 [retrieved on Sep. 5, 2017].
Anonymous: "UP10000480E66", Mar. 23, 2007 (Mar. 23, 2007), XP055403650, Retrieved from the Internet: URL:http://www.uniprot.org/uniparc/UPI0000480E66 [retrieved on Sep. 4, 2017].
Apparailly, M., et al., Adeno-Associated Virus Pseudotype 5 Vector Improves Gene Transfer in Arthritic Joints, Hum Gene Ther, Apr. 2005; 16(4): 426-34.
Ausubel, et al., (1987) Current Protocols in Molecular Biology. Wiley.
Bender, C, et al. (2009). Analysis of colorectal cancers for human cytomegalovirus presence. Infect Agent Cancer 4: 6.
Bernatchez, Chantale et al., Adoptive T Cell Transfer and Cell Therapy as Cancer Immunotherapy (CARS), Abstracts for the 27th Annual Scientific Meeting of the Society for Immunotherapy of Cancer (SITC), J. Immunother, vol. 35, No. 9, Nov. 9, Nov.-Dec. 2012, p. 721-791.
Bolotin, DA, et al. (2015), MIXCR: software for comprehensive adaptive immunity profiling. Nat Methods 12: 380-1.
Born, et al., Peptide antigens for gamma/delta T cells. 2011, Cell Mol. Life Sci., 68: 2335-2343.
Bosnes, Vidar et al.: "Recognition of a particular HLA-DQ heterodimer by a human y/6 T cell clone*", Eur. J. Immunol, Jan. 1, 1990 (Jan. 1, 1990), pp. 1429-1433, XP055406203, Retrieved from the Internet: URL:http://onlinelibrary.wiley.com/store/10.1002/eji.1830200704/asset/1830200704_ftp.pdf? v=1&t=j7iu67qt&s=6a5f4ca4b764249f46da541f127c2ef6eb44352a.
Bouchie, A. et al., 2017. Nature Biotechnology's academic spinouts of 2016, Nat Biotechnol 35: 322-33.
Bowness, P. et al., Th17 Cells Expressing KIR3DL2+ and Responsive to HLA-B27 Homodimers Are Increased in Ankylosing Spondylitis, The Journal of Immunology, vol. 186, No. 4, Feb. 15, 2011 (Feb. 15, 2011), pp. 2672-2680, XP55373331, US ISSN: 0022-1767, DOI: 10.4049/jimmunol.1002653.
Brauninger, A., (1999). Identification of common germinal-center B-cell precursors in two patients with both Hodgkin's disease and non-Hodgkin's lymphoma, N Engl J Med 340: 1239-47.
Bukowski, et al., (1998) Crucial Role of TCRgamma Chain Junctional Region in Prenyl Pyrophosphate Antigen Recognition by gamma delta T cells, J. Immunol. 161: 286-293.
Carillo et al. The Multiple Sequence Alignment Problem in Biology. SIAM J. Appl. Math 48(5):907-1082 (1988).
Castella, et al., (2011) V gamma 9 V delta 2 T cell-based immunotherapy in hematological malignancies: from bench to bedside, Cell Mol. Life Sci. 68: 2419-2432.
Chien, Y.H., et al., (2014) gammadelta T Cells: First Line of Defense and Beyond. Annu.Rev.Immunol., vol. 32:121-155.
Coffelt, S.B., (2015). IL-17-producing gammadelta T cells and neutrophils conspire to promote breast cancer metastasis. Nature 522: 345-8.
Colman et al., Effects of amino acid sequence changes on antibody-antigen interactions, Research in Immunology, 1994; 145(1):33-36.
Comparison matrix: BLOSSUM62 from Hentikoff and Hentikoff, Proc. Natl. Acad. Scio. USA, 89:10915-10919 (1992).
Corrected Notice of Allowability dated Aug. 23, 2016 for U.S. Appl. No. 14/388,675.
Corrected Notice of Allowability dated Dec. 13, 2016 for U.S. Appl. No. 14/388,675.
Couzin-Frankel, J., (2013), Breakthrough of the year 2013. Cancer immunotherapy. Science 342: 1432-3.
Dadi, S., et al. (2016). Cancer Immunosurveillance by Tissue-Resident Innate Lymphoid Cells and Innate-like T Cells. Cell 164: 365-77.
Davey, MS, et al., (2017), Clonal selection in the human Vdelta1 T cell repertoire indicates gamma delta TCR-dependent adaptive immune surveillance. Nat Commun 8: 14760.
David, A. et al., Transient Transgenesis in the Endocrine System: Viral Vectors for Gene Delivery (1999), J. Gen. Virol. 80: 3049-64.

(56) References Cited

OTHER PUBLICATIONS

Davis et al. Development of human anti-murine T-cell receptor antibodies in both responding and nonresponding patients enrolled in TCR gene therapy trials. Clin Cancer Res. Dec. 1, 2010;16(23):5852-61.
De Witte, M.A., et al. (2015), Orchestrating an immune response against cancer with engineered immune cells expressing alphabetaTCRs, CARs, and innate immune receptors: an immunological and regulatory challenge. Cancer Immunol Immunother 64: 893-902.
Deniger, D.C., et al., (2014), Clinical applications of gamma delta T cells with multivalent immunity. Front Immunol 5: 636.
Devereux et al., A comprehensive set of sequence analysis programs for the VAX. Nucleic Acids Res. Jan. 11, 1984;12(1 Pt 1):387-95.
Ding, Y., et al., (2015). Characteristics of the Vdelta2 CDR3 Sequence of Peripheral gamma delta T Cells in Patients with Pulmonary Tuberculosis and Identification of a New Tuberculosis-Related Antigen Peptide. Clin Vaccine Immunol 22: 761-8.
Elmaagacli, A.H., et al., (2016), Cytomegalovirus replication reduces the relapse incidence in patients with acute myeloid leukemia, Blood 128: 456-9.
EP17203843.2 European Search Report dated Mar. 9, 2018.
Federico, Maurizio, Lentiviruses as gene delivery vectors, (1999), Curr. Opin. Biotechnol.10: 448-53.
Fisch, P. et al. Recognition by Human V-Gamma-9-V-Delta-2 T Cells of a GroEL Homolog on Daudi Burkitt's Lymphoma Cell. vol. 250, No. 4985, pp. 1269-1273, 1990.
Fooksman, David et al., Clustering Class I Mhc Modulates Sensitivity of T-cell Recognition 1,2", Jun. 1, 2006 (Jun. 1, 2006), XP55406164, Retrieved from the Internet: URL:https://http://www.ncbi.nlm.nih.gov/pmc/articles/PMC1524854/pdf/nihms11101.pdf [retrieved on Sep. 13, 2017].
Gentles, A.J., et al., (2015). The prognostic landscape of genes and infiltrating immune cells across human cancers. Nat Med 21: 938-45.
Gomes, A., et al,. Targeting gamma delta T Lymphocytes for Cancer Immunotherapy: From Novel Mechanistic Insight to Clinical Application. 2010, Cancer Res. 70: 10024-10027.
Gonzalez-Villasana, et al., Rac1/Pak1/p38/MMP-2 Axis Regulates Angiogenesis in Ovarian Cancer, Clinical Cancer Research, vol. 21, No. 9,Jan. 16, 2015 (Jan. 16, 2015), pp. 2127-2137, XP055411010, US ISSN: 1078-0432, DOI: 10.1158/1078-0432.CCR-14-2279.
Grunder C., et al. Gamma 9-and Delta 2-CDR3 Domains Regulate Functional Avidity of T Cells Harboring c9d2 T Cell Receptors. Journal of Immunotherapy, vol. 35, No. 9, pp. 723, Nov. 2012.
Grunder C., et al., 2012. gamma9 and delta2CDR3 domains regulate functional avidity of T cells harboring gamma9delta2TCRs. Blood 120: 5153-62.
Grunder, et al. Individual T-Cell Receptors of γ9δ2T-Cells Mediate Differential Anti-Tumor-reactivity. Abstract Only. From Blood 2011; 118:4312.
Harly C., Guillaume Y, (2012), Key implication of CD277/butyrophilin-3 (BTN3A) in cellular stress sensing by a major human gammadelta T-cell subset. Blood 120: 2269-79.
Hentikoff and Hentikoff, (1992), Amino acid substitution matrices from protein blocks, Proc. Natl. Acad. Sci. USA. 89:10915-10919.
Hildalgo, J.V., et al., (2014). Histological Analysis of gammadelta T Lymphocytes Infiltrating Human Triple-Negative Breast Carcinomas. Front Immunol 5: 632.
Ho, S.N., et al., Site-directed mutagenesis by overlap extension using the polymerase chain reaction. Gene, 1989. 77(1): p. 51-9.
Holtmeier, W., et al. (1995), The delta T cell receptor repertoire in human colon and peripheral blood is oligoclonal irrespective of V region usage, J Clin Invest 96: 1108-17.
Huang, M., RhoB facilitates c-Myc turnover by supporting efficient nuclear ccumulation of GSK-3, Oncogene, vol. 25, No. 9, Oct. 17, 2005 (Oct. 17, 2005), pp. 1281-1289, XP055496792, London ISSN: 0950-9232, DOI: 10.1038/sj.onc.1209174.
InMunoGeneTics information system (http://www.imgt.org/IMGTScientificChart/Nomenclature/IMGT- 20 FRCDRdefinition.html), Feb. 13, 2019.
International Preliminary Report on Patentability dated May 23, 2017 for International PCT Patent Application No. PCT/EP2015/077286.
International Search Report dated Jan. 27, 2016 for International PCT Patent Application No. PCT/EP2015/077286.
International Search Report for PCT/NL2013/050235 dated Oct. 9, 2013.
Kabelitz, D., et al., (2007) Perspectives of T Cells in Tumor Immunology. Cancer Research, vol. 67, No. 1, pp. 5-8.
Kabelitz, D., et al.,Potential of Human gammadelta T Lymphocytes for Immunotherapy of Cancer. International Journal of Cancer, 112:727-732 (2004).
Kay et al., Viral vectors for gene therapy: the art of the turning infectious agents into vehicles of therapeutics, (2001), Nat. Med. 7: 33-40.
Kershaw et al. Gene-engineered T cells for cancer therapy. Nat Rev Cancer 13(8):525-541 (2013).
Kim, S.K., et al., (2005), Private specificities of CD8 T cell responses control patterns of heterologous immunity, J Exp Med 201: 523-33.
Kuball, et al. Increasing functional avidity of TCR-redirected T cells by removing defined N-glycosylation sites in the TCR constant domain. J Exp Med. Feb. 16, 2009;206(2):463-75.
Kuball, et al. Multipotent Vδ2-negative γδT-cells after CMV-reactivation in allogeneic stem cell transplantation (162.36). Abstract Only. From J Immunol May 1, 2012, 188 (1 Supplement) 162.36.
Kuball, J, et al, 2007, Facilitating matched pairing and expression of TCR chains introduced into human T cells. Blood 109: 2331-8.
Li, B., et al. (2016), Landscape of tumor-infiltrating T cell repertoire of human cancers. Nature Genetics 48,725-732.
Lim, W.A., (2017). The Principles of Engineering Immune Cells to Treat Cancer. Cell 168: 724-40.
Loi, S., et al., (2016), RAS/MAPK Activation Is Associated with Reduced Tumor-Infiltrating Lymphocytes in Triple-Negative Breast Cancer: Therapeutic Cooperation Between MEK and PD-1/PD-L1 Immune Checkpoint Inhibitors. Clin Cancer Res 22: 1499-509.
M. Ferez et al: "Cognate Peptide-MHC Complexes Are Expressed as Tightly Apposed Nanoclusters in Virus-Infected Cells to Allow TCR Crosslinking", The Journal of Immunology, vol. 192, No. 1, Dec. 4, 2013 (Dec. 4, 2013), pp. 52-58, XP55406156, US ISSN: 0022-1767, DOI: 10.4049/jimmunol.1301224.
Mamedov, I.Z., et al. (2013), Preparing unbiased T-cell receptor and antibody cDNA libraries for the deep next generation sequencing profiling, Front Immunol 4: 456.
Mami-Chouaib, F. et al: "Further evidence for a gamma/delta T cell receptor-mediated TCT.1/CD48 recognition", The Journal of Immunology, Nov. 1, 1991 (Nov. 1, 1991), pp. 2864-2867, XP055403236, United States Retrieved from the Internet: U RL:http://www.ji mmu nol.org/content/147/9/2864.full-text.pdf.
Mandel, R.J.,et al. Clinical trials in neurological disorders using AAV vectors: promises and Challenges (2004), Curr Opin Mol Ther. 6(5):482-90.
Marcu-Malina et al. Re-targeting T-cells against cancer by gene-transfer of tumor-reactive receptors. 2009, Expert Opin. Biol. Ther. 9: 579-591.
Marcu-Malina, V., et al., (2011), Redirecting alphabeta T cells against cancer cells by transfer of a broadly tumor-reactive gammadeltaT-cell receptor. Blood 118: 50-9.
Marin, M. et al., (1997) Towards efficient cell targeting by recombinant retroviruses, Mol. Med. Today 3: 396-403.
Martin, K.R.G., et al., (2004), Gene therapy for optic nerve disease, , Eye 18(11):1049-55.
Meeh, P.F., (2006), Characterization of the gammadelta T cell response to acute leukemia. Cancer Immunol.Immunother. 55: 1072-80.
Metzger, D., et al., (1988), The human oestrogen receptor functions in yeast, Nature, 334: 31-36.
Miles, JJ, et al., 2005. CTL recognition of a bulged viral peptide involves biased TCR selection. J Immunol 175: 3826-34.
Miyagawa, et al., (2001), Essential Contribution of Germline-Encoded Lysine Residues in J gamma1.2 Segment to the Recognition of Nonpeptide Antigens by Human gamma delta T Cells, J. Immunol. 167: 6773-6779.

(56) References Cited

OTHER PUBLICATIONS

Miyazaki, K., (2011) MEGAWHOP cloning: a method of creating random mutagenesis libraries via megaprimer PCR of whole plasmids. Methods Enzymol, 498: p. 399-406.
Moser Bernhard. Tumor-Killing [gamma] [delta]—TCRs take center stage. Blood, vol. 120, No. 26, pp. 5093-5094, Dec. 20, 2012, XP002700185.
Nathwani et al, N Eng' J Med. Dec. 2, 20112;365(25):2357-65.
Needleman, S. et al., (1970), A general method applicable to the search for similarities in the amino acid sequence of two proteins, J. Mol. Biol. 48:443-453.
Nicol, et al., (2011) Clinical evaluation of autologous gamma delta T cell-based immunotherapy for metastatic solid tumors, Br. J. Cancer 105: 778-786.
Nielsen, T.O., (2004), Immunohistochemical and clinical characterization of the basal-like subtype of invasive breast carcinoma. Clin Cancer Res 10: 5367-74.
Niemeyer, G., et al, Long-term correction of inhibitor-prone hemophilia B dogs treated with liver-directed AAV2-mediated factor IX gene therapy, Blood. Jan. 22, 2009;113(4):797-806.
Notice of Allowance dated Aug. 15, 2016 for U.S. Appl. No. 14/388,675.
Notice of Allowance dated Sep. 15, 2017 for U.S. Appl. No. 14/388,675.
Office Action dated Apr. 26, 2016 for U.S. Appl. No. 14/388,675.
Office Action dated Nov. 20, 2017 for U.S. Appl. No. 15/374,613.
Office Action dated Dec. 29, 2015 for U.S. Appl. No. 14/388,675.
Paterson et al: "Cost-effectiveness of Oral Clodronate Compared with Oral Ibandronate, Intravenous Zoledronate or Intravenous Pamidronate in Breast Cancer Patients", Journal of International Medical Research, vol. 36, No. 3, May 1, 2008 (May 1, 2008), pp. 400-413, XP055496644, GB ISSN: 0300-0605, DOI: 10.1177/147323000803600304.
Paul, Fundamental Immunology. 3rd Edition, pp. 292-295, Raven Press, 1993.
Pauza, C. David, et al, Evolution and function of the TCR Vgamma9 chain repertoire: It's good to be public, Cellular Immunology, vol. 296, No. 1, Jul. 1, 2015 (Jul. 1, 2015), pp. 22-30, XP055320697, US ISSN: 0008-8749, DOI: 10.1016/j.cellimm.2015.02.010.
Peng, K.W., et al., (1999), Viral vector targeting, Curr. Opin. Biotechnol. 10: 454-7.
Ravens, S., et al., (2017). Human gammadelta T cells are quickly reconstituted after stem-cell transplantation and show adaptive clonal expansion in response to viral infection. Nature Immunology, 18, 393-401.
Reiser, J. (2000), Production and concentration of pseudotyped HIV-1-based gene transfer vectors, Gene Ther. 7: 910-913.
Roberts, S. et al. (1987), Generation of an antibody with enhanced affinity and specificity for its antigen by protein engineering, Nature 328:731-734.
Rudikoff et al. Single amino acid substitution altering antigen-binding Specificity. PNAS USA 79:1979-1983 (1982).
Russell, W.C., 2000, Update on adenovirus and its vectors, J. Gen. Virol. 81: 2573-604.
Salgado, R, (2015), Tumor-Infiltrating Lymphocytes and Associations with Pathological Complete Response and Event-Free Survival in HER2-Positive Early-Stage Breast Cancer Treated With Lapatinib and Trastuzumab: A Secondary Analysis of the NeoALTTO Trial. JAMA Oncol 1: 448-54.
Sandstrom, A, (2014), The intracellular B30.2 domain of butyrophilin 3A1 binds phosphoantigens to mediate activation of human Vgamma9Vdelta2 T cells. Immunity 40: 490-500.
Scheper W., et al., (2013), gammadeltaT cells elicited by CMV reactivation after allo-SCT cross-recognize CMV and leukemia. Leukemia 27: 1328-38.
Scheper, et al. (2012) 477. Multipotent VΔ2-Negative γΔT-Cells after CMV-Reactivation in Allogeneic Stem Cell Transplantation. Molecular Therapy. Volume 20, Supplement 1, p. S185.
Scheper, W., et al., (2014), Cancer Immunotherapy Using gammadeltaT Cells: Dealing with Diversity. Front Immunol 5: 601.
Schneider, C.A., et al., (2012), NIH Image to ImageJ: 25 years of image analysis. Nat Methods 9: 671-5.
Sebestyen, Z. et al., (2016), RhoB Mediates Phosphoantigen Recognition by Vgamma9Vdelta2 T Cell Receptor. Cell Rep 15: 1973-85.
Shugay, M., et al., (2014). Towards error-free profiling of immune repertoires. Nat Methods 11: 653-5.
Simmonelli, Francesca et al, Gene Therapy for Leber's Congenital Amaurosis is Safe and Effective Through 1.5 Years After Vector Administration, American Society of Gene & Cell Ther. Mar. 2010;18(3):643-50. Epub Dec. 1, 2009.
Sittig, S.P,.et al.,( 2013), Clonal expansion of renal cell carcinoma-infiltrating T lymphocytes. Oncoimmunology 2: e26014.
Stanislawski et al., Circumventing tolerance to a human MDM2-derived tumor antigen by TCR gene transfer. Nat Immunol. 2001; 2(10): 962-970.
Straetemans T et al. Towards gamma/delta TCR gene therapy: the optimal gamma/delta TCR transgene cassette. Bone Marrow Transplantation, vol. 48 No. Suppl. 2, pp. S72, Apr. 2013, XP002700187.
Straetemans, T, (2015), Untouched GMP-Ready Purified Engineered Immune Cells to Treat Cancer. Clin Cancer Res 21: 3957-68.
Straetmans, T. et al., (2013) Towards gamma/delta TCR gene therapy: the optimal gamma/delta TCR transgene cassette. S72-S72, Bone Marrow Transplantation, Apr. 2013, vol. 48 Suppl 2, pp. S72-S72.
Tripodo, et al. Gamma-delta T-cell lymphomas. 2009, Nat. Rev. Clin. Oncol. 6: 707-717.
U.S. Appl. No. 15/374,613 Notice of Allowance dated Jul. 6, 2018.
U.S. Appl. No. 14/388,675 Office Action dated Jul. 20, 2017.
U.S. Appl. No. 15/374,613 Office Action dated Mar. 22, 2018.
U.S. Appl. No. 15/842,784 Office Action dated Jul. 5, 2018.
Uldrich, A.P., et al., (2013) CD1d-lipid antigen recognition by the gammadelta TCR. Nat Immunol 14: 1137-45.
Venturi V., et al., (2008), The molecular basis for public T-cell responses? Nat Rev Immunol 8: 231-8.
Vigna, E. et al., (2000), Lentiviral vectors: excellent tools for experimental gene transfer and promising candidates for gene therapy, J. Gene Med. 2: 308-16.
Voss, et al., (2005), Designing TCR for Cancer Immunotherapy. Adoptive Immunotherapy: Methods and Protocols pp. 229-256. Part of the Methods in Molecular Medicine™ book series, vol. 109.
Walther, W., et al., (2000), Viral Vectors for Gene Transfer, Drugs 60: 249-71.
Wang et al., A comprehensive study of optimal conditions for naked plasmid DNA transfer into skeletal muscle by electroporation, (2005), J Gene Med. Sept. 7(9):12325-45.
Wang, Hong et al. Vgamma2Vdelta2 T Cell Receptor Recognition of Prenyl Pyrophosphates Is Dependent on All CDRs. 2010, J. Immunol. 184: 6209-6222.
Wells, J.A., et al. (1985), Cassette mutagenesis: an efficient method for generation of multiple mutations at defined sites, Gene 34: 315-323.
Willcox, C.R., et al., (2012), Cytomegalovirus and tumor stress surveillance by binding of a human gammadelta T cell antigen receptor to endothelial protein C receptor, Nat.Immunol. 13: 872-9.
Xi, X. et al. The Recognition of TCR Protein Antigen Does Not Depend on the Hydrophobic 197 Residue of CDR3. International Immunology, vol. 22, No. 4, pp. 299-306, Apr. 1, 2010, XP055069895.
Xiang, Z., (2014), Targeted activation of human Vgamma9Vdelta2-T cells controls epstein-barr virus-induced B cell lymphoproliferative disease. Cancer Cell 26: 565-76<a></a>.
XP-002778544 (Database Geneseq [online] May 20, 2004 (May 20, 2004), "Human tumour-associated antigenic target (TAT) polypeptide #22.", XP002778544, retrieved from EBI accession No. GSP:ADL06523 Database accession No. ADL06523 & WO 2004016225 A2 Feb. 26, 2004—Genentech Inc [US]) (See WO 2004016225 A2).
XP-002778546 ( Database Geneseq [online] Mar. 5, 2009 (Mar. 5, 2009), "Human PRO amino acid sequence SEQ ID No. 2103.", XP002778546, retrieved from EBI accession No. GSP:AUZ26487 Database accession No. AUZ26487 & WO 2005016962 A2 Feb. 24, 2005—Genentech Inc [US], et al.) (See WO2005016962A2).

(56) References Cited

OTHER PUBLICATIONS

XP-002778547 (Database Geneseq [online] Jun. 15, 2007 (Jun. 15, 2007), "Human lymphocyte clone G 115 soluble TCR Vgamma chain.", XP002778547, retrieved from EBI accession No. GSP:AAR55705 Database accession No. AAR55705 & WO 9412648 A2 Jun. 9, 1994—Inst Nat Sante Rech Med [FR], et al.) (See WO 9412648 A2).

XP-002778548 ([X] Database USPTO Proteins [online] Aug. 10, 1998 (Aug. 10, 1998), "Sequence 17 from patent U.S. Pat. No. 5,723,309.", XP002778548, retrieved from EBI accession No. USPOP:I90500 Database accession No. AAC30862 & U.S. Pat. No. 5,723,309 A Mar. 3, 1998—Bonneville Marc [FR] (See U.S. Pat. No. 5,723,309).

Xu, C, et al., (2007), Gammadelta T cells recognize tumor cells via CDR3delta region. Mol Immunol 44: 302-10.

Xu, Chungping et al. γδ T Cells Recognize Tumor Cells via CDR3δ Region. Molecular Immunology, 2007, vol. 44, pp. 302-310.

Zhao, et al. CDR3δ-grafted γ9δ2T cells mediate effective antitumor reactivity. Cell Mol Immunol. Mar. 2012;9(2):147-54. doi: 10.1038/cmi.2011.28. Epub Sep. 12, 2011.

Allison T.J., et al., "Structure of Gammadelta T Cell Receptors and Their Recognition of Non-Peptide Antigens," Molecular Immunology, 2001, vol. 38, pp. 1051-1061.

Asnafi V., et al., "Analysis of TCR, pTalpha, and RAG-1 in T-Acute Lymphoblastic Leukemias Improves Understanding of Early Human T-Lymphoid Lineage Commitment," Blood, Apr. 1, 2003, vol. 101, No. 7, pp. 2693-2703.

Bethune M.T., et al., "Domain-Swapped T Cell Receptors Improve the Safety of TCR Gene Therapy," Elife, Nov. 8, 2016, vol. 5, 24 pages.

Betts M.R., et al., "Sensitive and Viable Identification of Antigen-Specific CD8+ T Cells by a Flow Cytometric Assay for Degranulation," Journal of Immunological Methods, 2003, vol. 281, pp. 65-78.

Born W., et al., "Immunoregulatory Functions of GammaDelta T Cells," Advances in Immunology, 1999, vol. 71, pp. 77-144.

Champagne E., "Gammadelta T Cell Receptor Ligands and Modes of Antigen Recognition," Archivum Immunologiae et Therapiae Experimentalis, 2011, vol. 59, pp. 117-137.

Couedel C., et al., "Allelic Exclusion at the TCR Delta Locus and Commitment to Gamma Delta Lineage: Different Modalities Apply to Distinct Human Gamma Delta Subsets," Journal of Immunology, May 1, 2004, vol. 172, No. 9, pp. 5544-5552.

Davodeau F., et al., "Close Correlation Between Daudi and Mycobacterial Antigen Recognition By Human Gamma Delta T Cells and Expression of V9jpc1 Gamma/v2djc Delta-encoded T Cell Receptors," The Journal of Immunology, Aug. 1, 1993, vol. 151, No. 3, pp. 1214-1223.

Davodeau F., et al., "Secretion of Disulfide-Linked Human T-Cell Receptor Gamma Delta Heterodimers," Journal of Biological Chemistry, Jul. 25, 1993, vol. 268, No. 21, pp. 15455-15460.

Eilat D., et al., "Secretion of a Soluble, Chimeric γδ T-Cell Receptor-Immunoglobulin Heterodimer," Proceedings of the National Academy of Sciences of the United States of America, Aug. 1992, vol. 89, pp. 6871-6875.

Garboczi D.N., et al., "Assembly, Specific Binding, and Crystallization of a Human TCR-Alphabeta with an Antigenic Tax Peptide from Human T Lymphotropic Virus Type 1 and the Class I MHC Molecule HLA-A2," Journal of Immunology, Dec. 15, 1996, vol. 157, No. 12, pp. 5403-5410.

Green A.E., et al., "Recognition of Nonpeptide Antigens by Human VGamma9VDelta2 T Cells Requires Contact with Cells of Human Origin," Clinical and Experimental Immunology, 2004, vol. 136, pp. 472-482.

Gregoire C., et al., "Engineered Secreted T-Cell Receptor Alpha Beta Heterodimers," Proceedings of the National Academy of Sciences of the United States of America, Sep. 1991, vol. 88, pp. 8077-8081.

Guo X-Z.J., et al., "Rapid Cloning, Expression, and Functional Characterization of Paired Aβ and γ6 T-cell Receptor Chains From Single-cell Analysis," Molecular Therapy-Methods & Clinical Development, 2016, vol. 3, 12 Pages.

Holtmeier W., et al., "The TCR-Delta Repertoire in Human Intestine Undergoes Characteristic Changes During Fetal to Adult Development," Journal of Immunology, Jun. 1997, vol. 158, No. 12, pp. 5632-5641.

Jones H.F., et al., "Empirical and Rational Design of T Cell Receptor-Based Immunotherapies," Frontiers in Immunology, Jan. 2021, vol. 11, No. 585385, 21 pages.

Kerrigan J.J., et al., "Production of Protein Complexes via Co-Expression," Protein Expression and Purification, Jan. 2011, vol. 75, No. 1, pp. 1-14.

Langerak A.W., et al., "Immunophenotypic and Immunogenotypic Characteristics of Tcrgammadelta+ T Cell Acute Lymphoblastic Leukemia," Leukemia, Feb. 1999, vol. 123, No. 21, pp. 206-214.

Li H., et al., "Structure of the Vdelta Domain of a Human Gammadelta T-Cell Antigen Receptor," Nature, Jan. 29, 1998, vol. 391, pp. 502-506.

Loh E.Y., et al., "Identification and Sequence of a Fourth Human T Cell Antigen Receptor Chain," Nature, Dec. 10, 1987, vol. 330, No. 6148, pp. 569-572.

MacDougall A.V., et al., "Vgamma2 TCR Repertoire Overlap in Different Anatomical Compartments of Healthy, Unrelated Rhesus Macaques," Journal of Immunology, Feb. 15, 2001, vol. 166, No. 4, pp. 2296-2302.

Mathioudakis G., et al., "Preferential Rearrangements of the V Gamma I Subgroup of the Gamma-Chain of the T-Cell Antigen Receptor to J Gamma 2C Gamma 2 Gene Segments in Peripheral Blood Lymphocyte Transcripts from Normal Donors," Scandinavian Journal of Immunology, 1993, vol. 38, pp. 31-36.

Ozawa T., et al., "The Binding Affinity of a Soluble TCR-Fc Fusion Protein is Significantly Improved by Crosslinkage with an Anti-CBeta antibody," Biochemical and Biophysical Research Communications, 2012, vol. 422, pp. 245-249.

Petersen T.R., et al., "A Chimeric T Cell Receptor with Super-Signaling Properties," International Immunology, May 17, 2004, 6 pages.

Sadelain, et al., "The Basic Principles of Chimeric Antigen Receptor Design," Cancer Discovery, Apr. 2013, vol. 3, Issue 4, pp. 388-398.

Scotet E., et al., "Tumor Recognition Following Vgamma9Vdelta2 T cell Receptor Interactions with a Surface F1-ATpase-Related Structure and Apolipoprotein A-I," Immunity, Jan. 2005, vol. 22, pp. 71-80.

Sebestyen Z., et al., "Translating Gammadelta (Gammadelta) T Cells and Their Receptors into Cancer Cell Therapies," Nature Reviews Drug Discovery, Mar. 2020, vol. 19, No. 3, pp. 169-184.

Spada F.M., et al., "Self-Recognition of CD1 by Gamma/Delta T Cells: Implications for Innate Immunity," Journal of Experimental Medicine, Mar. 20, 2000, vol. 191, No. 6, pp. 937-948.

Starick L., et al., "Butyrophilin 3A (BTN3A, CD277)-Specific Antibody 20.1 Differentially Activates Vgamma9Vdelta2 TCR Clonotypes and Interferes With Phosphoantigen Activation," European Journal of Immunology, 2017, vol. 47, pp. 982-992.

Tao C., et al., "Gammadelta TCR Immunoglobulin Constant Region Domain Exchange in Human Alfa-Betatcrs Improves TCR Pairing Without Altering TCR Gene-Modified T Cell Function," Molecular Medicine Reports, 2017, vol. 15, pp. 1555-1564.

Wang H., et al., "Conservation of Nonpeptide Antigen Recognition by Rhesus Monkey Vgamma2Vdelta2 T Cells," Journal of Immunology, Apr. 1, 2003, vol. 170, No. 7, pp. 3696-3706.

Wang Y., et al., "New Chimeric Antigen Receptor Design for Solid Tumors," Frontiers in Immunology, Dec. 22, 2017, vol. 8, No. 1934, 9 pages.

Wei H., et al., "Definition of APC Presentation of Phosphoantigen (E)-4-hydroxy-3-methyl-but-2-enyl Pyrophosphate to Vgamma2Vdelta 2 TCR," Journal of Immunology, Oct. 1, 2008, vol. 181, No. 7, pp. 4798-4806.

Xiong X., et al., "Identification of Guinea Pig Gammadelta T Cells and Characterization during Pulmonary Tuberculosis," Veterinary Immunology and Immunopathology, Nov. 2004, vol. 102, No. 1-2, pp. 33-44.

(56) References Cited

OTHER PUBLICATIONS

Xu B., et al., "Crystal Structure of a Gammadelta T-Cell Receptor Specific for the Human MHC Class I Homolog MICA, " Proceedings of the National Academy of Sciences of the United States of America, Feb. 8, 2011, vol. 108, No. 6, pp. 2414-2419.

Xu Y., et al., "Preclinical Development of-T-Cell Receptor-Engineered T-Cell Therapy Targeting the-5T4 Tumor Antigen on-Renal Cell Carcinoma," Cancer Immunology, Immunotherapy, 2019, vol. 68, pp. 1979-1993.

Zhang L., et al., "Gamma Delta T-Cell Receptors Confer Autonomous Responsiveness to the Insulin-Peptide B: 9-23," Journal of Autoimmunity, 2010, vol. 34, pp. 478-484.

Zheng J., et al., "A Novel Antibody-Like TCRGamma delta-Ig Fusion Protein Exhibits Antitumor Activity against Human Ovarian Carcinoma," Cancer Letters, 2013, 9 pages.

Adams, et al., "An autonomous CDR3delta is sufficient for recognition of the nonclassical MHC-I T10 and T22," Nature Immunology, Jul. 2008, 9(7), pp. 777-784.

Allison, et al., "Structure of a Human Yδ T-cell Antigen Receptor," Nature, 2001, vol. 411, pp. 820-824, DOI: 10.1038/35081115, XP055324441.

Bierer B.E, et al., "Cyclosporin A and FK506: Molecular Mechanisms of Immunosuppression and Probes for Transplantation Biology," Current Opinion in Immunology, 1993, vol. 5, pp. 763-773.

Bird, et al., "Single-Chain Antigen-Binding Proteins," Science, 1988, vol. 242, pp. 423-426.

Brash D.E, et al., "Strontium Phosphate Transfection of Human Cells in Primary Culture: Stable Expression of the Simian Virus 40 Large-T-Antigen Gene in Primary Human Bronchial Epithelial Cells," Molecular and Cellular Biology, May 1987, vol. 7, No. 5, pp. 2031-2034.

Colberre-Garapin F, et al., "A New Dominant Hybrid Selective Marker for Higher Eukaryotic Cells," Journal of Molecular Biology, 1981, vol. 150, 14 pages.

Conese, et al., "Gene Therapy Progress and Prospects: Episomally Maintained Self-Replicating Systems," Gene Therapy, 2004, vol. 11, pp. 1735-1741.

Dausset, et al., "Centre D'etude Dupolymorphisme Humain (Ceph): Collaborative Genetic Mapping of the Human Genome," Genomics, 1990, vol. 6, pp. 575-577.

Goncalves, "Adeno-Associated Virus: From Defective Virus to Effective Vector," Virology Journal, 2005, vol. 2, No. 1, 43, 17 pages.

Hapmap C., "The International HapMap Project", Nature, (20030000), vol. 426, pp. 789-796.

Henderson D.J, et al., "Comparison of the Effects of FK-506, Cyclosporin A and Rapamycin on IL-2 Production," Immunology, 1991, vol. 73, pp. 316-321.

Holliger P, et al., "Engineered Antibody Fragments and the Rise of Single Domains," Nature Biotechnology, 2005, vol. 23, No. 9, pp. 1126-1136.

Huang, et al., "Simultaneous Multiple-Emitter Fitting for Single Molecule Super-Resolution Imaging," Biomedical Optics Express, 2011, vol. 2, No. 5, pp. 1377-1393.

Huston J.S, et al., "Protein Engineering of Antibody Binding Sites: Recovery of Specific Activity in an Anti-Digoxin Single-Chain Fv Analogue Produced in *Escherichia coli*," Proceedings of the National Academy of Sciences of the United States of America, 1988, vol. 85, pp. 5879-5883.

International Preliminary Report on Patentability for International Application No. PCT/EP2018/063210, mailed Nov. 28, 2019, 9 Pages.

International Preliminary Report on Patentability for International Application No. PCT/EP2019/063004, mailed Dec. 3, 2020, 11 Pages.

International Search Report and Written Opinion for International Application No. PCT/EP2018/063210, mailed Aug. 21, 2018, 12 Pages.

Johnston S.A., "Biolistic Transformation: Microbes to Mice," Nature, 1990, vol. 346, pp. 776-777.

Kent, et al., "Ouabain Resistance Conferred by Expression of the cDNA for a Murine Na+, K+-ATPase Alpha Subunit," Science, 1987, vol. 237, pp. 901-903.

Lefranc M-P, et al., "The T Cell Receptor FactsBook," Academic Press, 2001, 413 pages.

Liu, et al., "Calcineurin is a common target of cyclophilin-cyclosporin A and FKBP-FK506 complexes," Cell, 1991, vol. 66, pp. 807-815.

Lowy, et al., "Isolation of Transforming DNA: Cloning the Hamster Aprt Gene," Cell, 1980, vol. 22, pp. 817-823.

Mulligan B.C., et al., "Selection for Animal Cells that Express the *Escherichia coli* Gene Coding for Xanthine-Guanine Phosphoribosyltransferase," Proceedings of the National Academy of Sciences of the United States of America, 1981, vol. 78, No. 4, pp. 2072-2076.

Murray E., "Methods in Molecular Biology," Gene Transfer and Expression Protocols, M Stockton Press, 1991, vol. 7, 420 pages.

O'Hare K, et al., "Transformation of Mouse Fibroblasts to Methotrexate Resistance by a Recombinant Plasmid Expressing a Prokaryotic Dihydrofolate Reductase," Proceedings of the National Academy of Sciences of the United States of America, 1981, vol. 78, No. 3, pp. 1527-1531.

Osbourn J.K, et al., "Directed Selection of MIP-1 Alpha Neutralizing CCR5 Antibodies from a Phage Display Human Antibody Library," National Biotechnology, 1998, vol. 16, pp. 778-781.

Riddel G., et al., "The Use of Anti-CD3 and Anti-CD28 Monoclonal Antibodies to Clone and Expand Human Antigen-Specific T Cells," Journal Immunology Methods 1990, vol. 128, No. 2, pp. 189-201.

Santerre R.F, et al., "Expression of Prokaryotic Genes for Hygromycin B and G418 Resistance as Dominant-Selection Markers in Mouse L Cells," Gene, 1984, vol. 30, pp. 147-156.

Smith, et al., "Fast, Single-Molecule Localization that Achieves Theoretically Minimum Uncertainty," Nature Methods, 2010, vol. 7, No. 5, pp. 373-377.

Szybalska, et al., "Genetics of Human Cell Lines, IV. DNA-Mediated Heritable Transformation of a Biochemical Trait," Proceedings of the National Academy of Sciences of the United States of America, 1962, vol. 48, pp. 2026-2034.

Trompeter H-I, et al., "Rapid and Highly Efficient Gene Transfer into Natural Killer Cells by Nucleofection," Journal of Immunological Methods, 2003, vol. 274, pp. 245-256.

Wigler, et al., "Transfer of Purified Herpes Virus Thymidine Kinase Gene to Cultured Mouse Cells," Cell, 1977, vol. 11, pp. 223-232.

Wigler M, et al., "Transformation of Mammalian Cells with an Amplifiable Dominant-Acting Gene," Proceedings of the National Academy of Sciences of the United States of America, 1980, vol. 77, No. 6, pp. 3567-3570.

\* cited by examiner

| CEPH line Coriel nr. | Numbering in this manuscript | Recognition phenotype | CEPH line Coriel nr. | Numbering in this manuscript | Recognition phenotype |
|---|---|---|---|---|---|
| 10846 | 1 | + | 12156 | 62 | + |
| 12145 | 4 | + | 10838 | 66 | + |
| 12146 | 5 | + | 12003 | 68 | + |
| 12239 | 6 | + | 12004 | 69 | + |
| 7029 | 7 | + | 12005 | 70 | + |
| 7019 | 8 | + | 12006 | 71 | + |
| 6994 | 9 | - | 12753 | 76 | + |
| 7022 | 12 | + | 12762 | 79 | + |
| 6991 | 16 | + | 12763 | 80 | + |
| 7034 | 18 | - | 12801 | 81 | + |
| 6993 | 20 | - | 12802 | 82 | + |
| 10851 | 22 | - | 12812 | 83 | - |
| 11839 | 36 | + | 12814 | 86 | + |
| 11840 | 37 | - | 12864 | 88 | + |
| 10860 | 48 | + | 12865 | 89 | + |
| 10861 | 49 | + | 12872 | 90 | + |
| 11993 | 51 | - | 12873 | 91 | + |
| 11994 | 52 | + | 12875 | 93 | - |
| 11995 | 53 | + | 12878 | 94 | + |
| 12155 | 61 | + | 12892 | 96 | + |

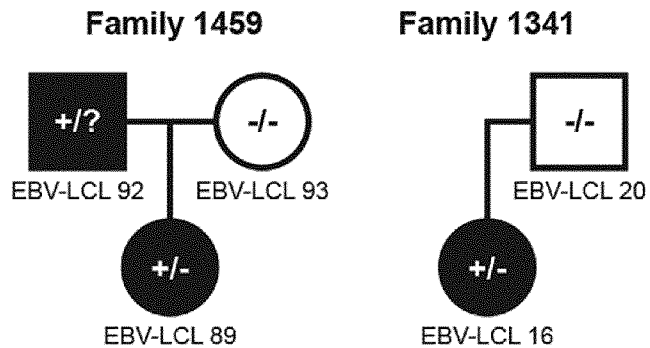

FIG 2A

| SNP ID | Chr. | Location | Closest gene | RNAi effect Vγ9Vδ2 | αβTCR |
|---|---|---|---|---|---|
| rs342782 | 1 | intergenic | RAB4A | ● | ● |
| rs13015314 | 2 | intergenic | RHOB | | |
| rs13015757 | 2 | intergenic | RHOB | ● | ○ |
| rs13021711 | 2 | intergenic | RHOB | | |
| rs12997448 | 2 | intergenic | RHOB | | |
| rs867544 | 2 | intron | CACNB4 | ○ | ○ |
| rs17041331 | 3 | intron | ITPR1 | ○ | ○ |
| rs13120675 | 4 | intron | UGT8 | ○ | ○ |
| rs6814569 | 4 | intron | UGT8 | | |
| rs1535281 | 6 | intergenic | TMEM200A | ○ | ○ |
| rs12526524 | 6 | intron | RIMS1 | ○ | ○ |
| rs3757827 | 7 | intron | UBE3C | ● | ● |
| rs11783360 | 8 | intergenic | LRP12 | ○ | ○ |
| rs2511107 | 11 | intergenic | RAB38 | ○ | ○ |
| rs11627657 | 14 | intergenic | DAAM1 | ○ | ● |
| rs12904257 | 15 | intron | ST20 | ○ | ○ |
| rs4075554 | 16 | intron | CDH13 | ○ | ○ |
| rs4075942 | 16 | intron | CDH13 | | |
| rs37038 | 16 | intron | NDRG4 | ○ | ● |
| rs11084914 | 19 | intergenic | SCAMP4 | ○ | ○ |
| rs12150939 | 19 | intron | ZNF383 | ○ | ○ |
| rs9978228 | 21 | intron | NCAM2 | ○ | ○ |

COMPOSITIONS AND METHODS FOR CELL TARGETING THERAPIES

CROSS-REFERENCE

This application is a U.S. National Stage entry of International Application No. PCT/EP2018/063210, filed May 18, 2018, which claims priority to U.S. Provisional Patent Application No. 62/508,272, filed May 18, 2017, and U.S. Provisional Patent Application No. 62/508,833, filed May 19, 2017, each of which is entirely incorporated herein by reference for all purposes.

BACKGROUND

Adoptive transfer of T cells with engineered anti-tumor specificity or anti-pathogen specificity are under development. In such strategies, an exogenous immune receptor such as an alpha beta T cell receptor, or a gamma delta T cell receptor or a chimeric antigen receptor having a particular anti-tumor specificity, or a particular anti-pathogen specificity is transferred to either autologous T cells from a patient, or, e.g. in case of an allogeneic stem cell transplantation into a patient, in corresponding allogeneic T cells. For example, a leukemic patient that is undergoing blood stem cell transplantation will during the treatment also be lymphodepleted. Hence, such a patient can also benefit from e.g. infusion of donor T cells that have been engineered to express a specific anti-leukemic T cell receptor. Described herein are compositions and methods comprising cells expressing receptors that selectively recognize a unique configuration in proteins expressed by one or more MHC associated genes, wherein said unique configuration is associated with one or more disease conditions.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SUMMARY

Provided herein is a pharmaceutical composition that comprises a dosage form of a polypeptide construct that selectively binds CD277 on a cancer cell or a dosage form of a cell expressing said polypeptide construct that selectively binds CD277 on said cancer cell; and at least one of (i) a dosage form of an agent that increases activity of RhoB GTPase in said cancer cell; and (ii) a dosage form of an agent that increases activity of a phosphoantigen in said cancer cell. In an aspect, a pharmaceutical composition comprises a dosage form of an agent that increases activity of RhoB GTPase and a dosage form of an agent that increases activity of a phosphoantigen. In an aspect, a pharmaceutical composition comprises a dosage form of an agent that increases activity of RhoB GTPase and a dosage form of an agent that increases activity of a phosphoantigen wherein an agent that increases activity of a phosphoantigen is administered prior to, concurrent with, or after an agent that increases activity of a RhoB GTPase. In an aspect, an agent that increases activity of a RhoB GTPase increases translocation of a RhoB GTPase to a cell membrane of a cancer cell, maintains RhoB GTPase at a cell membrane of a cancer cell, increases translocation of a RhoB GTPase away from a nucleus of a cancer cell, increases expression of a gene or transcript encoding a RhoB GTPase, increases stability of a RhoB GTPase, increases an interaction between a RhoB GTPase and CD277, activates RhoB GTPase, increases an interaction between a RhoB GTPase and GTP, reduces an interaction between a RhoB GTPase and GDP, increases an amount of GTP in a cancer cell, increases availability of GTP in a cancer cell, or any combination thereof. In an aspect, CD277 can be in a J-configuration. In an aspect, a polypeptide construct comprises at least one of a γ-TCR polypeptide sequence or a δ-TCR polypeptide sequence. In an aspect, a polypeptide construct comprises a variant or fragment of at least one of a γ-TCR polypeptide sequence or a δ-TCR polypeptide sequence. In an aspect, a polypeptide construct comprises a variant or fragment of at least one of a γ-TCR polypeptide sequence or a δ-TCR polypeptide sequence and wherein a γ-TCR polypeptide sequence can be a γ9-TCR polypeptide sequence or fragment thereof. In an aspect, a polypeptide construct comprises a variant or fragment of at least one of a γ-TCR polypeptide sequence or a δ-TCR polypeptide sequence and wherein a δ-TCR polypeptide sequence can be a δ2-TCR polypeptide sequence or a fragment thereof. In an aspect, a pharmaceutical composition can be administered to a subject comprising at least one of a solid cancer and leukemia. In an aspect, a pharmaceutical composition can be administered to a subject comprising acute myeloid leukemia. In an aspect, a pharmaceutical composition can be administered to a subject. A subject can comprise a mutation in a gene that correlates with RhoB GTPase expression or activity. In an aspect, a pharmaceutical composition can be administered to a subject wherein a subject comprises a mutation in a gene that correlates with reduced RhoB GTPase expression or activity. In an aspect, a pharmaceutical composition can be administered to a subject wherein a subject comprises a mutation in a gene that can correlate with reduced or inhibited interactions between CD277 and RhoB GTPase. In an aspect, an agent that increases activity of a RhoB GTPase can perform by indirectly or directly binding a RhoB GTPase. In an aspect, an agent that increases activity of a phosphoantigen can perform by indirectly or directly binding a RhoB GTPase. In an aspect, a dosage form of a polypeptide construct comprises a sequence that comprises at least 60% percent identity to a sequence from Table 3 or Table 4. In an aspect, an agent that increases activity of a phosphoantigen can be a mevalonate pathway inhibitor. In an aspect, an agent that increases activity of a phosphoantigen can be an aminobisphosphonate. In an aspect, an agent that increases activity of a phosphoantigen can be at least one of pamidronate and zoledronate. In an aspect, an agent that increases activity of a RhoB GTPase increases translocation of a RhoB GTPase to a cell membrane of a cancer cell, maintains RhoB GTPase at a cell membrane of a cancer cell, increases translocation of a RhoB GTPase away from a nucleus of a cancer cell, increases expression of a gene or transcript encoding a RhoB GTPase in a cancer cell, increases stability of a RhoB GTPase in a cancer cell, increases an interaction between a RhoB GTPase and CD277 in a cancer cell, activates RhoB GTPase in a cancer cell, increases an interaction between a RhoB GTPase and GTP in a cancer cell, reduces an interaction between a RhoB GTPase and GDP in a cancer cell, increases an amount of GTP in a cancer cell, increases availability of GTP in a cancer cell, or any combination thereof.

Disclosed herein is a method of treatment comprising administering a pharmaceutical composition to a subject in need thereof. In an aspect, a subject comprises a mutation in a gene that correlates with reduced or inhibited interactions between CD277 and RhoB GTPase. In an aspect, a subject comprises at least one of a solid cancer and leukemia.

Disclosed herein is a method of treatment comprising administering to a subject in need thereof a pharmaceutical composition that comprises an agent selected from the group consisting of: an agent that increases activity of a RhoB GTPase in a cancer cell of a subject, a pharmaceutical composition comprising a polypeptide construct that selectively binds CD277 on said cancer cell. In an aspect, a method can further comprise administering to a subject in need thereof an agent that increases activity of a phosphoantigen in a cancer cell of a subject in need thereof.

Disclosed herein is a method of treatment comprising administering to a subject in need thereof a dosage form of a polypeptide construct that selectively binds CD277 on a cancer cell or a dosage form of a cell expressing a polypeptide construct that selectively binds CD277 on a cancer cell; and at least one of (i) a dosage form of an agent that increases activity of RhoB GTPase in a cancer cell; and (ii) a dosage form of an agent that increases activity of a phosphoantigen in a cancer cell. In an aspect, a treatment comprises administering a dosage form of an agent that increases activity of RhoB GTPase and a dosage form of an agent that increases activity of a phosphoantigen. In an aspect, an agent that increases activity of a RhoB GTPase can be a mevalonate pathway inhibitor. In an aspect, an agent that increases activity of a RhoB GTPase can be a mevalonate pathway inhibitor that can be an aminobisphosphonate. In an aspect, an agent that increases activity of a RhoB GTPase can be a mevalonate pathway inhibitor that can be at least one of pamidronate and zoledronate. In an aspect, a polypeptide construct comprises a variant or fragment of at least one of a γ-TCR polypeptide sequence or a δ-TCR polypeptide sequence. In an aspect, a polypeptide construct comprises a variant or fragment of at least one of a γ-TCR polypeptide sequence or a δ-TCR polypeptide sequence and wherein a γ-TCR polypeptide sequence can be a γ9-TCR polypeptide sequence or fragment thereof. In an aspect, a polypeptide construct comprises a variant or fragment of at least one of a γ-TCR polypeptide sequence or a δ-TCR polypeptide sequence and wherein a δ-TCR polypeptide sequence can be a δ2-TCR polypeptide sequence or a fragment thereof. In an aspect, a cell can be an αβ T cell. In an aspect, an agent that increases activity of a phosphoantigen performs by indirectly or directly binding a phosphoantigen. In an aspect, a method can further comprise administering a dosage form comprising a cytokine. In an aspect, a dosage form of a polypeptide construct comprises a sequence that comprises at least 60% percent identity to a sequence from Table 3 or Table 4.

Disclosed herein is a method of treatment, comprising administering to a subject in need thereof a pharmaceutical composition comprising an agent that increases activity of a RhoB GTPase in a cancer cell of a subject, and a pharmaceutical composition that comprises a cell that expresses a Vγ9Vδ2 T cell receptor, wherein a T cell isolated from a subject secretes a small protein by at least one fold as compared to a comparable T cell isolated from a comparable subject absent an administering. In an aspect, a small protein can be a cytokine. In an aspect, a small protein can be a cytokine and is IFNγ. In an aspect, a T cell isolated from a subject secretes a small protein by at least 5 fold over to a comparable T cell isolated from a comparable subject absent an administering. In an aspect, a T cell isolated from a subject secretes a small protein by at least 10 fold over to a comparable T cell isolated from a comparable subject absent an administering.

Disclosed herein is a method of treatment comprising administering to a subject in need thereof a dosage form of an agent that increases activity of RhoB GTPase in a cancer cell and a dosage form of an agent that increases activity of a phosphoantigen in a cancer cell. In an aspect, an agent that increases activity of a RhoB GTPase can be a mevalonate pathway inhibitor. In an aspect, an agent that increases activity of a RhoB GTPase can be a mevalonate pathway inhibitor that can be an aminobisphosphonate. In an aspect, an agent that increases activity of a RhoB GTPase can be a mevalonate pathway inhibitor that can be at least one of pamidronate and zoledronate. In an aspect, an agent that increases activity of a phosphoantigen performs by indirectly or directly binding a phosphoantigen. In an aspect, a method can further comprise administering a dosage form of a polypeptide construct that selectively binds CD277 on a cancer cell or a dosage form of a cell expressing said polypeptide construct that selectively binds CD277 on a cancer cell.

Provided herein are compositions comprising engineered cells expressing a polypeptide construct that selectively binds a J-configuration or J-confirmation of CD277 on a target cell. In some cases is provided a polypeptide construct described herein that selectively binds a J-configuration of CD277 on a target cell, wherein said polypeptide construct is expressed in an engineered cell. Also provided are nucleotide sequences incorporating a polypeptide construct described herein that selectively binds a J-configuration of CD277 on a target cell.

Provided herein are methods and compositions comprising a polypeptide construct that selectively binds a J-configuration of CD277 on a target cell, nucleotides encoding said polypeptide construct or cells expressing said polypeptide construct. In some embodiments, a polypeptide construct that binds a J-configuration of CD277 on a target cell comprises at least one γδ T cell receptor or fragment or variant thereof.

Provided herein are compositions comprising engineered cells that express polypeptide constructs that selectively bind to a configuration of CD277 that is formed as a result of metabolic changes in distressed cells such as cancer cells, wherein said metabolic changes cause expression of generic stress molecules that are upregulated upon transformation or distress. In certain embodiments, this configuration can be the J-configuration. In some cases, the J-configuration of CD277 is formed as a result of RhoB transmigration within said distressed cell.

Provided herein are engineered cells expressing polypeptide constructs comprising γδT cell receptors (TCR) or fragments thereof, which selectively bind the J-configuration of CD277 on a target cell. In certain cases, the γδT cell receptors (TCR) or fragments thereof, comprise at least one of Vγ9 and Vδ2 chains and fragments thereof. In some cases are engineered cells described herein that can be provided to a subject in conjunction with at least one additional agent selected from an intermediate of the mammalian mevalonate pathway, such as isopentenyl pyrophosphate (IPP), and the microbial 2-C-methyl-D-erythiitol 4-phosphate (MEP) pathway.

Provided herein is an unbiased, genome-wide screening method that identifies mediators of the activation of predetermined receptors in specific cells, for instance tumor cells. Provided are systems, and kits for use in the unbiased genome-wide screening method. Further disclosed herein are compositions that target mediators identified by the screening method described herein. In specific embodiments are compositions useful to boost or restore optimal activation of a predetermined receptor such as Vγ9Vδ2 TCR.

In certain embodiments are methods of providing effective therapies for conditions that benefit from targeted cell clearance, such as cancer, said methods comprising providing a composition comprising a polypeptide construct described herein, nucleotide encoding the same, or cells expressing the same and optionally at least one agent useful to boost formation of the J-configuration of CD277, or the binding of the polypeptide construct to said J-configuration.

Provided herein is a pharmaceutical composition comprising a polypeptide construct that selectively binds a J-configuration of CD277 on a target cell, and wherein said polypeptide construct is expressed in an engineered cell. In some embodiments, the polypeptide construct binds the J-configuration of CD277 with higher selectivity as compared to a CD277 molecule which is not in said J-configuration. In some embodiments, the target cell is a cancer cell. In some embodiments, the target cell is a leukemia cell.

In some embodiments, the polypeptide construct comprises at least one of a γ-TCR polypeptide sequence or a δ-TCR polypeptide sequence, or a variant or fragment of at least one of a γ-TCR polypeptide sequence or a δ-TCR polypeptide sequence. In some embodiments, the γ-TCR polypeptide sequence is a γ9-TCR polypeptide sequence or fragment thereof. In some embodiments, the δ-TCR polypeptide sequence is a δ2-TCR polypeptide sequence or a fragment thereof. In yet another embodiment, the CD277 is present as a dimer.

Provided herein is a method of treating cancer in a subject comprising providing to the subject an effective amount of a pharmaceutical composition comprising a polypeptide construct that selectively binds CD277 on a cancer cell when said CD277 molecule is in a J-configuration, and wherein said polypeptide construct is optionally expressed in an engineered cell. Further provided herein is a method of clearing cancer cells in a subject in need thereof comprising providing to the subject an effective amount of a pharmaceutical composition comprising a polypeptide construct that selectively binds CD277 on said cancer cells when said CD277 is in a J-configuration, or an effective amount of engineered cells that express said polypeptide construct.

In some cases, the polypeptide construct recognizes the J-configuration of CD277 with higher selectivity as compared to a CD277 molecule which is not in said J-configuration. In some embodiments, the formation of said J-configuration requires at least an interaction of RhoB with CD277 and/or compartmentalization of CD277. In some embodiments, formation of said J-configuration requires interaction of intracellular phosphoantigen with CD277 subsequent to said interaction of RhoB with CD277. In some instances, the polypeptide construct comprises at least one of a γ-TCR polypeptide sequence or a δ-TCR polypeptide sequence, or a variant or fragment of at least one of a γ-TCR polypeptide sequence or a δ-TCR polypeptide sequence.

In some cases, the methods comprise administering an agent that increases translocation of RhoB GTPase to a cell membrane of said cancer cell, or administering an agent that modulates RhoB GTPase, wherein the agent targets at least one of a GTPase activating protein (GAP), a guanine nucleotide exchange factor (GEF), and a guanine nucleotide dissociation inhibitor (GDI). In some instances, the method comprises genotyping the subject for a mutation that correlates with RhoB GTPase expression or activity. In some instances, the method comprises genotyping a gene selected from a gene encoding a protein selected from a GTPase activating protein (GAP), a guanine nucleotide exchange factor (GEF), and a guanine nucleotide dissociation inhibitor (GDI), wherein the protein modulates RhoB GTPase.

Provided herein is a method of engineering T cells comprising a) providing immune-cells expressing low amounts of additional (innate) co-receptors; b) providing a nucleic acid sequence encoding a γ9-T-cell receptor chain, and a nucleic acid sequence encoding a δ2-T-cell receptor chain, wherein the γ9-T-cell receptor chain and the δ2-T cell receptor chain selectively bind CD277 when said CD277 is in a J-configuration; and c) introducing the nucleic acid sequences of step b) into the T-cells to provide for an engineered T-cell with a γ9δ2T-cell receptor comprising the γ9-T-cell receptor chain of step b) and the δ2-T-cell receptor chain of step b).

Further provided herein is a method of screening a target cell for a genetic or epigenetic variation that results in the lack of T cell receptor recognition comprising a) contacting a cell expressing a T cell receptor with a target cell; b) detecting a level of immune activation of the cell expressing a T cell receptor; c) identifying the target cell as one of i) having the genetic or epigenetic variation when immune activation is below a threshold level; or ii) not having the genetic or epigenetic variation when immune activation is above a threshold level; and d) comparing the target cell genotype to a control genotype when immune activation is below the threshold level to identify the genetic or epigenetic variation.

In some embodiments, the target cell is a cancer cell. In some instances, the T cell receptor is a Vγ9Vδ2 T cell receptor. In some cases, detecting the level of immune activation comprises quantifying production of at least one cytokine by the cell expressing a T cell receptor. In some embodiments, the cytokine is at least one of interferon-γ and TNF In some cases, the genetic or epigenetic variation is a single nucleotide polymorphism. In some cases, the zygosity of the target cell correlates with said having the genetic or epigenetic variation or said not having the genetic or epigenetic variation. In some instances, the method further comprises the step of identifying a gene proximal to the genetic or epigenetic variation. In some cases, the gene is located within about 300,000 base pairs of the genetic or epigenetic variation.

In some embodiments, the method further comprises the step of modulating the expression of the gene and assessing the effects of modulating on the quantity of immune activation of the cell expressing a T cell receptor. In some cases, said modulating comprises knocking out the gene. In some cases, the cell expressing a T cell receptor with a target cell is a T cell. In some instances, the control genotype is a genotype of a control cell, wherein the control cell causes immune activation of the cell expressing a T cell receptor when in contact with the cell expressing a T cell receptor. In some instances, said immune activation of the cell expressing the T cell receptor is characterized by at least a two-fold increase in production of a cytokine or analogous functional read out. In some instances, said immune activation of the cell expressing the T cell receptor is characterized by at least a ten-fold increase in production of a cytokine or analogous functional read out. In some instances, said immune activation of the cell expressing the T cell receptor is characterized by at least a hundred-fold increase in production of a cytokine or analogous functional read out. In some instances, said contacting comprises adding the cell expressing a T cell receptor and the control cell to the same container. In some instances, contacting comprises adding the cell expressing a T cell receptor and the control cell to the same container.

In some embodiments, the target cell is a B cell leukemia cell line. In some embodiments, the target cell is an Epstein Barr virus transformed cell. In some embodiments, the genetic mutation is located in a gene encoding a protein that regulates a RhoGTPase. In some instances, the protein is a GTPase activating protein or guanine nucleotide exchange factor. In some cases, the genetic mutation results in reducing or inhibiting interactions between CD277 and RhoB GTPase.

Provided herein is a method comprising a) screening a subject for a mutation in a gene encoding a protein, wherein the protein post-translationally regulates a RhoGTPase in a target cell of the subject; and b) treating the subject with a Vγ9Vδ2 TCR+ T cell-mediated therapy when the mutation does not reduce or inhibit formation of a J-configuration in CD277. In some embodiments, the target cell is a cancer cell. In some embodiments, the target cell is a leukemic cell. In some embodiments, the protein is a GTPase activating protein or guanine nucleotide exchange factor. In some embodiments, screening comprises genotyping the gene or a portion thereof. In some embodiments, screening comprises a method selected from nucleic acid amplification, sequencing, and oligonucleotide probe hybridization.

Provided herein is a method of clearing cancer cells in a subject in need thereof comprising a) administering an agent to the subject that increases activity of a RhoB GTPase in a cancer cell of the subject; and b) administering a T cell that expresses a Vγ9Vδ2 T cell receptor. In some embodiments, the agent increases translocation of the RhoB GTPase to a cell membrane of the cancer cell. In some embodiments, the agent maintains RhoB GTPase at a cell membrane of the cancer cell. In some embodiments, the agent increases translocation of the RhoB GTPase away from a nucleus of the cancer cell. In some embodiments, the agent increases expression of a gene or transcript encoding the RhoB GTPase. In some embodiments, the agent increases stability of the RhoB GTPase. In some embodiments, the agent increases an interaction between the RhoB GTPase and CD277. In some embodiments, the agent activates RhoB GTPase. In some embodiments, the agent increases an interaction between the RhoB GTPase and GTP. In some embodiments, the agent reduces an interaction between the RhoB GTPase and GDP.

In some cases, the agent increases an amount of GTP in the cancer cell. In some cases, the agent increases availability of GTP in the cancer cell. In some cases, the agent is conjugated to a moiety that binds a cell surface molecule on the cancer cell, thereby targeting the agent to the cancer cell. In some cases, the moiety comprises a small molecule compound. In some cases, the moiety comprises a peptide. In some cases, the moiety comprises an antibody or antigen binding fragment. In some cases, the agent increases an amount of an intracellular phosphoantigen in the cancer cell.

In some cases, the method comprises administering an additional agent that increases an amount of an intracellular phosphoantigen in the cancer cell. In some instances, the additional agent is a mevalonate pathway inhibitor. In some embodiments, the mevalonate pathway inhibitor is an aminobisphosphonate. In some embodiments, the aminobisphosphonate is at least one of pamidronate and zoledronate. In some cases, the subject has at least one of a solid cancer and leukemia. In some cases, the leukemia is acute myeloid leukemia. In some cases, the subject harbors a mutation in a gene that results in reduced RhoB GTPase expression or activity.

Provided herein is a method of clearing cancer cells in a subject in need thereof comprising: administering an agent to the subject that increases activity of a RhoB GTPase in a cancer cell of the subject. In some instances, the method comprises administering a T cell to the subject. In some instances, the T cell expresses a Vγ9Vδ2 T cell receptor. In some instances, the T cell has been engineered or genetically modified to express a Vγ9Vδ2 T cell receptor. In some instances, the T cell has been engineered or genetically modified to overexpress a Vγ9Vδ2 T cell receptor.

Provided herein is a system comprising a polypeptide construct and a cytotoxic cell, wherein the polypeptide construct selectively binds CD277 on a target cell when said CD277 is complexed to RhoB GTPase on said target cell, and wherein said polypeptide construct is expressed in an engineered cell.

Further provided herein is a method for identifying a genetic locus associated with activation of a receptor in a target cell, the method comprising a) identifying cells inducing a phenotype comprising said activation of the receptor in the target cell; b) identifying the zygocity of the cells exhibiting the phenotype; c) obtaining genotype information for the cells, the genotype information defining a genotype at each of multiple loci for different cells; and d) correlating the identified zygocity of the cells with the genotype at one of the multiple loci across the cells to identify the activating genetic locus.

In some embodiments, the genotype information defines a single nucleotide polymorphism at each of the multiple loci. In some instances, the receptor is a Vγ9Vδ2 T cell receptor or fragment thereof. In some cases, the target cell is a cancer cell. In some cases, the target cell is a leukemia cell. In some cases, said phenotype is production of IFNγ. In some cases, a gene is located proximal to at least one of the multiple loci. In some cases, said activation of the receptor involves a polypeptide construct of the target cell selectively binding a J-configuration of CD277 on a cell of the cell type. In some cases, said J-configuration is correlated with the activating genetic locus.

Provided herein is a method comprising a) obtaining target cells from a subject; b) contacting said target cells with at least one modified effector cell expressing an exogenous polypeptide construct; c) detecting a level of immune activation of said modified effector cell expressing said polypeptide construct; and d) identifying the target cells as having a nucleotide sequence polymorphism when said immune activation is above a threshold level.

In some cases, one or more of the target cells is a cancer cell. In some cases, the exogenous polypeptide construct comprises a Vγ9Vδ2 T cell receptor or fragment thereof. In some cases, said detecting the level of immune activation comprises quantifying production of at least one cytokine by the modified effector cell expressing the exogenous polypeptide construct. In some cases, the cytokine is interferon-γ. In some cases, the nucleotide sequence polymorphism is a single nucleotide polymorphism.

In some cases, the method further comprises the step of identifying a gene proximal to the nucleotide sequence polymorphism. In some instances, the gene is located within about 300,000 base pairs of the nucleotide sequence polymorphism. In some instances, the method further comprises the step of treating the subject with an effective amount of said exogenous polypeptide construct. In some instances, the modified effector cell expressing the polypeptide construct is a T cell. In some instances, said contacting the target cells with at least one modified effector cell expressing the exogenous polypeptide construct includes contacting a CD277 molecule on the surface of at least one of said target cells with said exogenous polypeptide construct. In some instances, said exogenous polypeptide construct selectively binds a J-configuration of the CD277 molecule.

Provided herein is a method comprising a) obtaining from a subject target cells expressing CD277; b) contacting the target cells with a cell expressing an exogenous polypeptide construct selectively binds a J-configuration of the CD277 molecule; and c) detecting recognition of the J-configuration of the CD277 molecule by the polypeptide construct. In some embodiments, one or more of the target cells is a cancer cell. In some cases, the polypeptide construct comprises a Vγ9Vδ2 T cell receptor or fragment thereof. In some cases, said detecting the recognition of the J-configuration of the CD277 molecule comprises quantifying production of at least one cytokine by the cell expressing the polypeptide construct. In some instances, the cytokine is interferon-γ. In some instances, the methods further comprises providing an effective amount of said polypeptide construct to said subject. In some cases, the cell expressing the polypeptide construct is a T cell.

Provided herein is a method of predicting a positive therapeutic response in a subject to treatment with a polypeptide construct capable of recognizing CD277, or an engineered cell expressing the polypeptide construct, the method comprising a) identifying target cells of the patient as having a nucleotide sequence polymorphism associated with the activity of RhoB; and b) predicting the subject to exhibit the positive therapeutic response based on said identifying the target cells as having the nucleotide sequence polymorphism. In some embodiments, the polypeptide construct recognizes a J-configuration of CD277 and binds to it directly, or indirectly thru one or more additional biological agents.

In some embodiments, the method further comprises administering the polypeptide construct to the subject. In some embodiments, one or more of the target cells is a cancer cell. In some cases, the nucleotide sequence polymorphism is a single nucleotide polymorphism. In some instances, said activity of RhoB is a high activity compared to a RhoB activity in a subject lacking the nucleotide sequence polymorphism. In some cases, the method further comprises the step of predicting a poor therapeutic response in a second subject based on identifying target cells of the second subject as lacking the nucleotide sequence polymorphism.

Provided herein is a method comprising a) obtaining from a first subject a first set of cells expressing a CD277 molecule; b) identifying said first set of cells as having at least one of i) a high activity of RhoB compared to a second set of target cells obtained from a second subject; and ii) a nucleotide sequence polymorphism associated with the high activity of RhoB; and c) administering to said first subject, a polypeptide construct that has selective affinity for the CD277 configuration on said first set of cells as compared to the CD277 configuration on said second group of cells, or an engineered cell expressing said polypeptide construct.

In some cases, one or more of said first group of cells is a cancer cell. In some cases, one or more of the first group of cells is a leukemic cell. In some instances, the CD277 configuration on said first set of cells is the J-configuration. In some embodiments, the nucleotide sequence polymorphism is a single nucleotide polymorphism.

Provided herein is a method of predicting a positive therapeutic response in a subject to treatment with a polypeptide construct capable of recognizing a CD277 molecule, or an engineered cell expressing the polypeptide construct, the method comprising a) obtaining from the subject target cells expressing the CD277 molecule; b) identifying a J-configuration of the CD277 molecule expressed in the target cells; and c) predicting the subject to exhibit the positive therapeutic response based on said identifying the J-configuration of the CD277 molecule.

In some cases, the method further comprises the step of administering the polypeptide construct to the subject. In some cases, the method further comprising the step of predicting a poor therapeutic response in a second subject based on identifying a CD277 molecule of target cells of the second subject as lacking the J-configuration. In some cases one or more of the target cells is a cancer cell. In some cases, the method further comprising the step of identifying a nucleotide sequence polymorphism associated with the activity of RhoB in the target cells. In some instances, said activity of RhoB is a high activity compared to a RhoB activity in a subject lacking the nucleotide sequence polymorphism. In some cases, the nucleotide sequence polymorphism is a single nucleotide polymorphism. In some embodiments, said predicting is based on both said identifying the J-configuration of the CD277 molecule and said identifying the nucleotide sequence polymorphism.

Provided herein is a method of treating a cancer in a subject wherein the subject has cancer cells that are CD277 positive, comprising administering to the subject an effective amount of a pharmaceutical composition comprising a pharmaceutically acceptable agent that selectively binds to the J-configuration or J-confirmation of CD277 on said cancer cell directly, or indirectly thru one or more additional biological agents. In some embodiments, the pharmaceutically acceptable agent comprises a polypeptide construct that selectively binds to the J-configuration of the CD277 on said cancer cell. In some embodiments, the polypeptide construct comprises at least one of a γ-TCR polypeptide sequence or a δ-TCR polypeptide sequence. In some embodiments, the polypeptide construct comprises a variant or fragment of at least one of a γ-TCR polypeptide sequence or a δ-TCR polypeptide sequence. In some instances the γ-TCR polypeptide sequence is a γ9-TCR polypeptide sequence or fragment thereof. In some cases, the δ-TCR polypeptide sequence is a δ2-TCR polypeptide sequence or a fragment thereof.

In some cases, the pharmaceutically acceptable agent binds the J-configuration of CD277 with higher selectivity as compared to a CD277 molecule which is not in said J-configuration, directly, or indirectly thru one or more additional biological agents. In some embodiments, the target cell is a cancer cell. In some embodiments, the target cell is a leukemia cell. In some cases, the CD277 is present as a dimer.

BRIEF DESCRIPTION OF THE DRAWINGS

The features of the present disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 1A shows recognition phenotype indicating whether EBV-LCL lines are recognized (+) or not (−) by Vγ9Vδ2 TCR+ T cells in three independent experiments. FIG. 1B shows recognition phenotype of EBV-LCLs (black bars: not activating; grey bars: activating) was assessed by IFN□-ELIspot assay, in which EBV-LCLs were used as targets against Vγ9Vδ2TCR+ T cells in the presence of ABP pamidronate. Figure shows the number of IFN□□ spots of a representative experiment.

FIG. 2A-2C show SNP-Associated comPutational Pathway Hunt Including shRNA Evaluation (SAPPHIRE) to identify genetic loci associated with the activation of a predetermined receptor in specific cells. FIG. 2A shows the recognition of CEPH EBV-LCL lines by Vγ9Vδ2 TCR+ T cells provided the basis for deducing hypothetical zygosities of candidate loci in each cell line (black: recognized; white: not recognized; square: male; circle: female; +/−: heterozygous; /−; homozygous negative; +/: undetermined). Members of two CEPH families are shown as examples. For CEPH ID numbers of cell lines, see FIG. 1A. FIG. 2B shows genetic association analysis revealed 17 SNPs of which genotypes correlated 100% ($r^2=1$) with predicted zygosities of cell lines. Locations and nearest neighboring genes of SNPs are indicated. The effect of knocking down candidate genes on recognition of EBV-LCL 48 by T cells transduced with either Vγ9Vδ2 TCR clone G115 or an HLA-A*0201-restricted $WT1_{126\_134}$-specific αβTCR are indicated by black circles (significant effect on T cell activation) and white circles (no effect). For testing recognition by WT1 αβTCR+ T cells, the EBV-LCL 48 line was pulsed with $WT1_{126\_134}$ peptide. FIG. 2C shows associating SNPs resulting from association analysis with candidate genes. The genetic region of the SNPs neighboring RhoB is shown as an example. Each bar represents one SNP and $r^2$ values represent correlation between predicted zygosities and SNP genotypes.

FIG. 4A shows RhoB was partially knocked out in the renal cancer cell line MZ1851RC using the CRISPR/Cas system. MZ1851RC cells were treated with either pamidronate or HLA-A*0201-restricted $WT1_{126+134}$ peptide and the effect on target cell recognition by engineered cells expressing polypeptide constructs described herein and WT1 o43TCR+ T cells, respectively, was determined by measuring IFNγ production. A guide RNA targeting an irrelevant sequence was used as control for knock out, while medium or irrelevant peptide loaded tumor cells were used as controls for T cell stimulation. Data show mean±S.E.M of three independent experiments, in duplicate samples. Level of knock out was determined by intracellular flow cytometry. FIG. 4B shows the effect of knock-out of RhoA, B and C in 293 HEK cells on recognition by engineered cells expressing polypeptide constructs described herein was assessed by measuring IFNγ production. A guide RNA targeting an irrelevant sequence was used as control. Figure shows IFNγ production normalized to irrelevant knock out samples of three independent experiments, in duplicate samples. FIG. 4C shows RNA expression of RhoB was measured by qPCR in either non-recognized (black bars) or recognized (white bars) EBV-LCLs and tumor cell lines. Data is representative of 2 repeated experiments. FIG. 4D shows the non-recognized EBV-LCL line 93 or the recognized EBV-LCL 48 were pretreated with either calpeptin or C3 transferase in combination with pamidronate or IPP and the effect on stimulation of Vγ9Vδ2 TCR+ T cells was assessed by measuring IFNγ. The effect of Rho-modulating compounds on recognition of $WT1_{126+134}$ peptide-pulsed EBV-LCL 48 cells by WT1 αβTCR+ T cells was measured in parallel. Data shows mean −1(4 S.E.M of at least three independent experiments. FIG. 4E shows HEK 293 cells were transfected with dominant-negative (RhoB-DN), constitutively active (RhoB-CA) or wild type RhoB (RhoB-WT) and the effect of activity variants on target cell recognition by Vγ9Vδ2 TCR+ T cells in the presence of pamidronate was determined by measuring IFNγ. Figure shows IFNγ production normalized to wild type RhoB samples of three independent experiments. Significance of data has been analyzed by Mann-Whitney test on FIGS. 4A, B and D, and by Knisltal-Wallis test and Dunn's multiple comparison test on FIG. 4E.

dark: nucleus [DAPI]).

FIG. 7A shows HEK 293 cells were transfected with CD277-emGFP fusion constructs and treated with medium, ABP zoledronate, or calpeptin. Zoledronate treatment was also applied to HEK 293 CD277-emGFP+ cells in which RhoB was knocked out by CRISPR/Cas or in cells that were also treated with C3-transferase. The figure shows the percentage of CD277 immobile fraction upon treatments applied (+). Symbols represent single cell measurements, of 2 experiments. FIG. 7B shows HEK 293 cells were pretreated with pamidronate or with calpeptin and BTN3 molecules and filamentous actin (F-actin) were stained using a fluorescently labeled anti-CD277 antibody and fluorescent phalloidin, respectively. The colocalization of CD277 and F-actin was subsequently assessed by determining the localization correlation of both signals. Symbols represent single cell measurements, of a single experiment. The center line and error bars represent average and S.E.M., p values indicate significance analyzed by using Mann-Whitney test.

FIG. 8A shows EBV-LCL 48 cells were treated either with medium or ABP pamidronate, loaded onto poly-L-lysine-coated coverslips and permeabilized. The interaction between RhoB and CD277 was subsequently assessed by Duolink PLA using anti-RhoB and anti-CD277 antibodies. Duolink PLA without antibodies against RhoB and BTN3 served as negative control (red: PLA signal; blue: nucleus [DAPI]; dotted line: cell membrane). Figures are representative of two independent experiments. FIG. 8B shows HEK 293 cells were treated with either medium or pamidronate and co-stained with equal amount of anti-CD277-PE (donor) as well as anti-CD277-DyLight 680 (acceptor) antibodies and FRET efficiency in cells was measured as described in Materials and Methods. Data shown is mean S.E.M. of three independent experiments, in triplicate samples, where Mann-Whitney test was used to analyze statistical significance. FIG. 8C shows HEK 293 cells were pretreated either with medium or pamidronate, trypsinized, permeabilized and stained with anti-RhoB-Alexa Fluor 488 (FRET donor) and anti-CD277-DyLight 680 (FRET acceptor) antibodies. FRET efficiency was subsequently measured by flow cytometry as described in Materials and Methods. Data show mean+S.E.M of three independent experiments, in triplicate samples, where Mann-Whitney test was used to analyze statistical significance. FIG. 8D shows concentration dependent binding of the full-length CD277 intracellular domain (BFI) with RhoGTPase in the presence or absence of the phosphoantigen cHDMAPP. Binding of BFI to RhoGTPase was measured using Biolayer Interferometry (BM) either in the absence of cHDMAPP (left panel) or presence of cHDMAPP (1:1) (right panel). Concentrations of CD277 BFI shown in the upper panel are 6.25, 12.5, 25, 50 and 100 uM shown in grey. The kinetics fitting curves are shown as black In the lower panel, concentrations of CD277 BFI shown are 3.75, 7.5, 15, 30 and 60 uM shown in grey The kinetics fitting curves are shown as black. FIG. 8E shows the same experimental setup but with recombinant CD277 B30.2 domain, lacking the N terminal region connector to the transmembrane domain. In the left panel, the interaction was measured without cHDMAPP. Concentrations of BTN3A1 B30.2 shown were 12.5, 25, 50, 100 and 200 uM shown in grey. The kinetics fitting curves are shown as black In the lower panel, the interaction was measured with cHDMAPP (1:1). Concentrations of B30.2 domain shown are 3.75, 7.5, 15, 30 and 60 uM shown in grey.

In FIG. 12A, EBV-LCL line 93, CLM cell line K562, as well as healthy donor derived CD3+ T cells, CD19+ B cells and CD14+ cells freshly isolated from peripheral blood were incubated with 100 uM Pamidronate and subsequently analysed for the intracellular distribution of RhoB via confocal microscopy. Shown is the ratio of RhoB signal detected outside vs inside of the nuclear area. In FIG. 12B, cells irradiated with 3500 cGy and pretreated with 100 uM Pamidronate were subsequently analysed for intracellular RhoB distribution as in FIG. 12A. Ratios indicate RhoB distribution changes when compared to non-irradiated cells.

DETAILED DESCRIPTION OF THE INVENTION

Figures 1A, 1B:
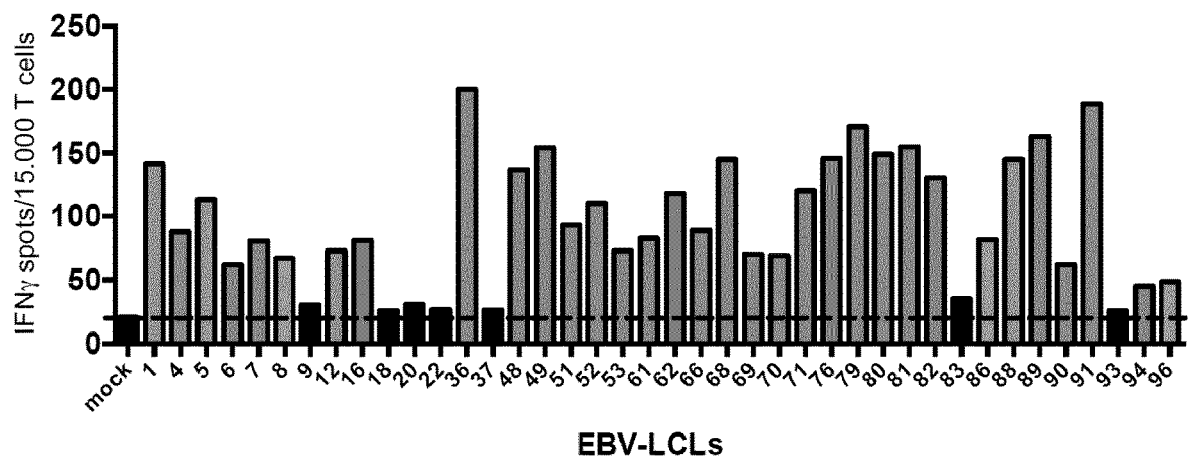
FIG. 1A-1B show CEPH EBV-LCL lines used for identifying genetic loci associated with engineered cells expressing a predetermined receptor, for instance Vγ9Vδ2TCR-mediated recognition.

In an aspect, provided herein are T cells that elicit robust antitumor responses. An antitumor response may be mediated by binding between an immune cell expressing a receptor, such as a γ9δ2 TCR, and a target, such as a tumor cell. The binding of a tumor cell to an immune cell may be bolstered by improved receptor-target interactions. In an aspect, provided herein can be compositions and methods that bolster binding between a target and an immune cell expressing a γ9δ2 TCR. In an aspect, a method can comprise increasing activity of a RhoB GTPase. In an aspect, a method can comprise increasing activity, such as accumulation, of a phosphoantigen. RhoB GTPase and phosphoantigen can be involved in bolstering expression of CD277 of a tumor cell surface thereby improving or allowing for an interaction between a tumor cell expressing CD277 and an immune cell comprising a γ9δ2 TCR. In an aspect, provided herein can be methods comprising improving an inside-out signaling of a tumor cell thereby allowing it to be recognized by immune cells. In an aspect, provided herein can be agents that enhance an inside out signaling of at umor cell by bolstering an expression of CD277 on a surface. Agents can act directly on CD277 or indirectly. Expression of CD277 can be bolstered by stimulating RhoB GTPase and phosphoantigena in a tumor cell. In an aspect, agents can act directly on RhoB GTPase or indirectly. In an aspect, agents can act directly on phosphoantigen or indirectly. In an aspect, an agent that can increase activity of RhoB GTPase, phosphoantigen, or a combination thereof can act indirectly or directly. In an aspect, an agent that can increase activity of RhoB GTPase, phosphoantigen, or a combination thereof can bind secondary factors that in turn increase activity of RhoB GTPase and/or phosphoantigen. In an aspect, an agent that can increase activity of RhoB GTPase, phosphoantigen, or a combination thereof can bind a number of upstream factors that in turn increase activity of RhoB GTPase and/or phosphoantigen. In an aspect, up to 10 factors upstream of RhoB GTPase or phosphoantigen can be stimulated and in turn actibity of RhoB GTPase and/or phosphoantigen is increased.

In an aspect, provided herein can be compositions of immune cells comprising γ9δ2 TCRs and compositions comprising agents that increase activity of RhoB GTPase and phosphoantigen. In an aspect, a γ9δ2TCR-mediated response can be enhanced by agents such as pamidronate, and alternatively through the expression of additional adhesion agents. In some aspects, activation can be followed by a recognition of a target, such as a cancerous cell expressing CD277. Recognition of a target may be mediated by the CDR3 region of the γ9δ2TCR, as well as configurational changes in CD277. In some aspects, T cell activation may utilize membrane flexibility to form a synapse comprising a T cell and a tumor cell. In some aspects, T cell activation may comprise microclustering of CD277 at a cell membrane through the interaction of a γ9δ2TCR.

All terms are intended to be understood as they would be understood by a person skilled in the art. Unless defined otherwise, all technical and scientific terms used herein have the same meaning as commonly understood by one of ordinary skill in the art to which the disclosure pertains.

The section headings used herein are for organizational purposes only and are not to be construed as limiting the subject matter described.

Although various features of the invention may be described in the context of a single embodiment, the features may also be provided separately or in any suitable combination. Conversely, although the invention may be described herein in the context of separate embodiments for clarity, the invention may also be implemented in a single embodiment.

The following definitions supplement those in the art and are directed to the current application and are not to be imputed to any related or unrelated case, e.g., to any commonly owned patent or application. Although any methods and materials similar or equivalent to those described herein can be used in the practice for testing of the present disclosure, the preferred materials and methods are described herein. Accordingly, the terminology used herein is for the purpose of describing particular embodiments only, and is not intended to be limiting.

In this application, the use of the singular includes the plural unless specifically stated otherwise. It must be noted that, as used in the specification, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

The term "autologous" and its grammatical equivalents as used herein can refer to as originating from the same being. For example, a sample (e.g., cells) can be removed, processed, and given back to the same subject (e.g., patient) at a later time. An autologous process is distinguished from an allogenic process where the donor and the recipient are different subjects.

The term "activation" and its grammatical equivalents as used herein can refer to a process whereby a cell transitions from a resting state to an active state. This process can comprise a response to an antigen, migration, and/or a phenotypic or genetic change to a functionally active state. For example, the term "activation" can refer to the stepwise process of T cell activation. For example, a T cell can require at least two signals to become fully activated. The first signal can occur after engagement of a TCR by the antigen-MHC complex, and the second signal can occur by engagement of co-stimulatory molecules. Anti-CD3 can mimic the first signal and anti-CD28 can mimic the second signal in vitro.

Reference in the specification to "some embodiments," "an embodiment," "one embodiment" or "other embodiments" means that a particular feature, structure, or characteristic described in connection with the embodiments is included in at least some embodiments, but not necessarily all embodiments, of the inventions.

As used in this specification and claim(s), the words "comprising" (and any form of comprising, such as "comprise" and "comprises"), "having" (and any form of having, such as "have" and "has"), "including" (and any form of including, such as "includes" and "include") or "containing"

(and any form of containing, such as "contains" and "contain") are inclusive or open-ended and do not exclude additional, unrecited elements or method steps. It is contemplated that any embodiment discussed in this specification can be implemented with respect to any method or composition of the invention, and vice versa. Furthermore, compositions of the invention can be used to achieve methods of the invention.

The term "about" in relation to a reference numerical value and its grammatical equivalents as used herein can include the numerical value itself and a range of values plus or minus 10% from that numerical value. For example, the amount "about 10" includes 10 and any amounts from 9 to 11. For example, the term "about" in relation to a reference numerical value can also include a range of values plus or minus 10%, 9%, 8%, 7%, 6%, 5%, 4%, 3%, 2%, or 1% from that value.

The term "cytotoxicity" as used in this specification, refers to an unintended or undesirable alteration in the normal state of a cell. The normal state of a cell may refer to a state that is manifested or exists prior to the cell's exposure to a cytotoxic composition, agent and/or condition. Generally, a cell that is in a normal state is one that is in homeostasis. An unintended or undesirable alteration in the normal state of a cell can be manifested in the form of, for example, cell death (e.g., programmed cell death), a decrease in replicative potential, a decrease in cellular integrity such as membrane integrity, a decrease in metabolic activity, a decrease in developmental capability, or any of the cytotoxic effects disclosed in the present application.

By "isolated" is meant the removal of a nucleic acid from its natural environment. By "purified" is meant that a given nucleic acid, whether one that has been removed from nature (including genomic DNA and mRNA) or synthesized (including cDNA) and/or amplified under laboratory conditions, has been increased in purity, wherein "purity" is a relative term, not "absolute purity." It is to be understood, however, that nucleic acids and proteins can be formulated with diluents or adjuvants and still for practical purposes be isolated. For example, nucleic acids typically are mixed with an acceptable carrier or diluent when used for introduction into cells.

The term "percent (%) identity," as used herein, refers to the percentage of amino acid (or nucleic acid) residues of a candidate sequence that are identical to the amino acid (or nucleic acid) residues of a reference sequence after aligning the sequences and introducing gaps, if necessary, to achieve the maximum percent identity (i.e., gaps can be introduced in one or both of the candidate and reference sequences for optimal alignment and non-homologous sequences can be disregarded for comparison purposes). Alignment, for purposes of determining percent identity, can be achieved in various ways that are within the skill in the art, for instance, using publicly available computer software such as BLAST, ALIGN, or Megalign (DNASTAR) software. Percent identity of two sequences can be calculated by aligning a test sequence with a comparison sequence using BLAST, determining the number of amino acids or nucleotides in the aligned test sequence that are identical to amino acids or nucleotides in the same position of the comparison sequence, and dividing the number of identical amino acids or nucleotides by the number of amino acids or nucleotides in the comparison sequence.

The term "peripheral blood lymphocytes" (PBL) and its grammatical equivalents as used herein can refer to lymphocytes that circulate in the blood (e.g., peripheral blood). Peripheral blood lymphocytes can refer to lymphocytes that are not localized to organs. Peripheral blood lymphocytes can comprise T cells, NK cells, B cell, or any combinations thereof.

The term "phenotype" and its grammatical equivalents as used herein can refer to a composite of an organism's observable characteristics or traits, such as its morphology, development, biochemical or physiological properties, phenology, behavior, and products of behavior. Depending on the context, the term "phenotype" can sometimes refer to a composite of a population's observable characteristics or traits.

"Polynucleotide" or "oligonucleotide" as used herein refers to a polymeric form of nucleotides of any length, either ribonucleotides or deoxyribonucleotides. This term refers only to the primary structure of the molecule. Thus, this term includes double and single stranded DNA, triplex DNA, as well as double and single stranded RNA. It also includes modified, for example, by methylation and/or by capping, and unmodified forms of the polynucleotide. The term is also meant to include molecules that include non-naturally occurring or synthetic nucleotides as well as nucleotide analogs.

The term "peripheral blood lymphocytes" (PBL) and its grammatical equivalents as used herein can refer to lymphocytes that circulate in the blood (e.g., peripheral blood). Peripheral blood lymphocytes can refer to lymphocytes that are not localized to organs. Peripheral blood lymphocytes can comprise T cells, NK cells, B cell, or any combinations thereof.

"Polypeptide" is used interchangeably with the terms "polypeptides" and "protein(s)," and refers to a polymer of amino acid residues. A "mature protein" is a protein which is full-length and which, optionally, includes glycosylation or other modifications typical for the protein in a given cellular environment.

Nucleic acids and/or nucleic acid sequences are "homologous" when they are derived, naturally or artificially, from a common ancestral nucleic acid or nucleic acid sequence. Proteins and/or protein sequences are homologous when their encoding DNAs are derived, naturally or artificially, from a common ancestral nucleic acid or nucleic acid sequence. The homologous molecules can be termed homologs. For example, any naturally occurring proteins, as described herein, can be modified by any available mutagenesis method. When expressed, this mutagenized nucleic acid encodes a polypeptide that is homologous to the protein encoded by the original nucleic acid. Homology is generally inferred from sequence identity between two or more nucleic acids or proteins (or sequences thereof). The precise percentage of identity between sequences that is useful in establishing homology varies with the nucleic acid and protein at issue, but as little as 25% sequence identity is routinely used to establish homology. Higher levels of sequence identity, e.g., 30%, 40%, 50%, 60%, 70%, 80%, 90%, 95% or 99% or more can also be used to establish homology.

The terms "identical" or "sequence identity" in the context of two nucleic acid sequences or amino acid sequences of polypeptides refers to the residues in the two sequences which are the same when aligned for maximum correspondence over a specified comparison window. In one class of embodiments, the polypeptides herein are at least 80%, 85%, 90%, 98% 99% or 100% identical to a reference polypeptide, or a fragment thereof, e.g., as measured by BLASTP (or CLUSTAL, or any other available alignment software) using default parameters. Similarly, nucleic acids can also be described with reference to a starting nucleic acid, e.g., they can be 50%, 60%, 70%, 75%, 80%, 85%, 90%, 98%, 99% or 100% identical to a reference nucleic acid or a fragment thereof, e.g., as measured by BLASTN (or CLUSTAL, or any other available alignment software) using default parameters. When one molecule is said to have certain percentage of sequence identity with a larger molecule, it means that when the two molecules are optimally aligned, said percentage of residues in the smaller molecule finds a match residue in the larger molecule in accordance with the order by which the two molecules are optimally aligned.

The term "T cell" and its grammatical equivalents as used herein can refer to a T cell from any origin. For example, a T cell can be a primary T cell, e.g., an autologous T cell, a cell line, etc. The T cell can also be human or non-human.

The term "TIL" or tumor infiltrating lymphocyte and its grammatical equivalents as used herein can refer to a cell isolated from a tumor. For example, a TIL can be a cell that has migrated to a tumor. A TIL can also be a cell that has infiltrated a tumor. A TIL can be any cell found within a tumor. For example, a TIL can be a T cell, B cell, monocyte, natural killer (NK) cell, or any combination thereof. A TIL can be a mixed population of cells. A population of TILs can comprise cells of different phenotypes, cells of different degrees of differentiation, cells of different lineages, or any combination thereof.

"Transposon" or "transposable element" (TE) is a vector DNA sequence that can change its position within the genome, sometimes creating or reversing mutations and altering the cell's genome size. Transposition often results in duplication of the TE. Class I TEs are copied in two stages: first, they are transcribed from DNA to RNA, and the RNA produced is then reverse transcribed to DNA. This copied DNA is then inserted at a new position into the genome. The reverse transcription step is catalyzed by a reverse transcriptase, which can be encoded by the TE itself. The characteristics of retrotransposons are similar to retroviruses, such as HIV. The cut-and-paste transposition mechanism of class II TEs does not involve an RNA intermediate. The transpositions are catalyzed by several transposase enzymes. Some transposases non-specifically bind to any target site in DNA, whereas others bind to specific DNA sequence targets. The transposase makes a staggered cut at the target site resulting in single-strand 5' or 3' DNA overhangs (sticky ends). This step cuts out the DNA transposon, which is then ligated into a new target site; this process involves activity of a DNA polymerase that fills in gaps and of a DNA ligase that closes the sugar-phosphate backbone. This results in duplication of the target site. The insertion sites of DNA transposons can be identified by short direct repeats which can be created by the staggered cut in the target DNA and filling in by DNA polymerase, followed by a series of inverted repeats important for the TE excision by transposase. Cut-and-paste TEs can be duplicated if their transposition takes place during S phase of the cell cycle when a donor site has already been replicated, but a target site has not yet been replicated. Transposition can be classified as either "autonomous" or "non-autonomous" in both Class I and Class II TEs. Autonomous TEs can move by themselves while non-autonomous TEs require the presence of another TE to move. This is often because non-autonomous TEs lack transposase (for class II) or reverse transcriptase (for class I).

"Transposase" refers an enzyme that binds to the end of a transposon and catalyzes the movement of the transposon to another part of the genome by a cut and paste mechanism or a replicative transposition mechanism. In some embodiments, the transposase's catalytic activity can be utilized to move gene(s) from a vector to the genome.

The nucleic acid sequences and vectors disclosed or contemplated herein can be introduced into a cell by "transfection," "transformation," "nucleofection" or "transduction." "Transfection," "transformation," or "transduction," as used herein, refer to the introduction of one or more exogenous polynucleotides into a host cell by using physical or chemical methods. Many transfection techniques are known in the art and include, for example, calcium phosphate DNA co-precipitation (see, e.g., Murray E. J. (ed.), Methods in Molecular Biology, Vol. 7, Gene Transfer and Expression Protocols, Humana Press (1991)); DEAE-dextran; electroporation; cationic liposome-mediated transfection; tungsten particle-facilitated microparticle bombardment (Johnston, Nature, 346: 776-777 (1990)); and strontium phosphate DNA co-precipitation (Brash et al., Mol. Cell Biol., 7: 2031-2034 (1987)); and nucleofection (Trompeter et al., J. Immunol. Methods 274:245-256 (2003). Phage or viral vectors can be introduced into host cells, after growth of infectious particles in suitable packaging cells, many of which are commercially available.

"Promoter" refers to a region of a polynucleotide that initiates transcription of a coding sequence. Promoters are located near the transcription start sites of genes, on the same strand and upstream on the DNA (towards the 5' region of the sense strand). Some promoters are constitutive as they are active in all circumstances in the cell, while others are regulated becoming active in response to specific stimuli, e.g., an inducible promoter.

The term "promoter activity" refers to the extent of expression of nucleotide sequence that is operably linked to the promoter whose activity is being measured. Promoter activity can be measured directly by determining the amount of RNA transcript produced, for example by Northern blot analysis or indirectly by determining the amount of product coded for by the linked nucleic acid sequence, such as a reporter nucleic acid sequence linked to the promoter.

"Inducible promoter" as used herein refers to a promoter which is induced into activity by the presence or absence of transcriptional regulators, e.g., biotic or abiotic factors. Inducible promoters are useful because the expression of genes operably linked to them can be turned on or off at certain stages of development of an organism or in a particular tissue. Examples of inducible promoters are alcohol-regulated promoters, tetracycline-regulated promoters, steroid-regulated promoters, metal-regulated promoters, pathogenesis-regulated promoters, temperature-regulated promoters and light-regulated promoters. In one embodiment, the inducible promoter is part of a genetic switch.

The term "enhancer," as used herein, refers to a DNA sequence that increases transcription of, for example, a nucleic acid sequence to which it is operably linked. Enhancers can be located many kilobases away from the coding region of the nucleic acid sequence and can mediate the binding of regulatory factors, patterns of DNA methylation, or changes in DNA structure. A large number of enhancers from a variety of different sources are well known in the art and are available as or within cloned polynucleotides (from, e.g., depositories such as the ATCC as well as other commercial or individual sources). A number of polynucleotides comprising promoters (such as the commonly-used CMV promoter) also comprise enhancer sequences. Enhancers can be located upstream, within, or downstream of coding sequences. The term "Ig enhancers" refers to enhancer elements derived from enhancer regions mapped within the immunoglobulin (Ig) locus (such enhancers include for example, the heavy chain (mu) 5' enhancers, light chain (kappa) 5' enhancers, kappa and mu intronic enhancers, and 3' enhancers (see generally Paul W. E. (ed), Fundamental Immunology, 3rd Edition, Raven Press, New York (1993), pages 353-363; and U.S. Pat. No. 5,885,827).

"Coding sequence" as used herein refers to a segment of a polynucleotide that codes for a polypeptide. The region or sequence is bounded nearer the 5' end by a start codon and nearer the 3' end with a stop codon. Coding sequences can also be referred to as open reading frames.

"Operably linked" as used herein refers to refers to the physical and/or functional linkage of a DNA segment to another DNA segment in such a way as to allow the segments to function in their intended manners. A DNA sequence encoding a gene product is operably linked to a regulatory sequence when it is linked to the regulatory sequence, such as, for example, promoters, enhancers and/or silencers, in a manner which allows modulation of transcription of the DNA sequence, directly or indirectly. For example, a DNA sequence is operably linked to a promoter when it is ligated to the promoter downstream with respect to the transcription initiation site of the promoter, in the correct reading frame with respect to the transcription initiation site and allows transcription elongation to proceed through the DNA sequence. An enhancer or silencer is operably linked to a DNA sequence coding for a gene product when it is ligated to the DNA sequence in such a manner as to increase or decrease, respectively, the transcription of the DNA sequence. Enhancers and silencers can be located upstream, downstream or embedded within the coding regions of the DNA sequence. A DNA for a signal sequence is operably linked to DNA coding for a polypeptide if the signal sequence is expressed as a preprotein that participates in the secretion of the polypeptide. Linkage of DNA sequences to regulatory sequences is typically accomplished by ligation at suitable restriction sites or via adapters or linkers inserted in the sequence using restriction endonucleases known to one of skill in the art.

The term "transcriptional regulator" refers to a biochemical element that acts to prevent or inhibit the transcription of a promoter-driven DNA sequence under certain environmental conditions (e.g., a repressor or nuclear inhibitory protein), or to permit or stimulate the transcription of the promoter-driven DNA sequence under certain environmental conditions (e.g., an inducer or an enhancer).

The term "induction" refers to an increase in nucleic acid sequence transcription, promoter activity and/or expression brought about by a transcriptional regulator, relative to some basal level of transcription.

A "target" gene or "heterologous" gene, or "gene of interest (GOI)" refers to a gene introduced into the host cell by gene transfer. In certain cases, a polypeptide construct described herein is encoded in an engineered cell as one or more heterologous genes.

"Recombinase" as used herein refers to a group of enzymes that can facilitate site-specific recombination between defined sites, where the sites are physically separated on a single DNA molecule or where the sites reside on separate DNA molecules. The DNA sequences of the defined recombination sites are not necessarily identical. Initiation of recombination depends on protein-DNA interaction, within the group there are large number of proteins that catalyze phage integration and excision (e.g., λ integrase, ΦC31), resolution of circular plasmids (e.g., Tn3, gamma delta, Cre, Flp), DNA inversion for expression of alternate genes (e.g., Hin, Gin, Pin), assembly of genes during development (e.g., *Anabaena* nitrogen fixation genes), and transposition (e.g., IS607 transposon). Most site-specific recombinases fall into one of the two families, based on evolutionary and mechanistic relatedness. These are λ integrase family or tyrosine recombinases (e.g., Cre, Flp, Xer D) and resolvase/integrase family or serine recombinase family (e.g., ΦC31, TP901-1, Tn3, gamma delta).

"Recombination attachment sites" are specific polynucleotide sequences that are recognized by the recombinase enzymes described herein. Typically, two different sites are involved (termed "complementary sites"), one present in the target nucleic acid (e.g., a chromosome or episome of a eukaryote or prokaryote) and another on the nucleic acid that is to be integrated at the target recombination site. The terms "attB" and "attP," which refer to attachment (or recombination) sites originally from a bacterial target and a phage donor, respectively, are used herein although recombination sites for particular enzymes can have different names. The recombination sites typically include left and right arms separated by a core or spacer region. Thus, an attB recombination site consists of BOB', where B and B' are the left and right arms, respectively, and O is the core region. Similarly, attP is POP', where P and P' are the arms and O is again the core region. Upon recombination between the attB and attP sites, and concomitant integration of a nucleic acid at the target, the recombination sites that flank the integrated DNA are referred to as "attL" and "attR." The attL and attR sites, using the terminology above, thus consist of BOP' and POB', respectively. In some representations herein, the "0" is omitted and attB and attP, for example, are designated as BB' and PP', respectively.

As used herein, the term "CRISPR" refers to a caspase-based endonuclease comprising a caspase, such as Cas9, and a guide RNA that directs DNA cleavage of the caspase by hybridizing to a recognition site in the genomic DNA.

The term "distressed cell" or "stressed cell" as used herein refers to a cell which manifests a diseased or disordered state. Manifestations of distress can include any alteration in cellular function relative to a normal or non-stressed state including changes in gene transcription or translation, post-transcriptional or post-translational modifications, protein or enzyme activities, polypeptide conformations, cell adhesion, cell surface characteristics, and the capacity to recognize or be recognized by other cells. In some embodiments, a particular phenotype of a distressed cell (e.g. altered pattern of gene expression) is related to an intracellular abnormality such as a genetic mutation. In other embodiments, a phenotype of a distressed cell is related to abnormalities or stressors in the extracellular environment. An example of a distressed cell is a tumor cell. In specific embodiments, a distressed cell can be characterized by a transmigration of RhoB to the cell membrane. In certain cases, a distressed cell is characterized by the presence of the J-configuration of CD277 on the cell surface.

The term "epigenetic change" or "epigenetic modification" as used herein refers to any covalent or non-covalent modification of DNA other than a change in DNA sequence. In certain embodiments, an epigenetic change affects or alters the regulation and/or expression of one or more genes. It is contemplated that an epigenetic change can impact regulation of genes which are relatively proximal (e.g. within 1 Mbp) to a chromosomal site of an epigenetic modification as well as distal (e.g. greater than 1 Mbp away along the same chromosome or on a different chromosome) to the site of the epigenetic modification. Non-limiting examples of an epigenetic change include DNA methylation and hydroxymethylation, histone modifications such as lysine acetylation, lysine and arginine methylation serine and threonine phosphorylation and lysine ubiquitination and sumoylation, and changes in chromatin structure.

In an aspect, provided can be compositions comprising γδT cells. A γδT can be an unconventional T cell population expressing a γδ T cell receptor. A γδT can be a merge of TCR-secured specificity and broad non HLA-restricted antitumor reactivity, the characteristics which may open a new avenue in cancer immunotherapy. For instance, detection of tumor-infiltrating γδT cells has been associated with a positive clinical outcome in cancer patients. In an aspect, γδT cells can be involved in early cancer immune surveillance. In an aspect, γδT can be heterogeneous in terms of function and receptor expression. In an aspect, a γδTCR can be introduced into an immune cell. For example, a γδTCR can be introduced into an αβT cell. In an aspect, a method comprising introducing a γδTCR into an immune cell, such as an αβT cell can improve persistence of a γδTCR-based therapeutic. In an aspect, a method comprising introducing a γδTCR into an immune cell, such as an αβT cell can improve proliferation of a γδTCR-based therapeutic. In an aspect, a method comprising introducing a γδTCR into an immune cell, such as an αβT cell can overcome clonal heterogeneity of tumor cells in patients with advanced cancer, an improvement over αβTCR-based approaches. In an aspect, this improvement may be due to the distinct HLA-independent activation cues of the γδTCR, such as changes in lipid metabolism. In an aspect, a γδTCR therapeutic may be administered to a subject comprising a cancer with a low mutational load.

In an aspect, provided herein can be a γδTCR therapeutic that binds a target, such as CD277 on a cancer cell. Binding of a γδTCR therapeutic can comprise spatial and/or conformational changes in CD277 expressed on a target. In an aspect, binding can refer to a direct interaction. In an aspect, binding can refer to an indirect interaction. Binding can refer to an agent that binds upstream of CD277. In an aspect, an agent that binds upstream of CD277 can bind from about 20, 19, 18, 17, 16, 15, 14, 13, 12, 11, 10, 9, 8, 7, 6, 5, 4, 3, 2, or 1 factor away from CD277. In some aspects, a cascade of events leading to the activating state of CD277, referred to as a J-configuration of CD277, or CD277J, can induce TCR-dependent γ9δ2T cell activation.

In an aspect, diversity in the CDR3 region of γ9δ2TCR can contribute to the functional heterogeneity within the γ9δ2 T cell population as well as the expression of additional co-receptors In an aspect. Functional heterogeneity within a γ9δ2 T cell population can be attributed to distinct phenotypic and transcriptional profiles. In an aspect, there can be clonal levels of different activation thresholds harbored within diverse γ9δ2T cell repertoires towards tumor cells. By expressing γδTCRs in αβT cells, there can exist variation in function of a γ9δ2 T cell clone. In some aspect, this variation may not be solely correlated to functional avidities mediated by distinct γ9δ2TCR. In an aspect, there can be a low affinity interaction of γ9δ2TCR with CD277J. In an aspect, there can be an initial scanning mode of the γδTCR towards its target. This initial scanning can be CDR3-independent and can utilize other contact residues of the γδTCR. In an aspect, a scanning can also utilize pamidronate induced adhesion molecules. A scanning mode can be followed by a CDR3-dependent cognate recognition, which can utilize membrane flexibility of the γ9δ2TCR and high-density recruitment during synapse formation to allow sensing the nano-clusters consisting of CD277J-configuration and possible additional membrane molecules at the target side. In an aspect, a TCR can comprise a percent identity from about 40%, 50%, 60%, 70%, 75%, 80%, 85%, 90%, 95%, 96%, 97%, 98%, 99%, or up to about 100% to a sequence in Table 4. In an aspect, a γ9δ2 can comprise a percent identity from about 40%, 50%, 60%, 70%, 75%, 80%, 85%, 90%, 95%, 96%, 97%, 98%, 99%, or up to about 100% to a sequence in Table 4. In an aspect, a γ9δ2 be generating using a sequence comprised in Table 3 or using a sequence comprising a percent identity from about 40%, 50%, 60%, 70%, 75%, 80%, 85%, 90%, 95%, 96%, 97%, 98%, 99%, or up to about 100% to a sequence in Table 3.

In an aspect, comparison of γδTCR repertoire diversity between naïve cord blood-derived γδ T cells and γδ T cells isolated from peripheral blood of adult healthy individuals can show preferential expansion of selected clonotypes. In an aspect, the skewing of the repertoire towards few dominant clonotypes may imply a certain functional benefit. In an aspect, there may not be a correlation between clonotype frequency and antitumor functional potential of the respective clone. In an aspect a repertoire focusing, occurring in parallel with acquisition of distinct phenotypic profiles can be a reflection of T cell antigenic stimulation history of an individual, rather than in vitro potency of a selected clone. In an aspect, other receptors than the γ9δ2TCR might be involved in the induction of tolerance of γ9δ2T cell clones.

In an aspect, a γ9δ2TCR taken outside of the environment of its parental clone, can be used to target very efficiently malignant diseases. In an aspect, a γ9δ2TCR affinity can be a determinant of an activation potential of αβTCRs when expressed on the same background. In an aspect, there may be intrinsic differences in activation potential, as measured by γ9δ2TCR-mediated functional avidity which may not be correlated to the intrinsic ability of the parental γδT cell clone.

In an aspect, an affinity of a γ9δ2 TCR can be in a range even lower than that of αβTCRs. For instance, by achieving detectable TCR binding only with increasing valency of γ9δ2TCR multimers to a size of a YG-bead with more than 104 γ9δ2TCRs at a bead surface. In an aspect, once having achieved sufficient interaction avidity, the difference in binding affinity between individual γ9δ2TCRs can be significant. In an aspect, a direct interaction between extracellular CD277 domains and γ9δ2TCR can occur.

In an aspect, CD277 may undergo spatial and conformational changes. In an aspect, a γ9δ2TCR may be involved in fluid cell membrane interactions with CD277 that may create higher local densities and stabilize the cell-cell interaction. In an aspect, a pamidronate stimulation of a cancer cell can lead to an upregulation of an adhesion molecule on the cancer cell increasing cell-cell contact as well as stabilizing the synapse and consequently avidity. In an aspect a CDR3 region of a γ9δ2TCR may be involved in recruitment to the synapse of a CD277 expressing cancer cell. In an aspect, an agent provide herein can induce special and conformational changes in CD277 directly or indirectly.

In an aspect, there can be an increase in cluster size of BTN3A1 as well as a reduction in cluster density. In an aspect, a change in cluster density creates most space for additional proteins within BTN3A clusters. In an aspect, about 10%, 20%, 30%, 40%, 50%, 60%, or more of a cluster surface can be occupied by BTN3A dimers. In an aspect, there can be involvement of an additional factor that moves into the CD277 synapse as well as conformational changes in CD277 orchestrated through RhoB.

In an aspect, there can be functional diversity and "repertoire focusing" of γ9δ2 T cells. Vector Polynucleotides encoding a polypeptide construct that selectively binds J-configuration of CD277 directly, or indirectly thru one or more additional biological agents can be incorporated in a vector described herein. An "expression vector" or "vector" is any genetic element, e.g., a plasmid, chromosome, virus, transposon, behaving either as an autonomous unit of polynucleotide replication within a cell. (i.e. capable of replication under its own control) or being rendered capable of replication by insertion into a cell chromosome, having attached to it another polynucleotide segment, so as to bring about the replication and/or expression of the attached segment. Suitable vectors include, but are not limited to, plasmids, transposons, bacteriophages and cosmids. Vectors can contain polynucleotide sequences which are necessary to effect ligation or insertion of the vector into a desired host cell and to effect the expression of the attached segment. Such sequences differ depending on the host organism; they include promoter sequences to effect transcription, enhancer sequences to increase transcription, ribosomal binding site sequences and transcription and translation termination sequences. Alternatively, expression vectors can be capable of directly expressing nucleic acid sequence products encoded therein without ligation or integration of the vector into host cell DNA sequences.

Vector also can comprise a "selectable marker gene." The term "selectable marker gene," as used herein, refers to a nucleic acid sequence that allows cells expressing the nucleic acid sequence to be specifically selected for or against, in the presence of a corresponding selective agent. Suitable selectable marker genes are known in the art and described in, e.g., International Patent Application Publications WO 1992/08796 and WO 1994/28143; Wigler et al., Proc. Natl. Acad. Sci. USA, 77: 3567 (1980); O'Hare et al., Proc. Natl. Acad. Sci. USA, 78: 1527 (1981); Mulligan & Berg, Proc. Natl. Acad. Sci. USA, 78: 2072 (1981); Colberre-Garapin et al., J. Mol. Biol., 150:1 (1981); Santerre et al., Gene, 30: 147 (1984); Kent et al., Science, 237: 901-903 (1987); Wigler et al., Cell, 11: 223 (1977); Szybalska & Szybalski, Proc. Natl. Acad. Sci. USA, 48: 2026 (1962); Lowy et al., Cell, 22: 817 (1980); and U.S. Pat. Nos. 5,122,464 and 5,770,359.

In some embodiments, the vector is an "episomal expression vector" or "episome," which is able to replicate in a host cell, and persists as an extrachromosomal segment of DNA within the host cell in the presence of appropriate selective pressure (see, e.g., Conese et al., Gene Therapy, 11:1735-1742 (2004)). Representative commercially available episomal expression vectors include, but are not limited to, episomal plasmids that utilize Epstein Barr Nuclear Antigen 1 (EBNA1) and the Epstein Barr Virus (EBV) origin of replication (oriP). The vectors pREP4, pCEP4, pREP7, and pcDNA3.1 from Invitrogen (Carlsbad, Calif.) and pBK-CMV from Stratagene (La Jolla, Calif.) represent non-limiting examples of an episomal vector that uses T-antigen and the SV40 origin of replication in lieu of EBNA1 and oriP.

Vector Modifications

A polynucleotide vector useful for the methods and compositions described herein can be a good manufacturing practices (GMP) compatible vector. For example, a GMP vector can be purer than a non-GMP vector. In some cases, purity can be measured by bioburden. For example, bioburden can be the presence or absence of aerobes, anaerobes, sporeformers, fungi, or combinations thereof in a vector composition. In some cases, a pure vector can be endotoxin low or endotoxin free. Purity can also be measured by double-stranded primer-walking sequencing. Plasmid identity can be a source of determining purity of a vector. A GMP vector of the invention can be from 10% to 99% more pure than a non-GMP vector. A GMP vector can be from 10%, 15%, 20%, 25%, 30%, 35%, 40%, 45%, 50%, 55%, 60%, 65%, 70%, 75%, 80%, 85%, 90%, 95%, 96%, 97%, 98%, or 99% more pure than a non-GMP vector as measured by the presence of bioburden, endotoxin, sequencing, or combinations thereof.

In some cases, a terminator sequence at the end of the first gene program is used. A terminator sequence can ensure that a transcript is terminating prior to initiating a second gene program. For example, an expression vectors can contain sequences necessary for the termination of transcription and for stabilizing an mRNA. Such sequences are commonly available from the 5' and, occasionally 3', untranslated regions of eukaryotic or viral DNAs or cDNAs. These regions can contain nucleotide segments transcribed as polyadenylated fragments in the untranslated portion of the mRNA. Cells comprising the expression vector are grown under conditions that provide for expression of the desired polypeptide, either in vivo or in vitro.

In some cases, a spacer sequence can be used at the end of a first polypeptide encoded by a polynucleotide in a vector. In other cases, a spacer sequence can be used at the end of a second gene in a vector. A spacer sequence can also be used following a first gene and a second gene in a vector.

These vectors can be used to express a polypeptide encoded by a gene, or portion of a gene of interest. A gene of portion or a gene can be inserted by using any method, viral or non-viral. For example; a method can be a non-viral based technique.

Linkers

In some embodiments, a polynucleotide linker can be utilized in a polynucleotide encoding a polypeptide construct described herein. A polynucleotide linker can be a double-stranded segment of DNA containing desired restriction sites that can be added to create end structures that are compatible with a vector comprising a polynucleotide described herein. In some cases, a polynucleotide linker can be useful for modifying vectors comprising polynucleotides described herein. For example, a vector modification comprising a polynucleotide linker can be a change in a multiple cloning site, or the addition of a poly-histidine tail. Polynucleotide linkers can also be used to adapt the ends of blunt insert DNA for cloning into a vector cleaved with a restriction enzyme with cohesive end termini. The use of polynucleotide linkers can be more efficient than a blunt ligation into a vector and can provide a method of releasing an insert from a vector in downstream applications. In some cases an insert can be a polynucleotide sequence encoding polypeptides useful for therapeutic applications.

A polynucleotide linker can be an oligomer. A polynucleotide linker can be a DNA double strand, single strand, or a combination thereof. In some cases, a linker can be RNA. A polynucleotide linker can be ligated into a vector comprising a polynucleotide described herein by a T4 ligase in some cases. To facilitate a ligation an excess of polynucleotide linkers can be added to a composition comprising an insert and a vector. In some cases, an insert and vector are pre-treated before a linker is introduced. For example, pre-treatment with a methylase can prevent unwanted cleavage of insert DNA.

In some embodiments, a linker can be utilized in a polynucleotide described herein. A linker can be a flexible linker, a rigid linker, an in vivo cleavable linker, or any combination thereof. In some cases, a linker can link functional domains together (as in flexible and rigid linkers) or releasing free functional domain in vivo as in in vivo cleavable linkers.

Linkers can improve biological activity, increase expression yield, and achieving desirable pharmacokinetic profiles. A linker can also comprise hydrazone, peptide, disulfide, or thioester.

In some cases, a linker sequence described herein can include a flexible linker. Flexible linkers can be applied when a joined domain requires a certain degree of movement or interaction. Flexible linkers can be composed of small, non-polar (e.g., Gly) or polar (e.g., Ser or Thr) amino acids. A flexible linker can have sequences consisting primarily of stretches of Gly and Ser residues ("GS" linker). An example of a flexible linker can have the sequence of (Gly-Gly-Gly-Gly-Ser)n. By adjusting the copy number "n", the length of this exemplary GS linker can be optimized to achieve appropriate separation of functional domains, or to maintain necessary inter-domain interactions. Besides GS linkers, other flexible linkers can be utilized for recombinant fusion proteins. In some cases, flexible linkers can also be rich in small or polar amino acids such as Gly and Ser, but can contain additional amino acids such as Thr and Ala to maintain flexibility. In other cases, polar amino acids such as Lys and Glu can be used to improve solubility.

J-Configuration of CD277

Herein "CD277" refers to the membrane-expressed protein butyrophilin BTN3A1, a key molecule in phosphoantigen-induced activation of engineered cells described herein. The CD277 protein is a cell-surface protein that can assume multiple configurations, as shown for example in FIG. 11 herein. The J-configuration or J-confirmation of CD277 is facilitated when GTP-bound RhoB facilitates spatial redistribution of CD277 by promoting cytoskeletal trapping in the plasma membrane binding to the B30.2 domain proximal connector region of CD277. Dissociation of GTP-bound RhoB and corresponding binding of intracellular phosphoantigen (pAG) to the B30.2 domain of CD277 triggers a conformational change of the extracellular region of CD277, referred to herein as the J-configuration of CD277. The J-configuration is characteristically observed in tumor cells and other distressed cells, wherein metabolic changes can cause expression of certain stress molecules and resulting in the transmigration of RhoB within the tumor cell or distressed cell in a manner that eventually results in the formation of the J-configuration of CD277. Herein, as well as in any related patents and/or patent applications, the terms "J-configuration", "J-conformation", and "J-confirmation" are used interchangeably.

Provided herein in certain embodiments, are methods and compositions that comprise polypeptide constructs that specifically bind the J-configuration of CD277 on the surface of such tumor cells and distressed cells. In certain embodiments, the polypeptide constructs described herein comprise gamma delta TCRs or fragments thereof. In certain embodiments are polynucleotides encoding polypeptide constructs described herein, and vectors encoding said polynucleotides. In some cases are provided engineered cells encoding polypeptide constructs described herein.

Polypeptide Constructs

Provided herein, in some aspects, are pharmaceutical compositions that comprise a polypeptide construct, wherein the polypeptide construct specifically interacts with the J-configuration of CD277 on a target cell. In certain embodiments, the polypeptide construct is expressed on an engineered cell. In some embodiments, the CD277 is a human CD277. In some cases the polypeptide construct binds said J-configuration of CD277 with at least 20%, 25%, 30%, 35%, 40%, 45%, 50%, 55%, 60%, 65%, 70%, 75%, 80%, 85%, 90%, 95%, or 99% more selectivity than other configurations of CD277. In some cases, the polypeptide construct binds J-configuration of CD277 with at least two fold, three fold, four fold, five fold, six fold, seven fold or eight fold affinity as compared to other configurations of CD277. In some embodiments, the polypeptide construct binds to CD277 upon a conformational change of CD277 to the J-configuration of CD277, which conformational change is induced by interaction of CD277 with a RhoB GTPase upon transmigration of RhoB-GTPase to the cell membrane. In some embodiments, the polypeptide construct binds to CD277 after CD277 interacts with a RhoB GTPase. In some embodiments, the polypeptide construct binds to CD277 when CD277 is interacting with a phosphoantigen. In some embodiments, the polypeptide construct binds to CD277 when CD277 is interacting with a phosphoantigen, and after CD277 interacts with a RhoB GTPase. In some embodiments, the polypeptide construct binds to CD277 when RhoB GTPase localizes to the cell membrane of the target cell. In some embodiments, the polypeptide construct binds to CD277 when RhoB GTPase localizes away from the nucleus of the target cell.

The selectivity or affinity of a polypeptide construct described herein for the J-configuration of CD277 can be determined by any method known to the person skilled in the art. For example, a ligand binding assay can be used to detect the presence of CD277-polypeptide construct complex formation, as well as the extent or strength of binding of the polypeptide construct to the J-configuration of CD277. In some embodiments, Fluorescence Resonance Energy Transfer (FRET) is employed to determine the affinity of binding between the polypeptide construct and the J-configuration of CD277. FRET is capable of detecting and measuring energy transfer between a pair of light sensitive molecules (e.g., fluorophore) typically placed in close proximity. One of the light sensitive molecules, the donor molecule (e.g., donor fluorophore), is initially present in an electron excited state and is capable of transferring energy to the other light sensitive molecule, the acceptor molecule (e.g., acceptor fluorophore). Energy transfer from the donor to the acceptor can be for example by dipole-dipole coupling. Measurement of the energy transferred from the acceptor molecule to the donor molecule can be used to estimate the distance between the acceptor and donor on the basis that the efficiency of energy transfer (i.e. FRET efficiency) is inversely proportional to the sixth power of the distance between donor and acceptor. Measurement of FRET can be for example by a fluorescence-detecting microscope (e.g., confocal microscope) or by fluorescent-sensitive cell sorting (e.g., flow cytometry, fluorescent-activated cell sorting). Quantification of fluorescence using FRET can be by any one or more of a number of techniques, including sensitized emission, acceptor photobleaching, fluorescence-lifetime imaging microscopy (FLIM) FRET, spectral imaging, and/or Homo-FRET and polarization anisotropy imaging. In some embodiments, FRET is employed using a donor and acceptor fluorophore. In some embodiments, FRET is employed using one or more fluorescently labeled antibodies specific for an antigen on the cell surface. In some embodiments, FRET is employed using one or more fluorescently labeled dyes which are hydrophobic and are capable of binding to hydrophobic cellular components such as the plasma membrane. In some embodiments, a combination of one or more fluorescently labeled antibodies and one or more hydrophobic fluorescent dyes are used to carry out FRET. In some embodiments, the fluorescent lipid conjugate BODIPY FL is used in combination with a fluorescently labeled antibody specific for an epitope on the CD277 protein. In some embodiments, other ligand-binding assays are used either alone or in combination with FRET to detect the selectivity of a polypeptide construct described herein for CD277. Non-limiting examples of ligand-binding assays contemplated herein include other fluorescence-based methods such as fluorescence polarization, detection of changes in the angle of light reflection from cell surface components using surface plasmon resonance, radioactive-based ligand assays, and immunoprecipitation of antibody-labeled cell surface components followed by structure analysis.

In some embodiments, polypeptide constructs disclosed herein are expressed in a cell. In some embodiments, said polypeptide construct is expressed on the cell membrane of the cell. In some embodiments, the polypeptide construct can interact with a cell. In some embodiments, the polypeptide construct is capable of being bound by a cell surface protein of the cell. In some embodiments, the cell is a cytotoxic cell. Non-limiting examples of cytotoxic cells include T cells, cell expressing at least a functional portion (e.g., conveys immune activity) of a T cell receptor, and natural killer cells. In some embodiments, the cell expresses a T cell receptor. In some embodiments, the cell expresses at least a portion of a T cell receptor, wherein the portion has a T cell function (e.g., immune regulation). In some embodiments, the cell is engineered or genetically modified to express at least one chain of a T cell receptor. The at least one chain can be a γ-T-cell receptor chain. The at least one chain can be a δ-T-cell receptor chain or fragment thereof. The at least one chain can be a γ9-T-cell receptor chain or fragment thereof. The at least one chain can be a δ2-T-cell receptor chain or fragment thereof. In some embodiments, the polypeptide construct is thus a TCR having at least one chain or fragment thereof (e.g. a γ-T-cell receptor chain or fragment thereof; δ-T-cell receptor chain or fragment thereof; γ9-T-cell receptor chain or fragment thereof; or δ2-T-cell receptor chain or fragment thereof). In some embodiments, the polypeptide construct can be a TCR having more than one chain (e.g. a homodimer or heterodimer).

In some embodiments, polypeptide constructs disclosed herein are not expressed by a cell. In some embodiments, the polypeptide construct is synthetic (e.g., not produced by a cell). In some embodiments, the polypeptide construct is produced in vitro. In some embodiments, the polypeptide construct is capable of binding a target cell and a cytotoxic cell disclosed herein. In some embodiments, the polypeptide construct is capable of binding a target cell and a cytotoxic cell disclosed herein, thereby bringing the target cell into a proximity of the cytotoxic cell sufficient for the cytotoxic cell to be cytotoxic to the target cell.

Polypeptides and proteins disclosed herein (including functional portions and functional variants thereof) can comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenyl alanine, phenylglycine, α-naphthyl alanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, and α-tert-butylglycine.

"Antibody" as used herein refers to monoclonal or polyclonal antibodies. A whole antibody typically consists of four polypeptides: two identical copies of a heavy (H) chain polypeptide and two identical copies of a light (L) chain polypeptide. Each of the heavy chains contains one N-terminal variable (VH) region and three C-terminal constant (CH1, CH2 and CH3) regions, and each light chain contains one N-terminal variable (VL) region and one C-terminal constant (CL) region. The variable regions of each pair of light and heavy chains form the antigen binding site of an antibody. The VH and VL regions have a similar general structure, with each region comprising four framework regions, whose sequences are relatively conserved. The framework regions are connected by three complementarity determining regions (CDRs). The three CDRs, known as CDR1, CDR2, and CDR3, form the "hypervariable region" of an antibody, which is responsible for antigen binding.

"Antigen recognition moiety or domain" refers to a molecule or portion of a molecule that specifically binds to an antigen. In one embodiment, the antigen recognition moiety is an antibody, antibody like molecule or fragment thereof and the antigen is a tumor antigen.

"Antibody like molecules" can be for example proteins that are members of the Ig-superfamily which are able to selectively bind a partner. MHC molecules and T cell receptors are such molecules. In one embodiment the antibody-like molecule is a TCR.

The terms "fragment of an antibody," "antibody fragment," "functional fragment of an antibody," and "antigen-binding portion" are used interchangeably herein to mean one or more fragments or portions of an antibody that retain the ability to specifically bind to an antigen (see, generally, Holliger et al., Nat. Biotech., 23(9):1126-1129 (2005)). The antibody fragment desirably comprises, for example, one or more CDRs, the variable region (or portions thereof), the constant region (or portions thereof), or combinations thereof. Examples of antibody fragments include, but are not limited to, (i) a Fab fragment, which is a monovalent fragment consisting of the VL, VH, CL, and CH1 domains; (ii) a F(ab')2 fragment, which is a bivalent fragment comprising two Fab fragments linked by a disulfide bridge at the stalk region; (iii) a Fv fragment consisting of the VL and VH domains of a single arm of an antibody; (iv) a single chain Fv (scFv), which is a monovalent molecule consisting of the two domains of the Fv fragment (i.e., VL and VH) joined by a synthetic linker which enables the two domains to be synthesized as a single polypeptide chain (see, e.g., Bird et al., Science, 242: 423-426 (1988); Huston et al., Proc. Natl. Acad. Sci. USA, 85: 5879-5883 (1988); and Osbourn et al., Nat. Biotechnol., 16: 778 (1998)) and (v) a diabody, which is a dimer of polypeptide chains, wherein each polypeptide chain comprises a VH connected to a VL by a peptide linker that is too short to allow pairing between the VH and VL on the same polypeptide chain, thereby driving the pairing between the complementary domains on different VH-VL polypeptide chains to generate a dimeric molecule having two functional antigen binding sites. Antibody fragments are known in the art and are described in more detail in, e.g., U.S. Pat. No. 8,603,950.

Engineered T-Cell Receptor (TCR)

In some embodiments, a polypeptide construct that selectively binds the J-configuration of CD277, comprises a T-cell receptor (TCR), an engineered TCR, or fragment thereof. In some embodiments, the T cell receptor (TCR) is composed of two chains (αβ or γδ) that pair on the surface of the T cell to form a heterodimeric receptor. The αβ TCR is expressed on most T cells in the body and is known to be involved in the recognition of specific MHC-restricted antigens. Each α and β chain are composed of two domains: a constant domain (C) which anchors the protein to the cell membrane and is associated with invariant subunits of the CD3 signaling apparatus; and a variable domain (V) that confers antigen recognition through six loops, referred to as complementarity determining regions (CDRs). Each of the V domains comprises three CDRs; e.g., CDR1, CDR2 and CDR3 with CDR3 as the hypervariable region. These CDRs interact with a complex formed between an antigenic peptide bound to a protein encoded by the major histocompatibility complex (pepMHC) (e.g., HLA-A, HLA-B, HLA-C, HLA-DPA1, HLA-DPB1, HLA-DQA1, HLA-DQB1, HLA-DRA, or HLA-DRB1 complex). In some instances, the constant domain further comprises a joining region that connects the constant domain to the variable domain. In some cases, the beta chain further comprises a short diversity region which makes up part of the joining region.

In some cases, such TCR are reactive to specific tumor antigen, e.g. NY-ESO, Mage A3, Titin. In other cases, such TCR are reactive to specific neoantigens expressed within a patient's tumor (i.e. patient-specific, somatic, non-synonymous mutations expressed by tumors). In some cases, engineered TCRs can be affinity-enhanced.

In some embodiments, a TCR is described using the International Immunogenetics (IMGT) TCR nomenclature, and links to the IMGT public database of TCR sequences. For example, there can be several types of alpha chain variable (Vα) regions and several types of beta chain variable (Vβ) regions distinguished by their framework, CDR1, CDR2, and CDR3 sequences. As such, a Vα type can be referred to in IMGT nomenclature by a unique TRAV number. For example, "TRAV21" defines a TCR Vα region having unique framework and CDR1 and CDR2 sequences, and a CDR3 sequence which is partly defined by an amino acid sequence which is preserved from TCR to TCR but which also includes an amino acid sequence which varies from TCR to TCR. Similarly, "TRBV5-1" defines a TCR Vβ region having unique framework and CDR1 and CDR2 sequences, but with only a partly defined CDR3 sequence.

In some cases, the beta chain diversity region is referred to in IMGT nomenclature by the abbreviation TRBD.

In some instances, the unique sequences defined by the IMGT nomenclature are widely known and accessible to those working in the TCR field. For example, they can be found in the IMGT public database and in "T cell Receptor Factsbook", (2001) LeFranc and LeFranc, Academic Press, ISBN 0-12-441352-8.

In some embodiments, an αβ heterodimeric TCR is, for example, transfected as full length chains having both cytoplasmic and transmembrane domains. In some cases, the TCRs contain an introduced disulfide bond between residues of the respective constant domains, as described, for example, in WO 2006/000830.

In some instances, TCRs described herein are in single chain format, for example see WO 2004/033685. Single chain formats include αβ TCR polypeptides of the Vα-L-Vβ, Vβ-L-Vα, Vα-Cα-L-Vβ, Vα-L-Vβ-Cβ, Vα-Cα-L-Vβ-Cβ types, wherein Vα and Vβ are TCR α and β variable regions respectively, Cα and Cβ are TCR α and β constant regions respectively, and L is a linker sequence. In certain embodiments single chain TCRs of the present disclosure can have an introduced disulfide bond between residues of the respective constant domains, as described in WO 2004/033685.

In contrast to an αβ TCR, the γδ TCR is composed of one γ chain and one δ chain. Although much less abundant in the body than αβ Tcells, γδ T cells combine potent anti-tumor effector functions with the recognition of broadly expressed tumor-associated molecules, and therefore are strong candidates for clinical application in cancer immunotherapy. The majority of γδ T cells are activated in an MHC-independent manner and do not require antigen processing, which is in contrast to MHC-restricted αβ T cells. Instead, γδ T cells rely on cell-cell contact with antigen-presenting cells and directly recognize antigens in the form of intact proteins or non-peptidic compounds. For this interaction, the CDR3 domains of the variable region is of particular importance. For this interaction, the CDR3 domains of the variable region is of particular importance. The orientation of the variable (V) and constant (C) regions of the γδ TCR is unique in comparison to αβ TCRs or antibodies, and results from a small angle between the Vγ and Cγ domains. Although the γδ TCR V domains are similar in structure to those of αβ TCRs, γδ TCR C domains are markedly different. Structural differences in Cγ and Cδ, including the location of the disulphide bond between them, may enable γδ TCRs to form different recognition/signalling complexes than αβ TCRs (Allison et al., "Structure of a human γδ T-cell antigen receptor," *Nature*, 411: 820-824). Activation of γδ T cells by TCR-mediated antigen recognition on a target cell can lead to production of cytokines and chemokines as well as cytoloysis of the target cell (e.g., tumor cell).

Vγ9Vδ2 T cells, the major γδ T cell subset in human peripheral blood, express γδ TCRs composed of Vγ9 and Vδ2 chains, and are specifically activated by intermediates of the mammalian mevalonate pathway such as isopentenyl pyrophosphate (IPP) or the microbial 2-C-methyl-D-erythritol 4-phosphate (MEP) pathway. Intracellular phosphoantigen (pAg) levels accumulate in tumor cells due to dysregulation of the mevalonate pathway or upon microbial infection, allowing the targeting of transformed or infected cells by Vγ9Vδ2 cells. Similarly, intracellular pAg levels can be pharmaceutically increased by treating cells with mevalonate pathway inhibitors such as aminobisphosphonates (ABPs), thereby sensitizing cells toward recognition by Vγ9Vδ2 T cells.

In some embodiments, a TCR endogenously expressed by Vγ9Vδ2 T cells can be expressed in αβ T cells engineered to express one or more Vγ9Vδ2 TCRs, thereby reprogramming the αβ T cells. For example, CD4⁺αβ T cells engineered to express one defined Vγ9Vδ2 TCR can be used to functionally screen tumor cells for proteins important for T cell recognition, in order to eliminate fluctuations in recognition by a diverse γδ TCR repertoire.

In some embodiments, a Vγ9Vδ2 TCR described herein recognizes a CD277 (BTN3A1) protein expressed by a target cell (e.g., tumor cell). In some embodiments, a Vγ9Vδ2 TCR described herein recognizes an epitope that includes the J configuration of the CD277 protein expressed on the surface of a target cell. In some embodiments, a Vγ9Vδ2 TCR described herein recognizes an epitope that is limited to the J configuration of the CD277 protein expressed on the surface of a target cell.

In some embodiments, a pharmaceutical composition described herein comprises a polypeptide construct which includes a Vγ9Vδ2 TCR comprising at least one of a γ-TCR amino acid sequence or a δ-TCR amino acid sequence capable of recognizing a CD277 protein on a cell surface of a target cell (e.g. tumor cell). In some embodiments, the polypeptide construct comprises a variant or a fragment of at least one of a γ-TCR amino acid sequence or a δ-TCR amino acid sequence capable of recognizing a CD277 protein on a cell surface of a target cell. The present disclosure contemplates polypeptide constructs comprising any portion or fragment or variation of a γδTCR capable of recognizing a target cell (e.g. tumor cell) via a CD277 cell surface molecule. In some embodiments, the polypeptide construct comprises at least a portion of a Cγ or C6 region and at least a portion of a Vγ or a Vδ region of a γδTCR. In some embodiments, the polypeptide construct comprises at least a portion of a Cγ or C6 region and at least a CDR3 domain of either a Vγ or a Vδ domain of a γδTCR. In some embodiments, the polypeptide construct comprises all CDR regions of the Vγ9Vδ2 TCR, and all of the CDR regions can be involved in binding to a cell surface molecule (e.g. CD277 molecule) on the surface of a target cell (e.g., see Wang et al., "V{gamma}2V{delta}2 T cell receptor recognition of prenyl pyrophosphates is dependent on all CDRs," *J Immunol*, 184, 6209-6222 (2010)).

A TCR described herein can be associated with a detectable label, a therapeutic agent or a PK modifying moiety.

Exemplary detectable labels for diagnostic purposes include, but are not limited to, fluorescent labels, radiolabels, enzymes, nucleic acid probes and contrast reagents.

Effector Cells

Provided are effector cells modified to express one or more heterologous genes or genes encoding polypeptide constructs disclosed herein, wherein said polypeptide constructs selectively bind the J-configuration of CD277.

"αβT cells" or "alpha beta. T cells" may be defined with respect to the function of T lymphocytes that express an αβTcR, which recognises peptides bound to WIC molecules (major histocompatibility complex), which are expressed on the surface of various cells. MHCs present peptides derived from the proteins of a cell. When for example a cell is infected with a virus, the MHC will present viral peptides, and the interaction between the αβTCR and the MHC-complex activates specific types of T-cells which initiate and immune responses to eliminate the infected cell. Hence, αβT cells may be functionally defined as being cells capable of recognizing peptides bound to MHC molecules. αβT-cells can be identified using an antibody specific for the αβ T-cell receptor such as described below (e.g. the BW242 antibody that is specific for a human αβ TCR). αβT cells can be selected from peripheral blood for example via the CD3 antigen, as the large majority of T cells have the αβTCR. Such a selection will also include γδT-cells. From such selected cells, the nucleic acid (or amino acid) sequence corresponding to the αT-cell receptor chain and the βT-cell receptor chain can be determined. Hence, αβT-cells can also be defined as being cells comprising a nucleic acid (or amino acid) sequence corresponding to the αT-cell receptor chain and/or the βT-cell receptor chain.

"γδT cells" or "gamma delta T cells" represent a small subset of T cells for which the antigenic molecules that trigger their activation is largely unknown. Gamma delta T cells can be considered a component of adaptive immunity in that they rearrange TCR genes to produce junctional diversity and will develop a memory phenotype. However, various subsets can also be considered part of the innate immunity where a restricted TCR is used as a pattern recognition receptor. γδT-cells can be identified using an antibody specific for the γδ T-cell receptor. Antibodies suitable for FACS are widely available. Conditions are selected, such as provided by the antibody manufacturer that allows the selection of negative and/or positive cells. Examples of antibodies that can be suitable are available from BD Pharmingen (BD, 1 Becton Drive, Franklin Lakes, NJ USA), TCR-APC (clone B1, #555718) or as available from Beckman Coulter, pan-TCR-PE (clone MMU510, #I M1418U). Also, from such selected cells, the nucleic acid (or amino acid sequence) sequence corresponding to the γT cell receptor chain and/or the δT cell receptor chain can be determined. Hence, γδT cells can also be defined as being cells comprising a nucleic acid (or amino acid) sequence corresponding to a γT-cell receptor chain.

In an aspect, compositions disclosed herein can utilize cells. Cells can be primary cells. Cells can be recombinant cells. Cells can be obtained from a number of non-limiting sources, including peripheral blood mononuclear cells, bone marrow, lymph node tissue, cord blood, thymus tissue, tissue from a site of infection, ascites, pleural effusion, spleen tissue, and tumors. For example, any T cell lines can be used. Alternatively, the cell can be derived from a healthy donor, from a patient diagnosed with cancer, or from a patient diagnosed with an infection. In another embodiment, the cell can be part of a mixed population of cells which present different phenotypic characteristics. A cell can also be obtained from a cell therapy bank. Disrupted cells resistant to an immunosuppressive treatment can be obtained. A desirable cell population can also be selected prior to modification. A selection can include at least one of: magnetic separation, flow cytometric selection, antibiotic selection. The one or more cells can be any blood cells, such as peripheral blood mononuclear cell (PBMC), lymphocytes, monocytes or macrophages. The one or more cells can be any immune cells such as lymphocytes, B cells, or T cells. Cells can also be obtained from whole food, apheresis, or a tumor sample of a subject. A cell can be a tumor infiltrating lymphocytes (TIL). In some cases an apheresis can be a leukapheresis. Leukapheresis can be a procedure in which blood cells are isolated from blood. During a leukapheresis, blood can be removed from a needle in an arm of a subject, circulated through a machine that divides whole blood into red cells, plasma and lymphocytes, and then the plasma and red cells are returned to the subject through a needle in the other arm. In some cases, cells are isolated after an administration of a treatment regime and cellular therapy. For example, an apheresis can be performed in sequence or concurrent with a cellular administration. In some cases, an apheresis is performed prior to and up to about 6 weeks following administration of a cellular product. In some cases, an apheresis is performed −3 weeks, −2 weeks, −1 week, 0, 1 week, 2 weeks, 3 weeks, 4 weeks, 1 month, 2 months, 3 months, 4 months, 5 months, 6 months, 7 months, 8 months, 9 months, 10 months, 11 months, 1 year, 2 years, 3 years, 4 years, 5 years, 6 years, 7 years, 8 years, 9 years, or up to about 10 years after an administration of a cellular product. In some cases, cells acquired by an apheresis can undergo testing for specific lysis, cytokine release, metabolomics studies, bioenergetics studies, intracellular FACs of cytokine production, ELISA-spot assays, and lymphocyte subset analysis. In some cases, samples of cellular products or apheresis products can be cryopreserved for retrospective analysis of infused cell phenotype and function.

In an aspect, a composition provided herein can comprise a TIL. A TIL can be isolated from an organ afflicted with a cancer. One or more cells can be isolated from an organ with a cancer that can be a brain, heart, lungs, eye, stomach, pancreas, kidneys, liver, intestines, uterus, bladder, skin, hair, nails, ears, glands, nose, mouth, lips, spleen, gums, teeth, tongue, salivary glands, tonsils, pharynx, esophagus, large intestine, small intestine, rectum, anus, thyroid gland, thymus gland, bones, cartilage, tendons, ligaments, suprarenal capsule, skeletal muscles, smooth muscles, blood vessels, blood, spinal cord, trachea, ureters, urethra, hypothalamus, pituitary, pylorus, adrenal glands, ovaries, oviducts, uterus, vagina, mammary glands, testes, seminal vesicles, penis, lymph, lymph nodes or lymph vessels. One or more TILs can be from a brain, heart, liver, skin, intestine, lung, kidney, eye, small bowel, or pancreas. TILs can be from a pancreas, kidney, eye, liver, small bowel, lung, or heart. TILs can be from a pancreas. The one or more cells can be pancreatic islet cells, for example, pancreatic β cells. In some cases, a TIL can be from a gastrointestinal cancer. A TIL culture can be prepared a number of ways. For example, a tumor can be trimmed from non-cancerous tissue or necrotic areas. A tumor can then be fragmented to about 2-3 mm in length. In some cases, a tumor can be fragmented from about 0.5 mm to about 5 mm in size, from about 1 mm to about 2 mm, from about 2 mm to about 3 mm, from about 3 mm to about 4 mm, or from about 4 mm to about 5 mm. Tumor fragments can then be cultured in vitro utilizing media and a cellular stimulating agent such as a cytokine. In some cases, IL-2 can be utilized to expand TILs from a tumor fragment.

In some embodiments, modified effector cells are modified immune cells that comprise T cells and/or natural killer cells which are modified to encode specific nucleic acid sequence(s) for expressing a polypeptide construct described herein.

Engineered T cells with exogenous immune receptors described herein are T cells that have been engineered such that they express an exogenous receptor, for instance a polypeptide construct that specifically binds to J-configuration of CD277. The exogenous receptor can be expressed from a transgene construct and not from endogenous loci. An exogenous receptor can be of a different origin, Le, from another species, as compared to the origin of the T cells that were engineered to provide for the engineered T cells with exogenous receptors. An exogenous receptor can be of the same origin, i.e. from the same species, as compared to the origin of the T cells that were engineered to provide for the engineered T cells with exogenous receptors. An exogenous receptor can also be an engineered γδ T cell receptor or an engineered αβ T cell receptor, which are engineered to selectively bind to J-configuration of CD277.

In some cases, an engineered T cell receptor is a T cell receptor of which the amino acid sequence has been modified such that it has a different amino acid sequence as compared to the corresponding amino acid sequence of an endogenous T cell receptor.

T helper cells (TH cells) assist other white blood cells in immunologic processes, including maturation of B cells into plasma cells and memory B cells, and activation of cytotoxic T cells and macrophages. In some instances, TH cells are known as CD4+ T cells due to expression of the CD4 glycoprotein on the cell surfaces. Helper T cells become activated when they are presented with peptide antigens by MHC class II molecules, which are expressed on the surface of antigen-presenting cells (APCs). Once activated, they divide rapidly and secrete small proteins called cytokines that regulate or assist in the active immune response. These cells can differentiate into one of several subtypes, including TH1, TH2, TH3, TH17, Th9, or TFH, which secrete different cytokines to facilitate different types of immune responses. Signaling from the APC directs T cells into particular subtypes.

Cytotoxic T cells (TC cells or CTLs) destroy virus-infected cells and tumor cells, and are also implicated in transplant rejection. These cells are also known as CD8+ T cells since they express the CD8 glycoprotein on their surfaces. These cells recognize their targets by binding to antigen associated with WIC class I molecules, which are present on the surface of all nucleated cells. Through IL-10, adenosine, and other molecules secreted by regulatory T cells, the CD8+ cells can be inactivated to an anergic state, which prevents autoimmune diseases.

Memory T cells are a subset of antigen-specific T cells that persist long-term after an infection has resolved. They quickly expand to large numbers of effector T cells upon re-exposure to their cognate antigen, thus providing the immune system with "memory" against past infections. Memory T cells comprise subtypes: stem memory T cells (TSCM), central memory T cells (TCM cells) and two types of effector memory T cells (TEM cells and TEMRA cells). Memory cells can be either CD4$^+$ or CD8$^+$. Memory T cells can express the cell surface proteins CD45RO, CD45RA and/or CCR7.

Regulatory T cells (Treg cells), formerly known as suppressor T cells, play a role in the maintenance of immunological tolerance. Their major role is to shut down T cell-mediated immunity toward the end of an immune reaction and to suppress autoreactive T cells that escaped the process of negative selection in the thymus.

Natural killer T cells (NKT cells) bridge the adaptive immune system with the innate immune system. Unlike conventional T cells that recognize peptide antigens presented by major histocompatibility complex (WIC) molecules, NKT cells recognize glycolipid antigen presented by a molecule called CD1d. Once activated, these cells can perform functions ascribed to both Th and Tc cells (i.e., cytokine production and release of cytolytic/cell killing molecules). They are also able to recognize and eliminate some tumor cells and cells infected with herpes viruses.

Natural killer (NK) cells are a type of cytotoxic lymphocyte of the innate immune system. In some instances, NK cells provide a first line defense against viral infections and/or tumor formation. NK cells can detect MHC presented on infected or cancerous cells, triggering cytokine release, and subsequently induce lysis and apoptosis. NK cells can further detect stressed cells in the absence of antibodies and/or MHC, thereby allowing a rapid immune response.

In some cases, a cell that can be utilized in a cellular therapy or a cell that can be used in a method provided herein can be positive or negative for a given factor. In some embodiments, a cell may be a CD3+ cell, CD3– cell, a CD5+ cell, CD5– cell, a CD7+ cell, CD7– cell, a CD14+ cell, CD14– cell, CD8+ cell, a CD8– cell, a CD103+ cell, CD103– cell, CD11b+ cell, CD11b– cell, a BDCA1+ cell, a BDCA1– cell, an L-selectin+ cell, an L-selectin– cell, a CD25+, a CD25– cell, a CD27+, a CD27– cell, a CD28+ cell, CD28– cell, a CD44+ cell, a CD44– cell, a CD56+ cell, a CD56– cell, a CD57+ cell, a CD57– cell, a CD62L+ cell, a CD62L– cell, a CD69+ cell, a CD69– cell, a CD45RO+ cell, a CD45RO– cell, a CD127+ cell, a CD127– cell, a CD132+ cell, a CD132– cell, an IL-7+ cell, an IL-7– cell, an IL-15+ cell, an IL-15– cell, a lectin-like receptor G1 positive cell, a lectin-like receptor G1 negative cell, or an differentiated or de-differentiated cell thereof. The examples of factors expressed by cells is not intended to be limiting, and a person having skill in the art will appreciate that a cell may be positive or negative for any factor known in the art. In some embodiments, a cell may be positive for two or more factors. For example, a cell may be CD4+ and CD8+. In some embodiments, a cell may be negative for two or more factors. For example, a cell may be CD25−, CD44−, and CD69−. In some embodiments, a cell may be positive for one or more factors, and negative for one or more factors. For example, a cell may be CD4+ and CD8−. The selected cells can then be infused into a subject. In some embodiments, the cells may be selected for having or not having one or more given factors (e.g., cells may be separated based on the presence or absence of one or more factors). In some embodiments, the selected cells can also be expanded in vitro. The selected cells can be expanded in vitro prior to infusion. It should be understood that cells used in any of the methods disclosed herein may be a mixture (e.g., two or more different cells) of any of the cells disclosed herein. For example, a method of the present disclosure may comprise cells, and the cells are a mixture of CD4+ cells and CD8+ cells. In another example, a method of the present disclosure may comprise cells, and the cells are a mixture of CD4+ cells and naïve cells. In some cases, a cell can be a stem memory $T_{SCM}$ cell comprised of CD45RO (−), CCR7(+), CD45RA (+), CD62L+(L-selectin), CD27+, CD28+ and IL-7Rα+, stem memory cells can also express CD95, IL-2Rβ, CXCR3, and LFA-1, and show numerous functional attributes distinctive of stem memory cells. Engineered cells can also be central memory $T_{CM}$ cells comprising L-selectin and CCR7, where the central memory cells can secrete, for example, IL-2, but not IFNγ or IL-4. Engineered cells can also be effector memory $T_{EM}$ cells comprising L-selectin or CCR7 and produce, for example, effector cytokines such as IFNγ and IL-4. In some cases a population of cells can be introduced to a subject. For example, a population of cells can be a combination of T cells and NK cells. In other cases, a population can be a combination of naïve cells and effector cells. A population of cells can be TILs.

In particular, T cell populations can be stimulated in vitro such as by contact with an anti-CD3 antibody or antigen-binding fragment thereof, or an anti-CD2 antibody immobilized on a surface, or by contact with a protein kinase C activator (e.g., bryostatin) sometimes in conjunction with a calcium ionophore. For co-stimulation of an accessory molecule on the surface of the T cells, a ligand that binds the accessory molecule can be used. For example, a population of T cells can be contacted with an anti-CD3 antibody and an anti-CD28 antibody, under conditions that can stimulate proliferation of the T cells. In some cases, 4-1BB can be used to stimulate cells. For example, cells can be stimulated with 4-1BB and IL-21 or another cytokine. To stimulate proliferation of either CD4 T cells or CD8 T cells, an anti-CD3 antibody and an anti-CD28 antibody can be used. For example, the agents providing a signal may be in solution or coupled to a surface. The ratio of particles to cells may depend on particle size relative to the target cell. In further embodiments, the cells, such as T cells, can be combined with agent-coated beads, where the beads and the cells can be subsequently separated, and optionally cultured. Each bead can be coated with either anti-CD3 antibody or an anti-CD28 antibody, or in some cases, a combination of the two. In an alternative embodiment, prior to culture, the agent-coated beads and cells are not separated but are cultured together. Cell surface proteins may be ligated by allowing paramagnetic beads to which anti-CD3 and anti-CD28 can be attached (3×28 beads) to contact the T cells. In some cases cells and beads (for example, DYNABEADS® M-450 CD3/CD28 T paramagnetic beads at a ratio of 1:1) are combined in a buffer, for example, phosphate buffered saline (PBS) (e.g., without divalent cations such as, calcium and magnesium). Any cell concentration may be used. The mixture may be cultured for or for about several hours (e.g., about 3 hours) to or to about 14 days or any hourly integer value in between. In another embodiment, the mixture may be cultured for or for about 21 days or for up to or for up to about 21 days. Conditions appropriate for T cell culture can include an appropriate media (e.g., Minimal Essential Media or RPMI Media 1640 or, X-vivo 5, (Lonza)) that may contain factors necessary for proliferation and viability, including serum (e.g., fetal bovine or human serum), interleukin-2 (IL-2), insulin, IFN-g, IL-4, IL-7, GM-CSF, IL-10, IL-21, IL-15, TGF beta, and TNF alpha or any other additives for the growth of cells. Other additives for the growth of cells include, but are not limited to, surfactant, plasmanate, and reducing agents such as N-acetyl-cysteine and 2-mercaptoethanol. Media can include RPMI 1640, A1 M-V, DMEM, MEM, α-MEM, F-12, X-Vivo 1, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. In some cases, an 865 mL bottle of RPMI may have 100 mL of human serum, 25 mL of Hepes 1M, 10 mL of Penicillin/streptomycin at 10,000 U/mL and 10,000 μg/mL, and 0.2 mL of gentamycin at 50 mg/mL. After addition of additives an RPMI media may be filtered using a 0.2 μm×1 L filter and stored at 4° C. In some embodiments, antibiotics, e.g., penicillin and streptomycin, are included only in experimental cultures but not in cultures of cells that are to be infused into a subject. In some cases, human serum can be thawed in a 37° C. water bath, and then heat inactivated (e.g., at 56° C. for 30 min for 100 mL bottle). The sera can be filtered through a 0.8 μm and 0.45 μm filter prior to addition of medium.

In an aspect, cells can be maintained under conditions necessary to support growth; for example, an appropriate temperature (e.g., 37° C.) and atmosphere (e.g., air plus 5% $CO_2$). In some instances, T cells that have been exposed to varied stimulation times may exhibit different characteristics. In some cases, a soluble monospecific tetrameric antibody against human CD3, CD28, CD2, or any combination thereof may be used.

Modified Effector Cell Doses

Provided herein are modified effector cells encoding a polypeptide construct that selectively binds the J-configuration of cell surface CD277. In some embodiments, an amount of modified effector cells is administered to a subject in need thereof and the amount is determined based on the efficacy and the potential of inducing a cytokine-associated toxicity. In some cases, an amount of modified effector cells comprises about $10^3$ to about $10^{10}$ modified effector cells/kg. In some cases, an amount of modified effector cells comprises about $10^4$ to about $10^8$ modified effector cells/kg. In some cases, an amount of modified effector cells comprises about $10^5$ to about $10^7$ modified effector cells/kg. In some cases, an amount of modified effector cells comprises about $10^6$ to about $10^9$ modified effector cells/kg. In some cases, an amount of modified effector cells comprises about $10^6$ to about $10^8$ modified effector cells/kg. In some cases, an amount of modified effector cells comprises about $10^7$ to about $10^8$ modified effector cells/kg. In some cases, an amount of modified effector cells comprises about $10^5$ to about $10^6$ modified effector cells/kg. In some cases, an amount of modified effector cells comprises about $10^6$ to about $10^7$ modified effector cells/kg. In some cases, an amount of modified effector cells comprises about $10^7$ to about $10^8$ modified effector cells/kg. In some cases, an amount of modified effector cells comprises about $10^8$ to about $10^9$ modified effector cells/kg. In some instances, an amount of modified effector cells comprises about $10^9$ modified effector cells/kg. In some instances, an amount of modified effector cells comprises about $10^8$ modified effector cells/kg. In some instances, an amount of modified effector cells comprises about $10^7$ modified effector cells/kg. In some instances, an amount of modified effector cells comprises about $10^6$ modified effector cells/kg. In some instances, an amount of modified effector cells comprises about $10^5$ modified effector cells/kg.

In some embodiments, the modified effector cells are modified T cells encoding gamma delta TCR of fragment thereof that selectively bind J-configuration of CD277. In some cases, an amount of engineered gamma delta TCR T-cells comprises about $10^5$ to about $10^9$ gamma delta TCR cells/kg. In some cases, an amount of engineered gamma delta TCR cells comprises about $10^5$ to about $10^8$ gamma delta TCR cells/kg. In some cases, an amount of engineered gamma delta TCR cells comprises about $10^7$ to about $10^9$ gamma delta TCR cells/kg. In some cases, an amount of engineered gamma delta TCR cells comprises about $10^5$ to about $10^6$ gamma delta TCR cells/kg.

Cytokines

Provided herein are polynucleotides encoding a polypeptide construct described herein and a cytokine, or variant or derivative thereof, and methods and systems incorporating the same. Cytokine is a category of small proteins between about 5-20 kDa that are involved in cell signaling. In some instances, cytokines include chemokines, interferons, interleukins, colony-stimulating factors or tumor necrosis factors. In some embodiments, chemokines play a role as a chemoattractant to guide the migration of cells, and is classified into four subfamilies: CXC, CC, CX3C, and XC. Exemplary chemokines include chemokines from the CC subfamily: CCL1, CCL2 (MCP-1), CCL3, CCL4, CCL5 (RANTES), CCL6, CCL7, CCL8, CCL9 (or CCL10), CCL11, CCL12, CCL13, CCL14, CCL15, CCL16, CCL17, CCL18, CCL19, CCL20, CCL21, CCL22, CCL23, CCL24, CCL25, CCL26, CCL27, and CCL28; the CXC subfamily: CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, and CXCL17; the XC subfamily: XCL1 and XCL2; and the CX3C subfamily CX3CL1.

Interferons (IFNs) comprise interferon type I (e.g. IFN-α, IFN-β, IFN-ε, IFN-κ, and IFN-ω), interferon type II (e.g. IFN-γ), and interferon type III. In some embodiments, IFN-α is further classified into about 13 subtypes including IFNA1, IFNA2, IFNA4, IFNA5, IFNA6, IFNA7, IFNA8, IFNA10, IFNA13, IFNA14, IFNA16, IFNA17, and IFNA21.

Interleukins are expressed by leukocytes or white blood cells and they promote the development and differentiation of T and B lymphocytes and hematopoietic cells. Exemplary interleukines include IL-1, IL-2, IL-3, IL-4, IL-5, IL-6, IL-7, IL-8 (CXCL8), IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-35, and IL-36.

Tumor necrosis factors (TNFs) are a group of cytokines that modulate apoptosis. In some instances, there are about 19 members within the TNF family, including, not limited to, TNFα, lymphotoxin-alpha (LT-alpha), lymphotoxin-beta (LT-beta), T cell antigen gp39 (CD40L), CD27L, CD30L, FASL, 4-1BBL, OX40L, and TNF-related apoptosis inducing ligand (TRAIL).

Colony-stimulating factors (CSFs) are secreted glycoproteins that interact with receptor proteins on the surface of hemopoietic stem cells, which subsequently modulates cell proliferation and differentiation into specific kind of blood cells. In some instances, a CSF comprises macrophage colony-stimulating factor, granulocyte macrophage colony-stimulating factor (GM-CSF), granulocyte colony-stimulating factor (G-CSF) or promegapoietin.

In some embodiments, one or more methods described herein further comprise administration of a cytokine. In some instances, the cytokine comprises a chemokine, an interferon, an interleukin, a colony-stimulating factor or a tumor necrosis factor. In some instances, one or more methods described herein further comprise administration of a cytokine selected from a chemokine, an interferon, an interleukin, a colony-stimulating factor or a tumor necrosis factor.

Indications

In some embodiments, disclosed herein are methods of administering a modified effector cell encoding a polynucleotide described herein to a subject having a disorder, for instance a cancer. In some cases, the cancer is a metastatic cancer. In other cases, the cancer is a relapsed or refractory cancer.

In some cases, a cancer is a solid tumor or a hematologic malignancy. In some instances, the cancer is a solid tumor. In other instances, the cancer is a hematologic malignancy.

In some instances, the cancer is a solid tumor. Exemplary solid tumors include, but are not limited to, anal cancer; appendix cancer; bile duct cancer (i.e., cholangiocarcinoma); bladder cancer; brain tumor; breast cancer; cervical cancer; colon cancer; cancer of Unknown Primary (CUP); esophageal cancer; eye cancer; fallopian tube cancer; gastroenterological cancer; kidney cancer; liver cancer; lung cancer; medulloblastoma; melanoma; oral cancer; ovarian cancer; pancreatic cancer; parathyroid disease; penile cancer; pituitary tumor; prostate cancer; rectal cancer; skin cancer; stomach cancer; testicular cancer; throat cancer; thyroid cancer; uterine cancer; vaginal cancer; or vulvar cancer.

In some instances, the cancer is a hematologic malignancy. In some cases, a hematologic malignancy comprises a lymphoma, a leukemia, a myeloma, or a B-cell malignancy. In some cases, a hematologic malignancy comprises a lymphoma, a leukemia or a myeloma. In some instances, exemplary hematologic malignancies include chronic lymphocytic leukemia (CLL), small lymphocytic lymphoma (SLL), high risk CLL, non-CLL/SLL lymphoma, prolymphocytic leukemia (PLL), follicular lymphoma (FL), diffuse large B-cell lymphoma (DLBCL), mantle cell lymphoma (MCL), Waldenstrom's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis. In some embodiments, the hematologic malignancy comprises a myeloid leukemia. In some embodiments, the hematologic malignancy comprises acute myeloid leukemia (AML) or chronic myeloid leukemia (CML).

In some instances, disclosed herein are methods of administering to a subject having a hematologic malignancy selected from chronic lymphocytic leukemia (CLL), small lymphocytic lymphoma (SLL), high risk CLL, non-CLL/SLL lymphoma, prolymphocytic leukemia (PLL), follicular lymphoma (FL), diffuse large B-cell lymphoma (DLBCL), mantle cell lymphoma (MCL), Waldenstrom's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis a modified effector cell described herein. In some instances, disclosed herein are methods of administering to a subject having a hematologic malignancy selected from AML or CML a modified effector cell to the subject.

Immune Effector Cell Sources

In certain aspects, the embodiments described herein include methods of making and/or expanding the immune effector cells (e.g., T-cells, NK-cell or NK T-cells) that comprises transfecting the cells with an expression vector containing a DNA (or RNA) construct encoding polypeptides that selectively binds the J-configuration of cell surface CD277, then, optionally, stimulating the cells with feeder cells, recombinant antigen, or an antibody to the receptor to cause the cells to proliferate. In certain aspects, the cell (or cell population) engineered to express polypeptides that selectively binds the J-configuration of cell surface CD277 is a stem cell, iPS cell, immune effector cell or a precursor of these cells.

Sources of immune effector cells can include both allogeneic and autologous sources. In some cases immune effector cells can be differentiated from stem cells or induced pluripotent stem cells (iPSCs). Thus, cell for engineering according to the embodiments can be isolated from umbilical cord blood, peripheral blood, human embryonic stem cells, or iPSCs. For example, allogeneic T cells can be modified to include a chimeric antigen receptor (and optionally, to lack functional TCR). In some aspects, the immune effector cells are primary human T cells such as T cells derived from human peripheral blood mononuclear cells (PBMC). PBMCs can be collected from the peripheral blood or after stimulation with G-CSF (Granulocyte colony stimulating factor) from the bone marrow, or umbilical cord blood. Following transfection or transduction (e.g., with a CAR expression construct), the cells can be immediately infused or can be cryo-preserved. In certain aspects, following transfection, the cells can be propagated for days, weeks, or months ex vivo as a bulk population within about 1, 2, 3, 4, 5 days or more following gene transfer into cells. In a further aspect, following transfection, the transfectants are cloned and a clone demonstrating presence of a single integrated or episomally maintained expression cassette or plasmid, and expression of the chimeric antigen receptor is expanded ex vivo. The clone selected for expansion demonstrates the capacity to specifically recognize and lyse antigen-expressing target cells. The recombinant T cells can be expanded by stimulation with IL-2, or other cytokines that bind the common gamma-chain (e.g., IL-7, IL-12, IL-15, IL-21, and others). The recombinant T cells can be expanded by stimulation with artificial antigen presenting cells. The recombinant T cells can be expanded on artificial antigen presenting cell or with an antibody, such as OKT3, which cross links CD3 on the T cell surface. Subsets of the recombinant T cells can be further selected with the use of magnetic bead based isolation methods and/or fluorescence activated cell sorting technology and further cultured with the AaPCs. In a further aspect, the genetically modified cells can be cryopreserved.

T cells can also be obtained from a number of sources, including peripheral blood, bone marrow, lymph node tissue, cord blood, thymus tissue, tissue from a site of infection, ascites, pleural effusion, spleen tissue, and tumor (tumor-infiltrating lymphocytes). In certain embodiments of the present disclosure, any number of T cell lines available in the art, can be used. In certain embodiments of the present disclosure, T cells can be obtained from a unit of blood collected from a subject using any number of techniques known to the skilled artisan, such as Ficoll® separation. In embodiments, cells from the circulating blood of an individual are obtained by apheresis. The apheresis product typically contains lymphocytes, including T cells, monocytes, granulocytes, B cells, other nucleated white blood cells, red blood cells, and platelets. In one embodiment, the cells collected by apheresis can be washed to remove the plasma fraction and to place the cells in an appropriate buffer or media for subsequent processing steps. In one embodiment of the present disclosure, the cells are washed with phosphate buffered saline (PBS). In an alternative embodiment, the wash solution lacks calcium and can lack magnesium or can lack many if not all divalent cations. Initial activation steps in the absence of calcium lead to magnified activation. As those of ordinary skill in the art would readily appreciate a washing step can be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells can be resuspended in a variety of biocompatible buffers, such as, for example, Ca2+-free, Mg2+-free PBS, PlasmaLyte A, or other saline solution with or without buffer. Alternatively, the undesirable components of the apheresis sample can be removed and the cells directly resuspended in culture media.

In another embodiment, T cells are isolated from peripheral blood lymphocytes by lysing the red blood cells and depleting the monocytes, for example, by centrifugation through a PERCOLL® gradient or by counterflow centrifugal elutriation. A specific subpopulation of T cells, such as CD3+, CD28+, CD4+, CD8+, CD45RA+, and CD45RO+ T cells, can be further isolated by positive or negative selection techniques.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8. In certain embodiments, it can be desirable to enrich for or positively select for regulatory T cells which typically express CD4+, CD25+, CD62Lhi, GITR+, and FoxP3+. Alternatively, in certain embodiments, T regulatory cells are depleted by anti-CD25 conjugated beads or other similar method of selection.

For isolation of a desired population of cells by positive or negative selection, the concentration of cells and surface (e.g., particles such as beads) can be varied. In certain embodiments, it can be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that can weakly express target antigens of interest, such as CD28-negative T cells, or from samples where there are many tumor cells present (i.e., leukemic blood, tumor tissue, etc.). Such populations of cells can have therapeutic value and would be desirable to obtain. For example, using high concentration of cells allows more efficient selection of CD8+ T cells that normally have weaker CD28 expression.

In a related embodiment, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, CD4+ T cells express higher levels of CD28 and are more efficiently captured than CD8+ T cells in dilute concentrations. In one embodiment, the concentration of cells used is 5×106/ml. In other embodiments, the concentration used can be from about 1×105/ml to 1×106/ml, and any integer value in between.

In other embodiments, the cells can be incubated on a rotator for varying lengths of time at varying speeds at either 2-10° C. or at room temperature.

T cells for stimulation can also be frozen after a washing step. After the washing step that removes plasma and platelets, the cells can be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° per minute and stored in the vapor phase of a liquid nitrogen storage tank. Other methods of controlled freezing can be used as well as uncontrolled freezing immediately at −20° C. or in liquid nitrogen.

In certain embodiments, cryopreserved cells are thawed and washed as described herein and allowed to rest for one hour at room temperature prior to activation using the methods of the present disclosure.

Also contemplated in the context of the present disclosure is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In one embodiment a blood sample or an apheresis is taken from a generally healthy subject. In certain embodiments, a blood sample or an apheresis is taken from a generally healthy subject who is at risk of developing a disease, but who has not yet developed a disease, and the cells of interest are isolated and frozen for later use. In certain embodiments, the T cells can be expanded, frozen, and used at a later time. In certain embodiments, samples are collected from a patient shortly after diagnosis of a particular disease as described herein but prior to any treatments. In a further embodiment, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, rapamycin, mycophenolic acid, steroids, FR901228, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815, (1991); Henderson et al., Immun 73:316-321, (1991); Bierer et al., Curr. Opin. Immun 5:763-773, (1993)). In a further embodiment, the cells are isolated for a patient and frozen for later use in conjunction with (e.g., before, simultaneously or following) bone marrow or stem cell transplantation, T cell ablative therapy using either chemotherapy agents such as, fludarabine, external-beam radiation therapy (XRT), cyclophosphamide, or antibodies such as OKT3 or CAMPATH. In another embodiment, the cells are isolated prior to and can be frozen for later use for treatment following B-cell ablative therapy such as agents that react with CD20, e.g., Rituxan.

In a further embodiment of the present disclosure, T cells are obtained from a patient directly following treatment. In this regard, it has been observed that following certain cancer treatments, in particular treatments with drugs that damage the immune system, shortly after treatment during the period when patients would normally be recovering from the treatment, the quality of T cells obtained can be optimal or improved for their ability to expand ex vivo. Likewise, following ex vivo manipulation using the methods described herein, these cells can be in a preferred state for enhanced engraftment and in vivo expansion. Thus, it is contemplated within the context of the present disclosure to collect blood cells, including T cells, dendritic cells, or other cells of the hematopoietic lineage, during this recovery phase. Further, in certain embodiments, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

Activation and Expansion of T Cells

In certain embodiments are T cells comprising polynucleotides encoding polypeptide constructs described herein that selectively bind the J-configuration of CD277. Whether prior to or after genetic modification of the T cells to express the desired polypeptide construct, the T cells can be activated and expanded generally using methods as described, for example, in U.S. Pat. Nos. 6,352,694; 6,534,055; 6,905,680; 6,692,964; 5,858,358; 6,887,466; 6,905,681; 7,144, 575; 7,067,318; 7,172,869; 7,232,566; 7,175,843; 5,883, 223; 6,905,874; 6,797,514; 6,867,041; and U.S. Patent Application Publication No. 20060121005.

"Adoptive T cell transfer" refers to the isolation and ex vivo expansion of tumor specific T cells to achieve greater number of T cells than what could be obtained by vaccination alone or the patient's natural tumor response. With regard to the current disclosure, tumor specific T cells can be obtained, for instance, by engineering T cells to express a polypeptide construct described herein that selectively binds the J-configuration of cell surface CD277. The tumor specific T cells can then be infused into patients with cancer in an attempt to give their immune system the ability to overwhelm remaining tumor via T cells which can attack and kill cancer. There are many forms of adoptive T cell therapy being used for cancer treatment; culturing tumor infiltrating lymphocytes or TIL, isolating and expanding one particular T cell or clone, and even using T cells that have been engineered to potently recognize and attack tumors.

Pharmaceutical Compositions and Dosage Forms

In some embodiments, disclosed herein are compositions comprising a polypeptide construct disclosed herein, a polynucleotide encoding the same, or an engineered cell expressing the same, for administration in a subject. In some instances, are modified effector cell compositions encoding a polynucleotide or polypeptide disclosed herein, and optionally containing a cytokine and/or an additional therapeutic agent such as an intermediate of the mammalian mevalonate pathway, such as isopentenyl pyrophosphate (IPP), and the microbial 2-C-methyl-D-erythiitol 4-phosphate (MEP) pathway. In some embodiments, the pharmaceutical composition can comprise an agent that increases activity of a RhoB GTPase in a target cell (e.g. cancer cell) of a subject. In some embodiments, the agent can increases translocation of the RhoB GTPase to a cell membrane of the cancer cell. In some embodiments, the agent can maintain RhoB GTPase at a cell membrane of the cancer cell. In some embodiments, the agent can increase translocation of the RhoB GTPase away from a nucleus of the cancer cell. In some embodiments, the agent can increase expression of a gene or transcript encoding the RhoB GTPase. In some embodiments, the agent can increase stability of the RhoB GTPase. In some embodiments, the agent can increase an interaction between the RhoB GTPase and a BNT3 protein. In some embodiments, the agent can activate RhoB GTPase. In some embodiments, the agent can increase an interaction between the RhoB GTPase and GTP. In some embodiments, the agent can reduce an interaction between the RhoB GTPase and GDP. In some embodiments, the agent can increase an amount of GTP in the cancer cell. In some embodiments, the agent can increase availability of GTP in the cancer cell. In some embodiments, the agent can be conjugated to a moiety that binds a cell surface molecule on the cancer cell, thereby targeting the agent to the cancer cell. In some embodiments, the moiety comprises a small molecule compound, a peptide, or an antibody or antigen binding fragment. In an aspect, an agent that increases activity of a RhoB GTPase does so indirectly by binding to secondary factors that in turn stimulate activity of RhoB GTPase. A secondary factor can be involved in a RhoB GTPase activation cascade. In an aspect, a secondary factor may be involved in signaling, structural changes, conformational changes, configurational changes, and the like. In an aspect, an agent that increases activity of a RhoB GTPase may increase activity at any point upstream of a stimulatory pathway of RhoB GTPase. For example, an agent can be "A" which in turn stimulates "B" which in turn stimulates "C" which in turn stimulates RhoB GTPase. In an aspect, an agent directly stimulates RhoB GTPase without involvement of any secondary factors. An agent can increase activity of RhoB GTPase by about 5%, 10%, 20%, 30%, 40%, 50%, 60%, 70%, 80%, 90%, or up to about 100% as compared to a comparable method or composition absent the RhoB GTPase stimulatory agent.

In some embodiments, the agent can increase an amount of an intracellular phosphoantigen in the cancer cell. In some embodiments, the additional agent is a mevalonate pathway inhibitor. An inhibitor of the mevalonate pathway can inhibit a factor involved in the generation of mevalonate. In an aspect, an inhibitor of the mevalonate pathway can inhibit a reaction involved in the mevalonate pathway. In an aspect, a mevalonate inhibitor can inhibit an enzyme such as: acetoacetyl-CoA, 3-hydroxy-3-methylglutaryl-CoA (HMG-CoA), HMG-CoA reductase, mevalonate-5-phosphate, farnesyl pyrophosphate synthase (FPPS), mevalonate-5-kinase, mevalonate-3-phosphate-5-kinase, phosphomevalonate kinase, mevalonate-5-pyrophosphate decarboxylase, isopentenyl pyrophosphate isomerase, ATP, and combinations thereof. In some embodiments, the mevalonate pathway inhibitor is an aminobisphosphonate. In an aspect, an agent can be hydrogen sulfide ($H_2S$). In an aspect, an agent can be DM-22. In some embodiments, the aminobisphosphonate is zoledronate. In an aspect, an agent can be a statin. In an aspect, a statin can inhibit a mevalonate pathway. In an aspect, an agent can be used to treat bone disease, multiple myeloma, or a combination thereof. In an aspect, an agent that increases activity of a phosphoantigen can bind phosphoantigen directly to stimulate its activity. In an aspect, an agent that increases activity of a phosphoantigen does so indirectly by binding to secondary factors that in turn stimulate activity or accumulation of phosphoantigen in a cytoplasm of a tumor cell. A secondary factor can be involved in a phosphoantigen production cascade. In an aspect, a secondary factor may be involved in translation, signaling, structural changes, conformational changes, configurational changes, and the like. In an aspect, an agent that increases activity of a phosphoantigen may increase activity at any point upstream of a pathway of phosphoantigen. For example, an agent can be "A" which in turn stimulates "B" which in turn stimulates "C" which in turn stimulates phosphoantigen to accumulate in a cytoplasm. In an aspect, an agent directly stimulates phosphoantigen accumulation without involvement of any secondary factors. An agent can increase activity of phosphoantigen, such as phosphoantigena accumulation, by about 5%, 10%, 20%, 30%, 40%, 50%, 60%, 70%, 80%, 90%, or up to about 100% as compared to a comparable method or composition absent the phosphoantigen stimulatory agent.

In an aspect, provided herein can be a synergistic method for tumor cytotoxicity. In an aspect, a method of treatment may comprise administering one or more agents that bolster expression of CD277 on a surface of a cell. Agents that can bolster expression of CD277 can act by increasing activity of RhoB GTPase and/or phosphoantigen in a cytoplasm of a tumor cell. In an aspect, cytotoxicity of a tumor can be increased from about 10%, 20%, 30%, 40%, 50%, 60%, 70%, 80%, 90%, or up to about 100% as compared to a comparable method or composition absent the phosphoantigen stimulatory agent, absent the RhoGTPase stimulatory agent, or their combination.

In an aspect, provided can be a method of bolstering expression of CD277 on a tumor cell surface comprising increasing activity of intracellular agents that bind an interior portion of CD277.

In some embodiments, different pharmaceutically active ingredients described herein can be administered to a subject in need thereof in the same pharmaceutical composition. For example, an agent that increases activity of a RhoB GTPase in a target cell can administered in the same pharmaceutical composition as a polypeptide construct, a polynucleotide encoding the same, or an engineered cell expressing the same. Accordingly, in such pharmaceutical compositions containing multiple pharmaceutically active ingredients, the multiple pharmaceutically active ingredients are administered to a subject in need thereof simultaneously. In other embodiments, different pharmaceutically active ingredients described herein can be administered to a subject in need thereof in different pharmaceutical compositions. For example, an agent that increases activity of a RhoB GTPase in a target cell can be administered in a different pharmaceutical composition as a polypeptide construct, a polynucleotide encoding the same, or an engineered cell expressing the same. In such compositions, a first composition comprising a first pharmaceutically active ingredient can be administered prior to, subsequent to, or simultaneously with a second composition comprising a second pharmaceutically active ingredient. For example, in some embodiments, a first composition comprising a polypeptide construct, a polynucleotide construct encoding the same, or an engineered cell expressing the same is administered to a subject in need thereof prior to administration of a second composition comprising an agent that increases activity of a RhoB GTPase in a target cell. In some embodiments, a first composition comprising a polypeptide construct, a polynucleotide construct encoding the same, or an engineered cell expressing the same is administered to a subject in need thereof subsequent to administration of a second composition comprising an agent that increases activity of a RhoB GTPase in a target cell. In some embodiments, a first composition comprising a polypeptide construct, a polynucleotide construct encoding the same, or an engineered cell expressing the same is administered to a subject in need thereof simultaneously with a second composition comprising an agent that increases activity of a RhoB GTPase in a target cell. In some instances, a first composition comprising a first pharmaceutically active ingredient can be administered at a predetermined time interval with regard to a second composition comprising a second pharmaceutically active ingredient. In some instances a first composition comprising a polypeptide construct, a polynucleotide construct encoding the same, or an engineered cell expressing the same is administered to a subject in a single dose once a day and a second composition comprising an agent that increases activity of a RhoB GTPase in a target cell is delivered in multiple doses at various times during the day. In some instances, a composition comprising an agent that increases activity of a RhoB GTPase in a target cell is delivered as a controlled release formulation for sustained release over a predetermined period of time, and a second composition comprising a polypeptide construct described herein, a polynucleotide construct encoding the same, or an engineered cell is delivered at various intervals during said predetermined period of time.

In an aspect, a composition comprising a cell can include a dosage form of a cell. With the instant application in hand, the skilled worker can determine a therapeutically effective amount of cells for administration. In some cases, about $5 \times 10^{10}$ cells are administered to a subject. In some cases, about $5 \times 10^{10}$ cells represent the median amount of cells administered to a subject. In some embodiments, about $5 \times 10^{10}$ cells can be introduced to a subject. In some embodiments, at least about at least about $1 \times 10^6$ cells, at least about $2 \times 10^6$ cells, at least about $3 \times 10^6$ cells, at least about $4 \times 10^6$ cells, at least about $5 \times 10^6$ cells, at least about $6 \times 10^6$ cells, at least about $6 \times 10^6$ cells, at least about $8 \times 10^6$ cells, at least about $9 \times 10^6$ cells, $1 \times 10^7$ cells, at least about $2 \times 10^7$ cells, at least about $3 \times 10^7$ cells, at least about $4 \times 10^7$ cells, at least about $5 \times 10^7$ cells, at least about $6 \times 10^7$ cells, at least about $6 \times 10^7$ cells, at least about $8 \times 10^7$ cells, at least about $9 \times 10^7$ cells, at least about $1 \times 10^8$ cells, at least about $2 \times 10^8$ cells, at least about $3 \times 10^8$ cells, at least about $4 \times 10^8$ cells, at least about $5 \times 10^8$ cells, at least about $6 \times 10^8$ cells, at least about $6 \times 10^8$ cells, at least about $8 \times 10^8$ cells, at least about $9 \times 10^8$ cells, at least about $1 \times 10^9$ cells, at least about $2 \times 10^9$ cells, at least about $3 \times 10^9$ cells, at least about $4 \times 10^9$ cells, at least about $5 \times 10^9$ cells, at least about $6 \times 10^9$ cells, at least about $6 \times 10^9$ cells, at least about $8 \times 10^9$ cells, at least about $9 \times 10^9$ cells, at least about $1 \times 10^{10}$ cells, at least about $2 \times 10^{10}$ cells, at least about $3 \times 10^{10}$ cells, at least about $4 \times 10^{10}$ cells, at least about $5 \times 10^{10}$ cells, at least about $6 \times 10^{10}$ cells, at least about $6 \times 10^{10}$ cells, at least about $8 \times 10^{10}$ cells, at least about $9 \times 10^{10}$ cells, at least about $1 \times 10^{11}$ cells, at least about $2 \times 10^{11}$ cells, at least about $3 \times 10^{11}$ cells, at least about $4 \times 10^{11}$ cells, at least about $5 \times 10^{11}$ cells, at least about $6 \times 10^{11}$ cells, at least about $6 \times 10^{11}$ cells, at least about $8 \times 10^{11}$ cells, at least about $9 \times 10^{11}$ cells, or at least about $1 \times 10^{12}$ cells are administered to a subject.

In an aspect, a subject may receive additional treatments or therapeutics. The disclosed compositions and methods herein can comprise administration of other agents. For example additional agents can include cytotoxic/antineoplastic agents and anti-angiogenic agents. Cytotoxic/anti-neoplastic agents can be defined as agents who attack and kill cancer cells. Some cytotoxic/anti-neoplastic agents can be alkylating agents, which alkylate the genetic material in tumor cells, e.g., cis-platin, cyclophosphamide, nitrogen mustard, trimethylene thiophosphoramide, carmustine, busulfan, chlorambucil, belustine, uracil mustard, chlomaphazin, and dacabazine. Other cytotoxic/anti-neoplastic agents can be antimetabolites for tumor cells, e.g., cytosine arabinoside, fluorouracil, methotrexate, mercaptopuirine, azathioprime, and procarbazine. Other cytotoxic/anti-neoplastic agents can be antibiotics, e.g., doxorubicin, bleomycin, dactinomycin, daunorubicin, mithramycin, mitomycin, mytomycin C, and daunomycin. There are numerous liposomal formulations commercially available for these compounds. Still other cytotoxic/anti-neoplastic agents can be mitotic inhibitors (vinca alkaloids). These include vincristine, vinblastine and etoposide. Miscellaneous cytotoxic/anti-neoplastic agents include taxol and its derivatives, L-asparaginase, anti-tumor antibodies, dacarbazine, azacytidine, amsacrine, melphalan, VM-26, ifosfamide, mitoxantrone, and vindesine.

In some cases, an agent may comprise an immunostimulant. An immunostimulant can be specific or non-specific. A specific immunostimulant can provide antigenic specificity such as a vaccine or an antigen. A non-specific immunostimulant can augment an immune response or stimulate an immune response. A non-specific immunostimulant can be an adjuvant. Immunostimulants can be vaccines, colony stimulating agents, interferons, interleukins, viruses, antigens, co-stimulatory agents, immunogenicity agents, immunomodulators, or immunotherapeutic agents. An immunostimulant can be a cytokine such as an interleukin. One or more cytokines can be introduced with cells of the invention. Cytokines can be utilized to boost cytotoxic T lymphocytes (including adoptively transferred tumor-specific cytotoxic T lymphocytes) to expand within a tumor microenvironment.

In some cases, IL-2 can be used to facilitate expansion of the cells described herein. Cytokines such as IL-15 can also be employed. Other relevant cytokines in the field of immunotherapy can also be utilized, such as IL-2, IL-7, IL-12, IL-15, IL-21, or any combination thereof. In some cases, IL-2, IL-7, and IL-15 are used to culture cells of the invention. An interleukin can be IL-2, or aldeskeukin. Aldesleukin can be administered in low dose or high dose. A high dose aldesleukin regimen can involve administering aldesleukin intravenously every 8 hours, as tolerated, for up to about 14 doses at about 0.037 mg/kg (600,000 IU/kg). An immunostimulant (e.g., aldesleukin) can be administered within 24 hours after a cellular administration. An immunostimulant (e.g., aldesleukin) can be administered in as an infusion over about 15 minutes about every 8 hours for up to about 4 days after a cellular infusion. An immunostimulant (e.g., aldesleukin) can be administered at a dose from about 100,000 IU/kg, 200,000 IU/kg, 300,000 IU/kg, 400,000 IU/kg, 500,000 IU/kg, 600,000 IU/kg, 700,000 IU/kg, 800,000 IU/kg, 900,000 IU/kg, or up to about 1,000,000 IU/kg. In some cases, aldesleukin can be administered at a dose from about 100,000 IU/kg to 300,000 IU/kg, from 300,000 IU/kg to 500,000 IU/kg, from 500,000 IU/kg to 700,000 IU/kg, from 700,000 IU/kg to about 1,000,000 IU/kg. An immunostimulant (e.g., aldesleukin) can be administered from 1 dose to about 14 doses.

In some cases, an additional agent may comprise an immunosuppressive agent as part of a therapy regime. An immunosuppressive agent can refer to a radiotherapeutic, a biologic, or a chemical agent. In some cases, an immunosuppressive agent can include a chemical agent. For example, a chemical agent can comprise at least one member from the group consisting of: cyclophosphamide, mechlorethamine, chlorambucil, melphalan, ifosfamide, thiotepa, hexamethylmelamine, busulfan, fludarabine, nitrosoureas, platinum, methotrexate, azathioprine, mercaptopurine, procarbazine, dacarbazine, temozolomide, carmustine, lomustine, streptozocin, fluorouracil, dactinomycin, anthracycline, mitomycin C, bleomycin, and mithramycin. A chemical agent can be cyclophosphamide or fludarabine.

Additionally, immunosuppressive agents can include glucocorticoids, cytostatic, antibodies, anti-immunophilins, or any derivatives thereof. A glucocorticoid can suppress an allergic response, inflammation, and autoimmune conditions. Glucocorticoids can be prednisone, dexamethasone, and hydrocortisone. Immunosuppressive therapy can comprise any treatment that suppresses the immune system. Immunosuppressive therapy can help to alleviate, minimize, or eliminate transplant rejection in a recipient. For example, immunosuppressive therapy can comprise immuno-suppressive drugs. Immunosuppressive drugs that can be used before, during and/or after transplant, but are not limited to, MMF (mycophenolate mofetil (Cellcept)), ATG (anti-thymocyte globulin), anti-CD154 (CD40L), anti-CD40 (2C10, ASKP1240, CCFZ533X2201), alemtuzumab (Campath), anti-CD20 (rituximab), anti-IL-6R antibody (tocilizumab, Actemra), anti-IL-6 antibody (sarilumab, olokizumab), CTLA4-Ig (Abatacept/Orencia), belatacept (LEA29Y), sirolimus (Rapimune), everolimus, tacrolimus (Prograf), daclizumab (Ze-napax), basiliximab (Simulect), infliximab (Remicade), cyclosporin, deoxyspergualin, soluble complement receptor 1, cobra venom factor, compstatin, anti C5 antibody (eculizumab/Soliris), methylprednisolone, FTY720, everolimus, leflunomide, anti-IL-2R-Ab, rapamycin, anti-CXCR3 antibody, anti-ICOS antibody, anti-OX40 antibody, and anti-CD122 antibody. Furthermore, one or more than one immunosuppressive agents/drugs can be used together or sequentially. One or more than one immunosuppressive agents/drugs can be used for induction therapy or for maintenance therapy. The same or different drugs can be used during induction and maintenance stages. In some cases, daclizumab (Zenapax) can be used for induction therapy and tacrolimus (Prograf) and sirolimus (Rapimune) can be used for maintenance therapy. Daclizumab (Zenapax) can also be used for induction therapy and low dose tacrolimus (Prograf) and low dose sirolimus (Rapimune) can be used for maintenance therapy. Immunosuppression can also be achieved using non-drug regimens including, but not limited to, whole body irradiation, thymic irradiation, and full and/or partial splenectomy.

In some instances, pharmaceutical compositions are formulated in a conventional manner using one or more physiologically acceptable carriers including excipients and auxiliaries which facilitate processing of the active compounds into preparations which can be used pharmaceutically. Proper formulation is dependent upon the route of administration chosen. A summary of pharmaceutical compositions described herein is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999).

Pharmaceutical compositions are optionally manufactured in a conventional manner, such as, by way of example only, by means of conventional mixing, dissolving, granulating, dragee-making, levigating, emulsifying, encapsulating, entrapping or compression processes.

In certain embodiments, compositions can also include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

In other embodiments, compositions can also include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

The pharmaceutical compositions described herein are administered by any suitable administration route, including but not limited to, oral, parenteral (e.g., intravenous, subcutaneous, intramuscular, intracerebral, intracerebroventricular, intra-articular, intraperitoneal, or intracranial), intranasal, buccal, sublingual, or rectal administration routes. In some instances, the pharmaceutical composition is formulated for parenteral (e.g., intravenous, subcutaneous, intramuscular, intracerebral, intracerebroventricular, intra-articular, intraperitoneal, or intracranial) administration.

The pharmaceutical compositions described herein are formulated into any suitable dosage form, including but not limited to, aqueous oral dispersions, liquids, gels, syrups, elixirs, slurries, suspensions and the like, for oral ingestion by an individual to be treated, solid oral dosage forms, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations. In some embodiments, the pharmaceutical compositions are formulated into capsules. In some embodiments, the pharmaceutical compositions are formulated into solutions (for example, for IV administration). In some cases, the pharmaceutical composition is formulated as an infusion. In some cases, the pharmaceutical composition is formulated as an injection.

The pharmaceutical solid dosage forms described herein optionally include a compound described herein and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof.

In still other aspects, using standard coating procedures, such as those described in Remington's Pharmaceutical Sciences, 20th Edition (2000), a film coating is provided around the compositions. In some embodiments, the compositions are formulated into particles (for example for administration by capsule) and some or all of the particles are coated. In some embodiments, the compositions are formulated into particles (for example for administration by capsule) and some or all of the particles are microencapsulated. In some embodiments, the compositions are formulated into particles (for example for administration by capsule) and some or all of the particles are not microencapsulated and are uncoated.

In certain embodiments, compositions provided herein can also include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

"Proliferative disease" as referred to herein means a unifying concept that excessive proliferation of cells and turnover of cellular matrix contribute significantly to the pathogenesis of several diseases, including cancer is presented.

"Subject" or "Patient" as used herein refers to a mammalian subject diagnosed with or suspected of having or developing a physiological condition, for instance a cancer or an autoimmune condition or an infection. In some embodiments, the term "patient" or "subject" refers to a mammalian subject with a higher than average likelihood of developing cancer. Exemplary patients can be humans, apes, dogs, pigs, cattle, cats, horses, goats, sheep, rodents and other mammalians that can benefit from the therapies disclosed herein. Exemplary human subjects can be male and/or female.

"Administering" is referred to herein as providing the compositions of the present disclosure to a patient. By way of example and not limitation, composition administration, e.g., injection, can be performed by intravenous (i.v.) injection, sub-cutaneous (s.c.) injection, intradermal (i.d.) injection, intraperitoneal (i.p.) injection, or intramuscular (i.m.) injection. One or more such routes can be employed. Parenteral administration can be, for example, by bolus injection or by gradual perfusion over time. Alternatively, or concurrently, administration can be by the oral route. Additionally, administration can also be by surgical deposition of a bolus or pellet of cells, or positioning of a medical device.

"A subject in need thereof" or "a patient in need thereof" is referred to herein as a subject or patient diagnosed with or suspected of having a disease or disorder, for instance, but not restricted to a proliferative disorder such as cancer. In one embodiment, the subject or patient has or is likely to develop solid tumors or leukemia. In some embodiments leukemia can be, for instance, acute lymphoblastic leukemia (ALL), acute myeloid leukemia (AML), chronic lymphocytic leukemia (CLL) and chronic myeloid leukemia (CML).

The compositions of the present disclosure can comprise engineered cells expressing nucleic acid sequences encoding polypeptide constructs that bind J-configuration of CD277, or a vector comprising the nucleic acid sequence, in an amount that is effective to treat or prevent proliferative disorders. As used herein, the terms "treatment," "treating," and the like refer to obtaining a desired pharmacologic and/or physiologic effect. In embodiments, the effect is therapeutic, i.e., the effect partially or completely cures a disease and/or adverse symptom attributable to the disease. To this end, the inventive method comprises administering a "therapeutically effective amount" of the composition comprising the host cells expressing the inventive nucleic acid sequence, or a vector comprising the inventive nucleic acid sequences.

A "therapeutically effective amount" refers to an amount effective, at dosages and for periods of time necessary, to achieve a desired therapeutic result. The therapeutically effective amount can vary according to factors such as the disease state, age, sex, and weight of the individual, and the ability of the inventive nucleic acid sequences to elicit a desired response in the individual.

Alternatively, the pharmacologic and/or physiologic effect can be "prophylactic," i.e., the effect completely or partially prevents a disease or symptom thereof.

A "prophylactically effective amount" refers to an amount effective, at dosages and for periods of time necessary, to achieve a desired prophylactic result (e.g., prevention of disease onset).

"Antifoaming agents" reduce foaming during processing which can result in coagulation of aqueous dispersions, bubbles in the finished film, or generally impair processing. Exemplary anti-foaming agents include silicon emulsions or sorbitan sesquoleate.

"Antioxidants" include, for example, butylated hydroxytoluene (BHT), sodium ascorbate, ascorbic acid, sodium metabisulfite and tocopherol. In certain embodiments, antioxidants enhance chemical stability where required.

Formulations described herein may benefit from antioxidants, metal chelating agents, thiol containing compounds and other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

"Binders" impart cohesive qualities and include, e.g., alginic acid and salts thereof; cellulose derivatives such as carboxymethylcellulose, methylcellulose (e.g., Methocel®), hydroxypropylmethylcellulose, hydroxyethyl cellulose, hydroxypropylcellulose (e.g., Klucel®), ethylcellulose (e.g., Ethocel®), and microcrystalline cellulose (e.g., Avicel®); microcrystalline dextrose; amylose; magnesium aluminum silicate; polysaccharide acids; bentonites; gelatin; polyvinylpyrrolidone/vinyl acetate copolymer; crospovidone; povidone; starch; pregelatinized starch; tragacanth, dextrin, a sugar, such as sucrose (e.g., Dipac®), glucose, dextrose, molasses, mannitol, sorbitol, xylitol (e.g., Xylitab®), and lactose; a natural or synthetic gum such as acacia, tragacanth, ghatti gum, mucilage of isapol husks, polyvinylpyrrolidone (e.g., Polyvidone® CL, Kollidon® CL, Polyplasdone® XL-10), larch arabogalactan, Veegum®, polyethylene glycol, waxes, sodium alginate, and the like.

A "carrier" or "carrier materials" include any commonly used excipients in pharmaceutics and should be selected on the basis of compatibility with compounds disclosed herein, such as, compounds of ibrutinib and An anticancer agent, and the release profile properties of the desired dosage form. Exemplary carrier materials include, e.g., binders, suspending agents, disintegration agents, filling agents, surfactants, solubilizers, stabilizers, lubricants, wetting agents, diluents, and the like. "Pharmaceutically compatible carrier materials" can include, but are not limited to, acacia, gelatin, colloidal silicon dioxide, calcium glycerophosphate, calcium lactate, maltodextrin, glycerine, magnesium silicate, polyvinylpyrrollidone (PVP), cholesterol, cholesterol esters, sodium caseinate, soy lecithin, taurocholic acid, phosphotidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like. See, e.g., Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999).

"Dispersing agents," and/or "viscosity modulating agents" include materials that control the diffusion and homogeneity of a drug through liquid media or a granulation method or blend method. In some embodiments, these agents also facilitate the effectiveness of a coating or eroding matrix. Exemplary diffusion facilitators/dispersing agents include, e.g., hydrophilic polymers, electrolytes, Tween® 60 or 80, PEG, polyvinylpyrrolidone (PVP; commercially known as Plasdone®), and the carbohydrate-based dispersing agents such as, for example, hydroxypropyl celluloses (e.g., HPC, HPC-SL, and HPC-L), hydroxypropyl methylcelluloses (e.g., HPMC K100, HPMC K4M, HPMC K15M, and HPMC K100M), carboxymethylcellulose sodium, methylcellulose, hydroxyethylcellulose, hydroxypropylcellulose, hydroxypropylmethylcellulose phthalate, hydroxypropylmethylcellulose acetate stearate (HPMCAS), noncrystalline cellulose, magnesium aluminum silicate, triethanolamine, polyvinyl alcohol (PVA), vinyl pyrrolidone/vinyl acetate copolymer (S630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine 908®), which is a tetrafunctional block copolymer derived from sequential addition of propylene oxide and ethylene oxide to ethylenediamine (BASF Corporation, Parsippany, N.J.)), polyvinylpyrrolidone K12, polyvinylpyrrolidone K17, polyvinylpyrrolidone K25, or polyvinylpyrrolidone K30, polyvinylpyrrolidone/vinyl acetate copolymer (S-630), polyethylene glycol, e.g., the polyethylene glycol can have a molecular weight of about 300 to about 6000, or about 3350 to about 4000, or about 7000 to about 5400, sodium carboxymethylcellulose, methylcellulose, polysorbate-80, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, polysorbate-80, sodium alginate, polyethoxylated sorbitan monolaurate, polyethoxylated sorbitan monolaurate, povidone, carbomers, polyvinyl alcohol (PVA), alginates, chitosans and combinations thereof. Plasticizers such as cellulose or triethyl cellulose can also be used as dispersing agents. Dispersing agents particularly useful in liposomal dispersions and self-emulsifying dispersions are dimyristoyl phosphatidyl choline, natural phosphatidyl choline from eggs, natural phosphatidyl glycerol from eggs, cholesterol and isopropyl myristate.

Combinations of one or more erosion facilitator with one or more diffusion facilitator can also be used in the present compositions.

The term "diluent" refers to chemical compounds that are used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution. In certain embodiments, diluents increase bulk of the composition to facilitate compression or create sufficient bulk for homogenous blend for capsule filling. Such compounds include e.g., lactose, starch, mannitol, sorbitol, dextrose, microcrystalline cellulose such as Avicel®; dibasic calcium phosphate, dicalcium phosphate dihydrate; tricalcium phosphate, calcium phosphate; anhydrous lactose, spray-dried lactose; pregelatinized starch, compressible sugar, such as Di-Pac® (Amstar); mannitol, hydroxypropylmethylcellulose, hydroxypropylmethylcellulose acetate stearate, sucrose-based diluents, confectioner's sugar; monobasic calcium sulfate monohydrate, calcium sulfate dihydrate; calcium lactate trihydrate, dextrates; hydrolyzed cereal solids, amylose; powdered cellulose, calcium carbonate; glycine, kaolin; mannitol, sodium chloride; inositol, bentonite, and the like.

"Filling agents" include compounds such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

"Lubricants" and "glidants" are compounds that prevent, reduce or inhibit adhesion or friction of materials. Exemplary lubricants include, e.g., stearic acid, calcium hydroxide, talc, sodium stearyl fumerate, a hydrocarbon such as mineral oil, or hydrogenated vegetable oil such as hydrogenated soybean oil (Sterotex®), higher fatty acids and their alkali-metal and alkaline earth metal salts, such as aluminum, calcium, magnesium, zinc, stearic acid, sodium stearates, glycerol, talc, waxes, Stearowet®, boric acid, sodium benzoate, sodium acetate, sodium chloride, leucine, a polyethylene glycol (e.g., PEG-4000) or a methoxypolyethylene glycol such as Carbowax™, sodium oleate, sodium benzoate, glyceryl behenate, polyethylene glycol, magnesium or sodium lauryl sulfate, colloidal silica such as Syloid™, Cab-O-Sil®, a starch such as corn starch, silicone oil, a surfactant, and the like.

"Plasticizers" are compounds used to soften the microencapsulation material or film coatings to make them less brittle. Suitable plasticizers include, e.g., polyethylene glycols such as PEG 300, PEG 400, PEG 600, PEG 1450, PEG 3350, and PEG 800, stearic acid, propylene glycol, oleic acid, triethyl cellulose and triacetin. In some embodiments, plasticizers can also function as dispersing agents or wetting agents.

"Solubilizers" include compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, and dimethyl isosorbide and the like.

"Stabilizers" include compounds such as any antioxidation agents, buffers, acids, preservatives and the like.

"Suspending agents" include compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol can have a molecular weight of about 300 to about 6000, or about 3350 to about 4000, or about 7000 to about 5400, sodium carboxymethylcellulose, methylcellulose, hydroxypropylmethylcellulose, hydroxymethylcellulose acetate stearate, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethyl cellulose, polysorbate-80, sodium alginate, polyethoxylated sorbitan monolaurate, polyethoxylated sorbitan monolaurate, povidone and the like.

"Surfactants" include compounds such as sodium lauryl sulfate, sodium docusate, Tween 60 or 80, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. Some other surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40. In some embodiments, surfactants can be included to enhance physical stability or for other purposes.

"Viscosity enhancing agents" include, e.g., methyl cellulose, xanthan gum, carboxymethyl cellulose, hydroxypropyl cellulose, hydroxypropylmethyl cellulose, hydroxypropylmethyl cellulose acetate stearate, hydroxypropylmethyl cellulose phthalate, carbomer, polyvinyl alcohol, alginates, acacia, chitosans and combinations thereof.

"Wetting agents" include compounds such as oleic acid, glyceryl monostearate, sorbitan monooleate, sorbitan monolaurate, triethanolamine oleate, polyoxyethylene sorbitan monooleate, polyoxyethylene sorbitan monolaurate, sodium docusate, sodium oleate, sodium lauryl sulfate, sodium doccusate, triacetin, Tween 80, vitamin E TPGS, ammonium salts and the like.

Kits/Article of Manufacture

Disclosed herein, in certain embodiments, are kits and articles of manufacture for use with one or more methods described herein. Such kits include a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In one embodiment, the containers are formed from a variety of materials such as glass or plastic.

The articles of manufacture provided herein contain packaging materials. Examples of pharmaceutical packaging materials include, but are not limited to, blister packs, bottles, tubes, bags, containers, bottles, and any packaging material suitable for a selected formulation and intended mode of administration and treatment.

For example, the container(s) include engineered cells expressing polypeptide construct that selectively binds J-configuration of CD277, and optionally in addition with cytokines and/or chemotherapeutic agents and/or additional agents disclosed herein, for instance an intermediate of the mammalian mevalonate pathway, such as isopentenyl pyrophosphate (IPP), and the microbial 2-C-methyl-D-erythiitol 4-phosphate (MEP) pathway. Such kits optionally include an identifying description or label or instructions relating to its use in the methods described herein.

A kit typically includes labels listing contents and/or instructions for use, and package inserts with instructions for use. A set of instructions will also typically be included.

In some embodiments, a label is on or associated with the container. In one embodiment, a label is on a container when letters, numbers or other characters forming the label are attached, molded or etched into the container itself; a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

Recognition Phenotypes

In certain embodiments provided herein a polypeptide construct, a nucleotide encoding the same, and/or an engineered cell harboring the same can recognize a target cell (e.g. tumor cell). In some embodiments, an engineered T cell can express a Vγ9Vδ2 TCR specific for a particular antigen (e.g. CD277) expressed on the surface of a target cell. Described herein are methods for identifying one or more T cells capable of recognizing a particular antigen on a target cell. A T cell or population of T cells capable of recognizing a particular antigen can be identified by assaying for a recognition phenotype that occurs as a result of a physical interaction between a TCR (e.g. Vγ9Vδ2 TCR) of the T cell and a protein, antigen, ligand or cell surface molecule (e.g. CD277) expressed on the surface of the target cell. In some embodiments, the recognition phenotype can be a change in cellular state that occurs in the T cell as a result of the recognition of the target cell by the Vγ9Vδ2 TCR. For example, a change in cellular state can include a change in the levels of interferon (IFN)-γ production resulting from Vγ9Vδ2 TCR-mediated activation of the T cell, which is detectable by methods known in the art (e.g. IFN-γ ELISPOT analysis). In other examples, a change in cellular state indicative of a recognition phenotype can involve molecular changes including qualitative or quantitative changes in gene expression (e.g. identified via qRT-PCR or microarray analysis) and/or protein expression (e.g. identified via Western blot or immunocytochemistry assays) resulting from Vγ9Vδ2 TCR-mediated recognition of a target cell. In other embodiments, a recognition phenotype can include physical manifestations of an interaction between a TCR of the T cell and a cell surface protein, ligand or antigen of the target cell. For example, a recognition phenotype can involve the physical binding of a Vγ9Vδ2 TCR of a T cell with a cell surface protein, ligand or antigen of a target cell. In certain embodiments, the recognition phenotype involves the formation of a physical complex comprising a Vγ9Vδ2 TCR and a J-configuration of a CD277 molecule on the surface of a target cell. Where the recognition phenotype involves formation of a complex comprising a receptor and a ligand, the phenotype can be identified by known methods, including immunoprecipitation, cell sorting, or immunocytochemistry.

In embodiments described herein, the recognition phenotypes can vary between different subjects and/or between cells obtained from different subjects. For example, in some embodiments, target cells obtained from different subjects can vary in the extent to which a Vγ9Vδ2 TCR expressed in an engineered cell recognizes the target cell (e.g. via a CD277 expressed on the surface of the target cell). Surface molecules of target cells obtained from some subjects can be recognized with high affinity by a Vγ9Vδ2 TCR expressed in an engineered cell. For target cells obtained from other subjects, surface molecules of the target cells can be recognized with low affinity or not recognized at all. The variation in recognition by a Vγ9Vδ2 TCR between target cells of different subjects can be manifested in variations in recognition phenotypes expressed by those cells. For example, following exposure to T cells expressing a Vγ9Vδ2 TCR, target cells of different subjects can vary in the amount of production of IFN-γ, gene or protein expression levels or patterns, and/or the extent of physical interaction between the a Vγ9Vδ2 TCR of the T cell and a cell surface protein (e.g. CD277) of the target cell.

The polypeptide constructs, polynucleotides encoding the same and engineered cells harboring the same described herein can have varying therapeutic effects when used to treat subjects in need thereof. Disclosed herein are methods comprising the stratification of a patient population (e.g. cancer patient population) into multiple therapy groups based on the strength of a particular phenotype exhibited by the patients or by cells of the patients. In some embodiments, the phenotype used to stratify patients into therapy groups is a recognition phenotype. For example, a patient population can be stratified into groups based on the presence, absence or extent of a recognition phenotype in target cells obtained from the patients following exposure to T cells expressing a Vγ9Vδ2 TCR, including the level of production of IFN-γ or the quantitative or qualitative pattern of gene expression. In some embodiments, the phenotype used to stratify patients into therapy groups is not a recognition phenotype that is based on the extent of recognition between a T cell expressing a Vγ9Vδ2 TCR and a target cell. Instead, the phenotype used as a basis for stratification can be a marker (i.e. biomarker) present in the target cells prior to exposure to a T cell. For example, the presence or absence of a J-configuration in the cell surface-expressed CD277 molecule can be a phenotype that varies between target cells (e.g. tumor cells) of patients and that can accordingly be used as a basis to separate or stratify patients into different groups having different probabilities of treatment success when administered the polypeptide constructs described herein.

In some embodiments, patients are stratified into at least two therapy groups including a stratification group with a positive treatment prognosis and a stratification group with a poor treatment prognosis. In some embodiments, patients classified into a positive treatment prognosis stratification group have target cells exhibiting recognition phenotypes such as IFN-γ production and physical interactions between a Vγ9Vδ2 TCR and a CD277 molecule of a target cell (e.g. in the form of a complex including both the TCR and the CD277 molecule). In some embodiments, patients classified into a positive treatment prognosis stratification group have target cells exhibiting CD277 cell surface molecules having a J-configuration prior to contact with Vγ9Vδ2 T cells. In some embodiments, patients classified into a poor treatment prognosis stratification group have target cells lacking or having reduced expression of one or more recognition phenotypes (e.g. IFN-γ production) or that fail to exhibit CD277 cell surface molecules having a J-configuration.

Polymorphic Variation and Genetic Association

The terms "nucleotide polymorphism", "genetic polymorphism" and nucleotide sequence polymorphism" are used interchangeably herein and refer to variation in nucleotide sequence at a specific position of the genome (i.e. a "locus") in a single individual or between individuals. In some cases, a genetic polymorphism exists at a locus within a cell or cells of an individual (i.e. the individual is heterozygous at a genetic locus for a particular nucleotide sequence). In other cases, the nucleotide sequence at a particular locus of an individual is invariant (i.e. the individual is homozygous for the nucleotide sequence at the particular locus), but the nucleotide sequence at the locus is polymorphic when compared to the DNA of a second individual. In certain embodiments, the nucleotide polymorphism includes variation at a single nucleotide at a locus. In such cases the nucleotide polymorphism is referred to as a single nucleotide polymorphism, or SNP. In other embodiments, the nucleotide polymorphism could include other types of DNA variation instead of or in addition to a SNP. Herein the term "polymorphism" contemplates any form of DNA variation, including single nucleotide polymorphisms and structural variations such as insertions, deletions, inversions and duplications.

In certain embodiments, a nucleotide polymorphism (e.g. SNP) can be a functional variation that causes a phenotypic difference between cells, tissues or organisms harboring different forms of the polymorphism. For example, a SNP can be located in the open reading frame of a gene and thereby directly impact the sequence of amino acids incorporated into a protein encoded by the gene. In other non-limiting examples, a polymorphism can produce phenotypic differences between individuals by altering splicing of mRNA transcribed from a gene (e.g. where a SNP is positioned at a splice site), altering the level of expression of a gene (e.g. where a SNP is positioned in the promoter of a gene), or impacting post-translational modifications of a protein (e.g. where a SNP affects the expression or function of a factor responsible for post-translationally modifying another protein. In certain other embodiments, a nucleotide polymorphism can be a non-function or neutral variation that does not directly lead to phenotypic differences between individuals harboring the different forms of the polymorphism.

In certain embodiments, a genetic polymorphism (either functional or non-functional) can be identified in association studies as being associated with a particular trait (e.g. cellular, tissue or organismal phenotype). Herein a "genetic association" exists where one or more genotypes within a population of individuals or a population of cells derived from different individuals co-occurs with a phenotypic trait more often than would be expected by chance. In some embodiments, the phenotypic trait can include a recognition phenotype manifesting as a result of the recognition of a target cell (e.g. tumor cell) by a T cell expressing a Vγ9Vδ2 TCR. In some embodiments, the phenotypic trait can include the conformation of one or more cell surface molecules of a target cell. In some embodiments, the phenotypic trait can include the presence or absence of a J-configuration in a cell-surface CD277 molecule of a target cell. In some embodiments, the phenotypic trait can include the zygosity of a particular individual at a particular genetic locus. In some embodiments, the phenotypic trait can include an activity of RhoB in a target cell (e.g. tumor cell). Herein the term "activity" when used with reference to a protein (e.g. RhoB) refers to the cellular function of the protein. The activity of a protein is influenced by many cellular events and factors, including the nucleotide sequence of the gene encoding the protein (e.g. where the gene is mutated), the level and timing of transcription of the gene, the pattern of splicing of the transcribed mRNA, post-translational modifications of the protein, the pattern of translocation of the protein or mRNA encoding the protein in the cell and the proper interaction of the protein with cellular factors influencing its function by for example changing its conformation and/or activity or positioning the protein at a proper location (e.g. cell surface) of the cell to perform its function. Accordingly, changing the activity of a protein (e.g. increasing or decreasing protein activity) contemplates any cellular mechanism that could result in alterations to a protein's function carried out in the cell. For example, with respect to RhoB, in some embodiments activity can be changed by affecting translocation of the RhoB GTPase to a cell membrane of the cancer cell. In some embodiments, activity can be changed by affecting whether the RhoB GTPase is maintained at a cell membrane of the cancer cell. In some embodiments, activity can be changed by effecting an increase or decrease of translocation of the RhoB GTPase away from a nucleus of the cancer cell. In some embodiments, activity can be changed by increasing or decreasing expression of a gene or transcript encoding the RhoB GTPase. In some embodiments, activity can be changed by altering the modification of a transcript (e.g. alternative splicing). In some embodiments, activity can be changed by increasing or decreasing stability of the RhoB GTPase in the cell. In some embodiments, activity can be changed by increasing or decreasing an interaction between the RhoB GTPase and a second protein (e.g. BNT3 protein). In some embodiments, activity can be changed by activating or deactivating RhoB GTPase. In some embodiments, activity can be changed by increasing or decreasing an interaction between the RhoB GTPase and a non-protein small molecule (e.g. GTP).

In some embodiments, the presence or absence of one or more nucleotide sequence polymorphisms is used to stratify patients into therapy groups, which may differ in their therapeutic response to a treatment with a polypeptide construct disclosed herein. For example, the presence of a particular form of a SNP may be found to be associated with a phenotypic trait (e.g. the presence/absence of a J configuration or a relatively high or low activity of RhoB) that is known to predict therapeutic success. Based on the identified genetic association, patients who are candidates for receiving a particular therapy disclosed herein may be screened (i.e. genotyped) for the presence or absence of the polymorphism correlating with the phenotypic trait. The screened patients can then be categorized into multiple patient populations or groups based on the presence or absence of the polymorphism. Each patient population can represent a stratification group which can be representative of the probability that a particular patient in the stratification group will respond to a particular therapeutic intervention with a positive response or poor response (i.e. patients in different stratification groups are assigned different likelihoods of responding positively to a therapeutic treatment). Herein the term "positive" when used with reference to a therapeutic response or stratification group refers to a result of treatment which accomplishes or partially accomplishes the purpose for which the treatment was applied. For example, in some embodiments, a positive patient response to treatment involves the clearing of at least some cancer cells by exposure to the compositions described herein. Herein a "positive" response is used relatively to a "poor" response, which in some embodiments is a response to treatment of a stratification group which is lesser than a response of a second stratification group exhibiting a positive response. In some embodiments, patients can be stratified into at least two patient groups where a first patient group is predicted to exhibit a positive response to treatment (i.e. positive treatment prognosis stratification group), whereas a second patient group is predicted to exhibit a relatively poor therapeutic response (i.e. poor treatment prognosis stratification group).

It will be understood from the above description that certain phenotypic traits (e.g. J-configuration of CD277, RhoB activity) and/or nucleotide sequence polymorphisms of target cells of a patient can be representative of one or more biomarkers which are predictive or prognostic of a therapeutic response of the patient to a treatment involving administration of the compositions disclosed herein. In some embodiments, patients can be stratified into different stratification groups based on the presence or absence of the biomarker in target cells of the patients. In some embodiments, the biomarker is a nucleotide sequence polymorphism (e.g. SNP) or epigenetic modification and patients having the nucleotide sequence polymorphism or epigenetic modification are stratified into a positive stratification group whereas patients lacking the nucleotide sequence polymorphism or epigenetic modification are stratified into a poor stratification group. In some embodiments, the biomarker is a nucleotide sequence polymorphism (e.g. SNP) or epigenetic modification and patients lacking the nucleotide sequence polymorphism or epigenetic modification are stratified into a positive stratification group whereas patients having the nucleotide sequence polymorphism or epigenetic modification are stratified into a poor stratification group. In some embodiments, as described above, the biomarker is a recognition phenotype (e.g. production of IFN-γ) or a target cell phenotype (e.g. presence of a J configuration in a cell surface CD277 molecule) which is associated with a poor or positive therapeutic response. In some embodiments, one biomarker is used to stratify patients into different stratification groups. In other embodiments, multiple biomarkers are used to stratify patients. For example, patients can be stratified into a positive stratification group where target cells of the patient exhibit both a particular nucleotide sequence polymorphism or epigenetic modification and a particular recognition phenotype or target cell phenotype.

The present disclosure contemplates the use of data collections which archive genomic information including nucleotide sequences, the presence and identity of polymorphisms, and zygosity at particular loci. An example of a data collection is the library of cell lines from the Centre d'Etude du Polymorphisms Huain (CEPH), which contains a large collection of Epstein Barr Virus (EBV)-transformed B cell lines (EBV-LCLs) obtained from several family pedigrees and genotyped for millions of SNPs. Another example of a data collection is the haplotype map generated by the International HapMap project. In some embodiments, the data collections can archive hypothetical or predicted genomic parameters. For example, hypothetical zygosities for candidate genetic loci can be deduced using classical Mendelian inheritance patterns from within family pedigrees.

Further disclosed herein are methods for identifying genetic and epigenetic variations in the target cells of a subject which are predictive or prognostic of a particular therapeutic response. For example, target cells (e.g. tumor cells) of a patient can be screened by contacting the cells with a composition comprising an engineered cell (e.g. T cell) expressing a T cell receptor and then detecting a recognition phenotype such as a level of immune activation of the cell (e.g. level or activity of IFN-γ) as a result of exposure to the composition. Depending on the response of the target cells to exposure to the composition, the subject can be categorized into a particular (e.g. positive) stratification group. For example, where exposure of the target cells to the composition invokes immune activation in the T cells, the patient can be classified into a positive stratification group. In some embodiments, the presence or absence of immune activation in a target cell can be associated with a genetic and/or epigenetic variation in the target cell. In some embodiments, genotypic or epigenetic information about the target cell is obtained (e.g. from a data collection) in order to associate a particular phenotypic trait (e.g. recognition phenotype) of the target cells with a genetic or epigenetic variant. The present disclosure contemplates any method for identifying genetic or epigenetic variation in target cells of a patient relative to cells of another patient in order to associate the genetic or epigenetic variation with a particular recognition phenotype and/or predicted therapeutic response. For example, a genome-wide association study (GWAS) can be carried out to determine if a particular genetic variant (e.g. SNP) is associated with a phenotypic trait (e.g. recognition phenotype) of the target cells. In other cases, epigenetic data (e.g. methylation status) of DNA from target cells of different subjects can be compared to identify candidate epigenetic marks which may be associated with a recognition phenotype and/or therapeutic response. In still other examples, zygosity at particular loci can be hypothesized using data from family pedigrees to identify candidate loci which may be associated with a particular phenotypic trait.

In certain embodiments, predicted zygosities at multiple loci correlate with SNP genotypes of CEPH individuals and can be calculated with a software tool such as ssSNPer. For example, proxy SNPs within 500 kb of SNPs produced y ssSNPer can be collected by querying the SNP Annotation and Proxy Search (SNAP) tool using $r^2=0.8$ as a threshold for linkage disequilibrium. eQTL analysis of ssSNPer SNPs and their proxies can be performed using the Genevar (GENe Expression VARiation) tool.

Sapphire

Disclosed herein is a method of identifying genetic loci associated with receptor mediated target cell recognition using a technique referred to as SNP-associated computational pathway hunt including shRNA evaluation (SAPPHIRE). For example, differences in the genetic backgrounds of tumor cells can affect recognition of these cells by Vγ9Vδ2 TCR engineered T cells, for instance cells described herein. In some embodiments, a library of cell lines can be used, which contains a large collection of EBV-transformed B cell lines (EBV-LCLs) obtained from several family pedigrees and genotyped for millions of SNPs (Dausset et al., Centre d'etude dupolymorphisme humain (CEPH): collaborative genetic mapping of the human genome. Genomics. 1990; 6:575-7; INTERNATIONAL HAPMAP, C. The International HapMap Project. Nature. 2003:426.789-96) The recognition phenotypes of EBV-LCLs by Vγ9Vδ2 TCR T cells can be assessed by means of IFNγ production. Using either CD4$^+$ or CD8$^+$ Vγ9Vδ2 T cells one can either reduce or increase the effect of NK like receptors on the phenotypic analysis. CD4$^+$ T cells express low amount of NK like receptors resulting in ease of analysis. Hypothetical zygosities for candidate genetic loci can be deduced using classical Mendelian inheritance patterns within CEPH family trios, where the influence of candidate alleles on receptor mediated recognition, for instance Vγ9Vδ2 TCR-mediated recognition can be assumed to be dominant. In one embodiment, the recognition phenotypes of EBV-LCLs by Vγ9Vδ2 TCR T cells assessed by means of IFNγ production can show an activating phenotype for a subset of EBV-LCLs and a non-activating phenotype for another subset of EBV-LCLs. Zygosities of activating and non-activating EBV-LCL subsets can then be predicted using recognition phenotypes combined with family pedigrees of the CEPH cell lines. Hypothetical loci zygosities can then be correlated with available genotype information of SNPs with the study's population, resulting in identification of SNPs whose genotypes have a strong correlation with predicted zygosities. Herein, "strong correlation" can refer in some embodiments to greater than 80%, greater than 85%, greater than 90%, greater than 95%, or greater than 99%.

In some embodiments, identified SNPs can be located on a chromosome proximal to a corresponding gene which is capable of impacting (e.g. via upregulation or downregulation of the gene) the immune activation of a cell expressing a T-cell receptor (e.g. Vγ9Vδ2 TCR T cells). In some embodiments, "proximal" refers to greater than 10,000 bp, greater than 50,000 bp, greater than 100,000 bp, greater than 200,000 bp, greater than 300,000 bp, greater than 500,000 bp or greater than 1 Mbp. In other embodiments, an identified SNP can be located on a different chromosome than a corresponding gene capable of impacting (e.g. via upregulation or downregulation of the gene) the immune activation of a cell expressing a T-cell receptor (e.g. Vγ9Vδ2 TCR T cells).

The description and examples illustrate embodiments of the invention in detail. It is to be understood that this invention is not limited to the particular embodiments described herein and as such can vary. Those of skill in the art will recognize that there are numerous variations and modifications of this invention, which are encompassed within its scope.

EXAMPLES

These examples are provided for illustrative purposes only and not to limit the scope of the claims provided herein.

Example 1. Identification of Genetic Loci Associated with Vγ9Vδ2 TCR-Mediated Target Cell Recognition by SNP-Associated Computational Pathway Hunt Including shRNA Evaluation (SAPPHIRE)

Figure 2C:
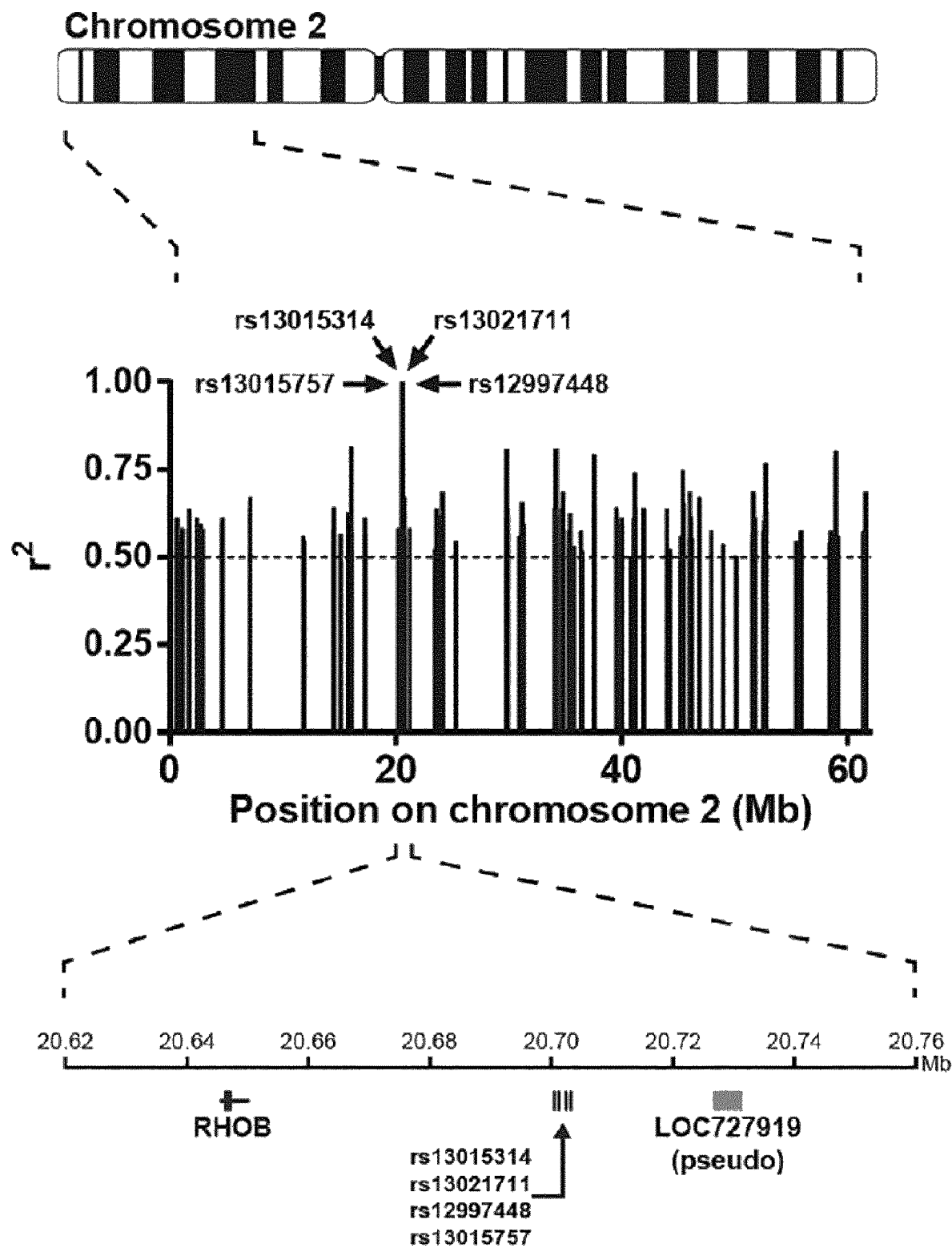

Differences in the genetic backgrounds of tumor cells affect recognition of these tumor cells by Vγ9Vδ2 TCR engineered T cells. Therefore, the library of cell lines from the Centre d'Etude du Polymorphisme Humain (CEPH) was utilized which contains a large collection of EBV-transformed B cell lines (EBV-LCLs) obtained from several family pedigrees (Dausset et al., 1990) and genotyped for millions of SNPs (International HapMap, 2003). CD4+αβT cells engineered to express one defined Vγ9Vδ2 TCR were utilized for the functional screening in order to eliminate fluctuations in recognition by a diverse γδTCR repertoire and varying expression of NK receptors. The recognition phenotypes of EBV-LCLs by Vγ9Vδ2 TCR T cells were assessed by means of IFNγ production and showed an activating phenotype for 33 EBV-LCLs, while 7 were non-activating (FIGS. 1A and 1B). A zygocity analysis revealed EBV-LCLs with a non-activating phenotype represent more power than those with an activating phenotype as analyzed with SAPPHIRE. Hypothetical zygosities for candidate genetic loci were deduced using classical Mendelian inheritance patterns within CEPH family trios, where the influence of candidate alleles on Vγ9Vδ2. TCR-mediated recognition was assumed to be dominant. The resulting recognition phenotypes combined with family pedigrees of the CEPH cell lines overcame the need to screen large numbers of LCL lines, and allowed the precise prediction of zygosities of candidate loci for 12 CEPH individuals (FIG. 2A. The hypothetical loci zygosities were then correlated with available genotype information of SNPs within the study's population, resulting in the identification of 17 SNPs whose genotypes correlated perfectly (100%) with predicted zygosities (FIG. 2B). Since none of these 17 SNPs, nor their proxy SNPs within high linkage disequilibrium ($r^2>0.8$), directly affected genes by causing changes in protein coding sequences, it was speculated that rather than playing direct roles, the SNPs identified could represent surrogate markers for genetic regions associated with susceptibility to Vγ9Vδ2 TCR+ T cell recognition. In addition, the genomic vicinity of the 17 SNPs were queried for neighboring candidate genes (FIG. 2C).

Figure 3A:
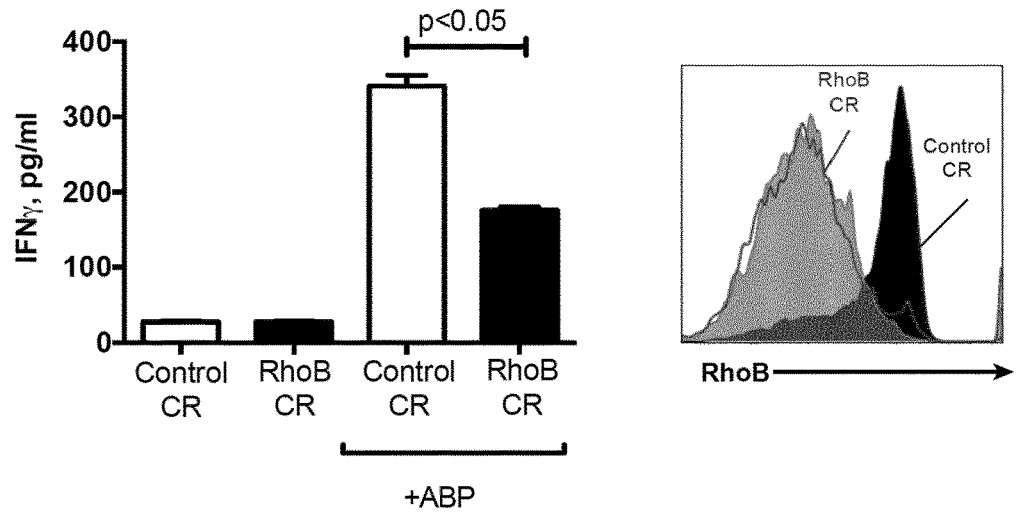
FIG. 3A shows RhoB was knocked out in 293 HEK cells using CRISPR/Cas system, and single cell clones were selected for stable complete knock out phenotype, and the effect of complete knock out on recognition by Vγ9Vδ2 TCR+ T cells was assessed by measuring IFNγ (left panel). A guide RNA targeting an irrelevant sequence was used as the control. Level of knock out was determined using intracellular flow cytometry (right panel). Data show mean±S.E.M of two independent experiments in duplicate samples, where Mann-Whitney test was used to analyze statistical significance.
Figure 3B:
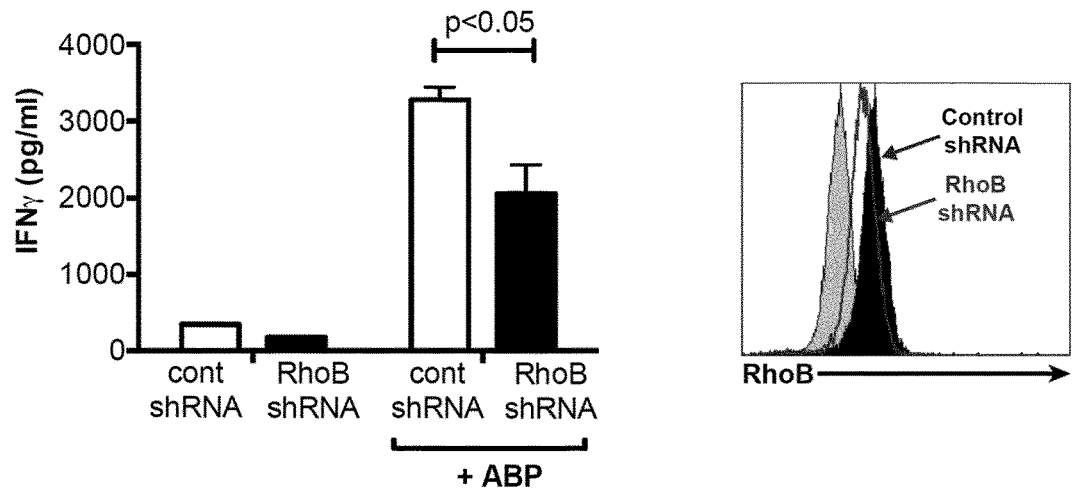
FIG. 3B shows Daudi cells were lentivirally transduced with shRNA targeting RhoB, and the effect of RhoB knockdown on recognition of a cell expressing surface CD277, by engineered cells expressing polypeptide constructs described herein was assessed by measuring IFNγ (left panel). Data show mean±S.E.M of three independent experiments in duplicate samples, where Mann-Whitney test was used to analyze statistical significance. A vector encoding an irrelevant shRNA served as negative control. Knock-down level of RhoB was determined by intracellular flow cytometry (right panel)
Figure 3C:
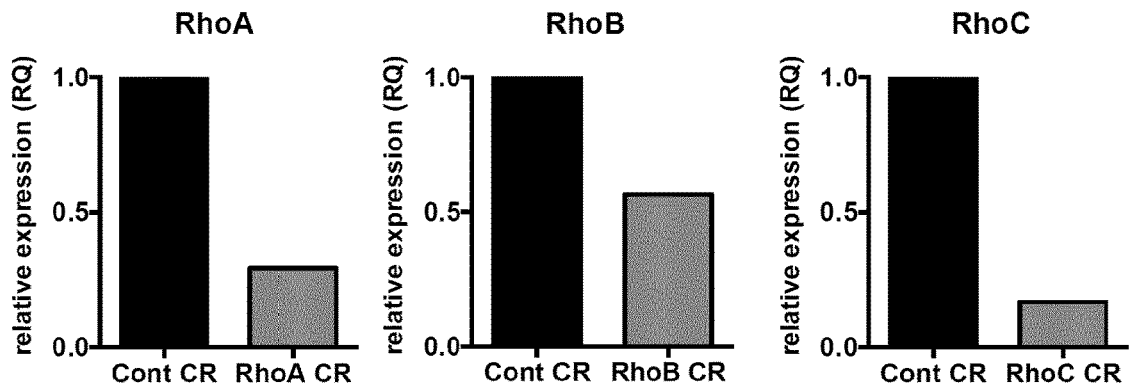
FIG. 3C shows RhoA, B and C were knocked out using CRISPR/Cas system in 293 HEK cells. A guide RNA targeting an irrelevant sequence was used as control. Level of knock out was determined using qPCR. Figure shows a representative experiment.
Figure 3D:
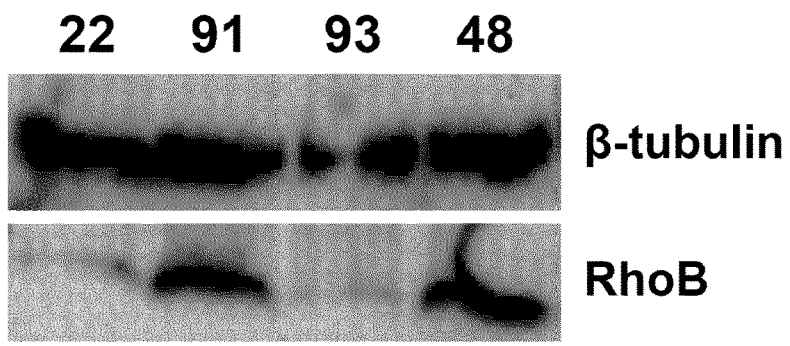
FIG. 3D shows RhoB protein levels were measured in the recognized EBV-LCL lines 48 and 91 and the non-recognized line 22 and 93 by western blot analysis. β-tubulin served as the loading control. Figure shows a representative experiment.
Figure 3E:
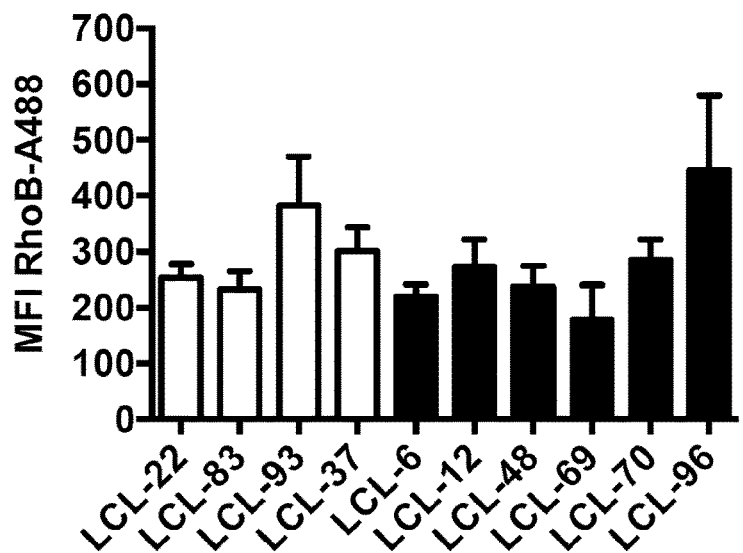
FIG. 3E shows RhoB protein levels were measured in the recognized EBV-LCL lines 6, 12, 48, 69, 70 and 99 and the non-recognized line 22, 83, 93 and 37 by intracellular flow cytometry analysis. Data show mean±S.E.M of at least three independent experiments.
Figure 4A:
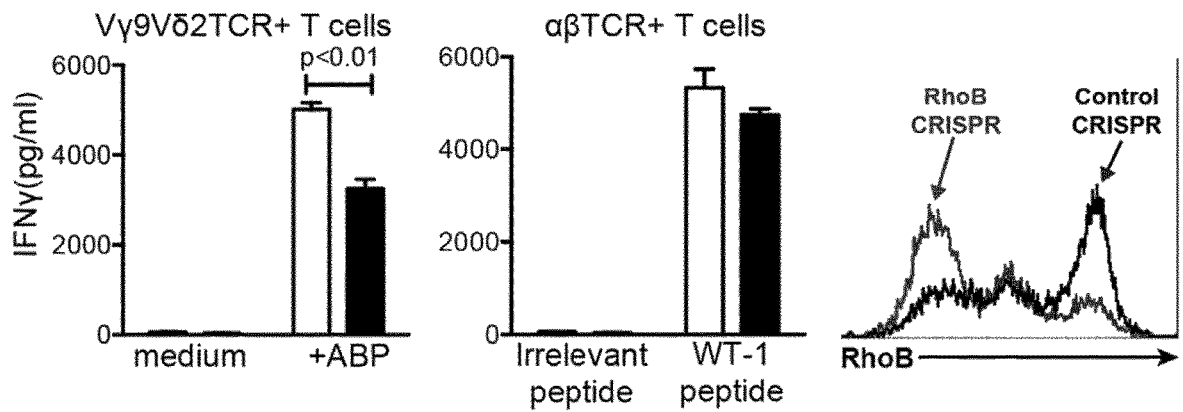
FIG. 4A-4E shows RhoB activity correlates with target cell recognition by engineered cells expressing polypeptide constructs described herein, based on the binding of said polypeptide constructs with the J-configuration of CD277.

To test the relevance of these genes for Vγ9Vδ2 TCR+ T cell-mediated target recognition, we knocked down all 17 SNP-adjacent genes in the Vγ9Vδ2 TCR+ T cell-activating EBV-LCL line 48. We then assessed the effect of knockdown on activation of Vγ9Vδ2 TCR+ T cells by measuring IFNγ production, which was reduced upon the knockdown of three genes (RAB4A, RHOB and UBE3C) (FIG. 2B). To ensure that potential knockdown effects pointed to genes that selectively affect Vγ9Vδ2 TCR-dependent activation, the three knockdown variants of EBV-LCL line 48 were pulsed with Wilm's tumor 1 (WT1) peptide and tested for recognition with T cells engineered to express the cognate WT1-specific αβTCR (Kuban et al., 2007). The selective knockdown of the small GTPase RhoB significantly affected the activation of Vγ9Vδ2 TCR—but not αβTCR-engineered T cells (FIG. 2B). Similar data were observed after partial knock down of RhoB in the prototypic Vγ9Vδ2 T cell target cell line Daudi (FIG. 3B), as well as after CRISPR/Cas-mediated partial RhoB knock out in the renal carcinoma cell line MZ1851RC (FIG. 4A). Interestingly, even complete knock out of RhoB in 293 HEK cells resulted only in partial depletion of target cell mediated Vγ9Vδ2 TCR T cell activation (FIG. 3A). In addition, knock out of either RhoA or RhoC genes in 293 HEK cells did not significantly influence their ability to activate Vγ9Vδ2 TCR+ T cells (FIG. 4B and FIG. 3C), emphasizing that RhoB modulates the recognition of tumor cells by a defined Vγ9Vδ2 TCR in a non-redundant role.

Figure 4B:
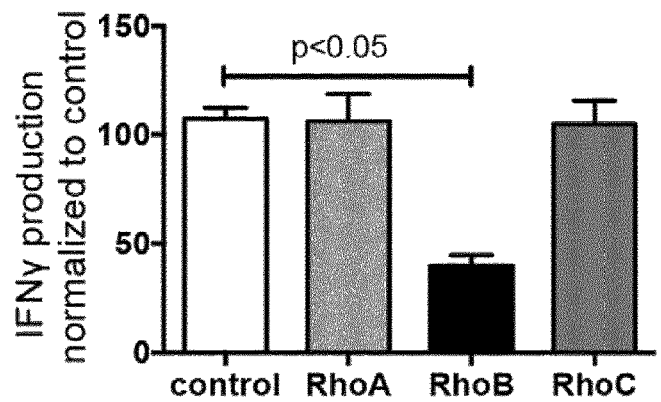
Figure 4C:
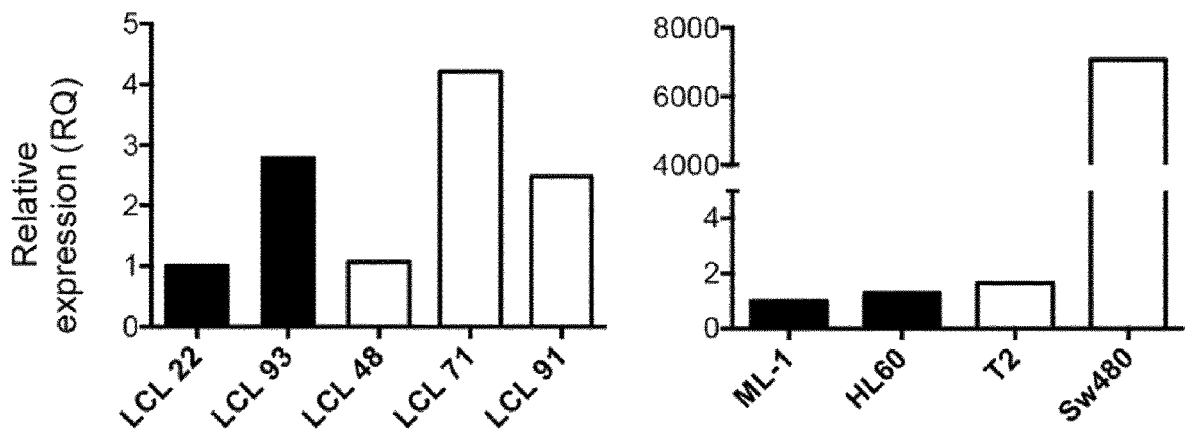
Figure 4D:
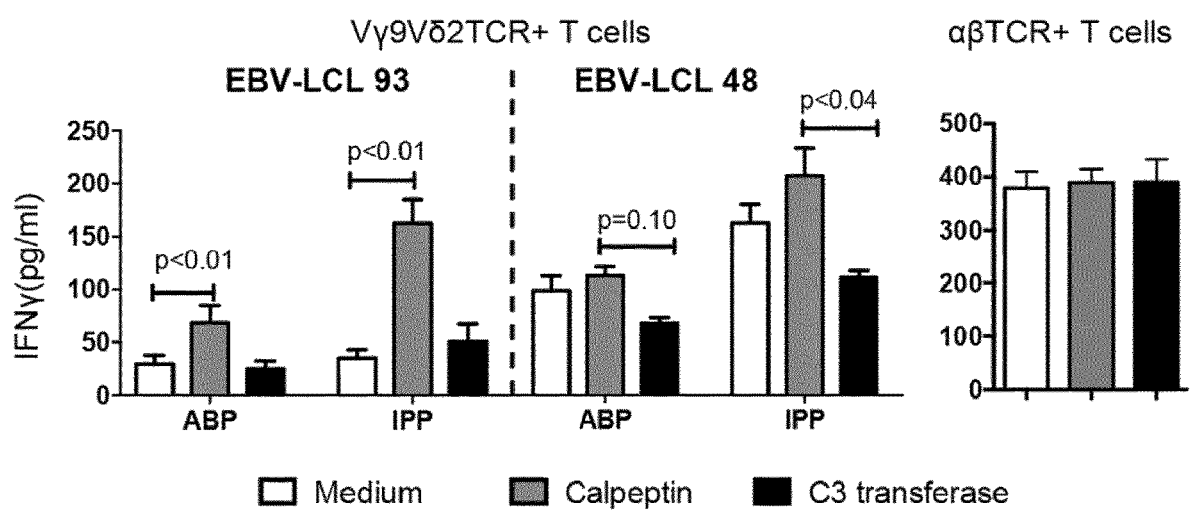
Figure 4E:
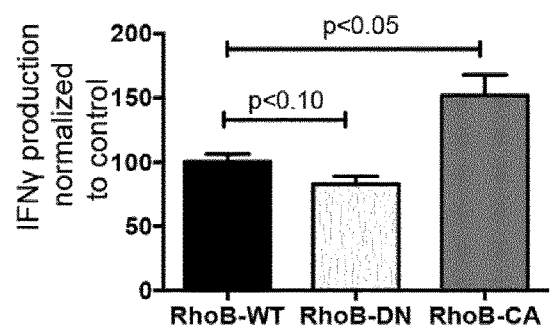

Example 2. Recognition of J-Configuration of CD277 on Target Cell by Polypeptide Constructs Described Herein Depends on Rho GTPase Activity The impact of RhoB GTPase activity on Vγ9Vδ2 TCR+ T cell activation was assessed by preheating different tumor cell lines with either the Rho GTPase activator calpeptin or inhibitor C3 transferase. Pretreatment with calpeptin significantly sensitized EBV-LCL 93 cells for recognition by Vγ9Vδ2 TCR+ T cells while, conversely, inhibition of Rho GTPase with C3 transferase resulted in significantly reduced activation of Vγ9Vδ2 TCR+ T cells by LCL 48 cells (FIG. 4D). Modulation of Rho GTPase activity did not affect the recognition of WT1 peptide-pulsed EBV-LCL 48 cells by WT1 αβTCR-transduced T cells. To specify that enzymatic activity of RhoB regulates tumor cell recognition by Vγ9Vδ2 TCR+ T cells, we transfected HEK 293 cells with wildtype or dominant negative form corresponding to the GDP-bound state (RhoB-DN), or with the constitutively active form corresponding to the GTP-bound form (RhoB-CA) of RhoB (Kamon et al., 2006) and used them as target cells for Vγ9Vδ2 TCR+ T cells (FIG. 4E). HEK cells overexpressing RhoB-CA mutants were able to trigger significantly stronger Vγ9Vδ2 TCR-specific responses than cells expressing wild type RhoB, while RhoB-DN-transfected HEK cells showed a significantly reduced ability to stimulate Vγ9Vδ2 TCR+ T cells compared to cells expressing wildtype RhoB. These results suggest that modulating the biochemical activity of RhoB GTPases in cancer cells can be useful for the recognition of those cancer cells by engineered cells expressing a polypeptide that selectively binds the J-configuration or J-confirmation of CD277, for instance, Vγ9Vδ2 TCR+ T cells.

Figure 5A:
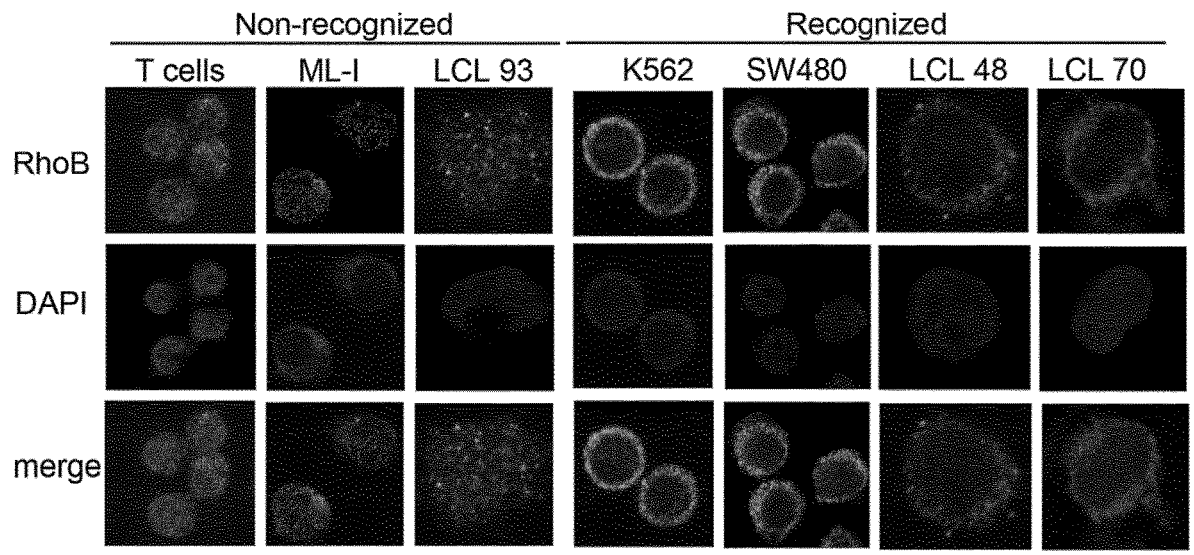
FIG. 5A shows non-recognized healthy T cells, leukemic cell line ML-I and EBV-LCL 93 cells, and recognized leukemia cell line K562, colon carcinoma cell line SW480, EBV-LCL 48 and EBV-LCL 70 cells were treated with pamidronate and loaded onto poly-L-lysine-coated coverslips. Attached cells were fixed and permeabilized, and stained using RhoB-specific antibody followed by an Alexa Fluor 488-conjugated secondary antibody. RhoB distribution was subsequently analyzed by confocal microscopy and representative images are shown (white: RhoB.
Figure 5B:
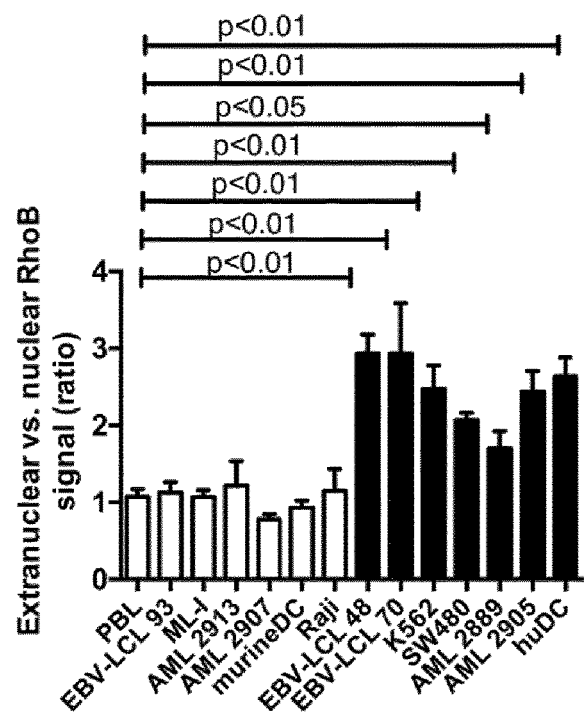
FIG. 5B shows T cells from healthy donors, EBV-LCL line 93, 48 and 70, tumor cell lines ML-I, K562, SW480, Raji, primary AML blasts AML2913, AML2907, AML2889, AML2905, and murine and human DCs were treated with pamidronate and analyzed for the intracellular distribution of RhoB in confocal microscopy. White bars represent target cells with a non-activating phenotype, while black bars indicate target cells that are able to activate engineered cells expressing polypeptide constructs described herein. The RhoB signal ratio between nuclear and extra nuclear cellular compartments was measured using ImageJ image analysis software. Graphs show average ratios of at least 10 different cells+S.E.M. Statistical significance compared to PBL was determined by using Kruskal-Wallis test and Dunn's multiple comparison test.
Figure 5C:
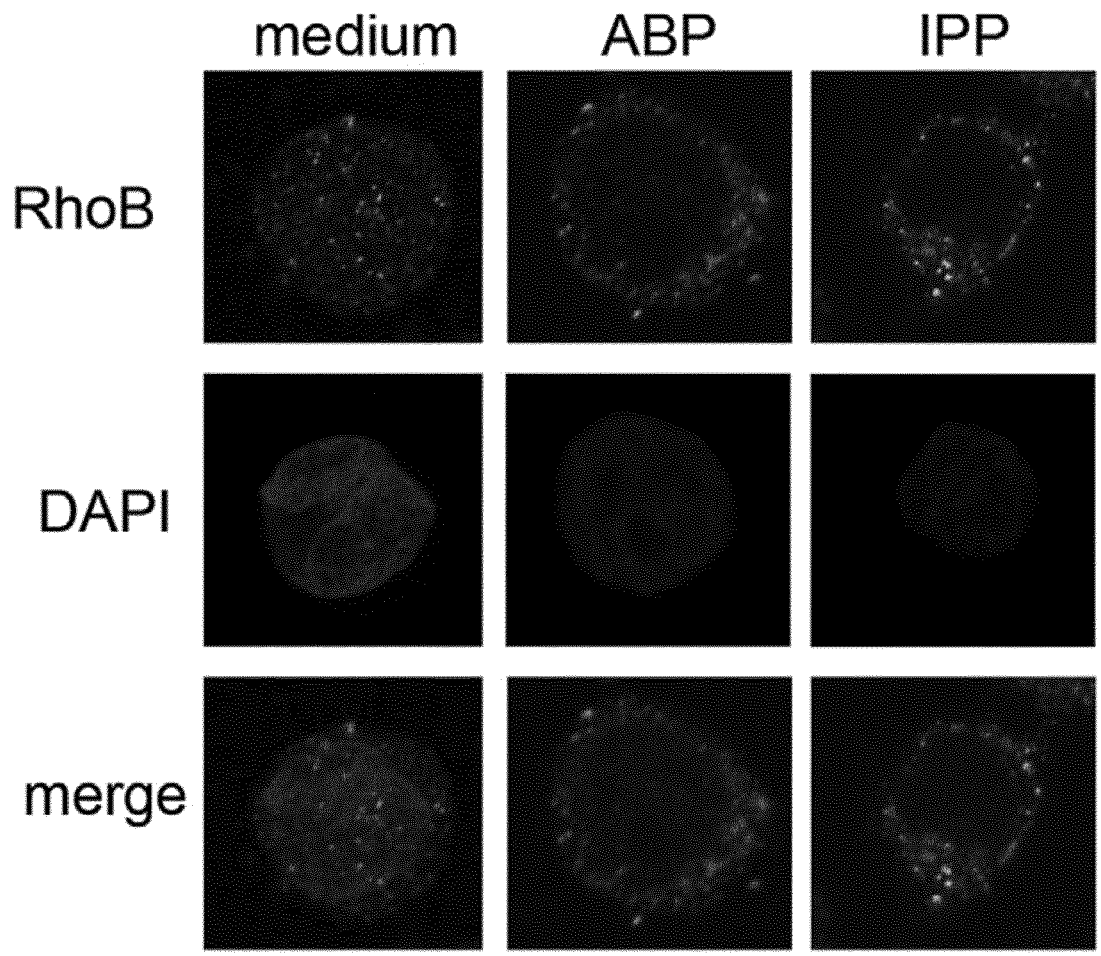
FIG. 5C shows the intracellular RhoB distribution and FIG. 5D the extranuclear/nuclear RhoB signal ratios, with ABP pamidronate and soluble IPP sensitization for recognized, ABP/IPP-sensitive EBV-LCL 48 analyzed as in A and B. Graphs show average ratios of at least 10 different cells+ S.E.M. Statistical significance compared to untreated EBV-LCL 48 was determined by using Mann-Whitney test.
Figure 5D:
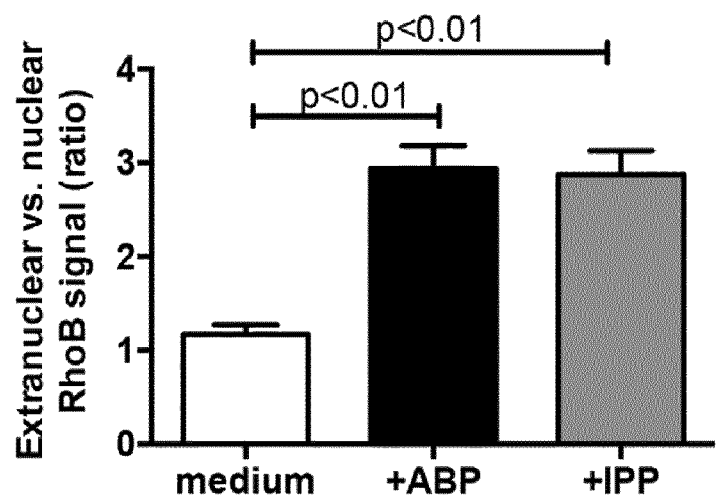
FIG. 5 shows intracellular distribution of RhoB correlates with the recognition of J-configuration of CD277 in target cells by engineered cells expressing polypeptide constructs described herein.
FIG. 5E shows the intracellular RhoB distribution in the presence or absence of ABP pamidronate was determined in monocyte derived human dendritic cells from two different donors. Bone marrow derived mouse dendritic cells (>95% CD11c+) were treated with ABP pamidronate and used for intracellular labeling of RhoB. Graphs show average ratios of at least 10 different cells+S.E.M. Statistical significance compared to LPS treated human DCs was determined by using Mann-Whitney test.
FIG. 5F shows CD34+CD38− leukemic stem cells were sorted from four patients of which leukemic blasts were recognized (AML 2889, AML 1665, AML 2575) and non-recognized (AML 2907), respectively, and the ratios between extranuclear and nuclear RhoB signal was measured. Graphs show average ratios of at least 10 different cells+S.E.M. Statistical significance compared to CD34+CD38− healthy stem cells was determined by using Mann-Whitney test.
Figure 5E:
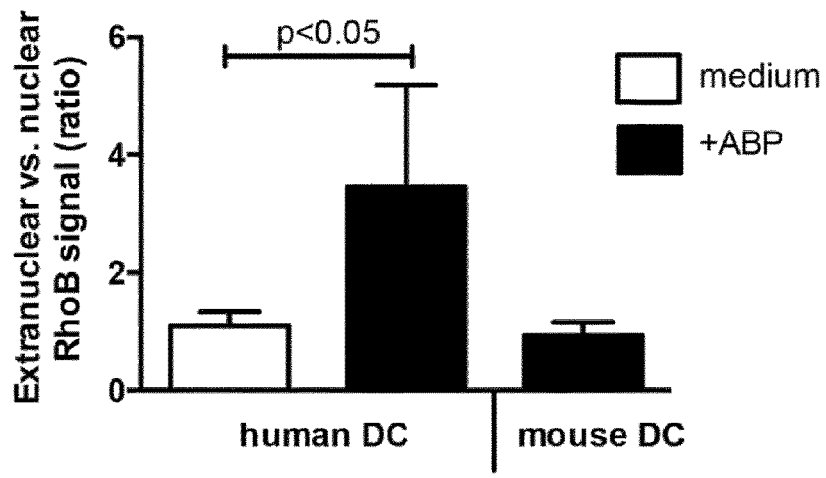
Figure 5F:
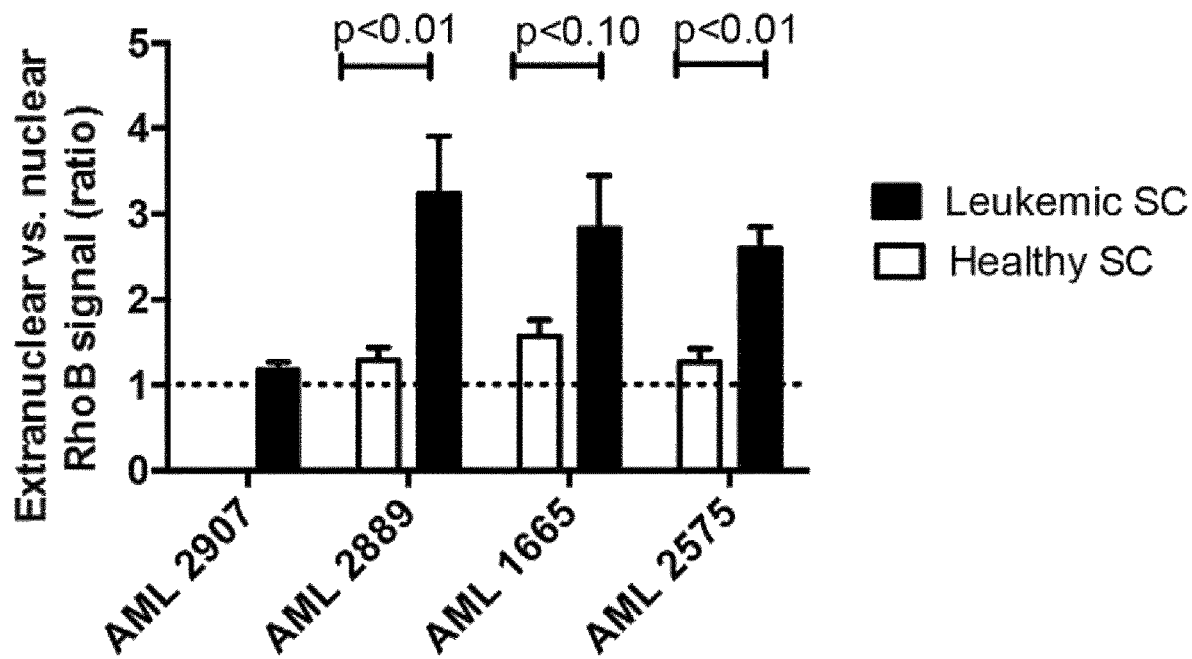
Figure 6A:
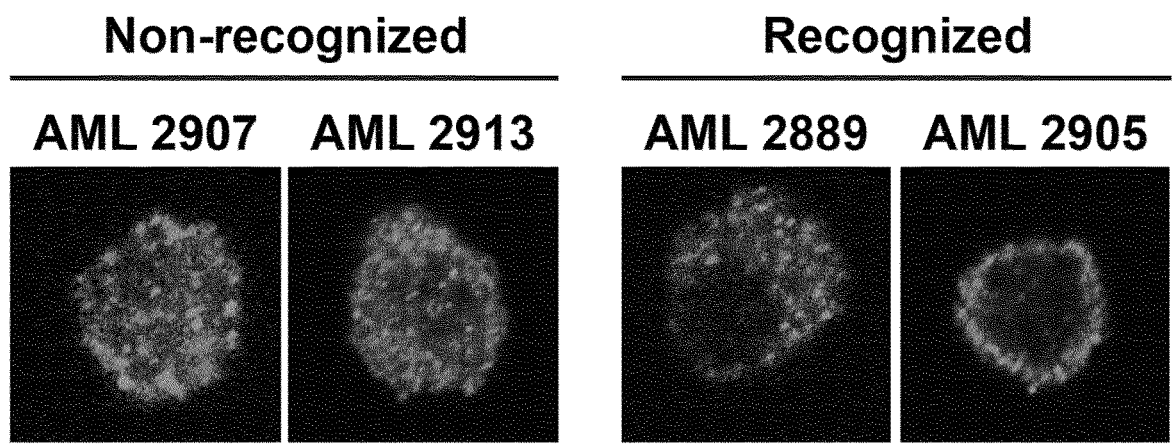
FIG. 6A shows representative images for the intracellular distribution of RhoB in recognized and non-recognized primary AML samples.
Figure 6B:
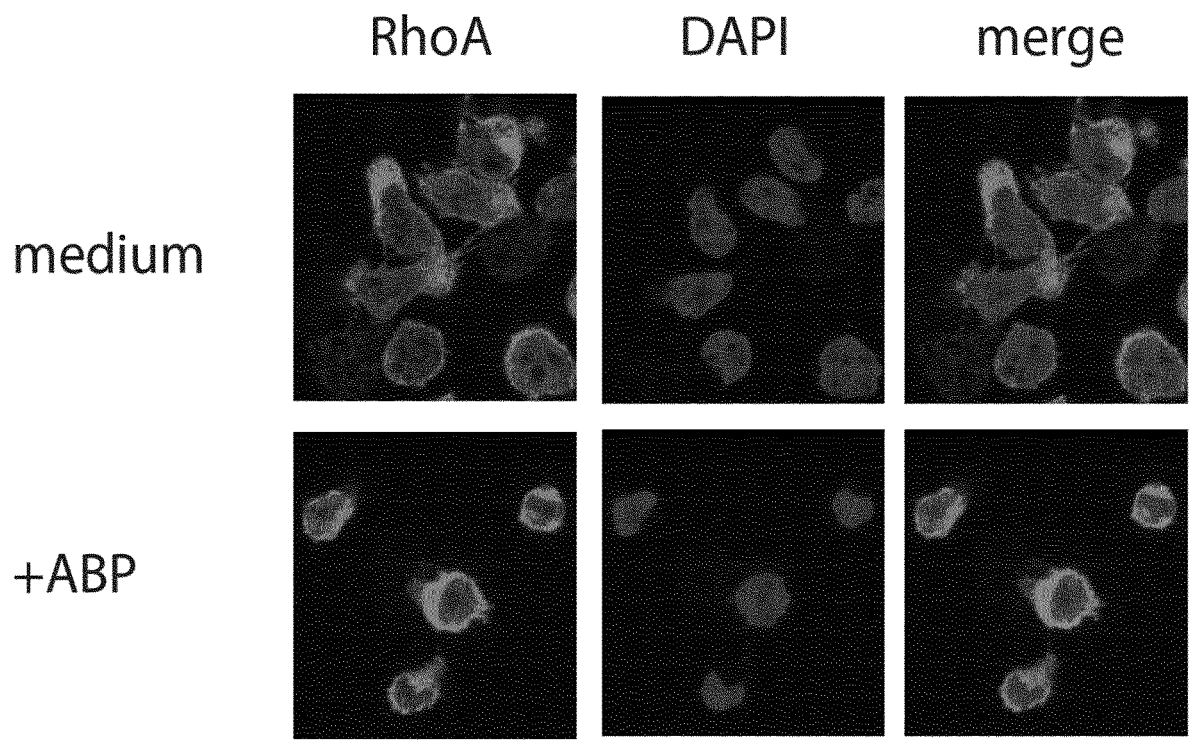
FIG. 6B shows the intracellular RhoA distribution in the presence or absence of ABP pamidronate was measured via confocal microscopy in EBV-LCL 48.
Figure 6C:
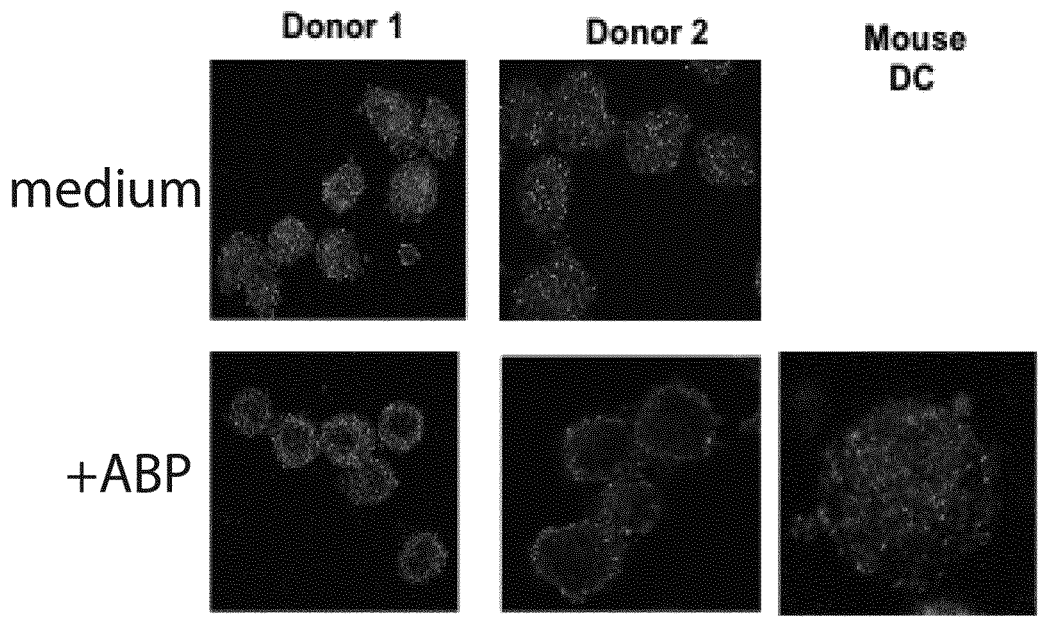
FIG. 6C shows the intracellular RhoB distribution in the presence or absence of ABP pamidronate was determined in monocyte derived human dendritic cells from two different donors. Mouse bone marrow derived dendritic cells (>95% CD11c+) were treated with ABP pamidronate and used for intracellular labeling of RhoB.
Figure 6D:
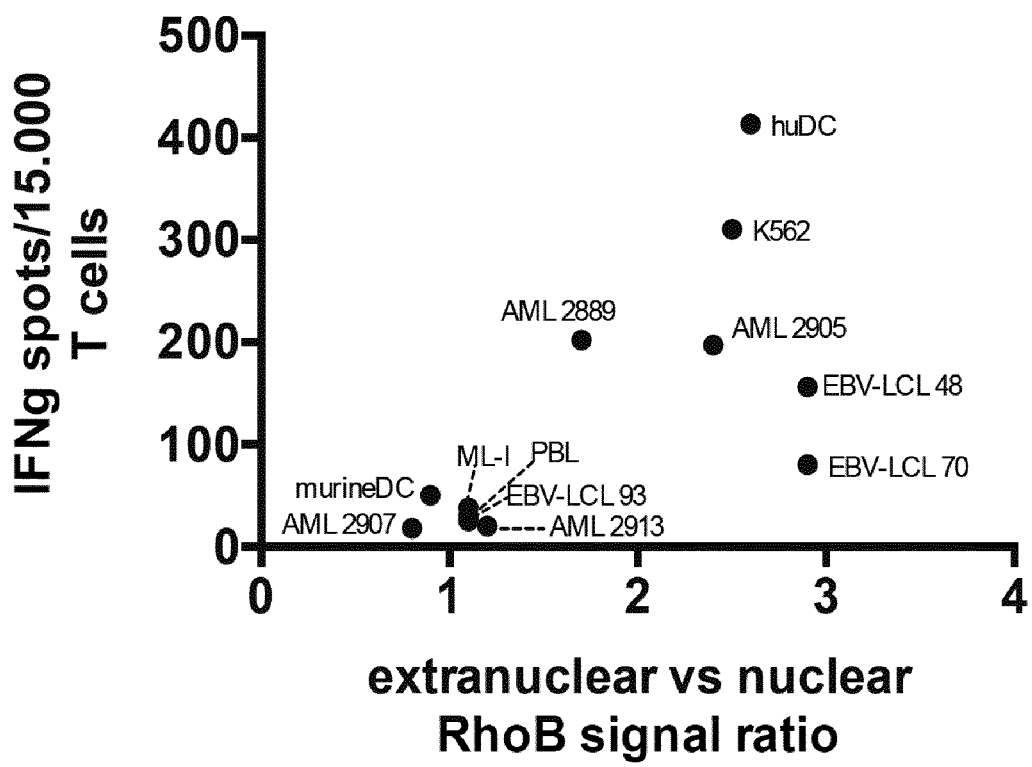
FIG. 6D shows the correlation of intracellular RhoB distribution to Vγ9Vδ2TCR T cell activation capacity of tumor target cells. Mean values of the extranuclear: nuclear RhoB intensity ratio in tumor cells were plotted against the number of IFNg spots when the same tumor cells were co-cultured with engineered cells expressing polypeptide constructs described herein.

Example 3. Recognition of J-Configuration of CD277 on Target Cell Depends on Intracellular Distribution of RhoB RhoB was selectively excluded from nuclear areas in cells that are able to activate Vγ9Vδ2 TCR+ T cells (FIG. 5A, FIG. 5B, FIG. 6A and FIG. 6D). Re-localization of RhoB from the nucleus, or from the nuclear membrane to extra-nuclear sites was induced by ABP as well as by soluble phosphoantigen IPP in cell lines (FIG. 5C and FIG. 5D), emphasizing that this process is dependent on accumulation of intracellular phosphoantigen. The homogenous intracellular distribution of other GTPases such as RhoA did not change upon ABP treatment (FIG. 6B), supporting the observation that RhoA knock down did not impact Vγ9Vδ2 TCR-mediated recognition (FIG. 4B). RhoB was excluded from the nucleus in human, but not in mouse dendritic cells selectively treated with ABP, even though RhoB protein sequences are identical in both species (FIG. 5E and FIG. 6C). In order to test whether redistribution of RhoB occurs upon ABP treatment in leukemic cancer stem cells also, leukemic blasts, cancer stem cells and healthy stem cells were sorted from the very same donor based on flow markers and distribution of RhoB was quantified. Indeed, in primary blasts from an acute myeloid leukemia patient donor, RhoB localization correlated with the recognition by Vγ9Vδ2 TCR-engineered T cells (FIG. 5B and FIG. 6A) including leukemic stem cells, but not healthy stem cells from the same donor (FIG. 5F). Taken together, these results suggest modulating intracellular distribution of the small GTPase RhoB (e.g., exclusion of RhoB from the nucleus) in tumor cells would increase their susceptibility to targeting by Vγ9Vδ2 TCR+ T cells.

Figure 7A:
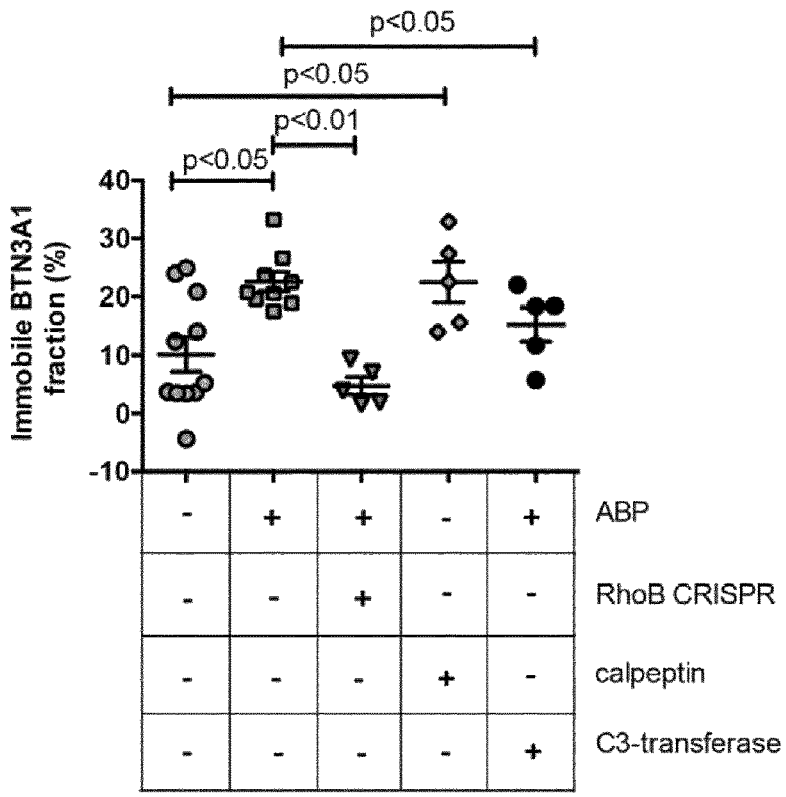
FIG. 7A-7B show RhoB activity modulates CD277 membrane mobility and its association with the actin cytoskeleton, thereby modulating formation of the J-configuration of CD277.

Example 4. RhoB Regulates Membrane Mobility of CD277, and the Formation of J-Configuration of CD277 on Cancer Cells The impact of ABP and RhoB, an important player in the cytoskeletal reorganization and formation of actin stress fibers, on mobility of CD277 was tested. Treating 293 HEK cells with the ABP zoledronate resulted in decreased CD277 membrane mobility. Strikingly, treatment with calpeptin induced immobilization of CD277 to similar levels as those of ABP treatment alone, while C3-transferase counteracted this ABP-effect (FIG. 7A). This points to the possibility that Rho GTPase activity acts on CD277 membrane immobilization upstream of the mevalonate pathway. Selective depletion of RhoB by CRISPR/Cas inhibited the ABP-induced immobilization of CD277 to levels comparable to those of medium controls, suggesting that ABP-mediated changes in CD277 mobility depend on RhoB.

Figure 7B:
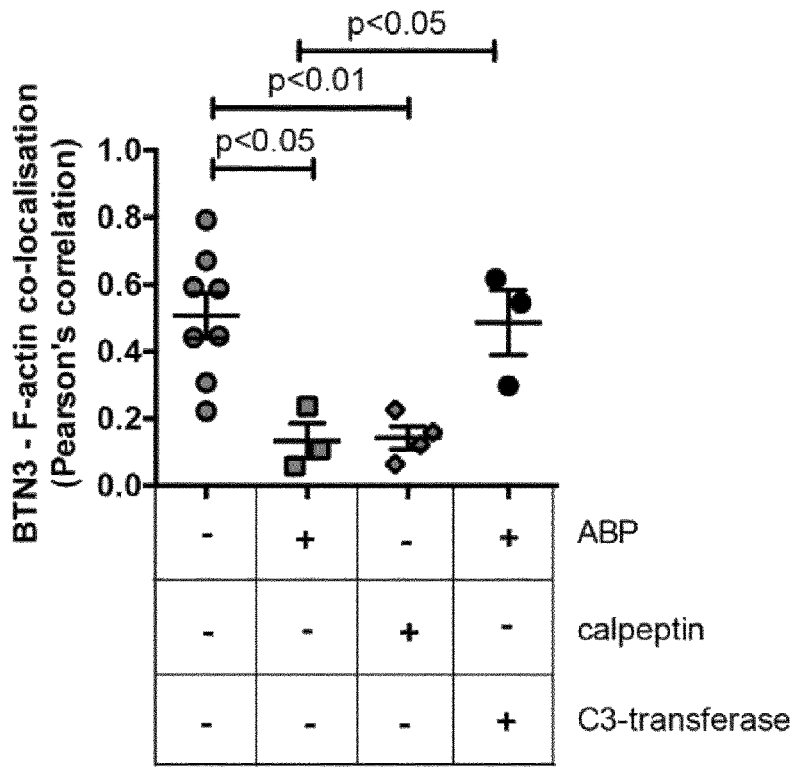

To next assess a role for RhoB-induced cytoskeletal rearrangements in mediating the observed changes in CD277 mobility, and J-configuration formation, the relation between CD277 molecules and F-actin was investigated by tantalization experiments. HEK 293 cells were stained with fluorescently labeled anti-CD277 and phalloidin, and tantalization coefficients were determined in response to treatment with ABP and calpeptin. In cells in a culture medium, a variable but considerable colocalization between CD277 and F-actin was observed, and was markedly reduced by ABP treatment (FIG. 7B). Strikingly, and similar to its effect on CD277 membrane mobility, calpeptin reduced tantalization between CD277 and F-actin to comparable levels observed with ABP treatment. This reduction suggests that both phosphoantigen accumulation and Rho activation can induce the formation of membrane domains surrounded by cytoskeleton, where CD277 molecules could be trapped and immobilized to form the J-configuration of CD277. Importantly, C3-transferase prevented ABP-induced CD277-actin segregation, indicating again the crucial involvement of active Rho in this process. Together, these data suggest that modulating CD277 membrane mobility through cytoskeletal rearrangements and forming the J-configuration of CD277 contributes to target recognition by engineered cells that express polypeptides that specifically bind the J-configuration, such as Vγ9Vδ2 TCR+ T cells.

Figure 8A:
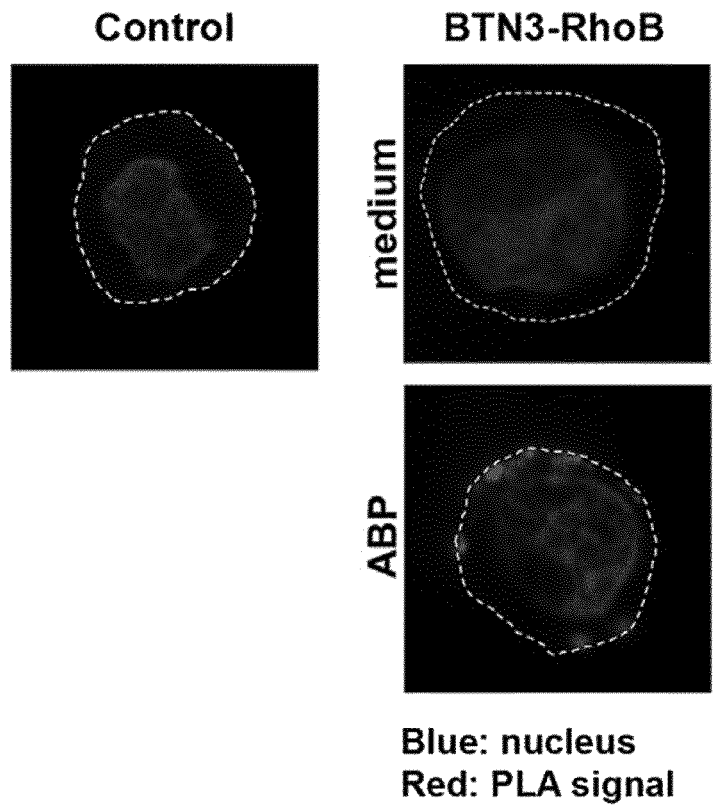
FIG. 8A-8E show RhoB interacts with CD277 molecules forming the J-configuration of CD277, and dissociates after phosphoantigen treatment.

Example 5. RhoB Interacts with CD277 Homodimers in Cancer Cells Recognized by Polypeptide Constructs Described Herein, for Instance Vγ9Vδ2 TCRs Given the strong requirement for RhoB activity in the membrane immobilization of CD277 to form the J-configuration, whether or not regulation of CD277 involves direct interactions with RhoB was tested. Using in sin/proximity ligation assay (PLA), RhoB and CD277 were observed to be in close proximity in recognized EBV-LCL 48 cells only when pretreated with the ABP (FIG. 8A FIG. 5A). Importantly, PLA signals were typically excluded from the nuclear area and distributed close to the plasma membrane, in line with our data that RhoB is involved in Vγ9Vδ2 TCR+ T cell recognition by regulating formation of J-configuration of membrane-expressed CD277.

Figure 8B:
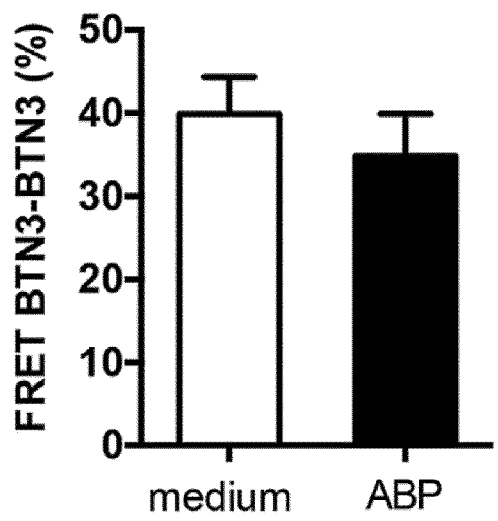
Figure 8C:
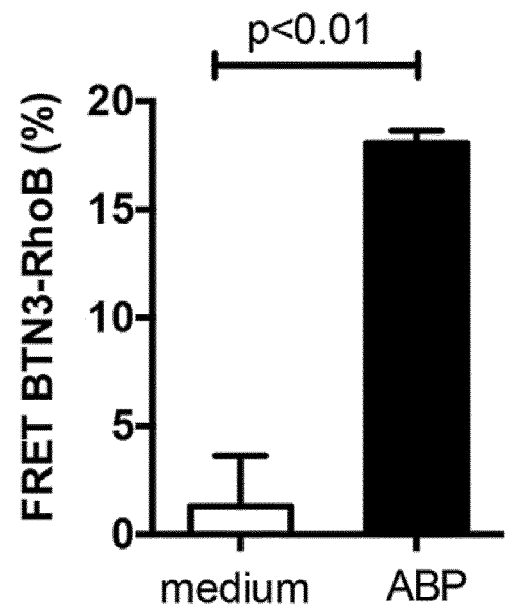
Figure 8D:
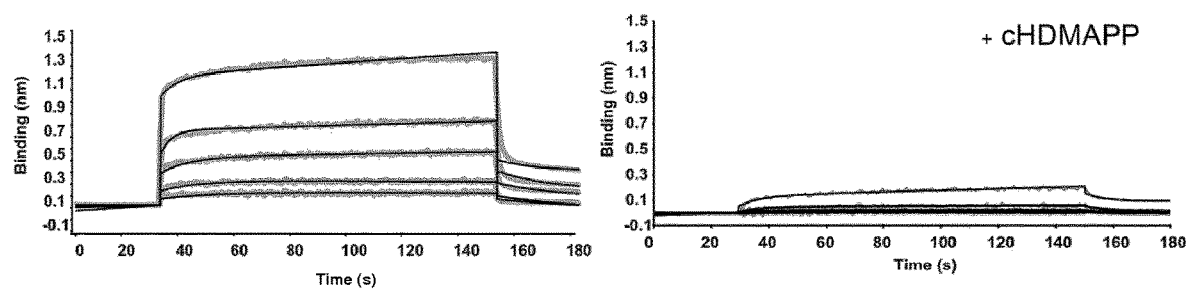
Figure 8E:
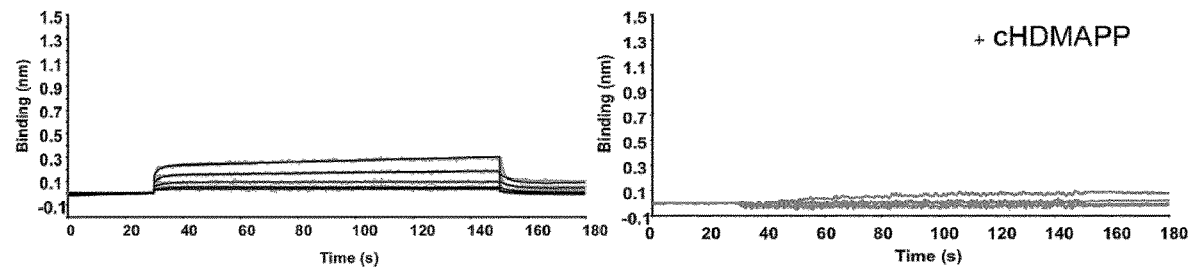
Figure 9A:
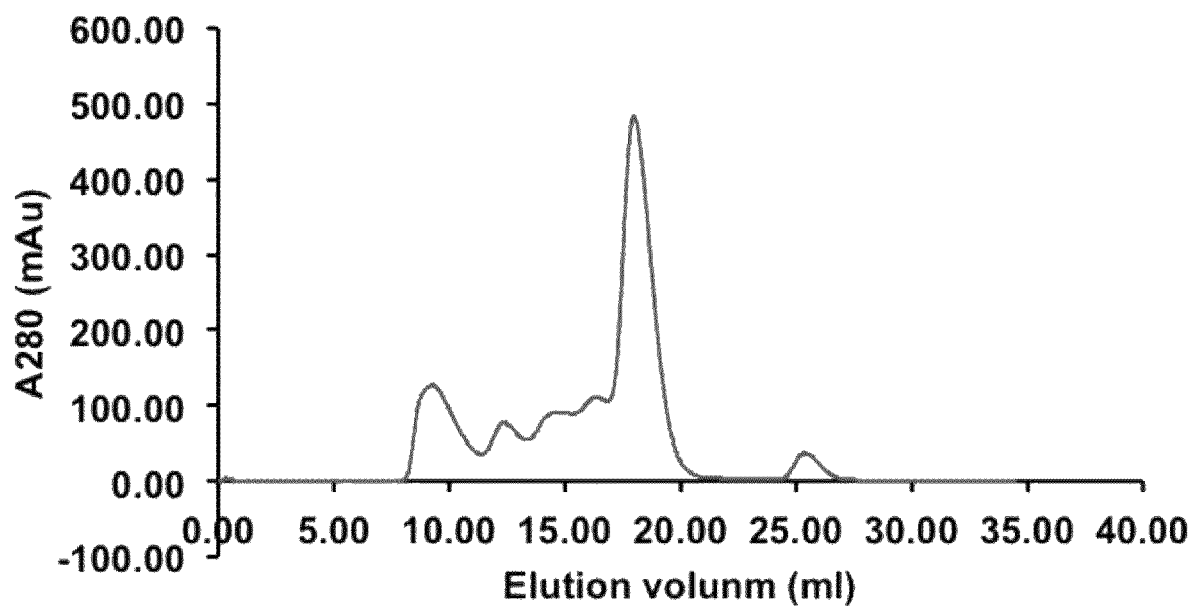
FIG. 9A Gel filtration profile of RhoB GTPase expressed in E coli. The peak from 17.8 ml to 19.2 ml contained purified RhoB GTPase monomer.
Figure 9B:
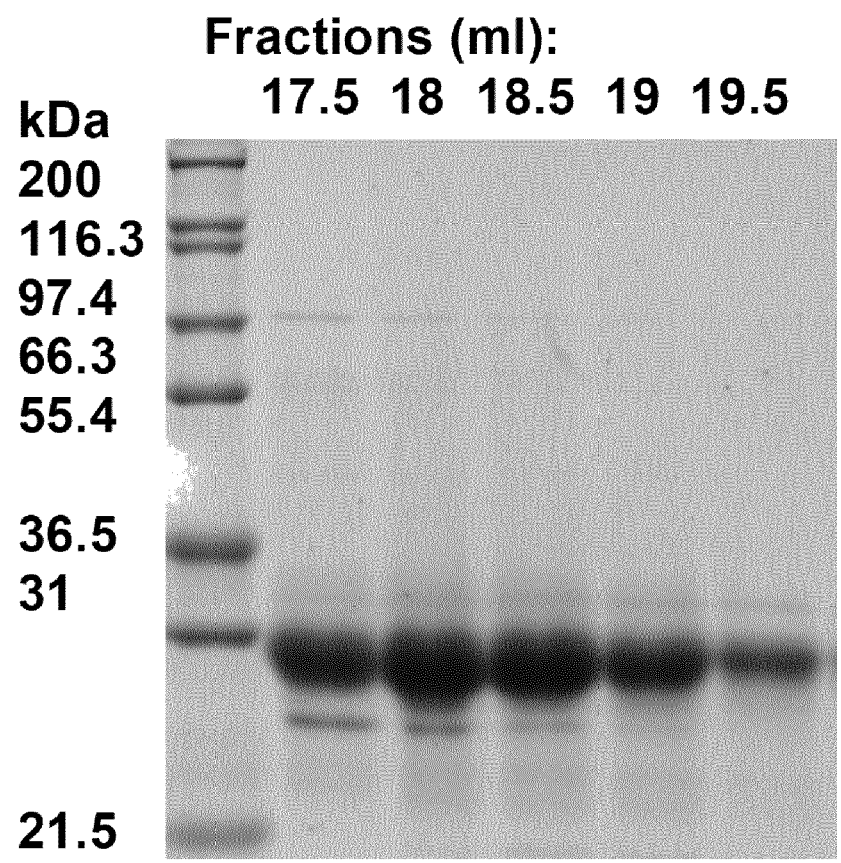
FIG. 9B shows SDS-PAGE showing the fractions (17.5-19.5 ml, 0.5 ml/fraction) containing RhoB GTPase collected from the gel filtration experiment.
Figure 9C:
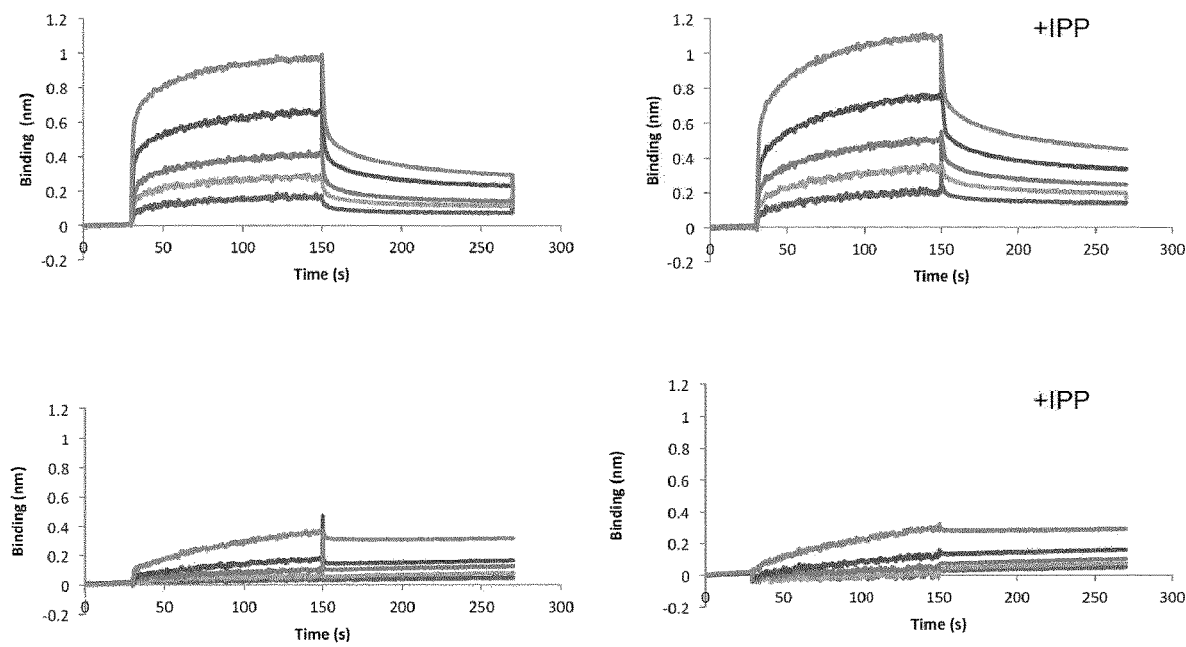
FIG. 9C shows concentration dependent binding of the full-length CD277 intracellular domain (BFI) with RhoGTPase in the presence or absence of the phosphoantigen IPP (upper panels). Binding of BFI to RhoGTPase was measured using Biolayer Interferometry (BLI) either in the absence of IPP (left panel) or presence of IPP (1:1) (right panel). Concentrations of CD277 BFI shown are 3.75, 7.5, 15, 30 and 60 uM shown in grey. Same experimental setup but with recombinant CD277 B30.2 domain, lacking the N terminal region connector to the transmembrane domain (lower panels). In the left panel, the interaction was measured without IPP. Concentrations of CD277 B30.2 shown were 3.75, 7.5, 15, 30 and 60 uM shown in grey. In the right panel, the interaction was measured with IPP (1:1).

To determine whether CD277 exists as a homodimer when expressed in a cellular context, and to study RhoB-CD277 interactions at even higher resolution, close interactions by utilizing fluorescence resonance energy transfer (FRET) were examined. Flow cytometry FRET measurements were performed on ABP-sensitive HEK 293 cells, by either overexpressing FRET compatible fusion proteins or labeling endogenous proteins with antibodies coupled to FRET-compatible fluorochromes. These experiments showed that CD277 molecules are expressed as homodimers on the cell surface of cancer cells (FIG. 8B), however the pairing of CD277 molecules was insensitive to ABP-induced phosphoantigen accumulation. Close association between RhoB and CD277 was undetectable in ABP-untreated HEK cells, but increased markedly after treating cells with the ABP (FIG. 8C). Biolayer Interferometry (BLI) was used to formally define a possible docking site for RhoB on the intracellular domain of CD277. RhoB binding was detected with recombinant full length BTN3A1 intracellular domain (BFI) (FIG. 8D; left panel and Table 1), yet was significantly reduced when using a recombinant CD277 B30.2 domain, lacking the N terminal region connector to the transmembrane domain (FIG. 8E; left panel). These data indicate an important role for the membrane proximal region of the CD277 intracellular domain in binding to RhoB GTPase. Interestingly, RhoB binding to BFI was almost completely abolished in the presence of soluble phosphoantigen cHDMAPP (FIG. 8D; right panel). When in the same experiment, the physiologically more relevant, but much lower affinity pAg IPP was applied, BLI was unable to resolve pAg-induced dissociation of RhoB from BFI (FIG. 9C), very likely due to the technical limitation of the assay. In summary, these data indicate that methods and compositions designed to promote close interaction of RhoB and CD277 molecules at the surface membrane would promote formation of the J-configuration and recognition thereof by Vγ9Vδ2 TCRs.

TABLE 1

Rate and affinity constants for binding interactions between RhoB GTPase and BFI or B30.2 domains, in the presence or absence of pAg

| Interaction | KD (μM) | $k_a$(1/Ms) | $k_d$ (1/s) | Chi^2 |
|---|---|---|---|---|
| RhoB-BFI | 19.7 | $2.2 \times 10^3$ | 0.04351 | $2.58 \times 10^{-4}$ |
| RhoB-B30.2 | 102 | $2.02 \times 10^3$ | 0.206 | $4.81 \times 10^{-6}$ |
| RhoB-BFI-cHDMAPP | 666 | 172 | 0.115 | $5.66 \times 10^{-6}$ |
| RhoB-B30.2-cHDMAPP | N.A | N.A | N.A | N.A. |

Figure 3F:
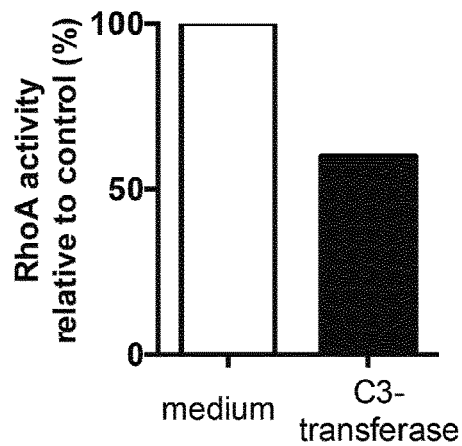
FIG. 3F shows Rho inhibition of 293 HEK cells following C3-transferase treatment was determined by using G-Lisa. Figure shows a representative experiment of the relative inhibition of RhoA activity compared to untreated sample.
Figure 10A:
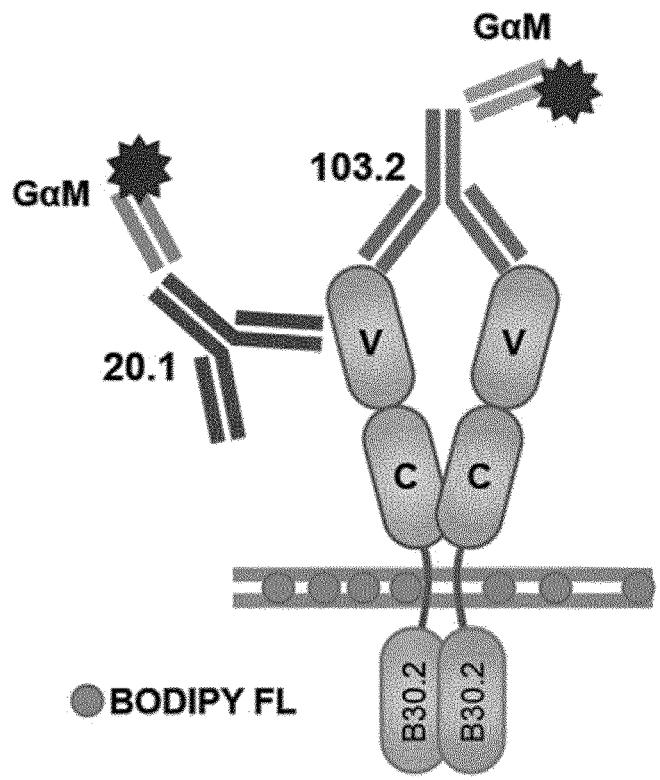
FIG. 10 shows intracellular phosphoantigen accumulation induces extracellular conformational changes in CD277, resulting in formation of the J-configuration of CD277. HEK 293 cells were pretreated with medium, C3 transferase and/or pamidronate and the surface membrane of cells was subsequently stained with the fluorescent lipid conjugate BODIPY FL (FRET donor) and BTN3 molecules were labeled with mouse anti-CD277 mAbs originating either from clone 20.1 or from the clone 103.2 followed by staining with secondary Alexa Fluor 594-conjugated Fab fragment (GaM) (FRET acceptor). FRET efficiency was measured by flow cytometry and data represent mean+S.E.M of at least three independent experiments in triplicate samples. Statistical significance of data was analyzed by Mann-Whitney test.
Figure 10B:
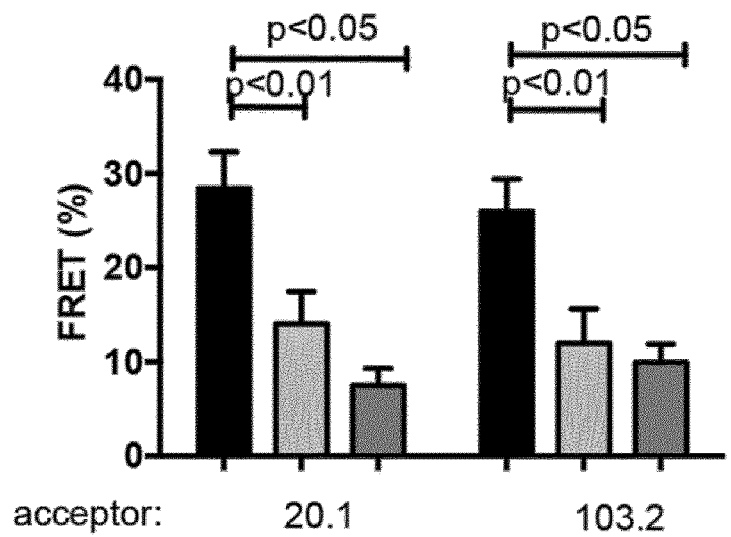

Example 6. Phosphoantigen Accumulation Associates with Conformational Changes of CD277 Dimers to the J-Configuration To study CD277 conformational changes to J-configuration in response to increased phosphoantigen levels, surface membranes of either unstimulated or ABP-stimulated HEK 293 cells were labeled with the fluorescent lipid conjugate BODIPY FL (donor), and subsequently stained with acceptor dye-labeled BTN3-specific antibodies on ice, in order to prevent conformational changes that could be driven by these antibodies under physiological circumstances. Without ABP stimulation, potent FRET efficiencies between stained membrane and both antibodies were observed (FIG. 10B), suggesting that the CD277 Ig-V domain is in close proximity to the cell membrane. Strikingly however, treatment of cells with ABP resulted in a marked reduction in FRET signals (FIG. 10B), demonstrating that intracellular phosphoantigen accumulation associates with a conformational change of BTN3 molecules. This change involves a pronounced distancing of the Ig-V domain from the cell membrane. Importantly, Rho-inhibitor C3-transferase treatment (FIG. 3F) of cells did not prevent ABP-driven conformational changes of the CD277 homodimer (FIG. 10B) indicating that this conformational change is independent of the enzymatic activity of RhoB. These data indicate that methods and compositions promoting CD277 dimerization act as, or contribute to a molecular signature recognized by Vγ9Vδ2 TCRs, namely the J-configuration of CD277.

Figure 11:
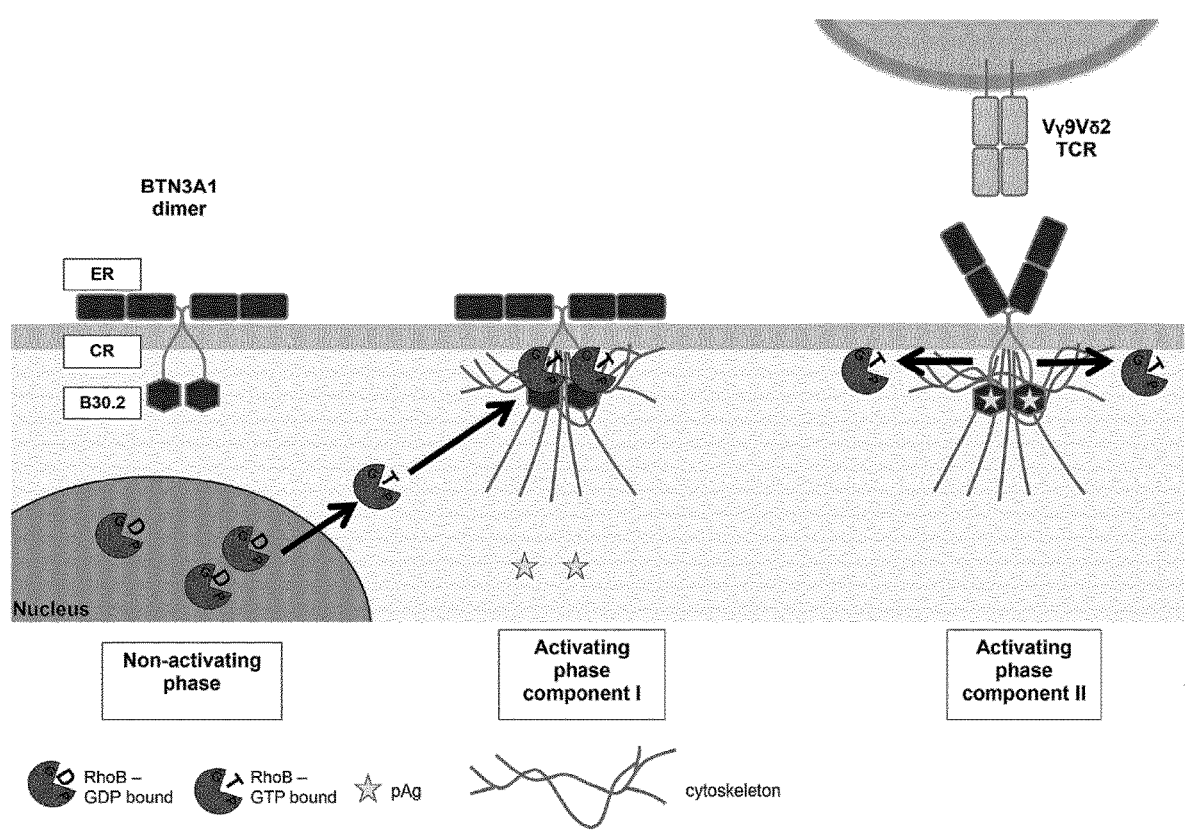
FIG. 11 shows a model of a two-component mechanism in tumor cells that leads to recognition of the J-configuration of CD277 by engineered cells expressing a polypeptide construct described herein TCR. Non-activating phase: no accumulation of phosphoantigens (pAg, yellow stars, which retains GDP-bound RhoB (red circles+GDP) from extranuclear areas. Activating phase component I: Accumulation of phosphoantigens is followed by more GTP-bound RhoB formation (red circles+GTP). GTP-bound RhoB undergoes subcellular re-compartmentalization (black arrows) accumulating at extranuclear areas and facilitates spatial redistribution of CD277 by promoting cytoskeletal trapping (lines extending from membrane) in the plasma membrane binding to the B30.2 domain proximal connector region (CR) of CD277 (blue hexagon). Activating phase component II: GTP-bound RhoB dissociates (black arrow) from while pAg binds to the B30.2 domain of CD277, which triggers a conformational change of the extracellular region (ER) of CD277, forming the J-configuration of CD277 leading to binding of a polypeptide construct described herein.

FIG. 11 shows a model of Vγ9Vδ2 TCR T cell activation based on data presented herein. During the non-activating phase, there is no accumulation of phosphoantigens (pAg, yellow stars, which retains GDP-bound RhoB (circles+GDP) from extranuclear areas. During activating phase component I, accumulation of phosphoantigens is followed by more GTP-bound RhoB formation (circles+GTP). GTP-bound RhoB undergoes subcellular re-compartmentalization (black arrows) accumulating at extranuclear areas and facilitates spatial redistribution of CD277 to J-configuration by promoting cytoskeletal trapping (lines extending from membrane) in the plasma membrane binding to the B30.2 domain proximal connector region (CR) of CD277 (blue hexagon). During the activating phase component II, GTP-bound RhoB dissociates (black arrow) from while pAg binds to the B30.2 domain of CD277, which triggers a conformational change of the extracellular legion (ER) of CD277 resulting in the formation of the J-configuration of CD277 and leading to Vγ9Vδ2 TCR T cell activation.

Example 7. Identified SNPs not Only Predict Recognition of LCL Lines but Also Other Tumor Cell Lines Including Solid Tumor Cell Lines The positive predictive value of the SNP A/G or G/G is stronger than the negative predictive value of A/A and depends on TCR affinity (see Table 2). In Table 2, clone 5 encodes a γ9δ2 TCR which has a higher affinity than the γ9δ2 TCR encoded by clone 115 (Marcu-Malina et al., "Redirecting αβ T cells against cancer cells by transfer of a broadly tumor-reactive γδ T-cell receptor," Blood, 118: 50-59 (2011)). Therefore, based on this data, the higher the TCR affinity:

1.) the better is the positive predictive value (i.e. an included patient has a high chance of being a responder)
2.) the worse is the negative predictive value (i.e. patients who are responders may be excluded).

With respect to the data in Table 2, the genotype of different tumor cells was assessed by sequencing. Recognition of tumor cells was assessed by IFN□-ELIspot assay or ELISA, in which indicated tumor cell lines were used as targets against Vγ9Vδ2TCR+ T cells expressing G115 or clone 5 chains. 0 indicates no recognition; 1 indicates significant recognition. Calculated are false negative and correct positive recognition for indicated SNPs.

Figure 12:
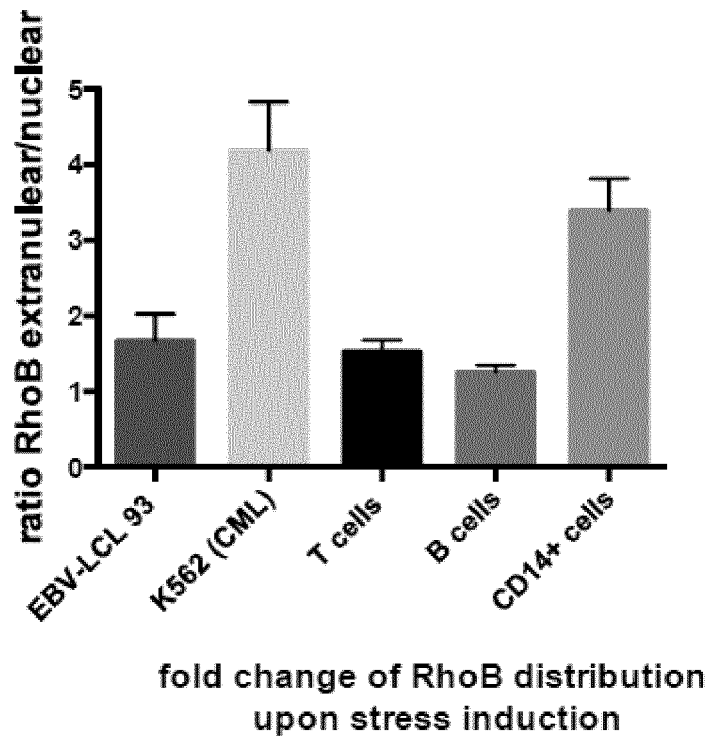
FIG. 12A-B show RhoB distribution in various cell types and its change upon cellular stress.
Figure 12:
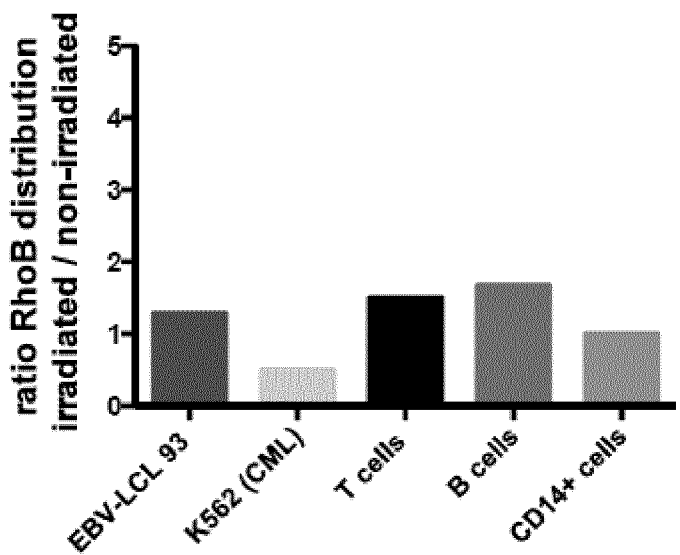

These data indicate that RhoB is an important modulator of recognition of tumor cells by T cells engineered to express a defined γδ TCR (i.e. "TEG cells"), and, that an increased affinity of a γ9δ2TCR can partially overcome this mechanism. In addition, stress like irradiation neither induces the mechanism (relocation of RhoB to the proximity of the cell membrane) nor induces recognition (see FIG. 12).

TABLE 2

Prediction of susceptibility of tumor cells to T cells engineered to express a defined TCR depends on the SNP genotype of the tumor as well as affinity of the γ9δ2TCR.

| | Tumor cell line | SNP 263 | G115 IFN-g production (pooled ELIspot + ELISA) effectorG115 TCR | cl5 (TEG001) IFN-g production (ELIspot) with effector clone 5 |
|---|---|---|---|---|
| 1 | Ca127 | A/A | 0 | 1 |
| 2 | Daudi | A/A | 1 | 1 |
| 3 | Hela | A/A | 0 | 1 |
| 4 | HL60 | A/A | 0 | 0 |
| 5 | K562 | A/A | 1 | 1 |
| 6 | LCL22 | A/A | 0 | 0 |
| 7 | LCL93 | A/A | 0 | 0 |
| 8 | LCL-TM | A/A | 0 | |
| 9 | MDA-MB231 | A/A | 1 | 1 |
| 10 | ML1 | A/A | 0 | 0 |
| 11 | Sw480 | A/A | 0 | 1 |
| | False negative prediction | | 0.27 | 0.60 |
| 1 | BV173 | A/G | 1 | 1 |
| 2 | HEK293ft | A/G | 1 | 1 |
| 3 | HEP-2 | A/G | 0 | 1 |
| 4 | HEPG2 | A/G | 0 | 1 |
| 5 | Jurkat | A/G | 0 | 1 |
| 6 | KCL22 | A/G | 1 | 0 |
| 7 | LCL48 | A/G | 1 | 1 |
| 8 | LCL71 | A/G | 1 | |
| 9 | MZ1851rc | G/A or G/G | 1 | 1 |
| 10 | NB4 | A/G | 1 | 1 |
| 11 | Raji | A/G | 0 | 1 |
| 12 | Saos2 | A/G | 1 | 1 |
| 13 | SCC9 | A/G | 1 | 1 |
| 14 | T2 | A/G | 0 | 1 |
| 15 | U266 | A/G | 0 | 1 |
| | Correct positive prediction | | 0.60 | 0.93 |

Example 8. SNPs Located Outside Rho-GTPase May Influence Rho-GTPase

In some cases, a defined SNP located within a gene of interest will directly influence expression or function of the protein encoded by the gene. However, in some cases identified SNPs may not be directly located within these regions, and splice variants may not be detected.

One hypothesis is that SNPs located outside Rho-GTPase may influence Rho-GTPase activity. Databases used for a SAPPHIRE strategy may not be complete, and thus may not cover all SNPs. To further identify genetic variations that correlate with the genotype of marker SNPs, extended genomic sequencing focusing primarily on the promoter region of Rho-GTPase will be performed. Rho-GTPase promoter regions differ between mice and humans, though the sequence of Rho-GTPase itself is identical. This observation could potentially explain why no γδ2 T cells are observed in mice. In addition, the recently released next generation database of SAPPHIRE will be used, which will allow a more profound SNP analysis to detect SNPs that are located within the genomic region of Rho-GTPase. A refined 2.0-version of SAPPHIRE will be developed by including proxy SNPs (i.e. SNPs in high LD with SNP hits, www-.broadinstitute.org/mpg/snap/ldsearch.php) as well as predicting functionality of (proxy) SNPs (e.g. missense, promoter, regulatory region, etc, e.g. http://fastsnp.ibms.sinica.edu.tw/). In addition, SNPs will be correlated to differential gene expression using expression quantitative trait loci (eQTL) analysis (http://www.sanger-.ac.uk/resources/software/genevar/), and common cellular processes or pathways among candidate genes will be deduced via NCBI Gene Ontology (GO) terms. In particular, genes encoding for Rho regulating proteins will be targeted, including some 130 genes that belong to GEF (Guanine nucleotide exchange factors), GAP (GTPase activating proteins) and GDI (Guanine nucleotide exchange inhibitors) molecular families. As such, genes are frequently located at the same chromosomal region as the Rho-GTPase, thus are also close to the marker SNPs. Such genes will be targeted for further computational and sequence analysis.

Predicted Outcome: SNPs e.g. within the promoter region or regulatory genes of Rho-GTPase which are linked to the marker SNPs may be identified. Follow up research can include either promoter studies to provide functional data on differential regulation of Rho-GTPase by defined SNPs, or studies overexpressing or inhibiting regulatory proteins of Rho-GTPase.

Example 9. Experimental Procedures

Cells and Reagents

Cells and reagents CEPH EBV-LCL lines (CEU population panel) were a kind gift from Tuna Mutis (UMC Utrecht, The Netherlands). Daudi, K562, SW480, HEK 293, HEK 293FT and Phoenix-Ampho cell lines were obtained from ATCC. LCL-TM (an EBV-LCL line separate from the CEPH panel) was kindly provided by Phil Greenberg (Seattle, U.S.A.). MZ1851RC was kindly provided by Barbara Seliger (University of Halle, Germany). Hek 293, Phoenix-Ampho, SW480, MZ1851RC cells were cultured in DMEM supplemented with 1% Pen/Strep (Invitrogen) and 10% FCS (Bodinco), all other cell lines in RPMI with 1% Pen/Strep and 10% FCS. Primary fresh PBMCs were isolated by Ficoll-Paque (GE Healthcare) from buffy coats supplied by Sanquin Blood Bank (Amsterdam, The Netherlands). Frozen primary acute myeloid leukemia (AML) samples were kindly provided by Matthias Theobald (Mainz, Germany) and were collected in compliance with GCP and Helsinki regulations.

The following reagents were used: pamidronate (Calbiochem), zoledronic acid monohydrate (zolidronate, Sigma-Aldrich), isopentenyl pyrophosphate (IPP) (Sigma-Aldrich), calpeptin (Rho activator II CN03, Cytoskeleton Inc), C3 transferase (Rho Inhibitor I CT04, Cytoskeleton Inc), the farnesyl transferase inhibitor (FTI) (Sigma-Aldrich), and the geranylgeranyltransferase inhibitor (GGTI) (Sigma-Aldrich).

Flow Cytometry

Antibodies used for flow cytometry included: pan-γδTCR-PE (clone IMMU510, Beckman Coulter), CD4-FITC (eBioscience), CD8-APC (BD), unconjugated rabbit polyclonal RhoB (AbCam), goat-anti-rabiit Alexa Fluor 488 (Jackson ImmunoResearch). Mouse a-CD277 mAb (clone #20.1 and 103.2) were kindly provided by D. Oliver (INSERM U891, Marseille, France). Samples were processed with FACSCalibur and FACSCanto-II flow cytometers (BD) and analyzed with FACSDiva software (BD). Primary leukemic stem cells and healthy progenitor cells were sorted according to phenotypic markers as previously described (Terwijn et al., 2014).

Cells were sorted using a FACS Aria SORP (with red, blue, and violet solid-state lasers; BD Biosciences). Cells were kept on ice during the whole procedure. Cells were labelled with AntiCD45RA Alexa Fluor 700, Anti-CD38APC, Anti-CD34 Horizon BV421, Anti-CD45 Horizon V500, all BD Biosciences, San Jose, CA, USA. CD34+ CD38− stem cells were sorted based on CD45RA expression: CD45RA positive cells are neoplastic and CD45RA negative cells are normal hematopoietic stem cells. Above that, CD34+CD38+ progenitors were sorted.

Retroviral Transduction of TCRs

Retroviral transduction of TCRs The Vγ9Vδ2-TCR clone G115 (Allison et al., 2001) and a HLA-A*0201-restricted WT1126-134-specific αβTCR (Kuball et al., 2007) were transduced into αβT cells as described (Marcu-Malina et al., 2011, Stanislawski et al., 2001). In brief, Phoenix-Ampho packaging cells were transfected with gag-pol (pHIT60), env (pCOLT-GALV) and pBullet retroviral constructs containing TCRγ/β-chain-IRES-neomycine or TCRδ/α-chain-IRES-puromycin, using Fugene6 (Promega). PBMCs pre-activated with αCD3 (30 ng/ml) (clone OKT3, Janssen-Cilag) and IL-2 (50U/ml) were transduced twice with viral supernatant within 48 hours in the presence of 50 U/ml IL-2 and 4 μg/ml polybrene (Sigma-Aldrich). Transduced T cells were expanded by stimulation with αCD3/CD28 Dynabeads (0.5×106 beads/106 cells) (Invitrogen) and IL-2 (50U/ml) and selected with 800 μg/ml geneticin (Gibco) and 5 μg/ml puromycin (Sigma-Aldrich) for one week. CD4+ TCR-transduced T cells were isolated by MACS-sorting using CD4-microbeads (Miltenyi Biotec).

Following transduction, transduced T cells were stimulated biweekly with 1 μg/ml PHA-L (Sigma-Aldrich), 50U/ml IL-2 (Novartis Pharma), 5 ng/ml IL-15 (R&D Systems), and irradiated allogeneic PBMCs, Daudi and LCL-TM cells. Fresh IL-2 was added twice a week. Transgenic TCR expression and purity of CD4+ populations was routinely assessed by flow cytometry.

Functional T Cell Assays

IFNγ ELISPOT was performed as previously described (Scheper et al., 2013, Marcu-Malina et al., 2011). Briefly, 15,000 Vγ9Vδ2 TCR-transduced or mock-transduced T cells and 50,000 target cells (ratio 0.3:1) were cocultured for 24 hrs in nitrocellulose-bottomed 96-well plates (Millipore)

precoated with anti-IFNγ antibody (clone 1-D1K) (Mabtech). Plates were washed and incubated with a second biotinylated anti-IFNγ antibody (clone 7-B6-1) (Mabtech) followed by streptavidin-HRP (Mabtech). IFNγ spots were visualized with TMB substrate (Sanquin) and the number of spots was quantified using ELISPOT Analysis Software (Aelvis).

Alternatively, Vγ9Vδ2 TCR-transduced T cells and target cells were cocultured as above in round-bottom 96-well plates, and IFNγ levels in supernatants were measured by ELISA. Where indicated, target cells were pretreated with pamidronate (100 μM), IPP (15 μM), FTI (10 μM), GGTI (50 μM), calpeptin (2 μg/ml) or C3 transferase (20 μg/ml) prior to coincubation. For testing stimulation of WT1 αβTCR-transduced T cells, the HLA-A2+ cell lines EBV-LCL 48 and MZ1851RC were pulsed with 10 μM $WT1_{126-134}$ peptide.

Zygosity/SNP Correlation Analysis

Recognition of CEPH EBV-LCL lines (pretreated with either medium, pamidronate (100 μM) or IPP (15 μM) by Vγ9Vδ2 TCR-transduced CD4+ T cells was determined by ELISPOT. Mocktransduced T cells were included as effector controls, and any EBV-LCL line that elicited IFNγ production by mock-transduced cells were excluded from the analysis. Recognition of EBV-LCL lines by Vγ9Vδ2 TCR+ T cells in a single assay was defined as an at least two-fold increase in IFNγ spots compared to those produced in response healthy control target cells, irrespective of EBV-LCL pretreatment (i.e. medium, pamidronate or IPP). EBV-LCL line was defined as activating when recognized in at least three out of five independent experiments. Hypothetical zygosities for candidate genetic loci were deduced using classical Mendelian inheritance patterns within CEPH family pedigrees, where the influence of candidate alleles on Vγ9Vδ2 TCR-mediated recognition was assumed to be dominant. Correlations of predicted zygosities with Hapmap SNP genotypes of CEPH individuals were subsequently calculated with the software tool ssSNPer, as previously described (Spaapen et al., 2008). Proxy SNPs within 500 kb of SNPs produced by ssSNPer were collected by querying the SNP Annotation and Proxy Search (SNAP) tool (Johnson et al., 2008), using $r^2=0.8$ as a threshold for linkage disequilibrium. eQTL analysis of ssSNPer SNP and their proxies was performed using the Genevar (GENe Expression VARiation) tool (Yang et al., 2010).

shRNA and CRISPR/Cas Genome Editing

HEK 293FT cells were transfected using Fugene 6 (Promega) with lentiviral constructs containing shRNAs (Sigma-Aldrich) together with lentiviral helper constructs VSVG and pspax2, against candidate genes of interest. EBV-LCL 48 cells were transduced with viral supernatants four days prior to functional T cell assays. Knockdown of targeted genes was confirmed using real-time Q-PCR, or in the case of RhoB, by flow cytometry.

We employed the CRISPR/Cas9 system (van de Weijer et al., 2014) to knock out RHOA, RHOB, or RHOC from MZ1851RC cells. For this, we used lentiviral CRISPR/Cas9 vectors (Ref Weijer et al) co-expressing *S. pyogenes* Cas9, PuroR and a human U6 promoter driving expression of anti RHOA guideRNAs (gRNA). The gene-specific regions of the gRNA sequences were designed by the CRISPR design tool from the Zhang lab (http://crispr.mit.edu/) and their sequences were GAACTATGTGGCAGATATCG (RHOA), GTGGTGGGCGACGGCGCGTG (RHOB), and GAAAGAAGCTGGTGATCGT (RHOC). As control gRNA, we targeted the eGFP gene with GTGAACCGCATCGAGCTGAA.

Lentiviruses were generated using standard $3^{rd}$ generation packaging vectors in 293T cells. MZ1851RC cells were transduced with indicated CRISPR/Cas9 lentiviruses, and cells were selected with 2 μg ml-1 puromycin. The efficiency of RhoB knockout was assessed using flow cytometry.

Western Blot Analysis

EBV-LCL lines 22, 48, 91 and 93 were treated with pamidronate overnight, and were lysed by lysis buffer containing NP-40. Lysates were centrifuged to remove cell debris and supernatants were separated by SDS-PAGE. Protein content was transferred to PVDF membranes (Millipore), blocked for 1 hr in blocking buffer (5% milk) and incubated overnight with rabbit polyclonal antibodies directed against RhoB (LifeSpan Biosciences) or β-tubulin (clone DM1A) (Sigma). Blots were subsequently incubated with HRP-conjugated secondary antibodies, and bands were visualized using Pierce ECL substrate (Thermpo Scientific).

Confocal Microscopy and Data Analysis

For intracellular immunofluorescence staining of RhoB, cells were treated with pamidronate overnight (where indicated) and were allowed to attach onto coverslips precoated with poly-Llysine (Sigma-Aldrich). Cells were subsequently permeabilized with Permeabilizing solution 2 (BD), blocked with blocking serum (50% pooled normal human serum in PBS), and stained with a rabbit polyclonal anti-RhoB antibody (AbCam) followed by a secondary Goat anti-Rabbit IgG Alexa Fluor 488-conjugated antibody (Jackson ImmunoResearch). Cells were washed with blocking serum, fixed with 4% paraformaldehyde, stained with DAPI (where indicated), and mounted onto microscopy slides using Mowiol. Images were acquired using a Zeiss confocal laser scanning microscope LSM 700. Ratios between nuclear and extranuclear signal of RhoB was determined using Volocity software (PerkinElmer) or Image J software, where DAPI staining was used, when available, to mark nuclei.

To determine colocalization between BTN3 molecules and the actin cytoskeleton, HEK 293 cells were grown onto poly-L-lysin-coated coverslips and pretreated with either calpeptin (2 μg/ml) or C3 transferase (20 μg/ml) prior to treating samples with pamidronate Cells were fixed, permeabilized and BTN3 and F-actin were stained with DyLight 680-conjugated BTN3 antibody (clone BT3.1, Novus Biologicals) and Fluorescein-coupled phalloidin (Sigma), respectively. The correlation coefficient between BTN3 and F-actin signal was determined as a measure of colocalization using Volocity software.

FRAP Microscopy

FRAP analysis was performed as previously described (Harly et al., 2012, Sandstrom et al., 2014). In brief, HEK293FT cells expressing either EmGFP-fused CD277 were laid on m-slides (Ibidi) and analyzed using a Nikon A1 RS confocal microscope (60×NA 1.40 oil immersion objective). Selected rectangular areas were photobleached for 500 ms by using full power of laser intensity (>90% of loss of fluorescence). Images were collected every 5 s, before (30 s) and after (120 s) bleaching using low laser intensity. Images were analyzed with Metamorph 7.5 (Molecular Devices, Universal Imaging) and NIS (Nikon) imaging software. The resulting curves were fitted using one-phase exponential equations.

Flow Cytometry FRET

To study association of RhoB and BTN3 molecules, cells were permeabilized by using Permeabilization solution 2 (BD), then blocked with PBS containing 50% Human serum and labeled with rabbit polyclonal anti-RhoB antibody (AbCam). After washing with PBS, samples were labeled with Alexa594-conjugated Goat anti-Rabbit IgG (acceptor)

(Jackson ImmunoResearch) and CD277-PE (donor) (BT3.1, Biollegend), respectively. The donor fluorescence was measured using a FACS Canto-II flow cytometer (BD) where donor fluorescence of the double-labeled samples was compared with that of samples labeled only with donor antibody. FRET efficiency was calculated from the fractional decrease of the donor fluorescence in the presence of the acceptor.

In order to determine homodimerization of CD277 molecules, cells were co-stained with equal amount of PE-conjugated anti-CD277 (donor) and Dyligth680-conjugated anti-CD277 (acceptor) and samples were measured using a FACS Canto-II flow cytometer (BD). FRET efficiency was calculated with equations according to Sebestyen and colleagues (Sebestyen et al., 2002) where donor fluorescence was excited at 488 nm and detected at 576±26 nm, acceptor fluorescence was excited at 635 nm and detected at 780±60 nm, whereas FRET intensity was excited at 488 nm and detected at 780±60 nm. Correction factors for the spectral overlap between the different fluorescence channels were obtained from data measured on unlabeled and single-labeled cells.

Conformational change of BTN3 molecule was determined similarly as described in (Gaspar et al., 2001). Cells were labeled with 5 ug/ml BODIPY-FL DPHE (donor) (Life Technologies) for 10 minutes on ice and then 10 minutes at 37 C, then washed extensively with ice-cold PBS. Cells were subsequently labeled with mouse anti-CD277 mAbs (either clone #20.1 or #103.2) and Alexa594-conjugated Goat anti-Mouse Fab fragments (Jackson ImmunoResearch). After washing, cells were resuspended in ice cold PBS and measured immediately using a FACS Canto-II flowcytometer (BD). FRET efficiency was calculated from the fractional decrease of the donor fluorescence in the presence of the acceptor.

Proximity Ligation Assay

HEK 293FT cells were grown onto poly-L-lysine coated coverslips and pre-treated with 100 uM pamidronate overnight prior to being fixed and permeabilized with Permeabilization buffer 2 (BD) for 15 minutes. Subsequently, cells were washed three times with PBS and blocked for 30 minutes at 22° C. in PBS containing 50% human serum. After blocking, cells were incubated for 60 min at 22° C. with rabbit anti-RhoB (AbCam) and mouse anti-CD277 (Novus Biologicals) in PBS containing 50% human serum. Cells were washed three times with PBST (0.05% Tween) and incubated with the secondary mouse PLUS and rabbit MINUS antibodies for 1.5 hours at 37° C. in the dark. Cells were washed three times in PBST before detection of the probe with the in situ PLA detection kit (Abnova). Cells were analyzed with a 63× objective on a Zeiss LSM 710 fluorescence microscope.

In Vitro Protein Expression and Purification

The full length RhoB protein was cloned into the pET 28a vector with an C-terminal six-HIS tag followed by a thrombin cleavage site using restriction enzyme sites NdeI and XhoI (5' primer: CGCCATATGATGGCCGCCATCCG; 3' primer: CGCCTCGAGTTAGCAGCAGTTGATGCAGC). The C-terminal CKVL motif of RhoB was deleted to prevent improper prenylation in *Escherichia coli*. The construct was expressed in BL21 strain *Escherichia coli*. Cells were grown in Terrific Broth (TB) at 37° C. to OD600=0.6 and then transferred to room temperature (25° C.). After 15 min of recovery, the cells were induced with 1 ml 1M Isopropyl β-D-1-thiogalactopyranoside (IPTG) per liter of culture for 12-16 hours. Protein was harvested and purified using Ni-NTA (Qiagen) IMAC chromatography in 20 mM Tris pH8.0, 400 mM NaCl, 20 mM Imidazole, 5 mM MgCl$_2$ and 4 mM 2-mercaptoethanol (BME), washed first with 1 mM ATP supplemented in the buffer mentioned above to dissociate potential chaperones from RhoB and then the buffer without ATP, and finally eluted with 20 mM Tris pH8.0, 400 mM NaCl, 250 mM Imidazole, 5 mM MgCl$_2$ and 4 mM BME. The eluted fractions was desalted into 10 mM Hepes 7.2, 150 mM NaCl, 0.02% azide, 5 mM MgCl$_2$ and 4 mM BME using an Econo-Pac 10DG column (Biorad). Protein was further purified by gel filtration over a Superdex 200 column (GE healthcare) in 10 mM Hepes pH7.2, 150 mM NaCl, 0.02% azide, 5 mM MgCl$_2$ and 4 mM BME. Protein concentration was measured by both BCA test and measuring A280 signal using ND-1000 spectrophotometer (NanoDrop Technologies, Inc.) using the theoretical extinction coefficient. The BTN3A1 B30.2 domain was expressed and purified as previously described (Sandstrom et al., 2014). The BTN3A1 full-length intracellular domain was cloned into pET28a with a 3C protease site followed by a carboxyl-terminus six-HIS tag using restriction enzyme sites NcoI and XhoI (5' primer: GCGCCATGGGGCAACAGCAGGAG-GAAAAA; 3' primer: CGCTCGAGGGGCCCCTG-GAACAGAACTTCCAGACCACCA-GACGCTGGACAAATAGTC).

The construct was expressed in BL21 strain *Escherichia coli*. Cells were grown to OD600=0.6 in Lysogeny Broth (LB) at 37° C. and induced with 1 ml 1M IPTG per liter of culture for four hours at room temperature. Protein was harvested and purified using Ni-NTA (Qiagen) IMAC chromatography in 20 mM Tris pH8.0, 400 mM NaCl, 20 mM Imidazole, 4 mM BME, and eluted with 20 mM Tris pH8.0, 400 mM NaCl, 250 mM Imidazole, 4 mM BME and desalted into 10 mM Hepes pH7.2, 150 mM NaCl, 0.02% azide, 4 mM BME using an Econo-Pac 10DG column (Biorad). Protein was cleaved overnight using 3C protease at 4° C. Protein concentration was measured as mentioned above (Figure S4A and S4B).

Biolayer Interferometry (BLI)

The interactions between RhoB and BTN3A1 full-length intracellular domain (BFI) or BTN3A1 B30.2 domain were measured using Biolayer interferometry (BLItz, FortéBio). The BLI buffer used in baseline equilibration and the dissociation step was prepared with 10 mM Hepes pH7.2, 150 mM NaCl, 0.02% azide, 5 mM MgCl$_2$, 4 mM BME. RhoB, at a concentration of 2 mg/ml, was immobilized on the Ni-NTA biosensor hydrated with the BLI buffer using the basic kinetics method with the following parameters: 30 s for baseline, 300 s for association and 300 s for dissociation. The RhoB-mounted biosensor was then blocked by 1 mg/ml BSA and equilibrated with the BLI buffer using a similar method with the following parameters: 30 s for baseline, 120 s for association and 120 s for dissociation. The buffer run served as a reference for the subsequent experiments. The interaction between RhoB and different concentrations of BFI (6.25, 12.5, 25, 50 and 100 uM) or B30.2 domain (12.5, 25, 50, 100 and 200 uM) were measured using the same method as mentioned above. The interaction between RhoB and different concentrations of BFI (3.75, 7.5, 15, 30 and 60 uM) or B30.2 domain (3.75, 7.5, 15, 30 and 60 uM) in the presence of (2E)-1-hydroxy-2-methylpent-2-enyl-pyrophosphonate (cHDAMPP) were also measured using the same method as mentioned above. The ratio between cHDMAPP and BFI or B30.2 domain was kept at 1:1 for these measurements. The rate and affinity constants for binding interactions were analyzed by Biaevulation (Biacore Life Sciences). The data was truncated to 180 s and the $k_a$ and $k_d$ were fitted simultaneously using 1:1 binding with drift baseline model.

G-Lisa Analysis

RhoA activity was assayed using a G-LISA RhoA Activation Assay Biochem kit (cat. no. BK124; Cytoskeleton, Inc., Denver, CO, USA), according to the manufacturer's instructions. Briefly, cell were lysed in ice-cold lysis buffer with a protease-inhibitor cocktail, and then centrifuged at 10000×g at 4° C. for 1 min. The supernatants were harvested and protein concentrations were measured using the Precision Red Advanced Protein Assay Reagent and were finally equalised with ice-cold lysis buffer to 1.0 mg/ml. Equalised protein extractions were transferred to a Rho-GTP-binding protein pre-coated plate. The plate was placed on an orbital microplate shaker at 0.72× g for 30 min at 4° C., and then incubated with monoclonal mouse anti-human anti-RhoA primary antibody (cat. no. GL01A; 1:250; Cytoskeleton, Inc.), followed by a polyclonal goat anti-mouse horseradish-conjugated secondary antibody (cat. no. GL02; 1:62.5; Cytoskeleton, Inc.), on an orbital microplate shaker (SSM1; Bibby Scientific Limited Group) at 0.72×g at room temperature, for 45 min each. The plate was then incubated with the HRP detection reagent at 37° C. for 15 min. Subsequent to the addition of HRP stop buffer, absorbance was read at 490 nm using a microplate reader.

Statistical Analysis

All experiments were independently repeated at least three times unless otherwise indicated. All data were shown as mean±SEM. Statistical significance was analysed by either Mann-Whitney or Kruskal-Wallis test and Dunn's multiple comparison test.

While preferred embodiments of the present disclosure have been shown and described herein, it will be obvious to those skilled in the art that such embodiments are provided by way of example only. Numerous variations, changes, and substitutions will now occur to those skilled in the art without departing from the present disclosure. It should be understood that various alternatives to the embodiments described herein, or combinations of one or more of these embodiments or aspects described therein may be employed in practicing the present disclosure. It is intended that the following claims define the scope of the present disclosure and that methods and structures within the scope of these claims and their equivalents be covered thereby Example 10: Experimental Methods Cell Lines The cell lines Daudi, LCL-TM, ML-1, JurMA and Jurkat-76 were cultured in RPMI (Gibco) supplemented with 10% FCS and 1% pen/strep (Gibco). HEK293FT cell line was cultured in DMEM (Gibco) supplemented with 10% FCS and 1% pen/strep. Human primary T cell clones were cultured in RPMI supplemented with 10% pooled human serum and 1% pen/strep. Human bulk primary T cells used for retroviral transductions were cultured in RPMI, supplemented with 2.5% pooled human serum and 1% pen/strep. All human primary T cells were cultured following the 2-week rapid expansion protocol (REP, including irradiated feeder cells (Daudi, LCL-TM and allogeneic PBMC)+PHA+IL-15+IL-2.

Generation, Expansion and Functional Testing of γ9δ2 T Cells Clones

PBMCs were stained with monoclonal antibody (mAb) to Vδ2 (Vδ2-FITC clone B6). The mAb-positive fraction was either sorted in bulk, expanded on REP, and thereafter cloned by limiting dilution (donor A) or single cell-sorted using FACS sort with collection of single cells in 96 well plates (donors B, C). All FACS sorts were performed on ARIAII (BD). Eight to twelve rounds of expansion on REP preceded functional testing. As soon as the cells expanded to sufficient numbers functional testing was performed: $5*10^4$ T cells were incubated overnight together with target cells at 1:1 E:T ratio in DMEM supplemented with 10% FCS and 1% pen/strep, without or in the presence of 100 uM Pamidronate Disodium salt (Calbiochem Cat #506600), supernatants were harvested the day after, and IFNγ concentration was measured using ELISA (eBioscience Ready-Set-Go! ELISA kit, Invitrogen Cat #88731688).

TCR Sequencing and Vector Generation

RNA was isolated from the primary T cell clones using the Qiagen RNeasy Minikit following the manufacturer's instructions. cDNA was synthesized with Superscript® II Reverse Transcriptase (Thermofisher), using a specific primer at the 3' constant region (TRDCRev TTCACCAGACAAGCGACA). cDNA was purified using a NucleoSpin Gel and PCR Clean-UP (Machery-Nagel). cDNA was amplified in a PCR amplification with the same reverse primer at constant region (TRDCRev TTCACCAGACAAGCGACA), and specific Vδ2 forward primer (TRDV2Fw TCTCTTCTGGGCAGGAGTC), using Q5® High Fidelity DNA polymerase (New England Biolabs) on a T100 Thermal Cycler (Biorad) and the following cycling parameters:

TCR gamma and delta chains were sequenced using primers specific for the variable and constant gene segments (TRDV2Fw TCTCTTCTGGGCAGGAGTC, TRDCRev TTCACCAGACAAGCGACA, TRGV9Fw TCCTTGGGGCTCTGTGTGT, TRGCRev GGGGAAACATCTGCATCA). Sanger sequencing was performed at Macrogen.

The TCRδ and TCRγ chains of a selection of the identified γδ T cell clones were reconstructed in retroviral expression vectors using overlap extension PCR to introduce the new CDR3 sequences. In brief, a set of primers was created based on the invariant sequences flanking the CDR3 region of a codon optimized construct encoding either the γ or δ chain of G115, the primers were extended with clone-specific nucleotides. A stretch of 15-20 bp within the overhang was designed to be reverse complement to its pair primer (see table 3):

TABLE 3

| | TCR Gamma and Delta sequences | | | |
|---|---|---|---|---|
| | Gamma | | Delta | |
| Torid | rev R1 5'-3' | fwd R2 5'-3' | rev R1 5'-3' | fwd R2 5'-3' |
| A1 | CCCAGCTCTT TCACCTCCCA CAGGGCGCAG | GGGAGGTGAAA GAGCTGGGCAA GAAAATCAAGG TGTTCG | GCTGTCGCCC AGAAGCAGCA GTGTGTCGCA GGCGCAGTAG TAG | CTGCTTCTGGGCGA CAGCAGCGACAAGC TGATCTTCGGCAAG G |

TABLE 3-continued

TCR Gamma and Delta sequences

| | Gamma | | Delta | |
|---|---|---|---|---|
| Torid | rev R1 5'-3' | fwd R2 5'-3' | rev R1 5'-3' | fwd R2 5'-3' |
| A2 | CCAGCTCTTG CACCTCCCAC AGGGCGCAG | GGGAGGTGCAA GAGCTGGGCAA GAAAATCAAGG TGTTCG | GTAGCCGCCA GGTTCAGCTG TGTCGCAGGC GCAGTAGTAG | GCTGAACCTGGCGG CTACAAGGACAAGC TGATCTTCGGCAAG G |
| A3 | CCAGCTCTTG CACCTCCCAC AGGGCGCAG | GGGAGGTGCAA GAGCTGGGCAA GAAAATCAAGG TGTTCG | TGTGTGGCCC CAGGCGTCGC AGGCGCAGTA GTAG | GCCTGGGGCCACAC AGACAAGCTGATCT TCGGCAAGG |
| A4 | CCCAGGCCTT CAACCTCCCA CAGGGCGCAG | GGAGGTTGAAG GCCTGGGCAAG AAAATCAAGGT GTTCG | GCTGCCTGTA TCGCCCAGGG CGTCGCAGGC | CTGGGCGATACAGG CAGCGACAAGCTGA TCTTCGGCAAGG |
| A5 | AGCTCGCCGG CCTCCCACAG GGCGCAG | GAGGCCGGCGA GCTGGGCAAGA AAATCAAGGTG TTCG | GTACAGCGCC CCCAGTGTGT CGCAGGCGCA GTAGTAG | CACTGGGGCGCTG TACACCGACAAGCT GATCTTCGG |
| A6 | CAGCTCTTGC CGCACCTCCC ACAGGGCGCA G | GAGGTGCGGCA AGAGCTGGGCA AGAAAATCAAG GTGTTCG | GGGGTCGCCC AGCTGGTCGC AGGCGCAGTA GTAG | CAGCTGGGCGACCC CGACAAGCTGATCT TCGGCAAGG |
| A7-1 | CAGCTCCCGC ACCTCCCACA GGGCGCAG | GGAGGTGCGGG AGCTGGGCAAG AAAATCAAGGT GTTCG | TATGCCCCAA TCGGGATCGC TGTCGCAGGC GCAGTAGTAG | GCGATCCCGATTGG GGCATACTGAACAC GGACAAGCTGATCT TCGGCAAGG |
| B1 | CCAGTTCCAC TTGAGCCTCC CACAGGGCGC AG | GGGAGGCTCAA GTGGAACTGGG CAAGAAAATCA AGGTGTTCG | AGTGTCCTGA GCAGCGGGAA TACCCCACGG AGTGTCGCAG GCGCAGTAGT AG | ACTCCGTGGGTAT TCCCGCTGCTCAGG ACACTGACAAGCTG ATCTTCGGCAAGG |
| B2, B5 | CAGCTTCTTG TAGTATCTCA CCTCCCACAG GGCGCAG | GGGAGGTGAGA TACTACAAGAA GCTGTTCGGCA GC | AGTAGTTCCC CAGGCTAGAA ACCTTGGGTC GCAGGCGCAG TAGTAG | CCAAGGTTTCTAGC CTGGGGAACTACTG ACAAGCTGATCTTC GGCAAGG |
| C1 | CAGCTCCCGC ACCTCCCACA GGGCGCAG | GGAGGTGCGGG AGCTGGGCAAG AAAATCAAGGT GTTCG | CGGTATCGTG GATAGAAGGT ACAGGGTCGC AGGCGCAGTA GTAG | CCTGTACCTTCTAT CCACGATACCGACA AGCTGATCTTCGGC |
| C2 | CAGCTCCCGC ACCTCCCACA GGGCGCAG | GGAGGTGCGGG AGCTGGGCAAG AAAATCAAGGT GTTCG | AGGGCCACCC GCTTGGTCGC AGGCGCAGTA GTAG | CAAGCGGGTGGCCC TGACAAGCTGATCT TCGGCAAGG |
| C3 | CCCAGGCCCA CCTCCCACAG GGCGCAG | GGAGGTGGGCCT GGGCAAGAAAAT CAAGGTGTTCGG CAGTAGTAGAAG G | CTGGTAGCCG CCAGACACTG TGTCGCAGGC | GTGTCTGGCGGCTA CCAGTACACTGACA AGCTGATCTTCGGC |
| C4, C14 | CAGCTCGCCA GACACCTCCC ACAGGGCGCA G | GGAGGTGTCTGG CGAGCTGGGCAA GAAAATCAAGGT GTTCG | CTTGTCTGTA TCTCCCAGAG CTAATGTGTC GCAGGCGCAG GTAGTAG | ACATTAGCTCTGGG AGATACAGACAAGC TGATCTTCGGCAAG G |
| C5 | CCAGCTCTTG CACCTCCCAC AGGGCGC | GGGAGGTGCAAG AGCTGGGCAAGA GAAAATCAAGGT AAGGTCGCAG GTTCG | GAGGTATCGC CAGGGGCAAG AAGGTCGCAG GCGCAGTAGT AG | GCCCCTGGCGATAC CTCTTTCACCGACA AGCTGATCTTCGGC |
| C6 | CCCAGCTCCC TCTTCACCTC | GAGGTGAAGAGG GAGCTGGGCAAG | ATCTCTGTAA CCACCTGTGC | CTTGGCACAGGTGG TTACAGAGATGACA |

TABLE 3-continued

TCR Gamma and Delta sequences

| Torid | Gamma | | Delta | |
|---|---|---|---|---|
| | rev R1 5'-3' | fwd R2 5'-3' | rev R1 5'-3' | fwd R2 5'-3' |
| | CCACAGGGCG CAG | AAAATCAAGGTG TTCG | CAAGCACCAC TGTGTCGCAG GCGCAGTAGT AG | AGCTGATCTTCGGC AAGG |
| C7, C11 | CAGCTCCCGC ACCTCCCACA GGGCGCAG | GGAGGTGCGGGA GCTGGGCAAGAA AATCAAGGTGTT CG | CCAAGAACTA GCATCACCCA TGTCGCAGGC GCAGTAGTAG | CGACATGGGTGATG CTAGTTCTTGGGAC ACTCGCCAAATG |

In PCR "R1" the V-(D)-J part (the variable domain and part of the CDR3 region) was amplified, using forward primers binding to the template chains δ and γ TCRG115 cloned into the retroviral pBullet vector and including the restriction sites (G115δFwd: CTGCCATGGAGCG-GATCAGC, G115γFwd: GCCATGGTGTCCCTGCTG, NcoI restriction site in italic), and the clone-specific reverse primer Rev R1 (Table 3). Similarly, in PCR "R2", the (D)-J-C part of the TCR chain was amplified using a constant reverse primer (G115δRev: ATGCGGATCCT-CACAGG, G115γRev: TAGTG-GATCCTCAGCTCTTCTC, BamHI restriction site in italic) and the clone-specific forward primer Fwd R2. After the gel-based size selection and purification with NucleoSpin Gel and PCR Clean-UP kit (Machery-Nagel), two of the PCR products (R1 and R2) were fused and amplified in PCR "R3" using G115δFwd/G115δRev and G115γFwd/G115γRev primer pairs to obtain TCR chains bearing the clone-specific CDR3 regions. All reactions were performed using Phusion High-Fidelity DNA polymerase (Thermo Fisher Scientific) on a T100 Thermal Cycler (Biorad) and the following parameters for R1-R2: 120 s at 98° C., 30 cycles of 20 sat 98° C., 20 s at 59° C., and 25 sat 72° C., followed by 600 sat 72° C.; for R3: 120 s at 98° C., 30 cycles of 20 s at 98° C., 20 s at 56° C., and 40 s at 72° C., followed by 600 s at 72° C.

After another gel-based size selection step, the newly synthetized TCR chains were purified and cloned into the retroviral pBullet vectors using NcoI and BamHI cloning sites. The TCR genes were cloned into pBullet-IRES-puromycin, the TCRγ genes were cloned into pBullet-IRES-neo. Sequence identity was confirmed with Sanger sequencing (Macrogen).

Retroviral Transduction of Plasmids

Vector pairs bearing the TCR chains of interest were transduced into the primary human T cells. Functional testing of the TCRs in the TEG format was performed in the same fashion as functional testing of the primary clones.

High Throughput Sequencing of TCRδ Chain

RNA was isolated using the Qiagen RNeasy Microkit following the manufacturer's instructions. cDNA was synthesized with Superscript® II Reverse Transcriptase (Thermofisher), using a specific primer at the 3' constant region (TRDCRev TTCACCAGACAAGCGACA). cDNA was purified using a NucleoSpin Gel and PCR Clean-UP (Machery-Nagel). cDNA was amplified in a PCR amplification with the same reverse primer at constant region (TRDCRev TTCACCAGACAAGCGACA), and specific Vδ2 forward primer (TRDV2Fw TCTCTTCTGGGCAGGAGTC), using Q5® High Fidelity DNA polymerase (New England Biolabs) on a T100 Thermal Cycler (Biorad) and the following cycling parameters: 300 s at 92° C., 30 cycles of 30 s at 92° C., 30 s at 63° C., and 45 s at 72° C., followed by 420 s at 72° C. After purification with NucleoSpin Gel and PCR Clean-UP, library preparation for HTS was done with HTSgo-LibrX kit with HTSgo-IndX indices from Gendx as recommended by the manufacturer. Cleanup of the samples was performed with HighPrep PCR beads from GC Biotech. High-throughput sequencing was performed on an Illumina MiSeq system 500 (2×250 bp) (Illumina). TCR sequence alignment, assembly and clonotype extraction were performed using the MiXCR (version-v2.1.1) program. In house R scripts were used for TCR repertoire analysis, data were filtered to exclude clonotypes with frequency of 1 read/clonotype.

Cloning, Expression, and Purification of Soluble TCRs

The extracellular domains of the TCR chains were amplified from synthetic DNA encoding the full length TCRs. The domain boundaries were based on ones published before for Vγ9Vδ2 TCR G115. The TCR chains were ligated in to a modified pBullet vector containing a μ-phosphatase signal peptide at the 5' end and fos zipper at the 3' end of the construct. The TCRγ chains were ligated in a modified pBullet vector containing a μ-phosphatase signal peptide at the 5' end and at the 3' a jun zipper followed by a biotin acceptor peptide and a poly-histidine tag. Synthetic DNA encoding for the bacterial biotin ligase BirA was also ligated in a pBullet vector containing a signal peptide. The expression of soluble γδTCRs was done in Freestyle 293-F cells (ThermoFisher). In short, plasmids containing TCRδ, TCRγ and BirA were mixed into a 45:45:10 ratio, combined with polyethylenimine (PEI) in a 2:3 ratio and incubated for 15' at room temperature. The DNA:PEI mix was added to the cells at a concentration of 1-1.5 μg plasmid/10^6 cells and after 6 h the media was supplemented with Pen/Strep (Gibco) and 100 μM biotin. 5 days after transfection the media was harvested, supplemented with phosphate buffer pH 7.5 and NaCl, at a final concentration of 20 and 300 mM respectively, and loaded on a 1 ml HisTrap Excel column (GE healthcare). A multi-step gradient, increasing the concentration of imidazole, was used to wash and elute the soluble TCR from the column. The eluted soluble TCR was loaded on a 1 ml HiTrapQ column (GE healthcare) in 20 mM Tris pH 8.2 and 20 mM NaCl. A linear gradient was used to elute the soluble TCR. Fractions containing the soluble TCR were pooled and concentrated. Tetramers and dextramers were prepared. Briefly, tetramers were prepared from monomers by adding one equivalent of SA-PE (1 μM) to six equivalents of sTCR (6 μM) in four steps over 20 min. Dextramers were prepared by preincubating SA-PE and sTCR in a molar ratio 1:3 for 15 min, and then doping the formed trimers with biotinylated dextran (MW 500 kDa, NanoCS) at a molar ratio 1:8 (dextran:SA-PE). For beads preparation, the biotinylated soluble TCRs were mixed with streptavidin conjugated fluorescent Yellow-Green microspheres (6 µm; Polysciences, Inc.) in excess to ensure fully coated beads, 10 sTCR/mg microspheres.

sTCR Multimer-Cell Conjugation Assay

For tetramer and dextramer staining, $1.0*10^5$ cells were incubated with 30 ul tetramer or dextramer solution (100 nM with respect to SA-PE) for 30 minutes at R.T. For beads staining, $7.5*10^4$ cells were incubated with 20 µl sTCR-YG-beads (0.33 mg beads/ml) for 30. Cells were subsequently stained with fixable viability dye eFluor780 (eBiosciences) for an additional 30'. For inhibition assay with anti-CD277 antibodies, either 20.1 or 103.2 (kind gift of Daniel Olive, Marseille, France), Daudi cells were pre-incubated with the antibodies at R.T. for 15' before the sTCR-YG-beads were added. The mixtures were fixed by adding 40 µl 2% formaldehyde for 15'. Samples were washed once with 1% formaldehyde and analyzed on a BD FACSCanto II (BD).

γδTCR enrichment to synapse and conjugate formation

HEK293FT cells were seeded in µ-slide poly-L-lysine pre coated chamber (Ibidi) to adhere overnight. Next day cells were treated with 100 µM PAM for one hour at 37° C. TEGs were added onto HEK293FT cells and incubated at 37° C. for 30-120 minutes. After co-incubation chambers were immediately placed onto ice and fixed with 4% PFA for 30 minutes. Samples were blocked with 1% BSA/FCS and labeled with CD3ε-Alexa Fluor 647 (BD Biosciences) at 2 µg/mL for two hours at room temperature, and finally fixed with 1% PFA+DAPI. Samples were imaged with Zeiss LSM-710 and analyzed with Volocity software (PerkinElmer). In order to quantify the number of conjugates between HEK293FT and TEG cells we calculated the ratio between CD3c positive objects and DAPI positive objects on each image taken. To analyse gamma delta TCR enrichment into the immunological synapse, we calculated the ratio of CD3c signal enrichment inside the contact area versus outside of contact area of the target and effector cell on 63× magnified images.

Super-Resolution Imaging

HEK293FT cells were plated in eight-well Lab-Tek chambers to adhere and treated with 100 uM pamidronate overnight. For super-resolution imaging, cells were labeled with AF647-CD277 at RT. After labeling, cells were washed with PBS and fixed with 4% PFA and 0.2% gluteraldehyde for 1-2 h. Prior to super-resolution imaging, 200 µL of fresh SRB (Super-resolution buffer: 50 mM Tris, 10 mM NaCl, 10% glucose, 168.8 U/mL glucose oxidase, 1404 U/mL catalase, 10 mM cysteamine hydrochloride, pH 8.0) was added to the well. dSTORM imaging was performed using an inverted microscope (IX71; Olympus America) equipped with an oil-immersion objective 1.45-NA total internal reflection fluorescence objective (U-APO 150×; Olympus America). A 637-nm diode laser (HL63133DG; Thorlabs) was used for AF647 excitation. A quad-band dichroic and emission filter set (LF405/488/561/635-A; Semrock) was used for sample illumination and emission. Emission light was separated onto different quadrants of an AndorIxon 897 electron-multiplying charge-coupled device (EM CCD) camera (Andor Technologies, South Windsor, CT), using a custom built 2-channel splitter with a 585 nm dichroic (Semrock) and additional emission filters (692/40 nm and 600/37). The sample chamber of the inverted microscope (IX71; Olympus America, Center Valley, PA) was mounted in a three-dimensional piezostage (Nano-LPS; Mad City Labs, Madison, WI) with a resolution along the xyz-axes of 0.2 nm. Sample drift was corrected for throughout the imaging procedure using a custom-built stage stabilization routine. Images were acquired at 57 frames/s in TIRF and between 10,000-20,000 frames were collected for each image reconstruction.

Super-Resolution Image Reconstruction and Data Analysis dSTORM images were analyzed and reconstructed with custom-built MATLAB functions as described previously (Smith et al 2010, Nat Methods: Huang et al 2011, Biomed Opt Express). For each image frame, subregions were selected based on local maximum intensity. Each subregion was then fitted to a pixelated Gaussian intensity distribution using a maximum likelihood estimator. Fitted results were rejected based on log-likelihood ratio and the fit precision, which was estimated using the Cramér-Rao lower bound values for each parameter, as well as intensity and background cut-offs. Analysis of dSTORM CD277 cluster data was performed using the density-based DBSCAN algorithm as part of a package of local clustering tools (http://stmc.health.unm.edu). Parameters chosen were a maximal distance between neighboring cluster points of epsilon=50 nm and a minimal cluster size of 6 observations. Cluster boundaries were produced with the MATLAB "boundary" function, using a default methodology that produced contours halfway between a convex hull and a maximally compact surface enclosing the points. The cluster areas within these boundaries were then converted into the radii of circles of equivalent area for a more intuitive interpretation. Regions of interest (ROIs) of size 2 µm×2 µm were selected from the set of images from which statistics for the equivalent radii were collected per ROI.

Example 11: Functional Profiling of γ9δ2T Cells

Figure 13A:
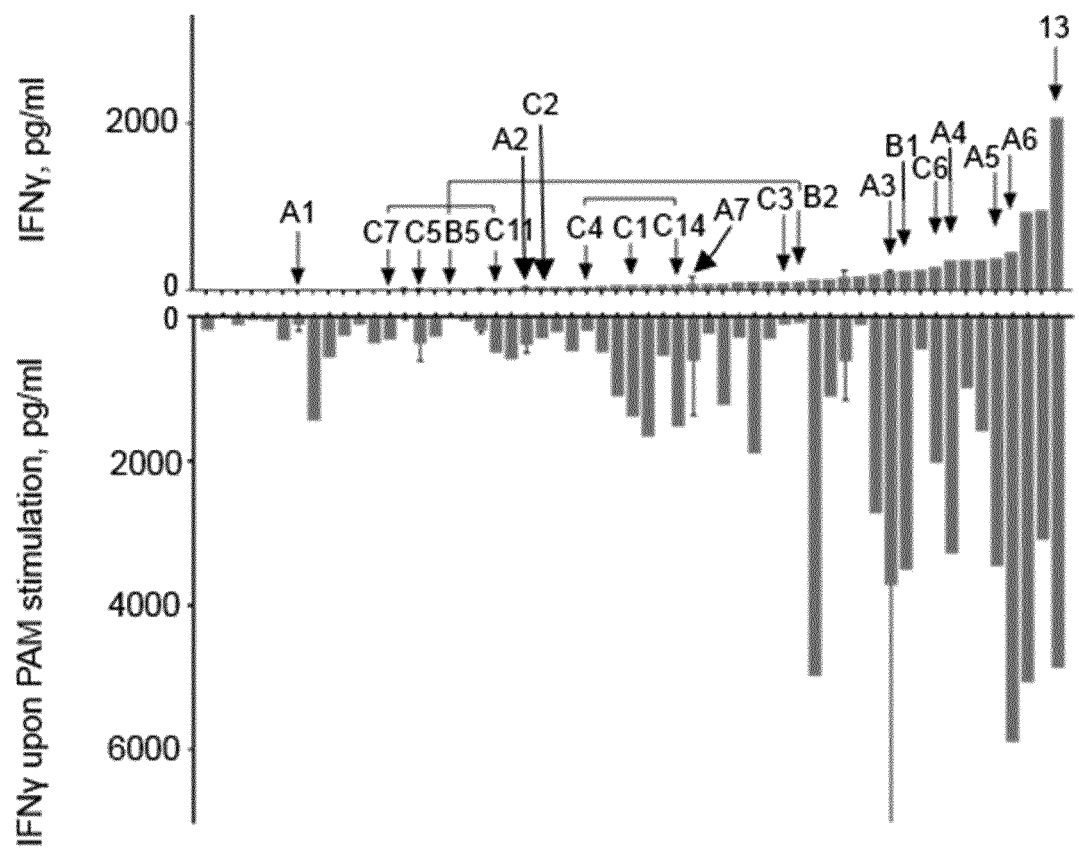
FIG. 13A shows antitumor reactivity of the isolated clones by IFNγ production. T cells were co-incubated overnight with the target cell line Daudi at 1:1 E:T ratio. Stimulation assay was performed without (upper plot) and in the presence of 100 μM PAM (lower plot). Bars are representative of 1 or 2 (where error bars are present) experiments. The error bars represent SEM of the 2 biological replicates. Arrows indicate clones with known TCR sequence.
Figure 13B:
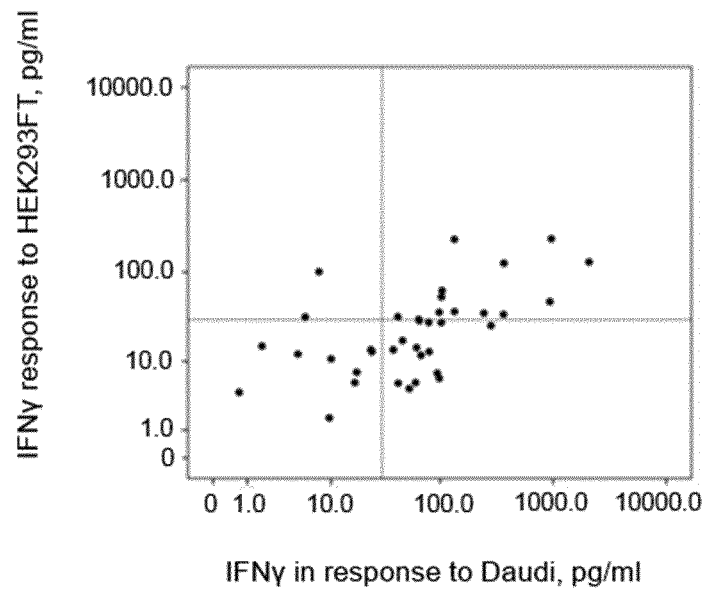
FIG. 13B shows a scatter plot of IFNγ production against Daudi vs HEK293FT cell lines without or in the presence of 100 uM PAM.
Figure 13C:
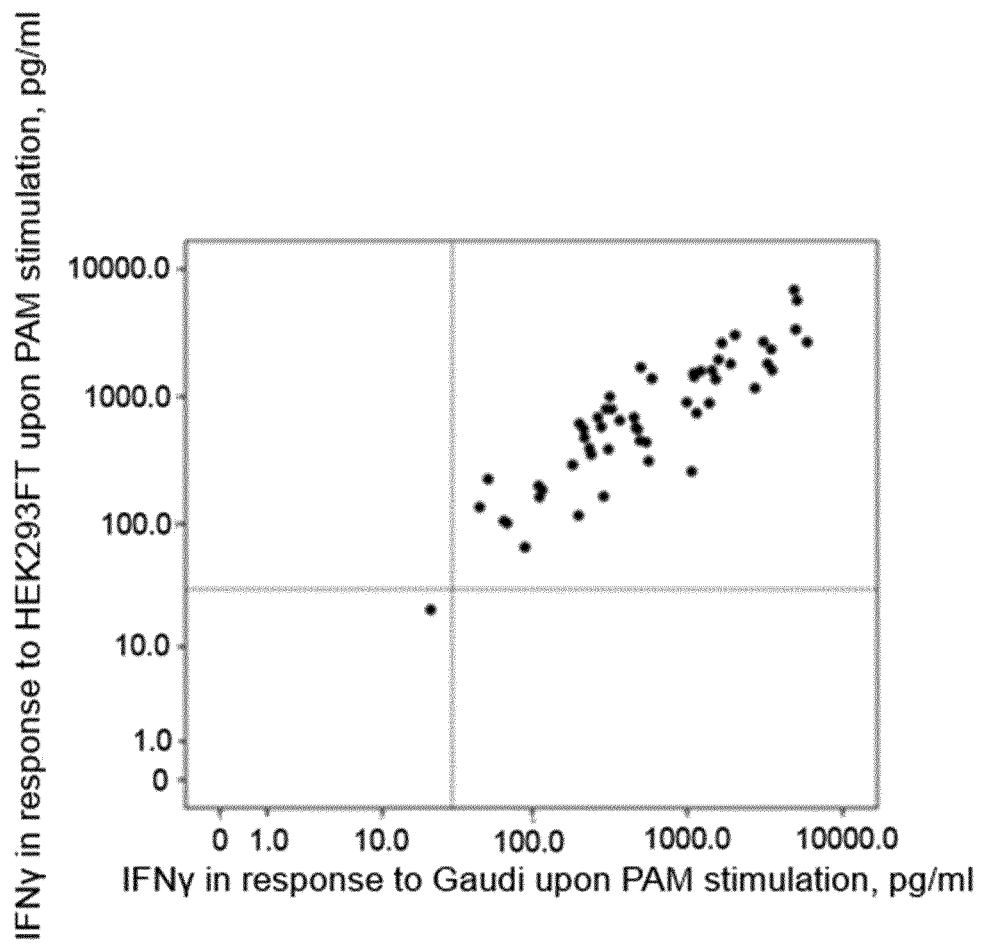
FIG. 13C shows a stimulation assay with HEK293FT cells as targets.

In order to assess on a broader range the impact of individual γ9δ2TCR on the functional activity of individual γ92δT cell clones γδ T cell clones were isolated by limiting dilution or FACS sorting. In vitro antitumor activity was determined by IFNγ production against the tumor cell line Daudi. Substantial antitumor functional heterogeneity was observed among the γ9δ2T cell clones (N=57) isolated from 4 healthy donors, with approximately 60% of the clones being reactive to the tumor cell line Daudi (FIG. 13A), when choosing a cut-off of 30 pg/ml for reliable measurement of IFNγ concentration. Bisphophsonates such as pamidronate (PAM) can enhance activity of γ9δ2T cells through induction of CD277J, facilitated by RhoB and sensed by the γ9δ2TCR. In the presence of 100 µM PAM the reactivity of investigated γ9δ2T cell clones was on average 10-fold enhanced (range 0.7-37.3; median 8.1) with >95% of the clones showing reactivity above the threshold when PAM was added (FIG. 13A). In order to assess whether activity profiles where exclusively observed for Daudi cells or also valid for other targets, the cell line HEK293FT, an additional well-characterized γδT cell target, was co-incubated with the isolated γδT cell clones. HEK293FT cell line elicited much lower cytokine secretion in the absence of PAM with only approximately 30% of γ9δ2T cell clones secreting IFNγ above cut-off (FIG. 13B). However, in the presence of PAM the reactivity of individual clones was comparable to their reactivity to Daudi, as evidenced by a strong correlation of IFNγ secretion when the very same clone was tested either against Daudi or HEK293FT (Spearman's r=0.893, p<0.0001 (n=54), FIG. 13B and FIG. 13C).

TABLE 4

CDR3 Clones

| clone ID | CDR3 Gamma | CDR3 Delta |
|---|---|---|
| A1 | CALWEVKELGKKIKVF | CACDTLLLLGDSSDKLIF |
| A2 | CALWEVQELGKKIKVF | CACDTAEPGGYKDKLIF |
| A3 | CALWEVQELGKKIKVF | CACDAWGHTDKLIF |
| A4 | CALWEVEGLGKKIKVF | CACDALGDTGSDKLIF |
| A5 | CALWEAGELGKKIKVF | CACDTLGALYTDKLIF |
| A6 | CALWEVRQELGKKIKVF | CACDQLGDPDKLIF |
| A7 | CALWEVRELGKKIKVF | CACDSDPDWGILNTDKLIF<br>CACDTVGHQGKLIF |
| B1 | CALWEAQVELGKKIKVF | CACDTPWGIPAAQDTDKLIF |
| B2, B5 | CALWEVRYYKKLF | CACDPRFLAWGTTDKLIF |
| C1 | CALWEVRELGKKIKVF | CACDPVPSIHDTDKLIF |
| C2 | CALWEVRELGKKIKVF | CACDQAGGPDKLIF |
| C3 | CALWEVGLGKKIKVF | CACDTVSGGYQYTDKLIF |
| C4, C14 | CALWEVSGELGKKIKVF | CACDTLALGDTDKLIF |
| C5 | CALWEVQELGKKIKVF | CACDLLAPGDTSFTDKLIF |
| C6 | CALWEVKRELGKKIKVF | CACDTVVLGTGGYRDDKLIF |
| C7, C11 | CALWEVRELGKKIKVF | CACDMGDASSWDTRQMFF |
| clone 13 | CALWEVIELGKKIKVF | CACVPLLADTDKLIF |

Example 12: Clonal Frequency of γ9δ2T Cells

Figure 14A:
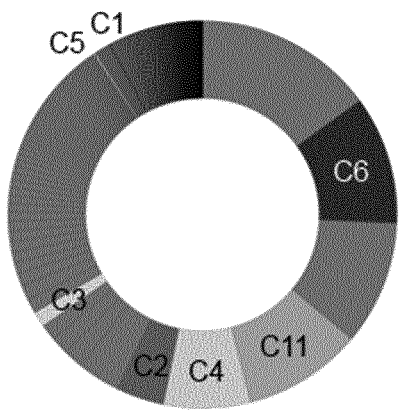
FIG. 14A shows the complete TRDV repertoire of the donor C. Percentages indicate prevalence of the clonotypes. Sequences with frequency of 1 read/clonotype are excluded from the analysis.

To further study the role of the γ9δ2TCR in the in vitro antitumor activity of individual γ9δ2T cell clones 20 out of 57 clones for γ9δ2TCR sequencing were chosen, these clones covered the full range of clonal activities as depicted in FIG. 13A. Several clone pairs (B2 and B5, C4 and C14, C7 and C11) were found to express the same TCR, ending with a total of 17 unique clonotypes. Among the individual clonotypes all δ chains were unique, whereas there existed some overlap in the γ chain in terms of CDR3 region sequence, both within and between donors (FIG. 14A).

Figure 14B:
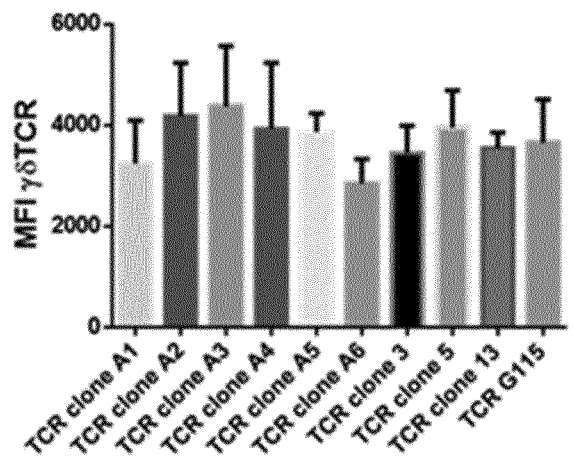
FIG. 14B shows MFI of γδTCR expression of the selected TCRs (n=7) after transduction into PBMCs and selection procedure, next to control TCRs.

High throughput sequencing (HTS) of the complete γ9δ2TCR repertoire of the same donors as used for single cell sorting was performed. Prevalence of a certain clonotype within the repertoire of a donor did not correlate with functional activity of the respective clone against Daudi or HEK293FT, as demonstrated on the example of the donor C: most prevalent clone C6 belonged to one of the most reactive γ9δ2T cell clones isolated from this donor, while three other prevalent clonotypes (C2, C4, C11) showed reactivity in the lower range (FIG. 14B), though we cannot exclude that the depicted δ chain, if combined with other γ chains, shows higher activity. Vice versa, very active γ9δ2T cell clones from donor A were not prevalent in the original donor. Therefore, clonal frequency did not correlate with functional activity of the individual γ9δ2T cells.

Example 13: Functional Activity of Parental γ9δ2T Cells

Figure 14C:
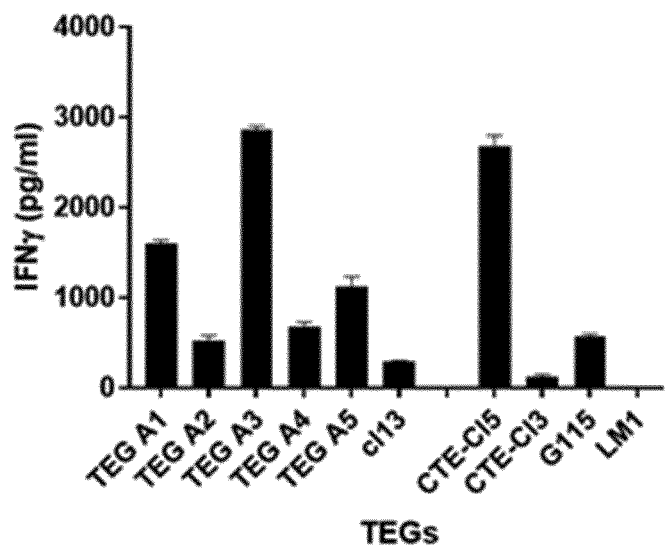
FIG. 14C shows functional avidity of the selected TCRs in the TEG format against cell line Daudi, next to control TCRs. TEGs were included in the graph based on comparable γδTCR expression.

A selection of sequenced γ and δ TCR genes were synthetized, cloned into the retroviral pBullet vector and expressed in primary αβT cells, allowing analysis of individual γδTCRs in the absence of other co-receptors of γδT cells. First, it was assessed whether variations within the CDR3 region impact TCR surface expression. As demonstrated in FIG. 14C, all generated TEGs expressed similar levels of γδTCRs as exemplified by the TCRs clone A1 to A6 and in clone 13 (C113), G115, clone 3 (C13) and clone 5 (C15). As demonstrated in FIG. 14D, substantial differences in activity could be observed between TEGs engineered with weak TCRs such as the artificially designed CTE-C13 and strong TCRs such as CTE-C15. Similarly, γ9δ2TCRs from the natural repertoire differed substantially in their ability to induce IFNγ secretion in the TEG format. However, functional activity did not correlate with the functional activity of the parental clone, as demonstrated by a highly reactive clone A4, A5 and C113 whose TCR was poorly activating in the TEG format (FIG. 14D), suggesting that other factors such as additional co-receptors or epigenetic regulations contribute to the functional response of a γ9δ2 T cell clone.

Example 14: γ9δ2TCR Target Interaction

Figure 15A:
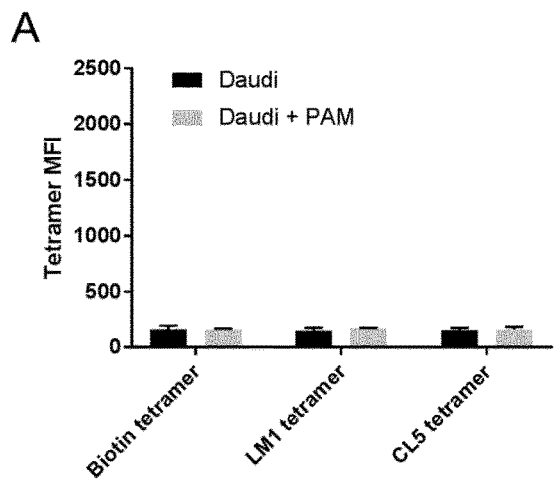
FIG. 15A shows staining of Daudi cells using TCR tetramers 1*10^5 Daudi cells (n=4) were stained for 30 minutes at room temperature with 100 nM SA-PE tetramer, either biotin control or containing γδTCR LM1 or CL5, and subsequently stained with fixable viability dye. Cells were incubated with 100 μM pamidronate (+PAM condition) for 2 h before staining. The stained cells were analyzed on a BD FACSCanto II (BD Bioscience).
Figure 15B:
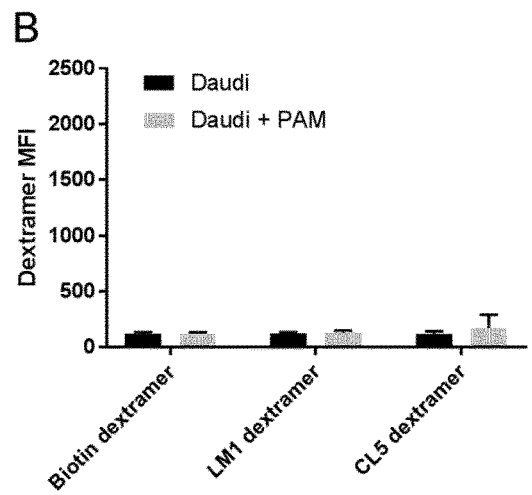
FIG. 15B shows staining of Daudi cells using TCR dextramers. 1*10^5 Daudi cells (n=4) were stained with 100 nM SA-PE dextramer and analysed in the same manner as in FIG. 15A.
Figure 15C:
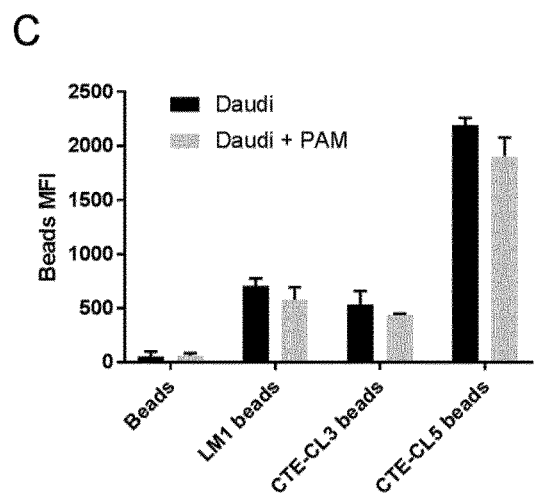
FIG. 15C shows staining of Daudi cells using YG-beads. 7.5*10^4 cells (n=3) were stained with 0.33 mg/ml YG beads (unconjugated or conjugated with γδTCRs LM1, CTE-CL3 or CTE-CL5) and analysed in the same manner as in FIG. 15A.
Figure 19:
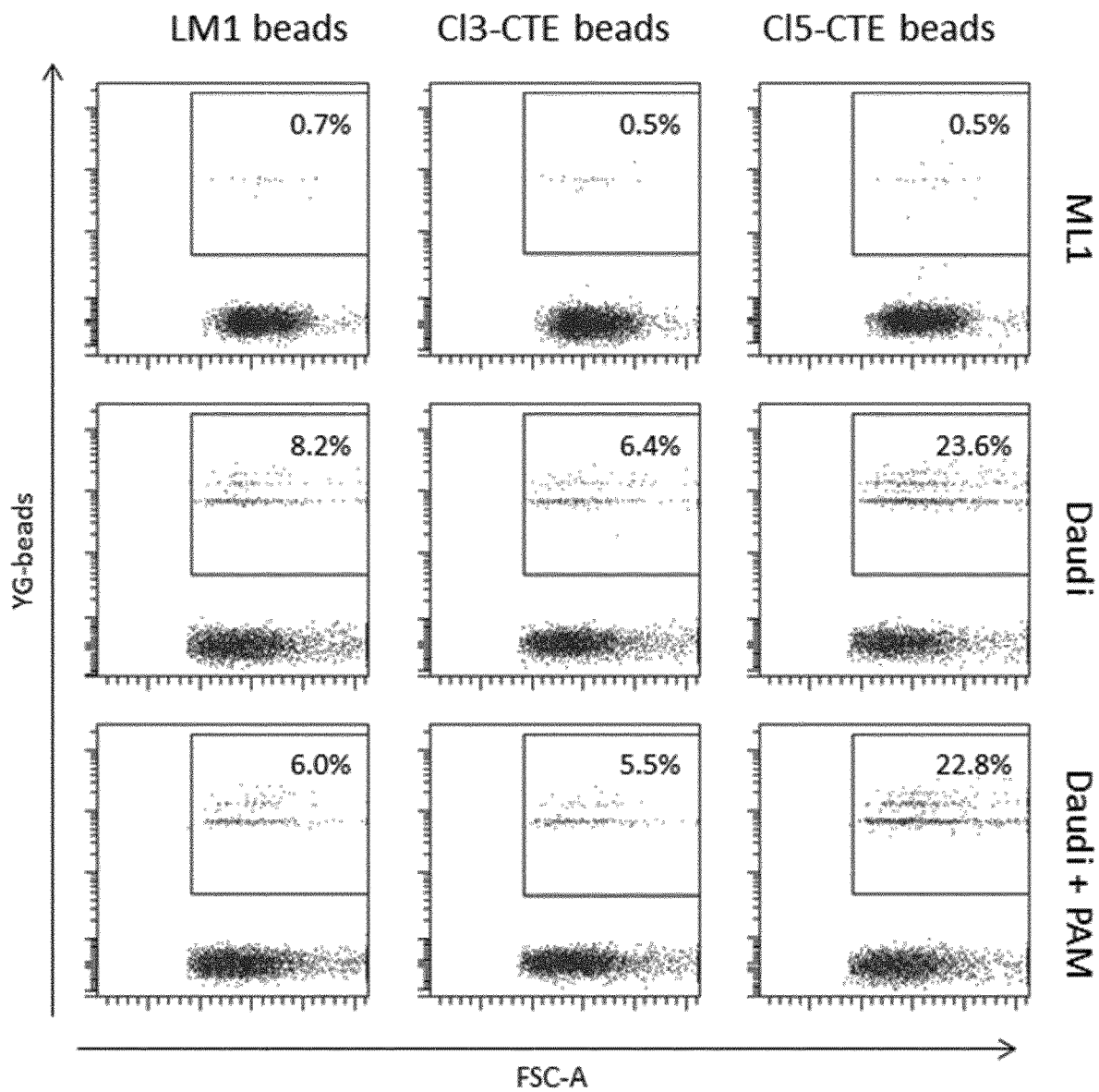
FIG. 19 shows representative flow cytometry dot plots of Daudi and ML1 cells stained with sTCR-conjugated beads.

Tetramers and dextramers were engineered that comprised γ9 and δ2TCR chains of γδTCR clone 5 and the non-functional length mutant LM1. In line with the low affinity interactions of γ9δ2TCR with its ligand which are used to sense CD277J-configuration, neither γ9δ2TCR tetramers nor dextramers did bind to the classical target Daudi (FIG. 15A and FIG. 15B). Next, the number of γδTCRs on a multimer was increased in order to reach a higher interaction avidity. The extracellular domains of the non-functional length mutant LM1, as well as γδTCRs CTE-C13 and CTE-C15, which mediate low and high functional avidity in the TEG format, were coupled to streptavidin conjugated Yellow-Green fluorescent beads (referred herein as YG-beads), which allowed at least $10^4$ γδTCR to be attached to the surface of a YG-bead. YG-beads expressing the γ9δ2TCRs were used to stain the known negative target cell line ML1, and the positive target cell line Daudi. No YG-bead conjugation to ML1 cells could be observed in case of any of the TCR-coated beads (FIG. 19A-FIG. 19D), whereas the amount of YG-bead conjugation to Daudi cells was dependent on the TCR used for coating the beads (FIG. 15C and FIG. 20). The non-functional γ9δ2TCR, LM1, showed little conjugation to Daudi cells, just like the low functional avidity (in the TEG format) TCR CTE-C13. The high functional avidity γ9δ2TCR, CTE-C15, showed markedly higher conjugation to Daudi cells, indicating that the functional avidity of γ9δ2TCRs is indeed linked to the γ9δ2TCR-ligand affinity. Beads conjugated with γδTCR clone 5 showed the same staining pattern as CTE-CL5 beads (FIG. 19D). Interestingly YG-beads did bind only to a fraction of tumor cells (FIG. 20), most likely rather reflecting technical limitations of bead to cell ratios than the heterogeneity of the ligand within the target population itself. The γ9δ2TCR senses CD277J-configuration.

Figure 15D:
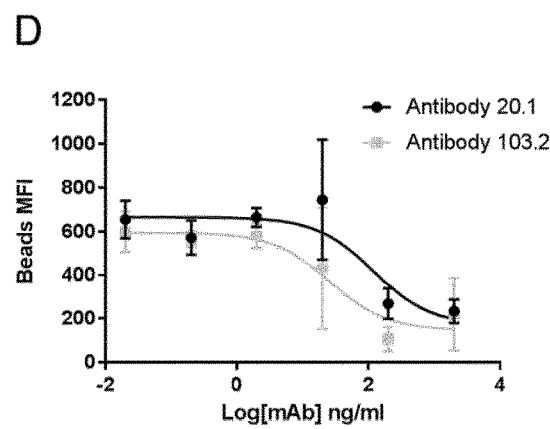
FIG. 15D shows staining of Daudi cells using YG-beads. Binding competition assay using 2 anti-CD277 monoclonal antibodies (20.1 and 103.2). 7.5 10$^4$ Daudi cells (n=2) were preincubated with the antibody and incubated with CL5-beads for 30 minutes at room temperature. All analyses of the FACS data were done in BD FACS Diva and graphs were generated in Graphpad Prism.

The binding of CTE-C15 YG-beads to Daudi cells allowed the assessment of whether CD277J is directly interacting with the γ9δ2TCR. CTE-C15 YG-beads were co-incubated with Daudi cells in the presence of two commonly used monoclonal antibodies against CD277, namely 20.1 and 103.2. The conjugation of CTE-C15 YG-beads with Daudi was inhibited by both monoclonal antibodies, indicating that CD277 is directly interacting with Vγ9Vδ2 TCRs (FIG. 15D). It was also determined whether static YG-beads can also sense CD277J induced by PAM. Adding PAM did not change intensity of TCR-YG-bead conjugation to Daudi cells (FIG. 15C), indicating that static TCR-YG-beads can capture different affinities of γ9δ2TCRs to CD277 but not fully mimic the mode of action of a γ9δ2TCR expressed within a cell membrane.

Example 15: Dynamic Interaction of a γ9δ2TCR with its Counterpart

Figure 16:
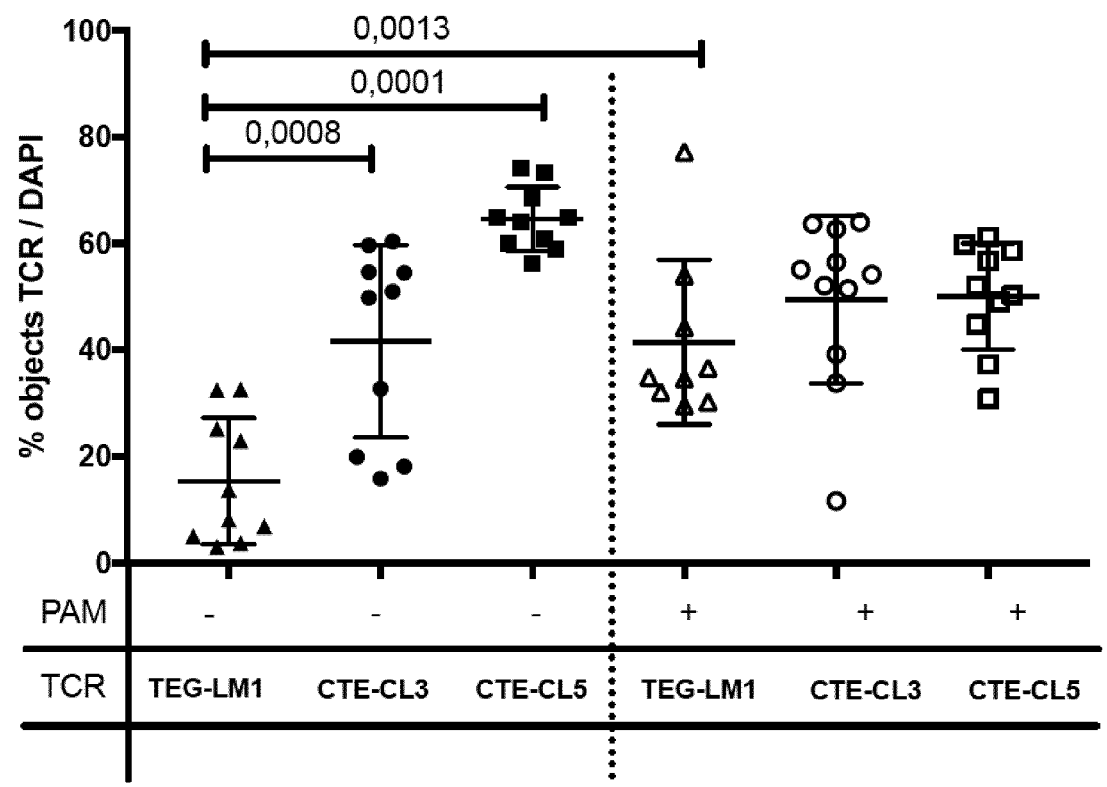
FIG. 16 shows TEGs expressing either non-functional TCR LM1, intermediate affinity CTE-CL3 or high affinity CTE-CL5 were co-incubated with HEK293FT cells that were either pre-incubated with 100 uM pamidronate or with medium. Co-incubation was done for up to 120 minutes where after the unconjugated cells were washed away. Samples were immunostained with anti-CD3e antibody and DAPI and used for confocal microscopy analysis. Images were quantified with respect to the number of DAPI+ cells (total cells) and CD3-positive cells (TEGs) and the ratios are represented. Analysis was done on at least ten independent images and significance was determined by non-parametric ANOVA. Results show individual measurements including mean and SD values.

To further assess whether distinct functional avidity of γ9δ2TCRs when expressed in the TEG format is regulated by their ability to mediate binding of TEGs to tumor cell targets a more dynamic model was utilized. Therefore, Jurma cells expressing comparable levels of various γδTCRs were co-incubated with HEK293FT tumor cells. Utilizing the adherent HEK293FT cells enabled discarding of TEGs not bound to tumor cells within 120 minutes after incubation by washing and was followed by staining with DAPI and anti-CD3 antibodies. The number of tumor cell-T cell conjugates was assessed. In contrast to YG-bead staining, not only the conjugate formation correlated with affinity of the used γ9δ2TCR in the absence of PAM, but PAM treatment also increased the number of conjugates, in particular in the case of the low affinity γ9δ2TCR as well as surprisingly also in the case of the non-functional mutant LM1. (FIG. 16). This finding suggests that physical binding of a distinct γ9δ2TCR to a defined protein expressed on tumor cells facilitates consecutive conjugate formation between a T cell expressing a γ9δ2TCR and the tumor cell. However, the conjugate formation can be independent of the CDR3 regions of the γ9δ2TCR. Thus, PAM can induce a γ9δ2TCR dependent but CDR3 independent conjugate formation, which is however not sufficient to fully activate a T cell. Additional steps must be involved in inducing full T cell activation.

Figure 17A:
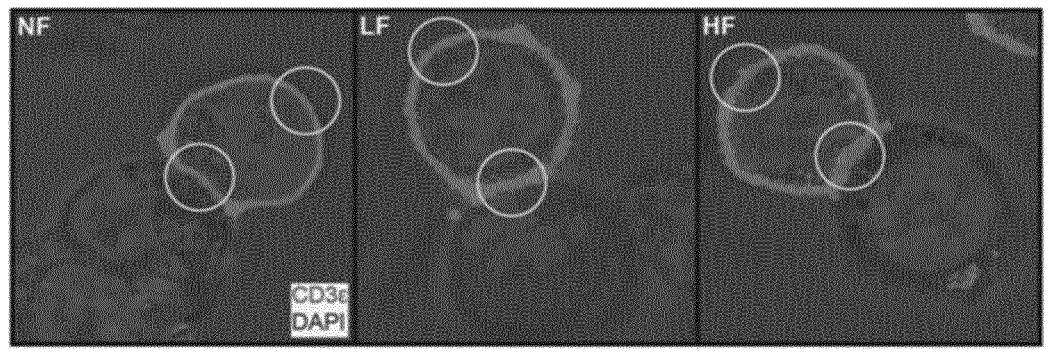
FIG. 17A shows immunological synapse and quantification method.
Figure 17B:
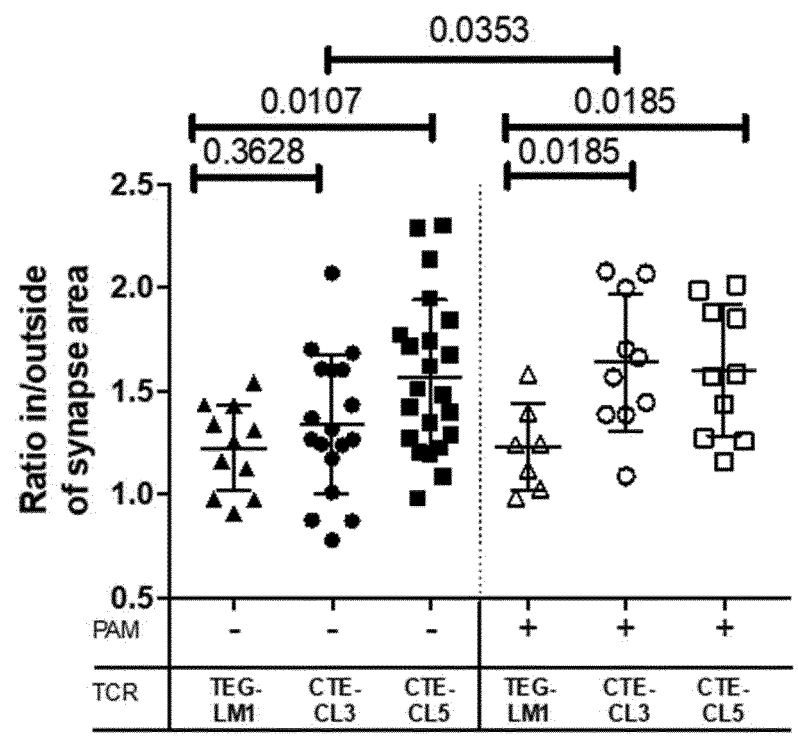
FIG. 17B shows enrichment of TCR in IS was determined by calculating the ratio of TCR signal intensity inside vs outside of synapse area. Analysis was done on at least seven independent images and significance was determined by non-parametric ANOVA. Results show individual measurements including mean and SD values.
Figures 17C, 17D, 17E, 17F:
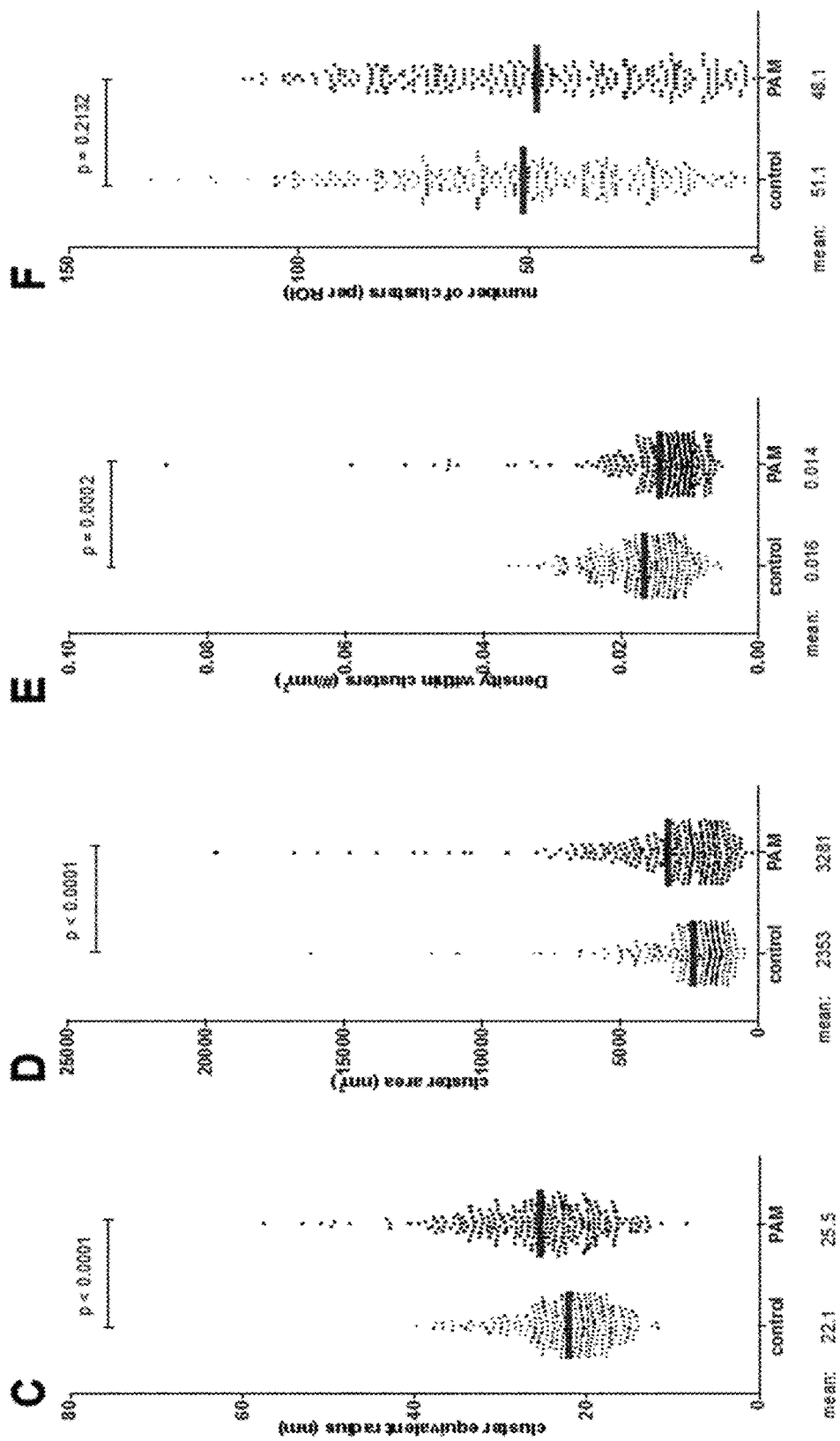
FIG. 17C and FIG. 17D show cluster size of target HEK-293FT tumor cells were either treated with 100 uM pamidronate or with medium and immunostained with CD277-AF647. Samples were subsequently used for analysis with super-resolution microscopy. Images were analysed with cluster algorithm DBSCAN.
FIG. 17E shows cluster compactness of immunological synapses.
FIG. 17F shows number of clusters per ROI.
Figure 18A:
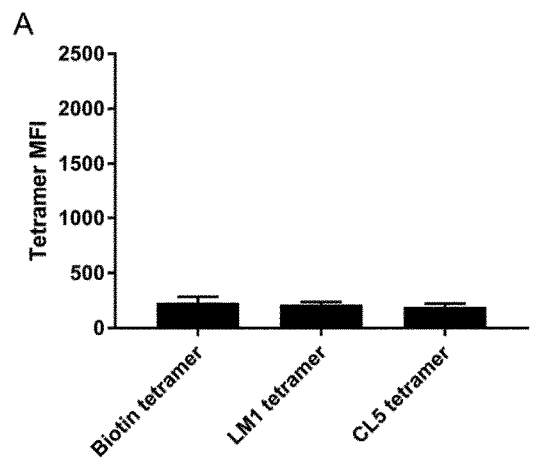
FIG. 18A shows staining of ML1 cells using TCR tetramers. 1*10^5 ML1 cells (n=4) were stained for 30 minutes at room temperature with 100 nM SA-PE tetramer, either biotin control or containing γδTCR "LM1" or "CL5", and subsequently stained with fixable viability dye. The stained cells were analyzed on a BD FACSCanto II (BD Bioscience).
Figure 18B:
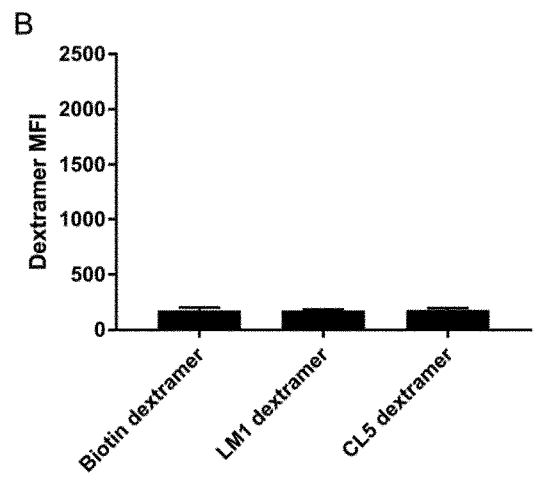
FIG. 18B shows staining of ML1 cells using dextramers. 1*10^5 ML1 cells (n=4) were stained with 100 nM SA-PE dextramer.
Figure 18C:
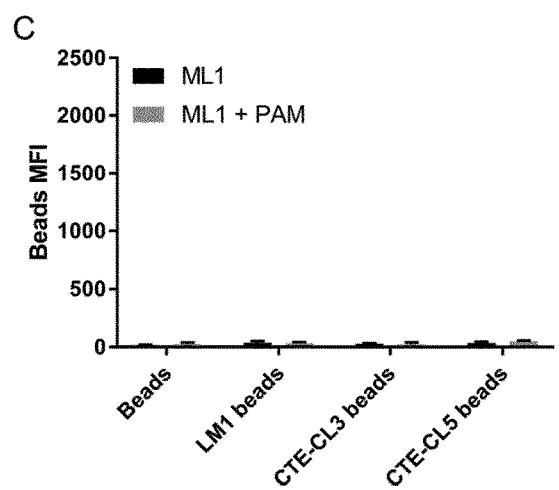
FIG. 18C and FIG. 18D show staining of ML1 cells using YG-beads. 7.5*10^4 ML1 cells (n=3) were stained with 0.33 mg/ml YG beads (unconjugated or conjugated with γδTCR "LM1", "CTE CL3" or "CTE CL5").
Figure 18D:
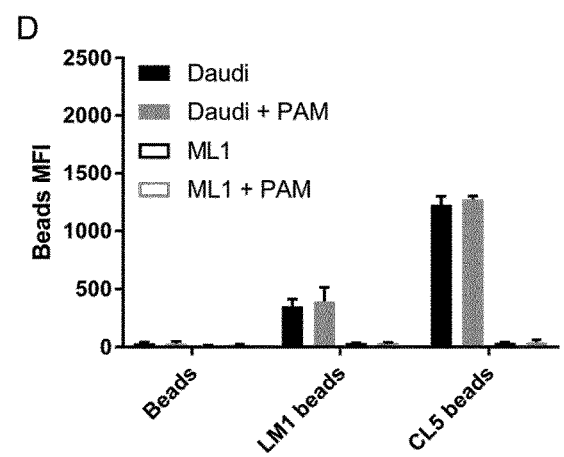

An additional step reported to be essential for activation of T cells expressing a γ9δ2TCR can be the CD277J-configuration at the cell membrane of the tumor cell. In order to investigate whether CD277J also associates with an increased clustering of γ9δ2TCR at the T cell side and whether such processes depend on the CDR3 region of the γ9δ2TCR, spatial changes in the plasma membrane in the context of distinct γδTCR affinities was analyzed. Confocal imaging of the late immunological synapses formed between Jurma T cells engineered to express non-functional TCR LM1, low affinity CTE-C13 and high affinity CTE-C15 was determined. The amount of γδTCRs that accumulated to the contact area between tumor targets and T cells, relative to T cell membrane areas distant from the immunological synapse is shown in FIG. 17A and FIG. 17B. Synapse enrichment of the γδTCR was significantly higher for CTE-C15 when compared to CTE-C13 and LM1 TCRs towards PAM-untreated tumor cells (at low phosphoantigen levels) (FIG. 17B). Even though T cells expressing a non-active TCR LM1 showed significant tumor cell binding (FIG. 16), LM1 TCR did not recruit to the immunological synapse even at high phosphoantigen levels when tumor cells were pre-treated with PAM (FIG. 17B). Neither did PAM pre-treatment affect the recruitment of the high affinity CTE-C15 TCR to the immune synapse. However, it significantly increased accumulation of the low affinity of CTE-C13 TCR in the synapse, suggesting that CDR3 region of the γ9δ2TCR has no impact on creating close vicinity between tumor cells and T cells, while it is instrumental for supporting recruitment of the γ9δ2TCR with lower affinities to the synapse. This finding implies that the affinity of the γ9δ2TCR dictates its recruitment to the immunological synapse and that complete synapse formation can be further enhanced by PAM.

Finally, in order to understand whether the enhanced recruitment of low affinity CTE-C13 TCR in the synapse was a result of changes in CD277 clustering due to the PAM treatment, direct stochastic optical reconstruction microscopy (dSTORM), a localization-based super-resolution imaging technique that provides ~20 nm resolution was performed. BTN3A molecules were labelled with AF647-CD277 antibody and super-resolution images were acquired at the basal membrane of HEK293FT cells. To quantify the images, a density-based spatial clustering application (DB-SCAN) was utilized. DBSCAN classifies localizations into clusters based on their relative local spatial density. Individual clusters were identified and comparisons between the distributions of clusters across different conditions were made. Treatment with PAM did not dramatically change localization cluster size, density or number (FIG. 17C, FIG. 17D, FIG. 17E, and FIG. 17F). Results were similar when using either Getis-G or Hierarchal cluster analysis methods. Choosing maximal distance between neighboring cluster points to an epsilon of 30, 40 or 50 nm gave similar BTN3A nano-clustering results.

What is claimed is:

1. A pharmaceutical composition comprising a polypeptide construct comprising:
   (A) a γ9 subunit or a fragment thereof comprising a γ9 complementarity-determining region 3 (γ9-CDR3) having a sequence selected from SEQ ID NOs: 74-84; and
   (B) a δ2 subunit or fragment thereof comprising a δ2 complementarity-determining region 3 (δ2-CDR3) having a sequence selected from SEQ ID NOs: 86-101 wherein the polypeptide selectively binds a J-configuration of CD277 on a target cell.

2. The pharmaceutical composition of claim 1, wherein said CD277 is present as a dimer.

3. The pharmaceutical composition of claim 1, wherein the polypeptide binds the J-configuration of CD277 with higher selectivity as compared to a CD277 molecule which is not in said J-configuration.

4. The pharmaceutical composition of claim 1, wherein the target cell is a cancer cell.

5. The pharmaceutical composition of claim 4, wherein the cancer cell is a leukemia cell or from a solid cancer.

6. A method of treating cancer in a subject in need thereof, wherein the subject has cancer cells that are CD277 positive, comprising providing to the subject an effective amount of a pharmaceutical composition comprising a polypeptide comprising:
- (A) a γ9 subunit or a fragment thereof comprising a γ9 complementarity-determining region 3 (γ9-CDR3) having a sequence selected from SEQ ID NOs: 74-84; and
- (B) a δ2 subunit or fragment thereof comprising a δ2 complementarity-determining region 3 (δ2-CDR3) having a sequence selected from SEQ ID NOs: 86-101 wherein the polypeptide selectively binds a J-configuration of CD277 on a target cell.

7. The method of claim 6, wherein formation of said J-configuration requires at least an interaction of RhoB with CD277 and/or compartmentalization of CD277.

8. The method of claim 7, wherein said formation of said J-configuration requires interaction of intracellular phosphoantigen with CD277 subsequent to said interaction of RhoB with CD277.

\* \* \* \* \*

UNITED STATES PATENT AND TRADEMARK OFFICE
CERTIFICATE OF CORRECTION

| | | |
|---|---|---|
| PATENT NO. | : 12,161,669 B2 | Page 1 of 1 |
| APPLICATION NO. | : 16/614691 | |
| DATED | : December 10, 2024 | |
| INVENTOR(S) | : Kuball et al. | |

It is certified that error appears in the above-identified patent and that said Letters Patent is hereby corrected as shown below:

In the Claims

Claim 1:
Column 125, Line 59-60 "A pharmaceutical composition comprising a polypep-tide construct comprising:" should be --A pharmaceutical composition comprising a polypeptide comprising:--.

Signed and Sealed this
Fourth Day of March, 2025

Coke Morgan Stewart
*Acting Director of the United States Patent and Trademark Office*

SEQUENCE LISTING

```
<160> NUMBER OF SEQ ID NOS: 102

<210> SEQ ID NO 1
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="See specification as filed for detailed
      description of substitutions and preferred embodiments"

<400> SEQUENCE: 1

Gly Gly Gly Gly Ser
1               5
```

-continued

```
<210> SEQ ID NO 2
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 2
gaactatgtg gcagatatcg                                                  20

<210> SEQ ID NO 3
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 3
gtggtgggcg acggcgcgtg                                                  20

<210> SEQ ID NO 4
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 4
gaaagaagct ggtgatcgt                                                   19

<210> SEQ ID NO 5
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 5
gtgaaccgca tcgagctgaa                                                  20

<210> SEQ ID NO 6
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 6

His His His His His His
1               5

<210> SEQ ID NO 7
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

-continued

```
<400> SEQUENCE: 7
cgccatatga tggccgccat ccg                                           23

<210> SEQ ID NO 8
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 8
cgcctcgagt tagcagcagt tgatgcagc                                     29

<210> SEQ ID NO 9
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Cys Lys Val Leu
1

<210> SEQ ID NO 10
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 10
gcgccatggg gcaacagcag gaggaaaaa                                     29

<210> SEQ ID NO 11
<211> LENGTH: 57
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 11
cgctcgaggg gccccctggaa cagaacttcc agaccaccag acgctggaca aatagtc     57

<210> SEQ ID NO 12
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 12
ttcaccagac aagcgaca                                                 18

<210> SEQ ID NO 13
<211> LENGTH: 19
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 13
tctcttctgg gcaggagtc                                                19

<210> SEQ ID NO 14
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 14
tccttggggc tctgtgtgt                                                19

<210> SEQ ID NO 15
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 15
ggggaaacat ctgcatca                                                 18

<210> SEQ ID NO 16
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 16
cccagctctt tcacctccca cagggcgcag                                    30

<210> SEQ ID NO 17
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 17
ccagctcttg cacctcccac agggcgcag                                     29

<210> SEQ ID NO 18
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

```
<400> SEQUENCE: 18
cccaggcctt caacctccca cagggcgcag                               30

<210> SEQ ID NO 19
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 19
agctcgccgg cctcccacag ggcgcag                                  27

<210> SEQ ID NO 20
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 20
cagctcttgc cgcacctccc acagggcgca g                             31

<210> SEQ ID NO 21
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 21
cagctcccgc acctcccaca gggcgcag                                 28

<210> SEQ ID NO 22
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 22
ccagttccac ttgagcctcc cacagggcgc ag                            32

<210> SEQ ID NO 23
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 23
cagcttcttg tagtatctca cctcccacag ggcgcag                       37

<210> SEQ ID NO 24
<211> LENGTH: 27
<212> TYPE: DNA
```

```
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 24
cccaggccca cctcccacag ggcgcag                                          27

<210> SEQ ID NO 25
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 25
cagctcgcca gacacctccc acagggcgca g                                    31

<210> SEQ ID NO 26
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 26
cccagctccc tcttcacctc ccacagggcg cag                                  33

<210> SEQ ID NO 27
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 27
gggaggtgaa agagctgggc aagaaaatca aggtgttcg                            39

<210> SEQ ID NO 28
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 28
gggaggtgca agagctgggc aagaaaatca aggtgttcg                            39

<210> SEQ ID NO 29
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 29
ggaggttgaa ggcctgggca agaaaatcaa ggtgttcg                             38
```

```
<210> SEQ ID NO 30
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 30
gaggccggcg agctgggcaa gaaaatcaag gtgttcg                              37

<210> SEQ ID NO 31
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 31
gaggtgcggc aagagctggg caagaaaatc aaggtgttcg                           40

<210> SEQ ID NO 32
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 32
ggaggtgcgg gagctgggca agaaaatcaa ggtgttcg                             38

<210> SEQ ID NO 33
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 33
gggaggctca agtggaactg ggcaagaaaa tcaaggtgtt cg                        42

<210> SEQ ID NO 34
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 34
gggaggtgag atactacaag aagctgttcg gcagc                                35

<210> SEQ ID NO 35
<211> LENGTH: 35
<212> TYPE: DNA
<213> ORGANISM: Artificial Sequence
<220> FEATURE:
```

```
<221> NAME/KEY: source
<223> OTHER INFORMATION: /note="Description of Artificial Sequence:
      Synthetic primer"

<400> SEQUENCE: 35
ggaggtgggc ctgggcaaga aaatcaaggt gttcg                                    35

<210> SEQ ID NO 36
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 36
ggaggtgtct ggcgagctgg gcaagaaaat caaggtgttc g                             41

<210> SEQ ID NO 37
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 37
gaggtgaaga gggagctggg caagaaaatc aaggtgttcg                               40

<210> SEQ ID NO 38
<211> LENGTH: 43
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 38
gctgtcgccc agaagcagca gtgtgtcgca ggcgcagtag tag                           43

<210> SEQ ID NO 39
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 39
gtagccgcca ggttcagctg tgtcgcaggc gcagtagtag                               40

<210> SEQ ID NO 40
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 40
tgtgtggccc caggcgtcgc aggcgcagta gtag                                     34
```

```
<210> SEQ ID NO 41
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 41
gctgcctgta tcgcccaggg cgtcgcaggc                                    30

<210> SEQ ID NO 42
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 42
gtacagcgcc cccagtgtgt cgcaggcgca gtagtag                            37

<210> SEQ ID NO 43
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 43
ggggtcgccc agctggtcgc aggcgcagta gtag                               34

<210> SEQ ID NO 44
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 44
tatgccccaa tcgggatcgc tgtcgcaggc gcagtagtag                         40

<210> SEQ ID NO 45
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 45
agtgtcctga gcagcgggaa taccccacgg agtgtcgcag gcgcagtagt ag           52

<210> SEQ ID NO 46
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

-continued

<400> SEQUENCE: 46
agtagttccc caggctagaa accttgggtc gcaggcgcag tagtag    46

<210> SEQ ID NO 47
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 47
cggtatcgtg gatagaaggt acagggtcgc aggcgcagta gtag    44

<210> SEQ ID NO 48
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 48
agggccaccc gcttggtcgc aggcgcagta gtag    34

<210> SEQ ID NO 49
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 49
ctggtagccg ccagacactg tgtcgcaggc gcagtagtag    40

<210> SEQ ID NO 50
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 50
cttgtctgta tctcccagag ctaatgtgtc gcaggcgcag tagtag    46

<210> SEQ ID NO 51
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 51
gaggtatcgc caggggcaag aaggtcgcag gcgcagtagt ag    42

<210> SEQ ID NO 52
<211> LENGTH: 52
<212> TYPE: DNA
<213> ORGANISM: Artificial Sequence -continued

```
<220> FEATURE:
<221> NAME/KEY: source
<223> OTHER INFORMATION: /note="Description of Artificial Sequence:
      Synthetic primer"

<400> SEQUENCE: 52
atctctgtaa ccacctgtgc caagcaccac tgtgtcgcag gcgcagtagt ag          52

<210> SEQ ID NO 53
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 53
ccaagaacta gcatcaccca tgtcgcaggc gcagtagtag                        40

<210> SEQ ID NO 54
<211> LENGTH: 43
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 54
ctgcttctgg gcgacagcag cgacaagctg atcttcggca agg                    43

<210> SEQ ID NO 55
<211> LENGTH: 43
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 55
gctgaacctg gcggctacaa ggacaagctg atcttcggca agg                    43

<210> SEQ ID NO 56
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 56
gcctggggcc acacagacaa gctgatcttc ggcaagg                           37

<210> SEQ ID NO 57
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 57
ctgggcgata caggcagcga caagctgatc ttcggcaagg                        40
```

<210> SEQ ID NO 58
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 58
cactgggggc gctgtacacc gacaagctga tcttcgg                    37

<210> SEQ ID NO 59
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 59
cagctgggcg accccgacaa gctgatcttc ggcaagg                    37

<210> SEQ ID NO 60
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 60
gcgatcccga ttggggcata ctgaacacgg acaagctgat cttcggcaag g    51

<210> SEQ ID NO 61
<211> LENGTH: 55
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 61
actccgtggg gtattcccgc tgctcaggac actgacaagc tgatcttcgg caagg   55

<210> SEQ ID NO 62
<211> LENGTH: 49
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 62
ccaaggtttc tagcctgggg aactactgac aagctgatct tcggcaagg       49

<210> SEQ ID NO 63
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 63
cctgtacctt ctatccacga taccgacaag ctgatcttcg gc        42

<210> SEQ ID NO 64
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 64
caagcgggtg gccctgacaa gctgatcttc ggcaagg        37

<210> SEQ ID NO 65
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 65
gtgtctggcg gctaccagta cactgacaag ctgatcttcg gcaagg        46

<210> SEQ ID NO 66
<211> LENGTH: 43
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 66
acattagctc tgggagatac agacaagctg atcttcggca agg        43

<210> SEQ ID NO 67
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 67
gcccctggcg atacctcttt caccgacaag ctgatcttcg gc        42

<210> SEQ ID NO 68
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 68
cttggcacag gtggttacag agatgacaag ctgatcttcg gcaagg        46

<210> SEQ ID NO 69
<211> LENGTH: 40
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 69
cgacatgggt gatgctagtt cttgggacac tcgccaaatg                    40

<210> SEQ ID NO 70
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 70
ctgccatgga gcggatcagc                                          20

<210> SEQ ID NO 71
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 71
gccatggtgt ccctgctg                                            18

<210> SEQ ID NO 72
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 72
atgcggatcc tcacagg                                             17

<210> SEQ ID NO 73
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 73
tagtggatcc tcagctcttc tc                                       22

<210> SEQ ID NO 74
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 74

Cys Ala Leu Trp Glu Val Lys Glu Leu Gly Lys Lys Ile Lys Val Phe
1               5                   10                  15

<210> SEQ ID NO 75
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 75

Cys Ala Leu Trp Glu Val Gln Glu Leu Gly Lys Lys Ile Lys Val Phe
1               5                   10                  15

<210> SEQ ID NO 76
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 76

Cys Ala Leu Trp Glu Val Glu Gly Leu Gly Lys Lys Ile Lys Val Phe
1               5                   10                  15

<210> SEQ ID NO 77
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 77

Cys Ala Leu Trp Glu Ala Gly Glu Leu Gly Lys Lys Ile Lys Val Phe
1               5                   10                  15

<210> SEQ ID NO 78
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 78

Cys Ala Leu Trp Glu Val Arg Gln Glu Leu Gly Lys Lys Ile Lys Val
1               5                   10                  15

Phe

<210> SEQ ID NO 79
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 79

Cys Ala Leu Trp Glu Val Arg Glu Leu Gly Lys Lys Ile Lys Val Phe
1               5                   10                  15

<210> SEQ ID NO 80
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 80

Cys Ala Leu Trp Glu Ala Gln Val Glu Leu Gly Lys Lys Ile Lys Val
1               5                   10                  15

Phe

<210> SEQ ID NO 81
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 81

Cys Ala Leu Trp Glu Val Arg Tyr Tyr Lys Lys Leu Phe
1               5                   10

<210> SEQ ID NO 82
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 82

Cys Ala Leu Trp Glu Val Gly Leu Gly Lys Lys Ile Lys Val Phe
1               5                   10                  15

<210> SEQ ID NO 83
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 83

Cys Ala Leu Trp Glu Val Ser Gly Glu Leu Gly Lys Lys Ile Lys Val
1               5                   10                  15

Phe

<210> SEQ ID NO 84
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 84

Cys Ala Leu Trp Glu Val Lys Arg Glu Leu Gly Lys Lys Ile Lys Val
1               5                   10                  15

Phe

<210> SEQ ID NO 85
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 85

Cys Ala Leu Trp Glu Val Ile Glu Leu Gly Lys Lys Ile Lys Val Phe
1               5                   10                  15

<210> SEQ ID NO 86
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 86

Cys Ala Cys Asp Thr Leu Leu Leu Leu Gly Asp Ser Ser Asp Lys Leu
1               5                   10                  15

Ile Phe

<210> SEQ ID NO 87
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 87

Cys Ala Cys Asp Thr Ala Glu Pro Gly Gly Tyr Lys Asp Lys Leu Ile
1               5                   10                  15

Phe

<210> SEQ ID NO 88
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 88

Cys Ala Cys Asp Ala Trp Gly His Thr Asp Lys Leu Ile Phe
1               5                   10

<210> SEQ ID NO 89
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 89

Cys Ala Cys Asp Ala Leu Gly Asp Thr Gly Ser Asp Lys Leu Ile Phe
1               5                   10                  15

<210> SEQ ID NO 90
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 90

Cys Ala Cys Asp Thr Leu Gly Ala Leu Tyr Thr Asp Lys Leu Ile Phe
1               5                   10                  15

<210> SEQ ID NO 91
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 91

Cys Ala Cys Asp Gln Leu Gly Asp Pro Asp Lys Leu Ile Phe
1               5                   10

<210> SEQ ID NO 92
<211> LENGTH: 33
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 92

Cys Ala Cys Asp Ser Asp Pro Asp Trp Gly Ile Leu Asn Thr Asp Lys
1               5                   10                  15

Leu Ile Phe Cys Ala Cys Asp Thr Val Gly His Gln Gly Lys Leu Ile
            20                  25                  30

Phe

<210> SEQ ID NO 93
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 93

Cys Ala Cys Asp Thr Pro Trp Gly Ile Pro Ala Gln Asp Thr Asp
1               5                   10                  15

Lys Leu Ile Phe
            20

<210> SEQ ID NO 94
<211> LENGTH: 18

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 94

Cys Ala Cys Asp Pro Arg Phe Leu Ala Trp Gly Thr Thr Asp Lys Leu
1               5                   10                  15

Ile Phe

<210> SEQ ID NO 95
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 95

Cys Ala Cys Asp Pro Val Pro Ser Ile His Asp Thr Asp Lys Leu Ile
1               5                   10                  15

Phe

<210> SEQ ID NO 96
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 96

Cys Ala Cys Asp Gln Ala Gly Gly Pro Asp Lys Leu Ile Phe
1               5                   10

<210> SEQ ID NO 97
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 97

Cys Ala Cys Asp Thr Val Ser Gly Gly Tyr Gln Tyr Thr Asp Lys Leu
1               5                   10                  15

Ile Phe

<210> SEQ ID NO 98
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 98

Cys Ala Cys Asp Thr Leu Ala Leu Gly Asp Thr Asp Lys Leu Ile Phe
1               5                   10                  15
```

```
<210> SEQ ID NO 99
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 99

Cys Ala Cys Asp Leu Leu Ala Pro Gly Asp Thr Ser Phe Thr Asp Lys
1               5                   10                  15

Leu Ile Phe

<210> SEQ ID NO 100
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 100

Cys Ala Cys Asp Thr Val Val Leu Gly Thr Gly Gly Tyr Arg Asp Asp
1               5                   10                  15

Lys Leu Ile Phe
            20

<210> SEQ ID NO 101
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 101

Cys Ala Cys Asp Met Gly Asp Ala Ser Ser Trp Asp Thr Arg Gln Met
1               5                   10                  15

Phe Phe

<210> SEQ ID NO 102
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 102

Cys Ala Cys Val Pro Leu Leu Ala Asp Thr Asp Lys Leu Ile Phe
1               5                   10                  15
```